(12) United States Patent
Jimenez et al.

(10) Patent No.: US 7,700,609 B2
(45) Date of Patent: Apr. 20, 2010

(54) COMPOSITIONS USEFUL AS INHIBITORS OF PROTEIN KINASES

(75) Inventors: Juan-Miguel Jimenez, Abingdon (GB); Jeremy Green, Burlington, MA (US); Huai Gao, Lincoln, MA (US); Young-Choon Moon, Belle Mead, NJ (US); Guy Brenchley, Wantage (GB); Ronald Knegtel, Abingdon (GB); Francoise Pierard, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 841 days.

(21) Appl. No.: 10/965,695

(22) Filed: Oct. 14, 2004

(65) Prior Publication Data

US 2005/0148603 A1 Jul. 7, 2005

Related U.S. Application Data

(60) Provisional application No. 60/510,881, filed on Oct. 14, 2003.

(51) Int. Cl.
*A61K 31/505* (2006.01)
*C07D 491/00* (2006.01)

(52) U.S. Cl. ...................... 514/267; 544/250
(58) Field of Classification Search .................. 514/267; 544/250
See application file for complete search history.

(56) References Cited

U.S. PATENT DOCUMENTS

| 5,304,121 A | 4/1994 | Sahatjian |
| 5,753,663 A | 5/1998 | Flippin et al. |
| 5,886,026 A | 3/1999 | Hunter et al. |
| 6,057,329 A | 5/2000 | Davis et al. |
| 6,099,562 A | 8/2000 | Ding et al. |
| 6,133,257 A | 10/2000 | Batchelor et al. |
| 6,599,908 B1 * | 7/2003 | Davis et al. .................. 514/267 |

FOREIGN PATENT DOCUMENTS

| EP | 0 260 642 A | 9/1987 |
| WO | WO9712880 | 4/1997 |
| WO | WO 98/28281 | 7/1998 |
| WO | WO 98/58926 | 12/1998 |
| WO | WO 99/65897 | 12/1999 |
| WO | WO 00/38675 | 7/2000 |
| WO | WO 01/87845 | 11/2001 |
| WO | WO 02/085909 | 10/2002 |
| WO | WO 2004/104007 | 12/2004 |
| WO | WO 2005/005438 | 1/2005 |

OTHER PUBLICATIONS

Adams, et al., "Chromosomal passengers and the (aurora) ABCs of mitosis," *Trends in Cell Biology* 11:49-54 (2001).

Behringer, H. and Falkenberg, K., "Synthesen von substituierten Thiophen-und 5-Amino-thiophen-carbonsäuren-(2)," *Chemische Berichte*, 99:3309-3315 (1966).

Berge et al., "Pharmaceutical Salts", *Journal of Pharmaceutical Sciences*, 66:1-19 (1977).

Biscardi et al., "c-Src, Receptor Tyrosine Kinases, and Human Cancer," *Advances in Cancer Research*, 76:61-119 (1999).

Bischoff et al., "A homologue of *Drosophila* aurora kinase is oncogenic and amplified in human colorectal cancers," *EMBO J*, 17:3052-3065 (1998).

Bischoff, J.R. and Plowman, G.D., "The Aurora/Ipl1p kinase family: regulators of chromosome segregation and cytokinesis," *Trends in Cell Biology*, 9:454-459 (1999).

Bolen et al., "Activation of pp60$^{c-src}$ protein kinase activity in human colon carcinoma," *Proc. Natl. Acad. Sci. USA*, 84:2251-2255. (1987).

Boschelli, D. and Boschelli, F., "Small molecule inhibitors of Src family kinases," *Drugs of the Future*, 2000, 25(7):717-736 (2000).

Brown et al., "Naphthyl Ketones: A New Class of Janus Kinase 3 Inhibitors," *Bioorg. Med. Chem. Lett.*, 10:575-579 (2000).

Brownlees et al., "Tau phosphorylation in transgenic mice expressing glycogen synthase kinase-3β transgenes," *Neuroreport*, 8:3251-3255 (1997).

Catlett-Falcone et al., "Constitutive Actvation of Stat3 Signaling Confers Resistance to Apoptosis in Human U266 Myeloma Cells," *Immunity*, 10:105-115 (1999).

Coghlan et al., "Selective small molecule inhibitors of glycogen synthase kinase-3 modulate glycogen metabolism and gene transcription," *Chemistry & Biology*, 7:793-803 (2000).

Cohen, P., "Dissection of the Protein Phosphorylation Cascades Involved in Insulin and Growth Factor Action," *Biochem. Soc. Trans.* 21:555-567 (1993).

Crimmins, et al., "Synthesis and Intramolecular Photocycloadditions of 2-Acyloxy-3-Hexenoyl Cyclohexenones: Diastereoselectivity in the Intramolecular [2+2] Photocycloadditions of Alkenes and Cyclohexenones Tethered by Four Atoms," *Tetrahedron* 53:8963-8974 (1997).

Cross et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf," *Biochem. J.* 303:21-26 (1994).

Dutertre, S., et al., "On the role of aurora-A in centrosome function," *Oncogene* 21:6175-6183 (2002).

(Continued)

*Primary Examiner*—James O Wilson
*Assistant Examiner*—Erich A Leeser
(74) *Attorney, Agent, or Firm*—Ropes & Gray LLP; James F. Haley, Jr.

(57) ABSTRACT

The present invention relates to compounds useful as inhibitors of protein kinases. The invention also provides processes for preparing the compounds, pharmaceutically acceptable compositions comprising the compounds, and methods of using the compounds and compositions in the treatment of various disease, conditions, or disorders.

63 Claims, No Drawings

OTHER PUBLICATIONS

Ellmeier et al., "Severe B Cell Deficiency in Mice Lacking the Tec Kinase Family Members Tec and Btk," *J Exp Med* 192:1611-1623 (2000).

Fischer, P.M. and Lane, D.P., "Inhibitors of Cyclin-Dependent Kinases as Anti-Cancer Therapeutics," *Current Medicinal Chemistry*, 7:1213-1245 (2000).

Flatt, P. and Pietenpol, J., "Mechanisms of Cell-Cycle Checkpoints: At the Crossroads Of Carcinogenesis and Drug Discovery," *Drug Metabolism Reviews*, 32:283-305 (2000).

Forrester, et al, "Iminyls. Part 7.[1] Intramolecular Hydrogen Abstraction; Synthesis of Heterocyclic Analogues of α—Tetralone,"*J. Chem. Soc., Perkin Trans.*, 1 3:984-987 (1981).

Fowell et al, "Impaired NFATc Translocation and Failure of Th2 Development in 1tk-Deficient CD4[+] T Cells," *Immunity*, 11:399-409 (1999).

Fox et al., "A single amino acid substitution makes ERK2 susceptible to pyridinyl imidazole inhibitors of p38 MAP kinase," *Protein Sci,*. 1998, 7:2249-2255 (1998).

Frank, D.A., "STAT Signaling in the Pathogenesis and Treatment of Cancer," *Mol. Med.* 1999, 5:432-456 (1999).

Fry, D.W. and Garrett, M.D., "Inhibitors of cyclin-dependent kinases as therapeutic agents for the treatment of cancer," *Current Opinion in Oncologic, Endocrine & Metabolic Investigational Drugs*, 2:40-59 (2000).

Galli, S.J., "New Concepts About The Mast Cell," *N. Engl. J. Med.*, 328:257-265 (1993).

Garcia-Bustos et al., "PIK1, an essential phosphatidylinositol 4-kinase associated with the yeast nucleus," *EMBO J.*, 13:2352-2361 (1994).

Giet, R. and Prigent, C., "Aurora/Ip11p-related kinases, a new oncogenic family of mitotic serine-threonine kinases," *Journal of Cell Science* 112:3591-3601 (1999).

Gordon et al., "Mast cells as a source of both preformed and immunologically inducible TNF-α/cachectin," *Nature*, 346:274-276 (1990).

Gritsko, T.M. et al., "Activation and Overexpression of Centrosome Kinase BTAK/Aurora-A in Human Ovarian Cancer[1]," *Clinical Cancer Research*, 9:1420-1426 (2003).

Hanks, S.K., Hunter, T., "The eukaryotic protein kinase superfamily: kinase (catalytic) domain structure and classification,[1]" *FASEB J.*, 9:576-596 (1995).

Haq, S. et al., "Glycogen Synthase Kinase-3β Is a Negative Regulator of Cardiomyocyte Hypertrophy," *J. Cell Biol.*, 151:117-129 (2000).

Hashimoto, M. et al., "Fibroblast Growth Factor 1 Regulates Signaling via the Glycogen Synthase Kinase-3β Pathway," *J. Biol. Chem.*, 277:32985-32991 (2002).

Hiles, I.D. et al., "Phosphatidylinositol 3-Kinase: Structure and Expression of the 110 kd Catalytic Subunit," *Cell*, 70:419-429 (1992).

Isola, J. J. et al. "Genetic Aberrations Detected by Comparative Genomic Hybridization Predict Outcome in Node-Negative Breast Cancer," *American Journal of Pathology*, 147:905-911 (1995).

Kämpf, A. et al., "Ueber Darstellung aromatisch substituirter Guanidine aus Cyanamid," *Chem. Ber.*, 32:1681-1684 (1904).

Katayama, H. et al., "Human AIM-1: cDNA cloning and reduced expression during endomitosis in megakaryocyte-lineage cells," *Gene*, 224:1-7 (1998).

Katayama, H. et al., "Mitotic Kinase Expression and Colorectal Cancer Progression," *Journal of the National Cancer Institute*, 91:1160-1162(1999).

Kaubisch, A., and Schwartz, G., "Cyclin-Dependent Kinase and Protein Kinase C Inhibitors: A Novel Class of Antineoplastic Agents in Clinical Development," *The Cancer Journal*, 6:192-212 (2000).

Kawakami, Y. et al., "Activation and Interaction with Protein Kinase C of a Cytoplasmic Tyrosine Kinase, 1tk/Tsk/Emt on FcεRI Cross-Linking on Mast Cells,[1]" *Journal of Immunology*, 155:3556-3562 (1995).

Kawakami, Y. et al., "Functions of Bruton's tyrosine kinase in mast and B cells," *Journal of Leukocyte Biology*, 65:286-290 (1999).

Kiefer, F. et al., "The Syk Protein Tyrosine Kinase Is Essential for Fcγ Receptor Signaling in Macrophages and Neutrophils," *Mol. Cell. Biol.*, 18:4209-4220 (1998).

Kim, L. and Kimmel, A.R., "GSK3, a master switch regulating cell-fate specification and tumorigenesis," *Curr. Opinion Genetics & Dev.*, 10:508-514 (2000).

Kimura, M. et al., "Cell Cycle-dependent Expression and Centrosome Localization of a Third Human Aurora/IpII-related Protein Kinase, AIK3*," *J. Biol. Chem.*, 274:7334-7340 (1999).

Kimura, M. et al., "Cell Cycle-dependent Expression and Spindle Pole Localization of a Novel Human Protein Kinase, Aik, Related to Aurora of *Drosophila* and Yeast Ip11,," *J. Biol. Chem.*, 272:13766-13771 (1997).

Kimura, M., et al., Cell Cycle-dependent Expression and Centrosome Localization of a Third Human Aurora/Ip11-related Protein Kinase, AIK3*, *J. Biol. Chem.*, 274:7334-7340 (1999).

Kirken, R.A., "Targeting JAK3 for Immune Suppression and Allograft Acceptance," *Transpl. Proc.*, 33:3268-3270 (2001).

Klein, N. P. et al., "Src kinases involved in hepatitis B virus replicataion," *EMBO J.*, 18:5019-5027 (1999).

Klein, N.P. and Schneider, R., "Activation of Src Family Kinases by Hepatitis B Virus HBx Protein and Coupled Signaling to Ras," *Mol. Cell. Biol.*, 17:6427-6436 (1997).

Klein, P.S. and Melton, D.A., "A molecular mechanism for the effect of lithium on development," *PNAS*, 93:8455-8459 (1996).

Knighton, D.R. et al., "Crystal Structure of the Catalytic Subunit of Cyclic Adenosine Monophosphate-Dependent Protein Kinase," *Science*, 253:407-414 (1991).

Kunz, J. et al., Target of Rapamycin in Yeast, TOR2, Is an Essential Phosphatidylinositol Kinase Homolog Required for $G_1$ Progression, *Cell*, 73:585-596 (1993).

Lawrence, D.S. and Niu, J., "Protein Kinase Inhibitors: The Tyrosine-Specific Protein Kinases," *Pharmacol. Ther.*, 77:81-114 (1998).

Lehmann, et al., 2-Substituierte 7-Oxo-4,5,6,7-tetrahydro-benzothiazole,*Z. Chem.*, 7.Jg.;422 (1967).

Li, D. et al., "Overexpression of Oncogenic STK15/BTAK/Aurora-A Kinase in Human Pancreatic Cancer," *Clin. Cancer Res.*, 9:991-997 (2003).

Lo, C.P. and Croxall, W.J., "5-Alkoxymethylenerhodanines and their Reactions with Rhodanines," *J. Am. Chem. Soc.*, 76:4166-4169 (1954).

Lovestone, S. et al., "Alzheimer's disease-like phosphorylation of the microtubule-associated protein tau by glycogen synthase kinase-3 in transfected mammalian cells," *Current Biology*, 4:1077-1086 (1994).

Lowell, C. and Berton, G., "Integrin signal transduction in myeloid leukocytes," *J. Leukoc. Biol.*, 65:313-320 (1999).

Lutz, M.P. et al., "Overexpression and Activation of the Tyrosine Kinase Src in Human Pancreatic Carcinoma," *Biochem. Biophys. Res.*, 243:503-508 (1998).

Lynch, S.A. et al., "Increased Expression of the src Proto-Oncogene in Hairy Cell Leukemia and a Subgroup of B-Cell Lymphomas," *Leukemia*, 7:1416-1422 (1993).

Maillard, J. et al., "Synthese de derives amines du tetrahydro-4,5,6,7 benzothiazole," *Eur. J. Med. Chem.*, 19:451-456 (1984).

Malaviya, R. et al., "Genetic and Biochemical Evidence for a Critical Role of Janus Kinase (JAK)-3 in Mast Cell-Mediated Type I Hypersensitivity Reactions," *Biochem. Biophys. Res. Commun.*, 257:807-813 (1999).

Malaviya, R. et al., "Targeting Janus Kinase 3 in Mast Cells Prevents Immediate Hypersensitivity Reactions and Anaphylaxis*," *J. Biol. Chem.*, 274:27028-27038 (1999).

Mandal, S.S. et al., "Studies in sulfur heterocycles, Part 15. Condensed heterocycles derived from thieno[2,3-c]- and thieno [3,2-c]-thiopyrans," *J. Chem. Soc. Perkin Trans.1*, 2639-2644 (1999).

Mani, S. et al., "Cyclin-dependent kinase inhibitors: novel anticancer agents," *Exp. Opin. Invest. Drugs*, 9:1849-1870 (2000).

Masaki, T. et al., "pp60$^{c-src}$ Activation in Hepatocellular Carcinoma of Humans and LEC Rats," *Hepatology*, 27:1257-1264 (1998).

Massillon, D. et al., "Identification of the glycogenic compound 5—iodotubercidin as a general protein kinase inhibitor," *Biochem J.*, 299:123-128 (1994).

Matsumoto, Y. et al., "Identification of Highly Expressed Genes in Peripheral Blood T Cells from Patients with Atopic Dermatitis," *Int. Arc. Aller. Immon.*, 129:327-340 (2002).

Meijer, L., "Cyclin-dependent kinases inhibitors as potential anticancer, antineurodegenerative, antiviral and antiparasitic agents," *Drug Resistance Updates*, 3:83-88 (2000).

Miller, A.T. and Berg, L.J., "New insights into the regulation and functions of Tec family tyrosine kinases in the immune system,", *Current Opinion in Immunology*, 14:331-340 (2002).

Miyoshi, Y. et al., "Association Of Centrosomal Kinase STK15/BTK mRNA Expression With Chromosomal Instability in Human Breast Cancers," *Int. J. Cancer*, 92:370-373 (2001).

Molina, T.J. et al., "Profound block in thymocyte development in mice lacking p56$^{lck}$," *Nature*, 357:161-164 (1992).

Mueller, C. and August, A., "Attenuation of Immunological Symptoms of Allergic Asthma in Mice Lacking the Tyrosine Kinase ITK," *J. Immunol.*, 170:5056-5063 (2003).

Mukhopadhyay, S. et al., "Macrophage Effector Functions Controlled by Bruton's Tyrosine Kinase Are More Crucial Than the Cytokine Balance of T Cell Responses for Microfilarial Clearance," *J. Immunol.*, 168:2914-2921 (2002).

Muller-Ladner, U. et al., "Activation of the IL-4 STAT Pathway in Rheumatoid Synovium," *J. Immunol.*, 164:3894-3901 (2000).

Nielsen, M. et al., "Constitutive activation of a slowly migrating isoform of Stat3 in mycosis fungoides: Tyrphostin AG490 inhibits Stat3 activation and growth of mycosis fungoides tumor cell lines," *Proc. Nat. Acad. Sci. U.S.A.*, 94:6764-6769 (1997).

Nigg, L.A., "Mitotic Kinases As Regulators Of Cell Division And Its Checkpoints," *Nature Reviews*, 2:21-32 (2001).

Nigg, E.A., "Mitotic Kinases As Regulators Of Cell Division And Its Checkpoints," *Nat. Rev. Mol. Cell Biol.*, 2:21-32 (2001).

Pei, J.J. et al., "Distribution, Levels, and Activity of Glycogen Synthase Kinase-3 in the Alzheimer Disease Brain," *J. Neuropathol. & Exp. Neur.*, 56:70-78 (1997).

Petersen U. and Heitzer, H., "Heterocyclensynthesenmit 4-Oxo-4H-chromen-3-carbaldehyd," *Justus Leibigs Annalen Der Chemie, Verlag Chemie GmbH*, Weinheim, DE, 7/8:1662-1673 (1976).

Pinna, G.A. et al., "Synthesis and pharmacological evaluation of thienocinnolin-3-(2H)-ones, bioisosters of antihypertensive and antithrombotic benzo(h)cinnolinones," *Eur. J. Med. Chem.*, 29:447-454 (1994).

Rosen, N. et al., "Analysis of pp60$^{c-src}$ Protein Kinase Activity in Human Tumor Cell Lines and Tissues," *J. Biol. Chem.*, 261:13754-13759 (1986).

Sakakura, C. et al. "Tumour-amplified Kinase BTAK is amplified and overexpressed in gastric cancers with possible involvement in aneuploid formation," *Brit. J. Cancer*, 84:824-831 (2001).

Sasaki, C. et al., "Different expression of glycogen synthase kinase-3β between young and old rat brains after transient middle cerebral artery occlusion," *Neurol Res.*, 23:588-92 (2001).

Schaeffer, E.M. et al., "Requirement for Tec Kinases Rlk and Itk in T Cell Receptor Signaling and Immunity," *Science*, 284:638-641 (1999).

Schaeffer, E.M. et al. "Mutation of Tec family kinases alters T helper cell differentiation," *Nat. Immunol.*, 2:1183-1188 (2001).

Schumacher, J.M. et al., "AIR-2: An Aurora/Ip11-related Protein Kinase Associated with Chromosomes and Midbody Microtubes Is Required for Polar Body Extrusion and Cytokineses in *Caenorhabditis elegans* Embryos," *J. Cell Biol.*, 143:1635-1646 (1998).

Schwaller, J. et al., "Transformation of hematopoietic cell lines to growth-factor independence and induction of a fatal myelo- and lymphoproliferative disease in mice by retrovirally transduced TEL/JAK2 fusion genes," *EMBO J.*, 17:5321-5333 (1998).

Seidel, H.M. et al., "Pharmaceutical intervention in the JAK/STAT signaling pathway," *Oncogene*, 19:2645-2656 (2000).

Sen, S. et al., "Amplification/Overexpression of a Mitotic Kinase Gene In Human Bladder Cancer," *J. Natl. Cancer Inst.*, 94:1320-1329 (2002).

Showalter, H.D.H. et al., "Tyrosine Kinase Inhibitors. 16. 6,5,6-Tricyclic Benzothieno[3,2-d]pyrimidines and Pyrimidol[5,4-b]-and—[4,5-b]indoles as Potent Inhibitors of the Epidermal Growth Factor Receptor Tyrosine Kinase," *J. Med. Chem.*, 42:5464-5474 (1999).

Soriano, P. et al., "Targeted Disruption of the c-src Proto-Oncogene Leads to Osteopetrosis in Mice," *Cell*, 64:693-702 (1991).

Staley, C.A. et al., "Decreased Tumorigenicity of a Human Colon Adenocarcinoma Cell Line by an Antisense Expression Vector Specific for c-Src," *Cell Growth & Diff.*, 8:269-274 (1997).

Stenton, G.R. et al., "Aerosolized Syk Antisense Suppresses Syk Expression, Mediator Release from Macrophages, and Pulmonary Inflammation,"*J. Immunol.*, 164:3790-3797 (2000).

Sudbeck, E.A. et al., "Structure-based Design of Specific Inhibitors of Janus Kinase 3 as Apoptosis-inducing Antileukemic Agents," *Clin. Cancer Res.*, 5:1569-1582 (1999).

Suzuki, K. et al., "Role of common cytokine receptor γ chain ($γ_c$)-and Jak3-dependent signaling in the proliferation and survival of murine mast cells," *Blood*, 96:2172-2180 (2000).

Takahashi, T. et al., "Centrosomal Kinases, HsAIRK1 and HsAIRK3, are Overexpressed in Primary Colorectal Cancers," *Jpn. J. Cancer Res.*, 91:1007-1014 (2000).

Takashima, A. et al., "tau protein kinase I is essential for amyloid β-protein-induced neurotoxicity," *Proc. Natl. Acad. Sci., USA*, 90:7789-7793 (1993).

Takayanagi, H. et al., "Suppression of arthritic bone destruction by adenovirus-mediated *csk* gene transfer to synoviocytes and osteoclasts," *J. Clin. Invest.*, 104:137-146 (1999).

Talamonti, M.S. et al., "Increase in Activity and Level of pp60$^{c-src}$ in Progressive Stages of Human Colorectal Cancer," *J. Clin. Invest.*, 91:53-60 (1993).

Tanaka, T., et al., "Centrosomal Kinase AIK1 Is Overexpressed in Invasive Ductal Carcinoma of the Breast," *Cancer Res.*, 59:2041-2044 (1999).

Tatosyan, A.G. and Mizenina, O.A., "Kinases of the Src Family: Structure and Functions," *Biochemistry* (Moscow), 65:49-58 (2000).

Tatsuka, M. et al., "Multinuclearity and Increased Ploidy Caused by Overexpression of the Aurora- and Ip11-like Midbody-associated Protein Mitotic Kinase in Human Cancer Cells," *Cancer Research*, 58:4811-4816 (1998).

Taylor, J.A. et al., "Activation of the High-Affinity Immunoglobulin E Receptor FceRI in RBL-2H3 Cells Is Inhibited by Syk SH2 Domains," *Mol. & Cell. Biol.*, 15:4149-4157 (1995).

Thomas, S.M. and Brugge, J.S., "Cellular Functions Regulated By Src Family Kinases," *Annu. Rev. Cell Dev. Biol.*, 13, 513-609 (1997).

Trieu, V.N. et al., "A Specific Inhibitor of Janus Kinase-3 Increases Survival in a Transgenic Mouse Model of Amyotrophic Lateral Sclerosis," *Biochem. Biophys. Res. Commun.*, 267:22-25 (2000).

Vihinen, M. et al., "Bruton Tyrosine Kinase (BTK) In X-Linked Agammaglobulinemia (XLA)," *Frontiers in Bioscience*, 5:917-927 (2000).

Wang, J.M. et al., "Reduction of ischemic brain injury by topical application of insulin-like growth factor-I after transient middle cerebral artery occlusion in rats," *Brain Res.*, 859:381-385 (2000).

Wiener, J.R. et al., "Decreased Src Tyrosine Kinase Activity Inhibits Malignant Human Ovarian Cancer Tumor Growth in a Nude Mouse Model," *Clin. Cancer Res.*, 5:2164-2170 (1999).

Williams, O., et al., "Activation of Cdk2 is a requirement for antigen-mediated thymic negative selection," *Eur. J. Immunol.*, 30:709-713 (2000).

Wong, G. et al., "Molecular Cloning and Nucleic Acid Binding Properties of the GAP-Associated Tyrosine Phosphoprotein p62," *Cell*, 69:551-558 (1992).

Yousefi, S. et al., "Requirement of Lyn and Syk Tyrosine Kinases for the Prevention of Apoptosis by Cytokines in Human Eosinophils," *J Exp. Med.*, 183:1407-1414 (1996).

Yu, C.L. et al., "Constitutive Activation of the Janus Kinase-STAT Pathway in T Lymphoma Overexpressing the Lck Protein Tyrosine Kinase," *J. Immunol.*, 159:5206-5210 (1997).

Zhang, Z. et al., "Destabilization of β-catenin by mutations in presenilin-1 potentiates neuronal apoptosis," *Nature*, 395:698-702 (1998).

Zhou, H. et al., "Tumour amplified kinase *STK15/BTAK* induces centrosome amplification, aneuploidy and transformation," *Nature Genetics*, 20:189-193 (1998).

CAS Chemcats Database search: Accession No. 1999:150853, Catalog Name: Bionet Screening Compounds.

CAS Chemcats Database search: Accession No. 1999:130670, Catalog Name: Bionet Screening Compounds.

Tauber, Claudia; Klade, Manfred; Sterk, Heinz; Junek, Hans, "Syntheses with nitriles. LXXXVI. The chemistry of 2,3-dihydro-3-oxobenzo[b]thiophene 1,1-dioxide" *Monatshefte fuer Chemie* (1990), 121(4), 299-309 (only English abstract available).

Junek, Hans; Klade, Manfred; Sterk, Heinz, "Syntheses with nitriles. LXXXIII. (Dicyanomethylene)aminoindenes, indanopyridazines, and Indanopyridines" Monatshefte fuer Chemie (1989), 120(8-9), 781-8 (only English abstract available).

\* cited by examiner

COMPOSITIONS USEFUL AS INHIBITORS OF PROTEIN KINASES

CROSS-REFERENCE TO RELATED APPLICATION(S)

This application claims the benefit under 35 U.S.C. §119 of U.S. Provisional Application 60/510,881, filed Oct. 14, 2003, the entire contents of the provisional application being incorporated herein by reference.

TECHNICAL FIELD OF THE INVENTION

The present invention relates to compounds useful as inhibitors of protein kinases. The invention also provides processes for preparing the compounds of the invention, pharmaceutically acceptable compositions comprising the compounds, and methods of using the compounds and compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological f unction. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Aurora family of serine/threonine kinases is essential for cell proliferation [Bischoff, J. R. & Plowman, G. D. (The Aurora/Ipl1p kinase family: regulators of chromosome segregation and cytokinesis) Trends in Cell Biology 9, 454-459 (1999); Giet, R. and Prigent, C. (Aurora/Ipl1p-related kinases, a new oncogenic family of mitotic serine-threonine kinases) Journal of Cell Science 112, 3591-3601 (1999); Nigg, E. A. (Mitotic kinases as regulators of cell division and its checkpoints) Nat. Rev. Mol. Cell Biol. 2, 21-32 (2001); Adams, R. R, Carmena, M., and Earnshaw, W. C. (Chromosomal passengers and the (aurora) ABCs of mitosis) Trends in Cell Biology 11, 49-54 (2001)]. Inhibitors of the Aurora kinase family therefore have the potential to block growth of all tumour types.

The three known mammalian family members, Aurora-A ("2"), B ("1") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, TPX2, all of which are required forcell division.

Since its discovery in 1997 the mammalian Aurora kinase family has been closely linked to tumorigenesis. The most compelling evidence for this is that over-expression of Aurora-A transforms rodent fibroblasts (Bischoff, J. R., et al. A homologue of *Drosophila* aurora kinase is oncogenic and amplified in human colorectal cancers. EMBO J. 17, 3052-3065 (1998)). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. (Miyoshi, Y., Iwao, K., Egawa, C., and Noguchi, S. Association of centrosomal kinase STK15/BTAK mRNA expression with chromosomal instability in human breast cancers. Int. J. Cancer 92, 370-373 (2001). (Sakakura, C. et al. Tumor-amplified kinase BTAK is amplified and overexpressed in gastric cancers with possible involvement in aneuploid formation. British Journal of Cancer 84, 824-831 (2001)). The Aurora kinases have been reported to be over-expressed in a wide range of human tumours. Elevated expression of Aurora-A has been detected in over 50% of colorectal cancers (Bischoff, J. R., et al. A homologue of *Drosophila* aurora kinase is oncogenic and amplified in human colorectal cancers. EMBO J. 17, 3052-3065 (1998)) (Takahashi, T., et al. Centrosomal kinases, HsAIRk1 and HsAIRK3, are overexpressed in primary colorectal cancers. Jpn. J. Cancer Res. 91, 1007-1014 (2000)), ovarian cancers (Gritsko, T. M. et al. Activation and overexpression of centrosome kinase BTAK/Aurora-A in human ovarian cancer. Clinical Cancer Research 9, 1420-1426 (2003)), and gastric tumors (Sakakura, C. et al. Tumor-amplified kinase BTAK is amplified and overexpressed in gastric cancers with possible involvement in aneuploid formation. British Journal of Cancer 84, 824-831 (2001)), and in 94% of invasive duct adenocarcinomas of the breast (Tanaka, T., et al. Centrosomal kinase AIK1 is overexpressed in invasive ductal carcinoma of the breast. Cancer Research. 59, 2041-2044 (1999)). High levels of Aurora-A have also been reported in renal, cervical, neuroblastoma, melanoma, lymphoma, pancreatic and prostate tumour cell lines. (Bischoff, J. R., et al. A homologue of *Drosophila* aurora kinase is oncogenic and amplified in human colorectal cancers. EMBO J. 17, 3052-3065 (1998) (Kimura, M., Matsuda, Y., Yoshioka, T., and Okano, Y. Cell cycle-dependent expression and centrosomal localization of a third human Aurora/Ipl1-related protein kinase, AIK3. Journal of Biological Chemistry 274, 7334-7340 (1999))(Zhou et al. Tumour amplified kinase STK15/BTAK induces centrosome amplification, aneuploidy and transformation Nature Genetics 20: 189-193 (1998))(Li et al. Overexpression of oncogenic STK15/BTAK/Aurora-A kinase in human pancreatic cancer Clin Cancer Res. 9(3): 991-7 (2003)). Amplification/overexpression of Aurora-A is observed in human bladder cancers and amplification of Aurora-A is associated with aneuploidy and aggressive clinical behaviour (Sen S. et al. "Amplification/overexpression of a mitotic kinase gene in human bladder cancer" *J. Natl. Cancer Inst.* 94(17):1320-9 (2002)). Moreover, amplification of the aurora-A locus (20q13) correlates with poor prognosis for patients with node-negative breast cancer (Isola, J. J., et al. "Genetic aberrations detected by comparative genomic hybridization predict outcome in node-negative breast cancer" *American Journal of Pathology* 147, 905-911 (1995)). Aurora-B is highly expressed in multiple human tumour cell lines, including leukemic cells (Katayama et al. Human AIM-1: cDNA cloning and reduced expression during endomitosis in megakaryocyte-lineage cells. Gene 244:1-7)). Levels of this enzyme increase as a function of Duke's stage in primary colorectal cancers (Katayama, H. et al. Mitotic kinase expression and colorectal cancer progression. Journal of the National Cancer Institute 91, 1160-1162 (1999)). Aurora-C, which is normally only found in germ cells, is also overexpressed in a high percentage of primary colorectal cancers and in a variety of tumour cell lines including cervical adenocarinoma and breast carcinoma cells (Kimura, M., Matsuda, Y., Yoshioka, T., and Okano, Y. Cell cycle-dependent expression and centrosomal localization of a third human Aurora/Ipl1-related protein kinase, AIK3. Journal of Biological Chemistry 274, 7334-7340 (1999). (Takahashi, T., et al. Centrosomal kinases, HsAIRk1 and HsAIRK3, are overexpressed in primary colorectal cancers. Jpn. J. Cancer Res. 91, 1007-1014 (2000)).

Based on the known function of the Aurora kinases, inhibition of their activity should disrupt mitosis leading to cell cycle arrest. In vivo, an Aurora inhibitor therefore slows tumor growth and induces regression.

Elevated levels of all Aurora family members are observed in a wide variety of tumour cell lines. Aurora kinases are over-expressed in many human tumors and this is reported to be associated with chromosomal instability in mammary tumors (Miyoshi et al. 2001 92, 370-373).

Aurora-2 is highly expressed in multiple human tumor cell lines and levels increase as a function of Duke's stage in primary colorectal cancers [Katayama, H. et al. (Mitotic kinase expression and colorectal cancer progression) Journal of the National Cancer Institute 91, 1160-1162 (1999)]. Aurora-2 plays a role in controlling the accurate segregation of chromosomes during mitosis. Misregulation of the cell cycle can lead to cellular proliferation and other abnormalities. In human colon cancer tissue, the Aurora-2 protein has been found to be over-expressed [Bischoff et al., EMBO J., 17, 3052-3065 (1998); Schumacher et al., J. Cell Biol., 143, 1635-1646 (1998); Kimura et al., *J. Biol. Chem.*, 272, 13766-13771 (1997)]. Aurora-2 is over-expressed in the majority of transformed cells. Bischoff et al. found high levels of Aurora-2 in 96% of cell lines derived from lung, colon, renal, melanoma and breast tumors (Bischoff et al. *EMBO J.* 1998 17, 3052-3065). Two extensive studies show elevated Aurora-2 in 54% and 68% (Bishoff et al. EMBO J. 1998 17, 3052-3065)(Takahashi et al. 2000 Jpn J Cancer Res. 91, 1007-1014) of colorectal tumours and in 94% of invasive duct adenocarcinomas of the breast (Tanaka et al. 1999 59, 2041-2044).

Aurora-1 expression is elevated in cell lines derived from tumors of the colon, breast, lung, melanoma, kidney, ovary, pancreas, CNS, gastric tract and leukemias (Tatsuka et al. 1998 58, 4811-4816).

High levels of Aurora-3 have been detected in several tumour cell lines, although it is restricted to testis in normal tissues (Kimura et al. 1999 274, 7334-7340). Over-expression of Aurora-3 in a high percentage (c. 50%) of colorectal cancers has also been documented (Takahashi et al. 2000 Jpn J Cancer Res. 91, 1007-1014). In contrast, the Aurora family is expressed at a low level in the majority of normal tissues, the exceptions being tissues with a high proportion of dividing cells such as the thymus and testis (Bischoff et al. EMBO J. 1998 17, 3052-3065).

For further review of the role Aurora kinases play in proliferative disorders, see Bischoff, J. R. & Plowman, G. D. (The Aurora/Ipl1p kinase family:regulators of chromosome segregation and cytokinesis) Trends in Cell Biology 9, 454-459 (1999); Giet, R. and Prigent, C. (Aurora/Ipl1p-related kinases, a new oncogenic family of mitotic serine-threonine kinases) Journal of Cell Science 112, 3591-3601 (1999); Nigg, E. A. (Mitotic kinases as regulators of cell division and its checkpoints) Nat. Rev. Mol. Cell Biol. 2, 21-32 (2001); Adams, R. R, Carmena, M., and Earnshaw, W. C. (Chromosomal passengers and the (aurora) ABCs of mitosis) Trends in Cell Biology 11, 49-54 (2001); and Dutertre, S., Descamps, S., & Prigent, P. (On the role of aurora-A in centrosome function) Oncogene 21, 6175-6183 (2002).

Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates* 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews* 2001, 2, 21-32; Flatt, P., Pietenpol, J., *Drug Metabolism Reviews* 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt, P., Pietenpol, J., *Drug Metabolism Reviews* 2000, 32, 283-305]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal* 2000, 6, 192-212].

CDKs, especially CDK2, also play a role in apoptosis and T-cell development. CDK2 has been identified as a key regulator of thymocyte apoptosis [Williams, O., et al, *European Journal of Immunology* 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus [Meijer, L., *Drug Resistance Updates* 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 2000 3, 83-88].

Glycogen synthase kinase-3 (GSK-3) is a serine/threonine protein kinase comprised of α and β isoforms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is associated with Alzheimer's disease. This disease is characterized by the well-known β-amyloid peptide and the formation of intracellular neurofibrillary tangles. The neurofibrillary tangles contain hyperphosphorylated Tau protein, in which Tau is phosphorylated on abnormal sites. GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is associated with stroke [Wang et al., *Brain Res* 2000, 859, 381-5; Sasaki et al., Neurol Res 2001, 23, 588-92; Hashimoto et al., *J. Biol. Chem* 2002, 277, 32985-32991].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank *Mol. Med.* 1999, 5, 432-456 and Seidel et al., *Oncogene* 2000, 19, 2645-2656].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al., *Blood* 2000, 96, 2172-2180].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al., *Nature* 1990, 346, 274-276 and Galli, *N. Engl. J. Med.* 1993, 328, 257-265]. A crucial role for JAK3 in IgE receptor-mediated mast cell responses in vitro and in vivo has been established [Malaviya et al., *Biochem. Biophys. Res. Commun.* 1999, 257, 807-813]. In addition, the prevention of type I hypersensitivity reactions, including anaphylaxis, mediated by mast cell-activation through inhibition of JAK3 has also been reported [Malaviya et al., *J. Biol. Chem.* 1999 274, 27028-27038]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 2001, 33, 3268-3270].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner et al., *J. Immunol.* 2000, 164, 3894-3901].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu et al., *Biochem. Biophys. Res. Commun.* 2000, 267, 22-25].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck et al., *Clin. Cancer Res.* 1999, 5, 1569-1582]. JAK3 specific compounds were shown to inhibit the clonogenic growth of JAK3-expressing cell lines DAUDI, RAMOS, LC1-19, NALM-6, MOLT-3 and HL-60.

In animal models, TEL/JAK2 fusion proteins have induced myeloproliferative disorders and in hematopoietic cell lines, and introduction of TEL/JAK2 resulted in activation of STAT1, STAT3, STAT5, and cytokine-independent growth [Schwaller et al., *EMBO J.* 1998, 17, 5321-5333].

Inhibition of JAK3 and TYK2 abrogated tyrosine phosphorylation of STAT3, and inhibited cell growth of mycosis fungoides, a form of cutaneous T-cell lymphoma. These results implicated JAK family kinases in the constitutively activated JAK/STAT pathway that is present in mycosis fungoides [Nielsen et al., *Proc. Nat. Acad. Sci. U.S.A.* 1997, 94, 6764-6769]. Similarly, STAT3, STAT5, JAK1 and JAK2 were demonstrated to be constitutively activated in mouse T-cell lymphoma characterized initially by LCK over-expression, thus further implicating the JAK/STAT pathway in abnormal cell growth [Yu et al., *J. Immunol.* 1997, 159, 5206-5210]. In addition, IL-6-mediated STAT3 activation was blocked by an inhibitor of JAK, leading to sensitization of myeloma cells to apoptosis [Catlett-Falcone et al., *Immunity* 1999, 10, 105-115].

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49-58; Boschelli et al., *Drugs of the Future* 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia* 1993, 7, 1416. Furthermore, antisense Src expressed in ovarian and colon tumor cells has been shown to inhibit tumor growth. Wiener et al., *Clin. Cancer Res.*, 1999, 5, 2164; Staley et al., *Cell Growth Diff* 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 1992, 357, 161. Hck, Fgr and Lyn have been identified as important mediators of integrin signaling in myeloid leukocytes. Lowell et al., *J. Leukoc. Biol.*, 1999, 65, 313. Inhibition of these kinase mediators may therefore be useful for treating inflammation. Boschelli et al., *Drugs of the Future* 2000, 25(7), 717.

Syk is a tyrosine kinase that plays a critical role in FcεRI mediated mast cell degranulation and eosinophil activation. Accordingly, Syk kinase is implicated in various allergic disorders, in particular asthma. It has been shown that Syk binds to the phosphorylated gamma chain of the FcεRI receptor via N-terminal SH2 domains and is essential for downstream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

The Tec family of non-receptor tyrosine kinases plays a central role in signalling through antigen-receptors such as the TCR, BCR and Fcεreceptors (reviewed in Miller A, et al. Current Opinion in Immunology 14;331-340 (2002). Tec family kinases are essential for T cell activation. Three members of the Tec family, Itk, Rlk and Tec, are activated downstream of antigen receptor engagement in T cells and transmit signals to downstream effectors, including PLC-γ. Deletion of Itk in mice results in reduced T cell receptor (TCR)-induced proliferation and secretion of the cytokines IL-2, IL-4, IL-5, IL-10 and IFN-γ (Schaeffer et al, Science 284; 638-641 (1999)), Fowell et al, Immunity 11;399-409 (1999), Schaeffer et al. Nature Immunology 2,12; 1183-1188 (2001))). The immunological symptoms of allergic asthma are attenuated in Itk−/− mice. Lung inflammation, eosinophil infiltration and mucous production are drastically reduced in Itk−/− mice in response to challenge with the allergen OVA (Mueller et al, Journal of Immunology 170: 5056-5063 (2003)). Itk has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International archives of Allergy and Immunology 129; 327-340 (2002)).

Splenocytes from Rlk−/− mice secrete half the IL-2 produced by wild type animals in response to TCR engagement (Schaeffer et al, Science 284; 638-641 (1999)), while combined deletion of Itk and Rlk in mice leads to a profound inhibition of TCR-induced responses including proliferation and production of the cytokines IL-2, IL-4, IL-5 and IFN-γ (Schaeffer et al. Nature Immunology 2,12; 1183-1188 (2001)), Schaeffer et al, Science 284; 638-641 (1999)). Intracellular signalling following TCR engagement is effected in Itk/Rlk deficient T cells; inositol triphosphate production, calcium mobilization, MAP kinase activation, and activation of the transcription factors NFAT and AP-1 are all reduced (Schaeffer et al, Science 284; 638-641 (1999), Schaeffer et al. Nature Immunology 2,12; 1183-1188 (2001)).

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al. Frontiers in Bioscience 5:d917-928). Mice deficient in Btk also have a reduced number of peripheral B cells and greatly decreased levels of IgM and IgG3. Btk deletion in mice has a profound effect on B cell proliferation induced by anti-IgM, and inhibits immune responses to thymus-independent type II antigens (Ellmeier et al, J Exp Med 192:1611-1623 (2000)).

Tec kinases also play a role in mast cell activation through the high-affinity IgE receptor (FcεRI). Itk and Btk are expressed in mast cells and are activated by FcεRI cross-linking (Kawakami et al, Journal of Immunology; 3556-3562 (1995)). Btk deficient murine mast cells have reduced degranulation and decreased production of proinflammatory cytokines following FcεRI cross-linking (Kawakami et al. Journal of leukocyte biology 65:286-290). Btk deficiency also results in a decrease of macrophage effector functions (Mukhopadhyay et al, Journal of Immunology; 168, 2914-2921 (2002)).

Accordingly, there is a great need to develop compounds useful as inhibitors of protein kinases. In particular, it would be desirable to develop compounds that are useful as inhibitors of GSK-3, SYK, Aurora-2, CDK-2, JAK-3, LCK, SRC, and Tec family (e.g., Tec, Btk, Itk/Emt/Tsk, Bmx, Txk/Rlk) protein kinases, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of GSK-3, SYK, Aurora-2, CDK-2, JAK-3, LCK, SRC, and Tec family (e.g., Tec, Btk, Itk/Emt/Tsk, Bmx, Txk/Rlk) protein kinases. These compounds have the general formula I:

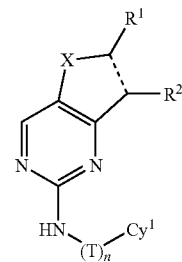

or a pharmaceutically acceptable salt thereof, wherein $R^1$, $R^2$, $Cy^1$, T, n and X are as defined below.

These compounds and pharmaceutically acceptable compositions thereof are useful for treating or preventing a variety of diseases, disorders or conditions, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention:
The present invention relates to a compound of formula I:

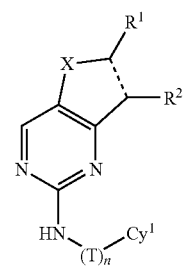

or a pharmaceutically acceptable salt thereof, wherein:
X is an optionally substituted $C_1$-$C_3$ alkylidene chain wherein one or two non-adjacent methylene units are independently optionally replaced by CO, CONR', NR'CO, SO, $SO_2$, NR'$SO_2$, $SO_2$NR', O, S, or NR';
$R^1$ and $R^2$, taken together with the carbon atoms to which they are bound form an optionally substituted 5- or 6-membered aryl or heteroaryl ring having 0-3 heteroatoms independently selected from nitrogen, oxygen, or sulfur,
wherein the ring formed by $R^1$ and $R^2$ taken together, and the $C_1$-$C_3$ alkylidene chain of X, are each optionally and independently substituted at one or more carbon atoms with y occurrences of —WR$^y$, wherein y is 0-5; and wherein one or more substitutable nitrogen atoms of the ring formed by R$^1$ and R$^2$ taken together are optionally substituted with —R$^3$;

each occurrence of W is independently a bond or is a C$_1$-C$_6$ alkylidene chain wherein up to two non-adjacent methylene units of W are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^y$ is independently selected from R', halogen, NO$_2$, or CN, or —WR$^y$ is =O, =S, or =NR';

T is CHR', CH$_2$CH(R'), —S(=O)$_2$, or C(=O);

n is 0 or 1;

Cy$^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur, wherein Cy$^1$ is optionally substituted at one or more carbon atoms with x independent occurrences of -QR$^X$; wherein x is 0-5; and at one or more substitutable nitrogen atoms with —R$^4$; wherein Q is a bond or is a C$_1$-C$_6$ alkylidene chain wherein up to two non-adjacent methylene units of Q are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^X$ is independently selected from R', halogen, NO$_2$, or CN, or -QR$^X$ is =O, =S, or =NR';

each occurrence of R$^3$ and R$^4$ is independently R', —COR', —CO$_2$(C$_{1-6}$ aliphatic), —CON(R')$_2$, or —SO$_2$R;

each occurrence of R is independently selected from hydrogen or an optionally substituted C$_{1-6}$ aliphatic group; and each occurrence of R' is independently selected from hydrogen or an optionally substituted group selected from C$_{1-8}$ aliphatic, C$_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form an optionally substituted 3-8 membered cycloalkyl, heterocyclyl, aryl, or heteroaryl ring having 0-3 heteroatoms independently selected from nitrogen, oxygen, or sulfur; and the dashed bond represents a single or double bond, as valency permits;

provided that:

a) when n is 0, Cy$^1$ is an optionally substituted aryl or heteroaryl group, and X is —(C(R)$_2$)$_2$—, —CH$_2$—O—, —O—CH$_2$—, —S—CH$_2$—, —CH$_2$—S—, —CH$_2$—N(R)—, —N(R)—CH$_2$—, —CH$_2$SO—, —SOCH$_2$—, wherein R is hydrogen or C$_{1-4}$alkyl, then R$^1$ and R$^2$, taken together with the carbon atoms to which they are bound do not form a phenyl ring optionally substituted with C$_{1-4}$alkyl, C$_{1-4}$alkoxy, halo, CONR$_2$, CO$_2$R, fused phenyl, NO$_2$, or trifluoromethyl;

b) when n is 0, Cy$^1$ is 3,4,5-trimethoxyphenyl, anc when X is —(CH$_2$)$_2$—, then R$^1$ and R$^2$, taken together with the carbon atoms to which they are bound, do not form an unsubstituted thieno ring; and c) when X is —(CH$_2$)$_2$—, n is 0 and Cy$^1$ is a phenyl group bearing one or more of the following substitutents: —(CH$_2$)$_2$OH, —O(CH$_2$)$_2$OH, —(CH$_2$)$_2$NMe$_2$, —O(CH$_2$)$_2$NHEt, —O(CH$_2$)$_2$NEt$_2$, —OMe and —O(CH$_2$)$_2$OS(O)$_2$-p-Tol, then R$^1$ and R$^2$, taken together with the carbon atoms to which they are bound, do not form a methoxy-substituted pyridyl ring.

In certain other embodiments for compounds described directly above:

a) when n is 0, Cy$^1$ is an optionally substituted aryl or heteroaryl group, and X is —(C(R)$_2$)$_2$—, —CH$_2$—O—, —O—CH$_2$—, —S—C(R)$_2$—, —C(R)$_2$—S—, —CH$_2$—N(R)—, —N(R)—CH$_2$—, —CH$_2$SO—, —SOCH$_2$—, —N(R)SO$_2$—, C=O, —CH$_2$—, C=C, —N(R)N(R)—, or N=N, wherein R is hydrogen or C$_{1-4}$alkyl, then R$^1$ and R$^2$, taken together with the carbon atoms to which they are bound do not form a phenyl ring optionally substituted with —C$_{1-4}$alkyl, —C$_{1-4}$alkoxy, -halo, —CONR$_2$, —CO$_2$R, fused phenyl, —NO$_2$, —NR$_2$, —N(CO)R, —NSO$_2$R, —N(CO)N(R)$_2$, —SCH$_3$, —SR, —CH$_2$OH, —OH, —C(O)H, —OCH$_2$Ph, —N(CO)OR, 2-furyl, or trifluoromethyl;

b) when n is 0 and Cy$^1$ is 3,4,5-trimethoxyphenyl then i) when X is —(CH$_2$)$_2$—, then R$^1$ and R$^2$, taken together with the carbon atoms to which they are bound, do not form an unsubstituted thieno ring; and ii) when X is —S—CR$_2$—, then R$^1$ and R$^2$, taken together with the carbon atoms to which they are bound, do not form an unsubstituted or a chloro-substituted phenyl ring (or in certain embodiments, an unsubstituted or a substituted phenyl); and iii) when X is —CH$_2$CH$_2$CH$_2$—, then R$^1$ and R$^2$, taken together with the carbon atoms to which they are bound, do not form an unsubstituted phenyl ring (or in certain embodiments, a substituted or unsubstituted phenyl); and c) when X is —(CH$_2$)$_2$—, n is 0 and Cy$^1$ is a phenyl group bearing one or more of the following substitutents: —(CH$_2$)$_2$OH, —O(CH$_2$)$_2$OH, —(CH$_2$)$_2$NMe$_2$, —O(CH$_2$)$_2$NHEt, —O(CH$_2$)$_2$NEt$_2$, —OMe and —O(CH$_2$)$_2$OS(O)$_2$-p-Tol, then R$^1$ and R$^2$, taken together with the carbon atoms to which they are bound, do not form a methoxy-substituted (or in certain embodiments, a substituted or unsubstituted) pyridyl ring.

d) when n is 1, T is CH$_2$, and X is —OC(H)(OH)—, Cy is not optionally substituted pyridyl.

In certain other embodiments for compounds described above:

a. when n is 0, Cy$^1$ is an optionally substituted phenyl, benzotriazolyl, benzothiazolyl, indolyl, or pyridyl group, and X is a C$_{1-2}$alkylene group optionally substituted with one or more halogen atoms or C$_{1-3}$alkyl groups, then R$^1$ and R$^2$, taken together with the carbon atoms to which they are bound do not form a pyridyl, or thienyl group, when the pyridyl or thienyl group is unsubstituted or is substituted with a substituent other than a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur;

b. when n is 0, Cy$^1$ is an optionally substituted C$_6$-C$_{1-2}$ mono- or bicyclic aromatic group, and X is a C$_{1-2}$alkylene group optionally substituted with one or more halogen atoms or C$_{1-3}$alkyl groups, then R$^1$ and R$^2$, taken together with the carbon atoms to which they are bound do not form a phenyl group, when the phenyl group is unsubstituted or is substituted with a substituent other than a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur;

c. when n is 0; $Cy^1$ is an aryl or heteroaryl group substituted with at least one optionally substituted cycloaliphatic or heterocycloaliphatic group, wherein the cycloaliphatic or heterocycloaliphatic groups are attached directly to $Cy^1$ or are attached to $Cy^1$ through an alkylidene chain; and X is an optionally substituted $C_{1-2}$alkylene group; then $R^1$ and $R^2$, taken together with the carbon atoms to which they are bound do not form an optionally substituted phenyl group.

In certain other embodiments, this invention provides a compound of formula I, wherein the optionally substituted ring containing X is an aromatic ring (either 5- or 6-membered aromatic ring) and $R^1$ and $R^2$, taken together with the carbon atoms to which they are bound form an optionally substituted 5- or 6-membered heteroaryl ring having 0-3 heteroatoms independently selected from nitrogen, oxygen, or sulfur. In preferred forms of this embodiment, the heteroaryl ring is an optionally substituted thienyl or thiazolyl ring. It should be understood that the optional substituents and the other variables in this embodiment are as defined above or in any embodiment herein.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{1-2}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkylene" or "alkylene group", as used herein, refers to a hydrocarbon group that is completely saturated.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I. It should be understood that 1) an aliphatic group (e.g., alkyl) substituted with a halogen could also be referred to as a haloaliphatic (e.g., haloalkyl, in the case of an halo-substituted alkyl group); and 2) that perfluorinated groups are within the scope of this invention.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S) R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring (provided that a nitrogen atom in the heterocyclic ring is optionally substituted with —R$^+$ or —C(O)R$^+$, wherein R$^+$ is (C$_{1-6}$alkyl), preferably (C$_{1-4}$alkyl)), phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O) R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O) R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N (R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$ (Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule, wherein one or more methylene units may optionally and independently be replaced with a group including, but not limited to, CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR.

As detailed above, in some embodiments, two independent occurrences of R° (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

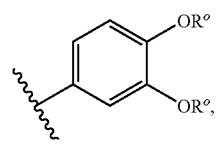

these two occurrences of R° are taken together with the oxygen atoms to which they are bound to form a fused 6-membered oxygen containing ring:

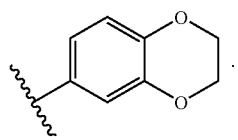

5

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

As described generally above for compounds of formula I, $R^1$ and $R^2$, taken together with the carbon atoms to which they are bound form an optionally substituted 5- or 6-membered aryl or heteroaryl ring having 0-3 heteroatoms independently selected from nitrogen, oxygen, or sulfur. In certain preferred embodiments, $R^1$ and $R^2$, taken together with the carbon atoms to which they are bound form an optionally substituted 5 or 6-membered aryl or heteroaryl ring selected from one of the following groups:

i

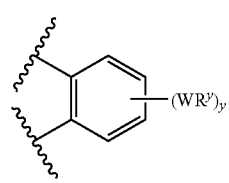

ii-1

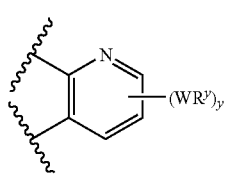

ii-2

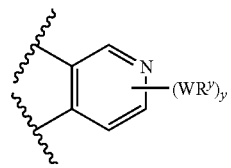

ii-3

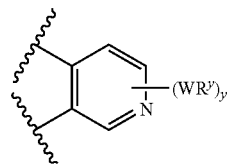

ii-4

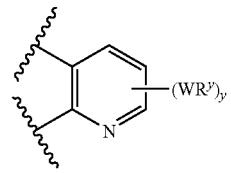

iii-1

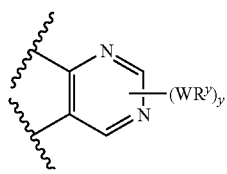

iii-2

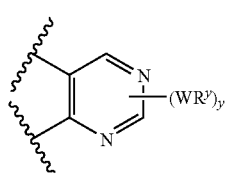

iii-3

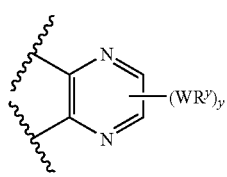

iv-1

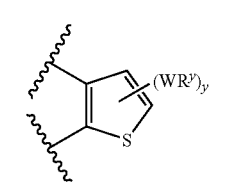

iv-2

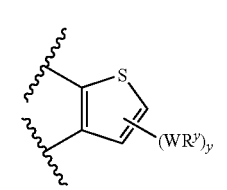

v-1

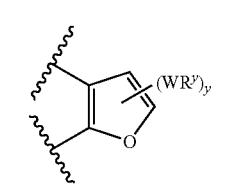

-continued
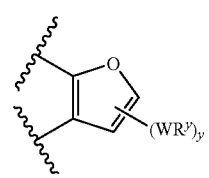 v-2
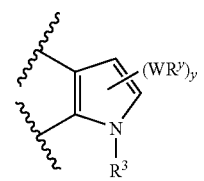 vi-1
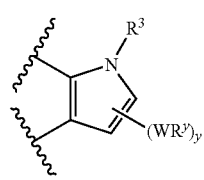 vi-2
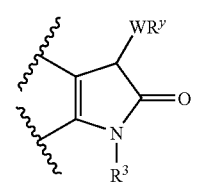 vii-1
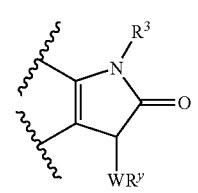 vii-2
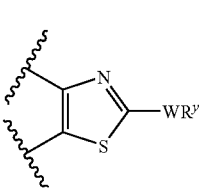 viii-1
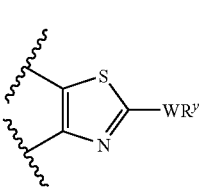 viii-2
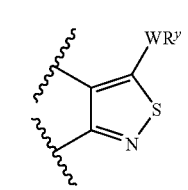 ix-1
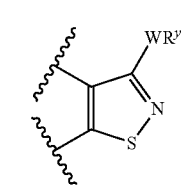 ix-2
-continued
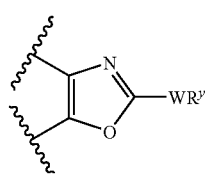 x-1
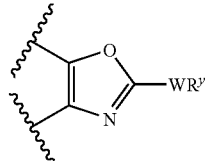 x-2
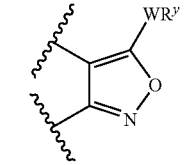 xi-1
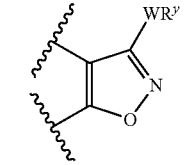 xi-2
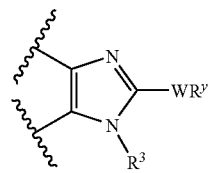 xii
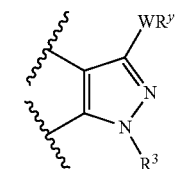 xiii-1
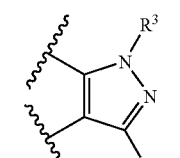 xiii-2
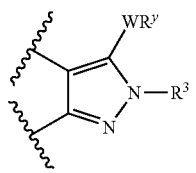 xiii-3
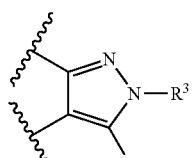 xiii-4

-continued

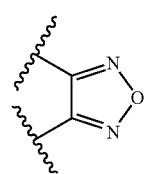
xiv

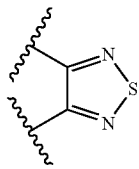
xv

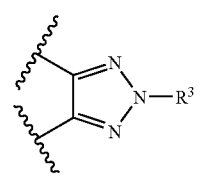
xvi

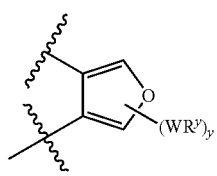
xvii

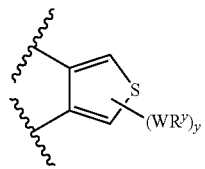
xviii

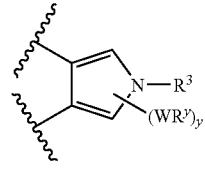
xix

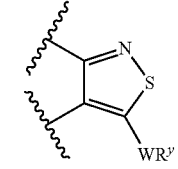
xx-1

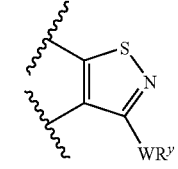
xx-2

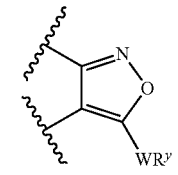
xxi-1

-continued

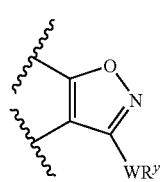
xxi-2 wherein W, $R^y$, y, and $R^3$ are as defined generally above and in classes and subclasses herein. It should be understood that the orientation of the rings i to xxi-2 relative to formula I is as follows:

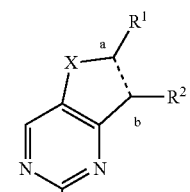
I

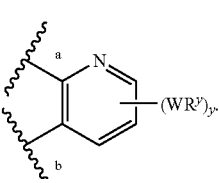
ii

In more preferred embodiments, $R^1$ and $R^2$, taken together with the carbon atoms to which they are bound form an optionally substituted 5- or 6-membered aryl or heteroaryl ring selected from phenyl (i), pyridyl (ii-1, ii-2, ii-3, ii-4), pyrazolyl (xiii-1, xiii-2, xiii-3, and xiii-4), oxadiazolyl (xiv), thiophenyl (iv-1, iv-2, and xviii), or thiazolyl (viii-1 and viii-2).

It will be appreciated that the ring formed by $R^1$ and $R^2$ taken together is optionally substituted at one or more carbon atoms with y independent occurrences of —$WR^y$, wherein y is 0-5; and is optionally substituted at one or more substitutable nitrogen atoms with —$R^3$. In preferred embodiments, each occurrence of $WR^y$, when present, is independently halogen, CN, $NO_2$, —$N(R')_2$, —$CH_2N(R')_2$, —OR', —$CH_2OR'$, —SR', —$CH_2SR'$, —COOR', —NRCOR', —$CON(R')_2$, —$S(O)_2N(R')_2$, or an optionally substituted group selected from $C_{1-4}$alkyl, aryl, or heteroaryl. In more preferred embodiments, —$WR^y$ groups are each independently F, Cl, Br, I, Me, Et, —CN, —OMe, —SMe, —$NMe_2$, —$NEt_2$, —COOMe, —COOH, —OH, —$SO_2NH_2$, —CON$(CH_3)_2$, —CO(optionally substituted N-piperazinyl), —CO(N-morpholinyl) (including optionally substituted N-morpholinyl), —CO(N-piperidinyl) (including optionally substituted N-piperidinyl), —$CH_2N(Me)_2$, —$CH_2N(Et)_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl. In another more preferred embodiment, —$WR^y$ groups are each independently $CF_3$, F, Cl, Br, I, Me, Et, —CN, —OMe, —SMe, —$NMe_2$, —$NEt_2$, —COOMe, —COOH, —OH, —$SO_2NH_2$, —CON$(CH_3)_2$, —CO(optionally substituted N-piperazinyl, —CO(N-morpholinyl) (including optionally substituted N-morpholinyl), —CO(N-piperidinyl) (including optionally substituted N-piperidinyl), —CO(pyrrolidinyl) (including optionally substituted pyrrolidinyl), —CO(N(H)-pyrrolidinyl) (including —CO(N-pyrrolidinyl), wherein each pyrrolidinyl is optionally substituted), —CH$_2$N(Me)$_2$, —CH$_2$N(Et)$_2$, or an optionally substituted group selected from C$_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or —N(H)pyrrolidinyl. In other preferred embodiments, y is 1 and WR$^y$ is an optionally substituted aryl or heteroaryl group. Preferred substituents for the optionally substituted aryl or heteroaryl group include —VR$^V$; wherein V is a bond or is a C$_1$-C$_6$ alkylidene chain wherein up to two non-adjacent methylene units of V are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^V$ is independently selected from R', halogen, NO$_2$, or CN, or -QR$^X$ is =O, =S, or =NR'. In still other embodiments, y is 1 and WR$^y$ is —CH$_2$N(R')$_2$, —N(R')$_2$, or —CON(R')$_2$. Most preferred WR$^y$ groups and substituents thereof include those shown below in Tables 1-8. In certain embodiments, y is 0.

Preferred T groups, when present, include, but are not limited to, —CH$_2$—, —CH$_2$CH$_2$—, —CO— and —SO$_2$—. Alternatively, T groups, when present are —C(H)(CH$_3$)—, —C(H)(CH$_3$)CH$_2$—, —CH$_2$C(H)(CH$_3$)—, or —CH$_2$CH$_2$CH$_2$—. In certain other preferred embodiments, n is 0 and T is absent. In most preferred embodiments, T is absent (n=0) or T is —CO—.

As described generally above, Cy$^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur. In certain embodiments, for compounds of general formula I, Cy$^1$ is selected from one of the following groups:

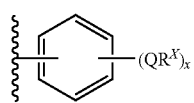
a

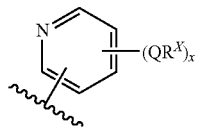
b

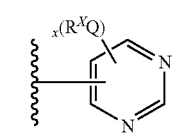
c

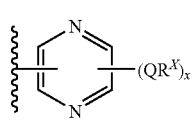
d

-continued

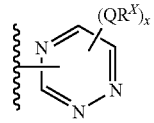
e

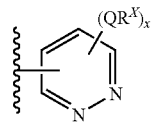
f

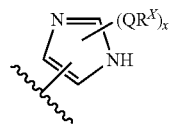
g

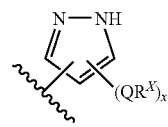
h

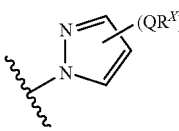
i

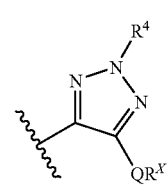
j

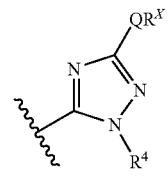
k

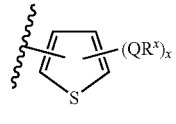
l

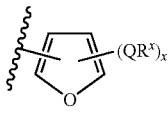
m

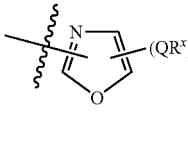
n

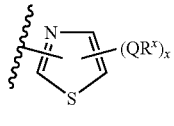
o

-continued
| | | |
|---|---|---|
| 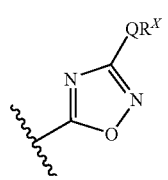 | p | 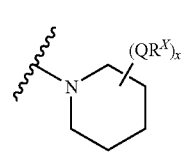 y |
| 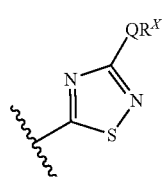 q | 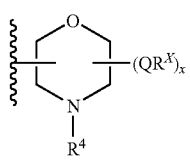 z |
| 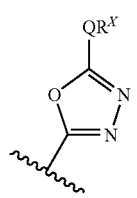 r | 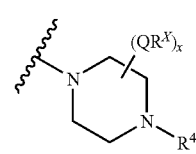 aa |
| 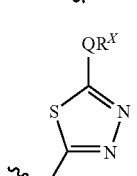 s | 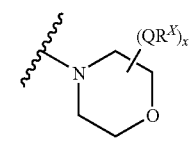 bb |
| 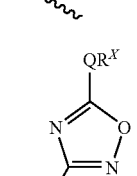 t | 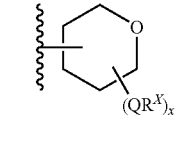 cc |
| 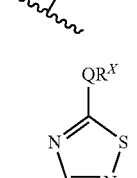 u | 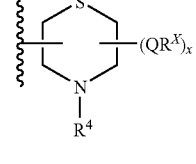 dd |
| 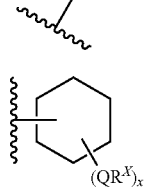 v | 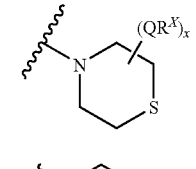 ee |
| 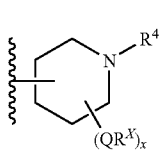 w | 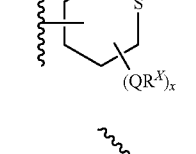 ff |
| 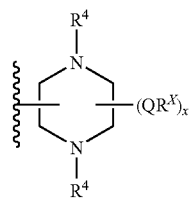 x | 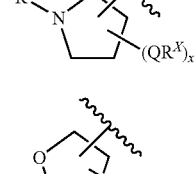 gg |
| | 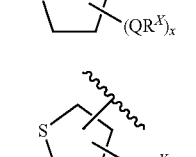 hh |

-continued

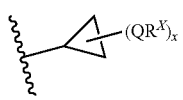
jj

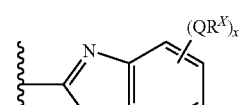
kk

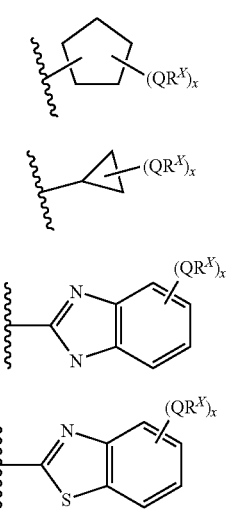
ll

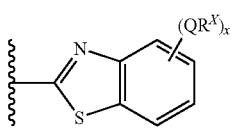
mm wherein Q, R⁴ and $R^X$ are as defined generally above and in classes and subclasses herein, and x is 0-5.

In more preferred embodiments, $Cy^1$ is selected from phenyl (a), pyridyl (b) (preferably attached in the 2-, 3, or 4-position as shown below by b-i, b-ii, and b-iii), pyrimidinyl (c) (preferably attached in the 2-, 4- or 5-position as shown by c-i, c-ii, and c-iii), imidazolyl (g) (preferably attached in the 2-, 4- or 5-position as shown by g-i), thienyl (l), thiazolyl (o) (preferably attached in the 2-position as shown by o-i), cyclohexyl (v), piperazinyl (aa), morpholinyl (bb), thiomorpholinyl (ff), pyrrolidinyl (gg), tetrahydrofuryl (hh), tetrahydrothiofuryl (ii), and cyclopropyl (kk):

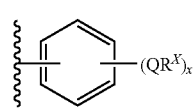
a

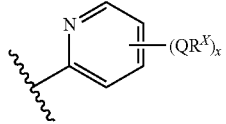
b-i

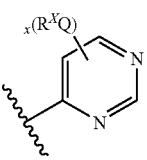
c-i

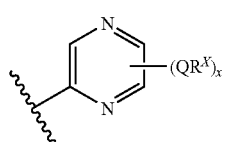
d

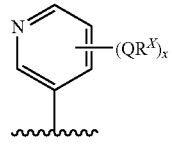
b-ii

-continued

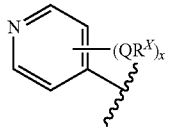
b-iii

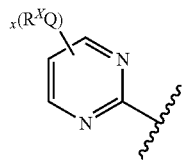
c-ii

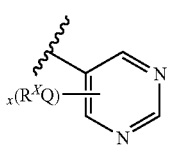
c-iii

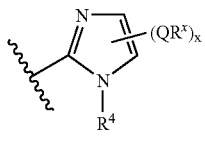
g-i

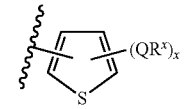
l

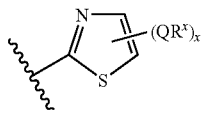
o-i

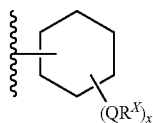
v

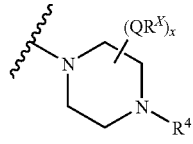
aa

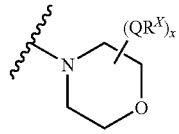
bb

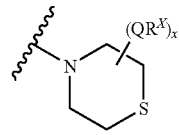
ff

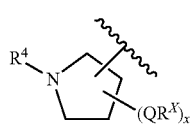
gg

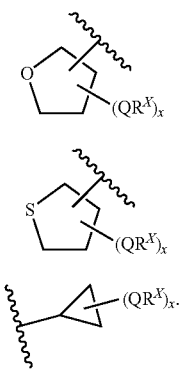

In other preferred embodiments, Cy¹ is selected from phenyl (a), pyridyl (b) (preferably attached in the 2-, 3-, or 4-position as shown by b-i, b-ii, and b-iii), imidazolyl (g) (preferably attached in the 2-, 4- or 5-position as shown by g-i), benzimidazol-2-yl (ll), thiazolyl (o) (preferably attached in the 2-position as shown by o-i), benzthiazol-2-yl (mm), and thienyl (l):

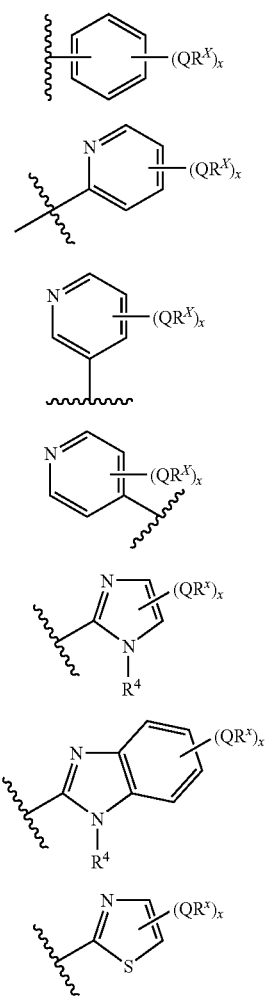

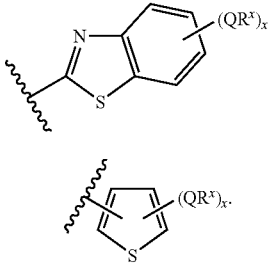

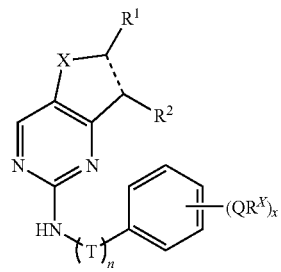

In most preferred embodiments Cy¹ is selected from phenyl (a), and compounds have the formula I-A:

I-A wherein X, $R^1$, $R^2$, n, T, Q and $R^X$ are as defined generally above and in classes and subclasses herein and x is 0-5.

As detailed above, Cy¹ can be optionally substituted with up to 5 occurrences of $QR^X$. In certain preferred embodiments, x is 0-3, and thus Cy¹ is substituted with 0-3 occurrences of $QR^X$. In still other preferred embodiments, x is 0 and Cy¹ is unsubstituted.

In preferred embodiments, $QR^X$ groups, when present, are each independently halogen, CN, NO₂, or an optionally substituted group selected from $C_{1-4}$alkyl, aryl, aralkyl, —N(R')₂, —CH₂N(R')₂, —OR', —CH₂OR', —SR', —CH₂SR', —COOR', —NRCOR', —CON(R')₂, —SO₂R', NR'SO₂R', or —SO₂N(R')₂. Alternatively, $QR^X$ groups, when present, are each independently halogen, CN, NO₂, or an optionally substituted group selected from $C_{1-4}$alkyl, —CF₃, aryl, heteroaryl, aralkyl, —N(R')₂, —CH₂N(R')₂, —OR', —CH₂OR', —SR', —CH₂SR', —COOR', —NRCOR', —CON(R')₂, —SO₂R', NR'SO₂R', SO₂N═R', or —SO₂N(R')₂. In more preferred embodiments, $QR^X$ groups are each independently Cl, Br, F, CF₃, methyl, ethyl, isopropyl, n-propyl, n-butyl, tert-butyl, NO₂, —OH, —SO₂NH₂, SO₂CH₃, NH₂, SO₂NHCH₃, NHSO₂CH₃, or an optionally substituted group selected from $C_{1-4}$alkoxy, phenyl, phenyloxy, benzyl, or benzyloxy. Most preferred $QR^X$ groups include those shown below in Tables 1-8.

As described generally above, X is an optionally substituted $C_1$-$C_3$ alkylidene chain wherein one or two non-adjacent methylene units are independently optionally replaced by CO, CONR', NR'CO, SO, SO₂, NR'SO₂, SO₂NR', O, S, or NR'. In certain preferred embodiments, compounds of special interest include those compounds wherein X is an optionally substituted methylene group and compounds have the general formula II:

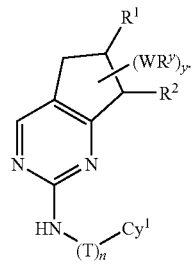

II

As described generally above, in certain preferred embodiments, Cy¹ is selected from any one of a through mm depicted above (including certain subsets b-i, c-i, b-ii, b-iii, c-ii, c-iii, g-i, ll, o-i or mm). It will be appreciated, however, that for compounds of formula II as described above, certain additional compounds are of special interest. For example, in certain exemplary embodiments, for compounds of general formula II above, compounds of special interest include those compounds where Cy¹ is optionally substituted phenyl, and compounds have the formula II-A:

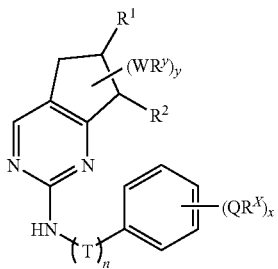

II-A wherein X, R¹, R², n, x, T, Q and $R^X$ are as defined generally above and in classes and subclasses herein.

For certain other compounds of interest, R¹ and R², taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2), and compounds have one of the structures II-B, II-C, II-D, II-E, II-F, II-G, II-H, II-I, II-J, II-K, II-L, or II-M:

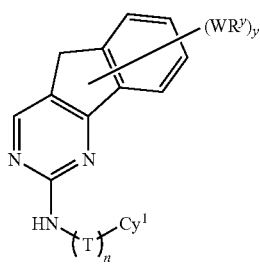

II-B

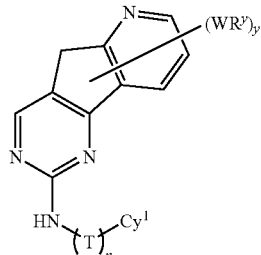

II-C

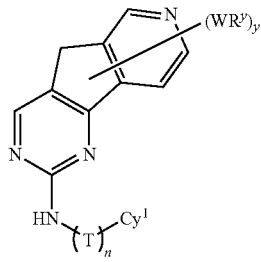

II-D

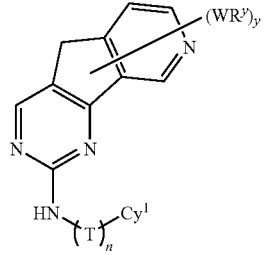

II-E

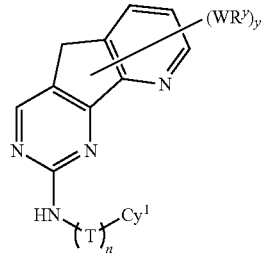

II-F

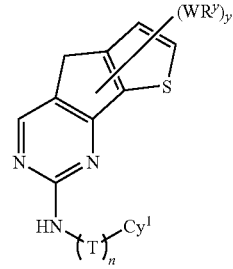

II-G

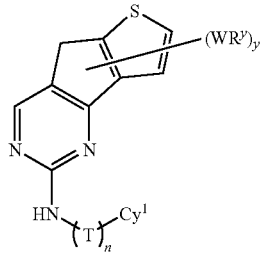

II-H

II-I

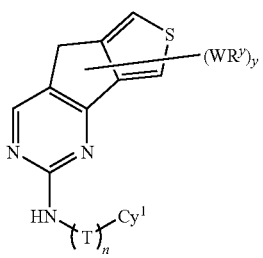

II-J

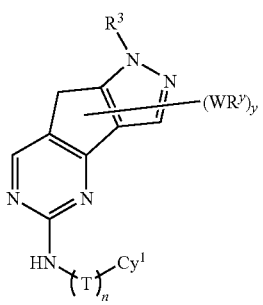

II-K

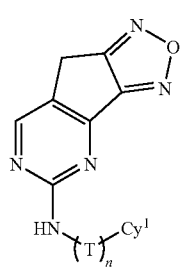

II-L

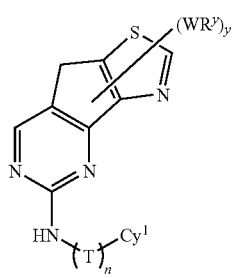

II-M

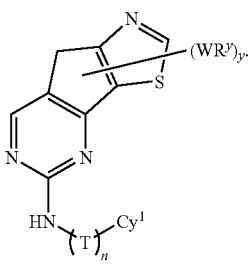

It will be appreciated that certain subclasses of the foregoing compounds of formulas II and II-A through II-M, are of particular interest.

For example, in certain preferred embodiments, for compounds of formulas II and II-A through II-M, $Cy^1$ is phenyl, optionally substituted with 0-3 occurrences of $QR^X$. In more preferred embodiments for compounds described above, n is 0, or n is 1 and T is $CH_2$, —$CH_2CH_2$—, —CO— or —$SO_2$—; x is 0-3; and each occurrence of $QR^X$ is independently halogen, CN, $NO_2$, or an optionally substituted group selected from $C_{1-4}$alkyl, aryl, aralkyl, —N(R')$_2$, -$CH_2N(R')_2$, —OR', —$CH_2OR'$, —SR', —$CH_2SR'$, —COOR', —NRCOR', —CON(R')$_2$, —$SO_2R'$, NR'$SO_2R'$, or —$SO_2N(R')_2$. Alternatively, T is —C(H)(CH$_3$)— —C(H)(CH$_3$)CH$_2$—, —$CH_2C$(H)(CH$_3$)—, or —$CH_2CH_2CH_2$—.

In more preferred embodiments, $QR^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optionally substituted group selected from $C_{1-4}$alkoxy, phenyl, phenyloxy, benzyl, or benzyloxy.

In certain preferred embodiments, for compounds of formula II-A, x is 0-3; and each occurrence of $QR^X$ is independently halogen, CN, NO$_2$, or an optionally substituted group selected from $C_{1-4}$alkyl, aryl, aralkyl, —N(R')$_2$, —$CH_2N$(R')$_2$, —OR', —$CH_2OR'$, —SR', —$CH_2SR'$, —COOR', —NRCOR', —CON(R')$_2$, —SO$_2$R', NR'SO$_2$R', or —SO$_2$N(R')$_2$. In more preferred embodiments, $QR^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optionally substituted group selected from $C_{1-4}$alkoxy, phenyl, phenyloxy, benzyl, or benzyloxy.

In certain preferred embodiments, for compounds of formulae II-B through II-M, y is 0-3; and each occurrence of WR$^y$ is independently halogen, CN, NO$_2$, or an optionally substituted group selected from $C_{1-4}$alkyl, aryl, heteroaryl, —N(R')$_2$, —$CH_2N$(R')$_2$, —OR', —$CH_2OR'$, —SR', —$CH_2SR'$, —COOR', —NRCOR', —CON(R')$_2$, or —S(O)$_2$N(R')$_2$. In more preferred embodiments, —WR$^y$ groups are each independently F, Cl, Br, I, Me, Et, —CN, —OMe, —SMe, —NMe$_2$, —NEt$_2$, —COOMe, —COOH, —OH, —SO$_2$NH$_2$, —CON(CH$_3$)$_2$, —CO(optionally substituted N-piperazinyl), —CO(N-morpholinyl) (including optionally substituted N-morpholinyl), —CO(N-piperidinyl) (including optionally substituted N-piperidinyl), —CH$_2$N(Me)$_2$, —CH$_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl. Alternatively, —WR$^y$ groups are each independently CF$_3$, F, Cl, Br, I, Me, Et, —CN, —OMe, —SMe, —NMe$_2$, —NEt$_2$, —COOMe, —COOH, —OH, —SO$_2$NH$_2$, —CON(CH$_3$)$_2$, —CO(optionally substituted N-piperazinyl), —CO(N-morpholinyl) (including optionally substituted N-morpholinyl), —CO(N-piperidinyl) (including optionally substituted N-piperidinyl), —CO(pyrrolidinyl) (including optionally substituted pyrrolidinyl), —CO(N(H)pyrrolidinyl) (including —CO(N-pyrrolidinyl), wherein each pyrrolidinyl is optionally substituted), —CH$_2$N(Me)$_2$, —CH$_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or N(H)pyrrolidinyl.

In other preferred embodiments, y is 1 and WR$^y$ is an optionally substituted aryl or heteroaryl group. Preferred substituents for the optionally substituted aryl or heteroaryl group include —VR$^V$; wherein V is a bond or is a $C_1$-$C_6$ alkylidene chain wherein up to two non-adjacent methylene units of V are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^V$ is independently selected from R', halogen, NO$_2$, or CN, or QR$^X$ is =O, =S, or =NR'. In still other embodiments, y is 1 and WR$^y$ is —CH$_2$N(R')$_2$, —N(R')$_2$, or —CON(R')$_2$. Most preferred WR$^y$ groups and substituents thereof include those shown below in Tables 1-8. In certain embodiments, y is 0.

In still other preferred embodiments, compounds have the general formula II-H and one occurrence of WR$^y$ is an optionally substituted aryl or heteroaryl group, denoted by Ar$^1$ in formula II-H-i below:

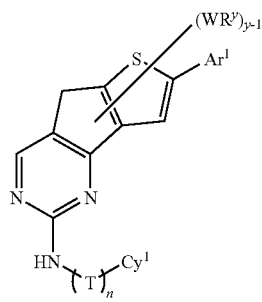

II-H-i

In still other preferred embodiments, Ar$^1$ is an optionally substituted phenyl, pyridyl, pyrimidinyl, thiophenyl, or furanyl group. Preferred substituents for the optionally substituted aryl or heteroaryl group include —VR$^V$; wherein V is a bond or is a C$_1$-C$_6$ alkylidene chain wherein up to two non-adjacent methylene units of V are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^V$ is independently selected from R', halogen, NO$_2$, or CN, or -QR$^X$ is =O, =S, or =NR'.

In certain other embodiments, for compounds of formulae II and II-A through II-M, n is 0, or n is 1 and T is CH$_2$, —CH$_2$CH$_2$—, —CO— or —SO$_2$. Alternatively, T is —C(H)(CH$_3$)—C(H)(CH$_3$)CH$_2$—, —CH$_2$C(H)(CH$_3$)—, or —CH$_2$CH$_2$CH$_2$—.

In certain other embodiments, for compounds of formula II and II-A through II-M, n is 0, or n is 1 and T is CH$_2$, —CH$_2$CH$_2$—, —CO— or —SO$_2$—; x is 0-3; and each occurrence of QR$^X$ is independently halogen, CN, NO$_2$, or an optionally substituted group selected from C$_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, —SO$_2$R', NR'SO$_2$R', or —SO$_2$N(R')$_2$. Alternatively, T is —C(H)(CH$_3$)—C(H)(CH$_3$)CH$_2$—, —CH$_2$C(H)(CH$_3$)—, or —CH$_2$CH$_2$CH$_2$—. In more preferred embodiments, QR$^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optional substituted group selected from C$_{1-4}$alkoxy, phenyl, phenyloxy, benzyl, or benzyloxy. Most preferred QR$^X$ groups include those shown below in Tables 1-8.

In other preferred embodiments, X is an optionally substituted C$_2$-alkylidene chain wherein zero, one or two methylene units are optionally replaced by S, O, or —SO$_2$N(R')—, and the compounds have one of the structures III, IV, V, VI, VII, VIII, or IX:

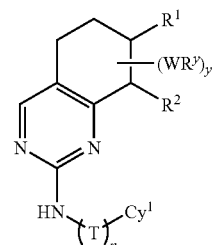

III

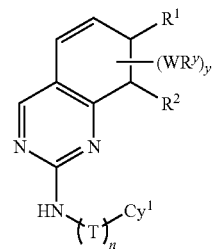

IV

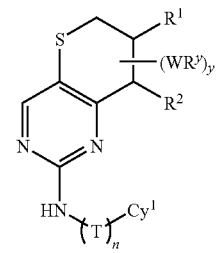

V

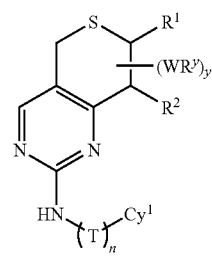

VI

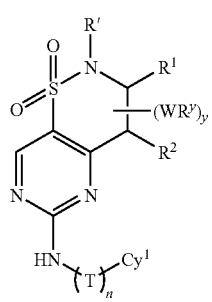

VII

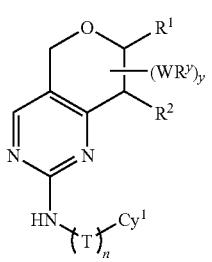

VIII

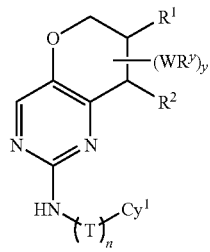

IX wherein W, $R^y$, y, and R' are as defined generally above and in classes and subclasses herein; wherein the dashed bond denoted a single or double bond, as valency permits.

As described generally above, in certain preferred embodiments, $Cy^1$ is selected from any one of a through mm depicted above (including certain subsets b-i, c-i, b-ii, b-iii, c-ii, c-iii, g-i, ll, o-i or mm). It will be appreciated, however, that for compounds of formulae III through VI as described above, certain additional compounds are of special interest. For example, in certain exemplary embodiments, for compounds of general formulae II through VI above, compounds of special interest include those compounds where $Cy^1$ is optionally substituted phenyl, and compounds have one of formulae III-A through VI-A:

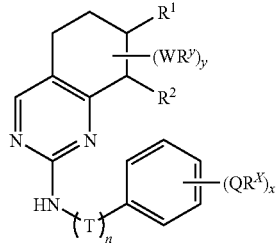

III-A

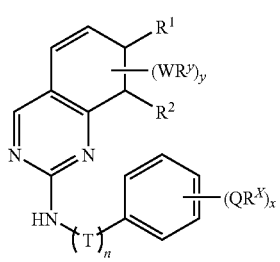

IV-A

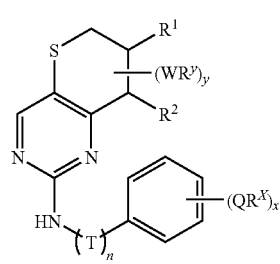

V-A

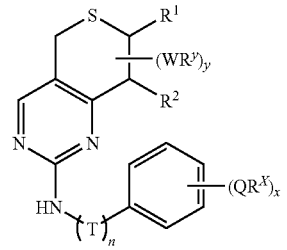

VI-A

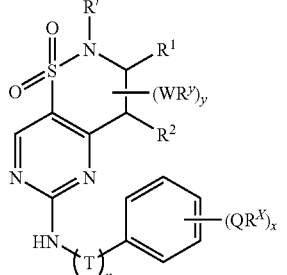

VII-A

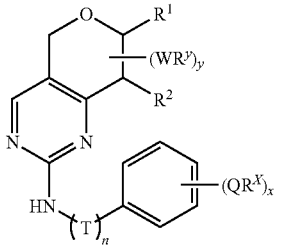

VIII-A

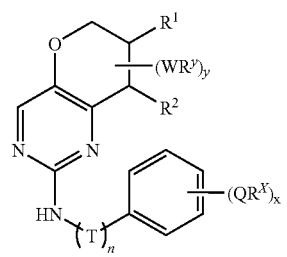

IX-A wherein X, $R^1$, $R^2$, n, x, T, Q and $R^X$ are as defined generally above and in classes and subclasses herein.

In certain preferred embodiments, for compounds of formulas III through IX, $R^1$ and $R^2$, taken together with the carbon atoms to which they are bound form an optionally substituted 5 or 6-membered aryl or heteroaryl ring selected from phenyl (i), pyridyl (ii-l, ii-2, ii-3, ii-4), pyrazolyl (xiii-2), oxadiazolyl (xiv) and thiophenyl (iv-1, iv-2, and xviii), or thiazolyl (viii-1 and viii-2). In more preferred embodiments, for compounds of general formula III, $R^1$ and $R^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2), and compounds have one of the formulas III-B, III-C, III-D, III-E, III-F, III-G, III-H, III-I, III-J, III-K, III-L, or III-M:

III-B 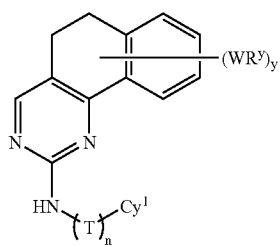 III-H 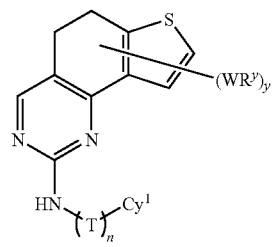
III-C 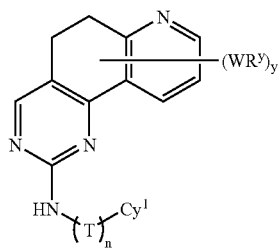 III-I 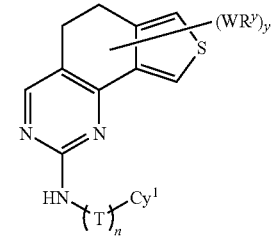
III-D 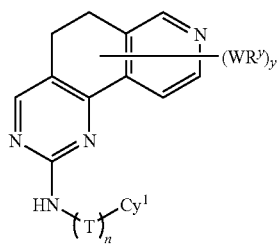 III-J 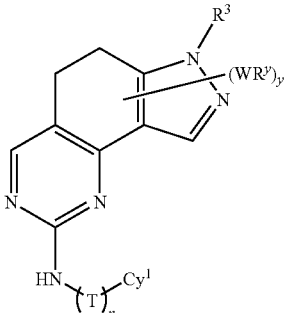
III-E 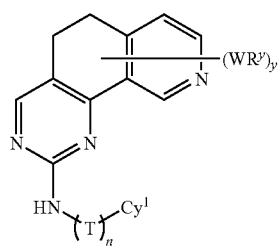 III-K 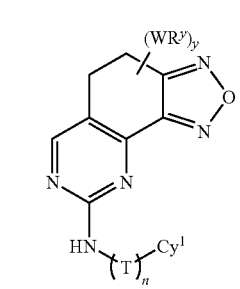
III-F 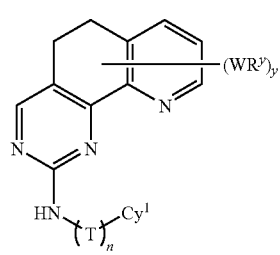 III-L 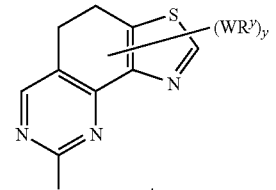
III-G 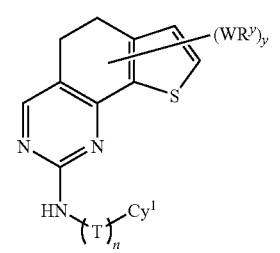 III-M 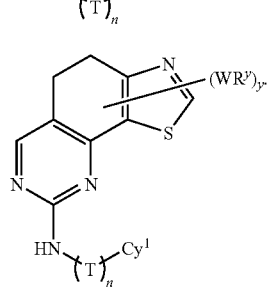

It should be understood that a substituent on a bond passing through more than one ring indicates that any of those rings may be substituted with the subsituent. That is, a compound of formula III-B may be substituted on either the cyclohexyl or the phenyl with WR$^y$ (wherein the total number of y1 and y2 is equal to y):

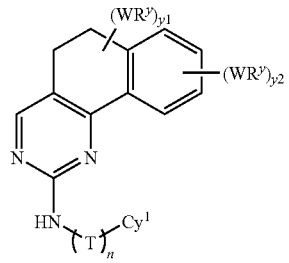

In other preferred embodiments, for compounds of general formula IV, $R^1$ and $R^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2), and compounds have one of the formulas IV-B, IV-C, IV-D, IV-E, IV-F, IV-G, IV-H, IV-I, IV-J, IV-K, IV-L, or IV-M:

IV-B

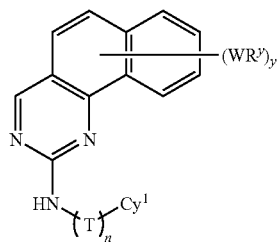

IV-C

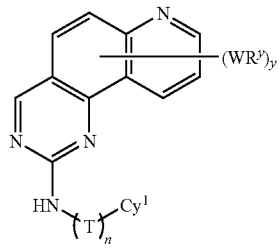

IV-D

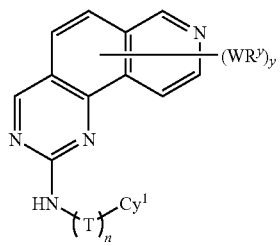

IV-E

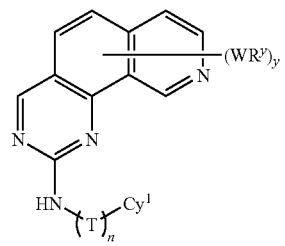

IV-F

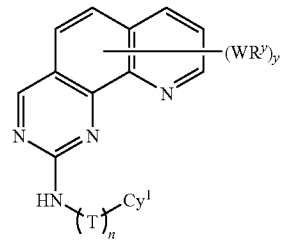

IV-G

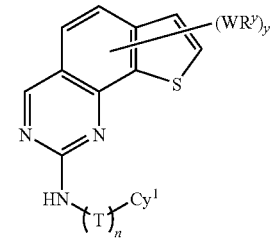

IV-H

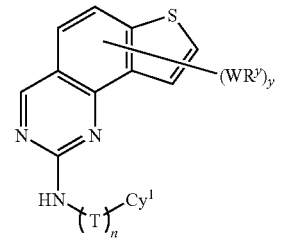

IV-I

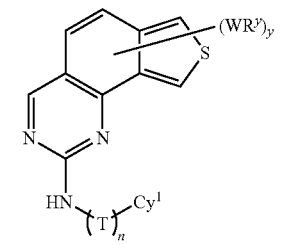

IV-J

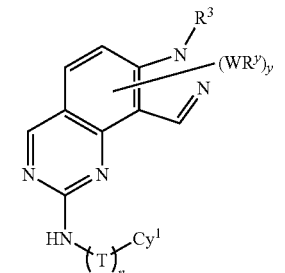

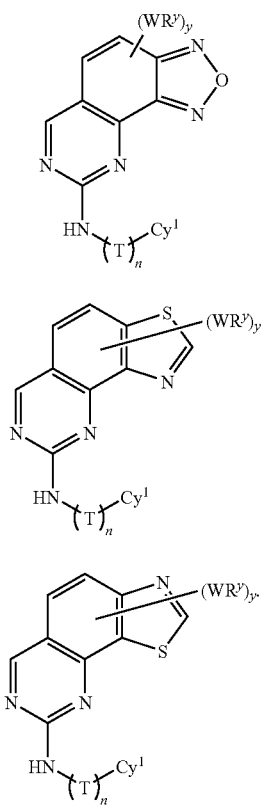

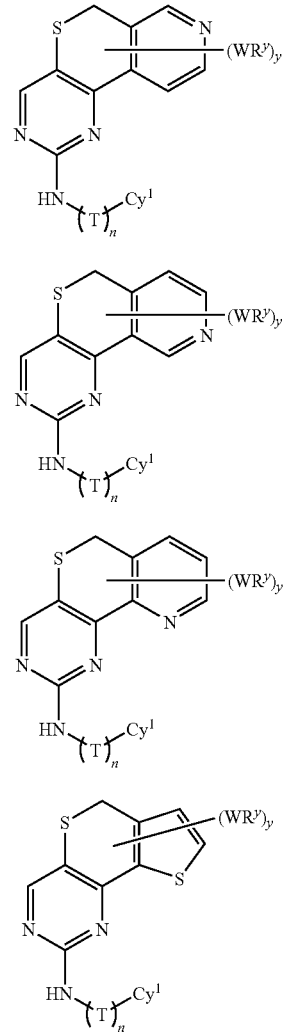

In other preferred embodiments, for compounds of general formula V, $R^1$ and $R^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2), and compounds have one of the formulas V-B, V-C, V-D, V-E, V-F, V-G, V-H, V-I, V-J, V-K, V-L, or V-M:

-continued

V-J
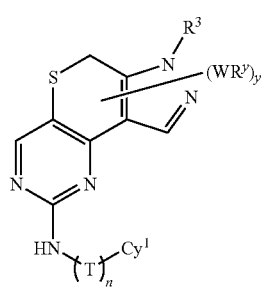

V-K
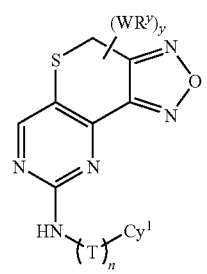

V-L
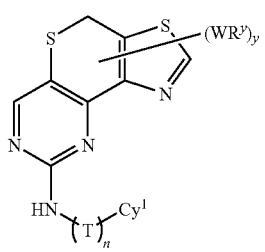

V-M
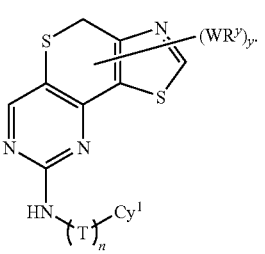

In other preferred embodiments, for compounds of general formula IX, $R^1$ and $R^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2), and compounds have one of the formulas IX-B, IX-C, IX-D, IX-E, IX-F, IX-G, IX-H, IX-I, IX-J, IX-K, IX-L, or IX-M:

IX-B
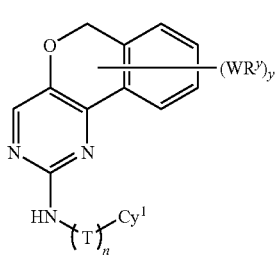

-continued

IX-C
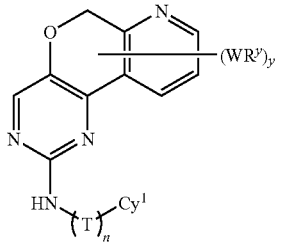

IX-D
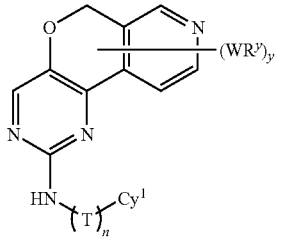

IX-E
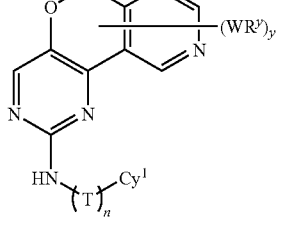

IX-F
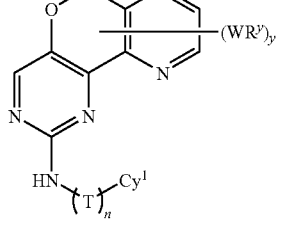

IX-G
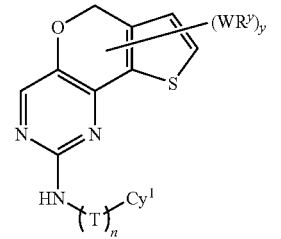

IX-H
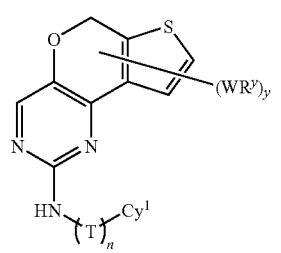

-continued

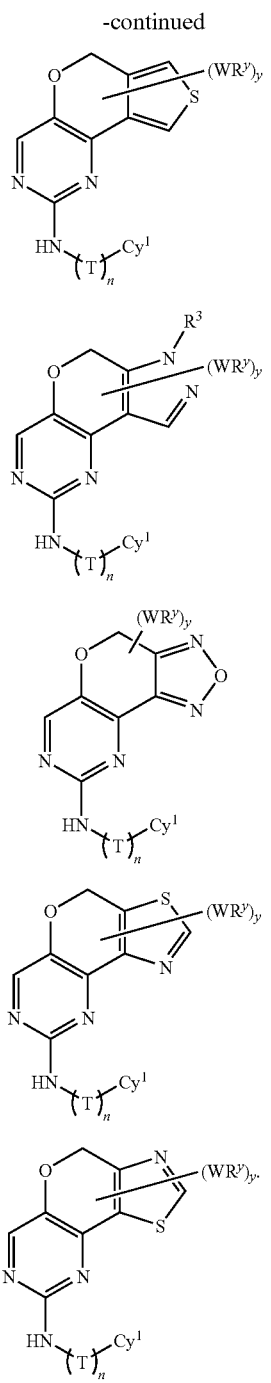

IX-I

IX-J

IX-K

IX-L

IX-M

It will be appreciated that certain subclasses of the foregoing compounds are of particular interest.

For example, in certain preferred embodiments, for compounds described directly above $Cy^1$ is phenyl, optionally substituted with 0-3 occurrences of $QR^X$. In more preferred embodiments for compounds described above, n is 0, or n is 1 and T is $CH_2$, —$CH_2CH_2$—, —CO— or —$SO_2$—; x is 0-3; and each occurrence of $QR^X$ is independently halogen, CN, $NO_2$, or an optionally substituted group selected from $C_{1-4}$alkyl, aryl, aralkyl, —$N(R')_2$, —$CH_2N(R')_2$, —OR', —$CH_2OR'$, —SR', —$CH_2SR'$, —COOR', —NRCOR', —$CON(R')_2$, —$SO_2R'$, $NR'SO_2R'$, or —$SO_2N(R')_2$. Alternatively, T is —C(H)(CH_3)— —C(H)(CH_3)CH_2—, —CH_2C(H)(CH_3)—, or —CH_2CH_2CH_2—. In more preferred embodiments, $QR^X$ groups are each independently Cl, Br, F, $CF_3$, methyl, ethyl, isopropyl, n-propyl, n-butyl, tert-butyl, $NO_2$, —OH, —$SO_2NH_2$, $SO_2CH_3$, $NH_2$, $SO_2NHCH_3$, $NHSO_2CH_3$, or an optionally substitute group selected from $C_{1-4}$alkoxy, phenyl, phenyloxy, benzyl, or benzyloxy.

In certain preferred embodiments, for compounds described directly above, y is 0-3; and each occurrence of $WR^y$ is independently halogen, CN, $NO_2$, or an optionally substituted group selected from $C_{1-4}$alkyl, aryl, heteroaryl, —$N(R')_2$, —$CH_2N(R')_2$, —OR', —$CH_2OR'$, —SR', —$CH_2SR'$, —COOR', —NRCOR', —$CON(R')_2$, or —$S(O)_2N(R')_2$. In more preferred embodiments, —$WR^y$ groups are each independently F, Cl, Br, I, Me, Et, —CN, —OMe, —SMe, —$NMe_2$, —$NEt_2$, —COOMe, —COOH, —OH, —$SO_2NH_2$, —$CON(CH_3)_2$, —CO(optionally substituted N-piperazinyl), —CO(N-morpholinyl) (including optionally substituted N-morpholinyl), —CO(N-piperidinyl) (including optionally substituted N-piperidinyl), —$CH_2N(Me)_2$, —$CH_2N(Et)_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl. Alternatively, —$WR^y$ groups are each independently $CF_3$, F, Cl, Br, I, Me, Et, —CN, —OMe, —SMe, —$NMe_2$, —$NEt_2$, —COOMe, —COOH, —OH, —$SO_2NH_2$, —$CON(CH_3)_2$, —CO(optionally substituted N-piperazinyl), -CO(N-morpholinyl) (including optionally substituted N-morpholinyl), —CO(N-piperidinyl) (including optionally substituted N-piperidinyl), —CO(pyrrolidinyl) (including optionally substituted pyrrolidinyl), —CO(N(H)pyrrolidinyl) (including —CO(N-pyrrolidinyl), wherein each pyrrolidinyl is optionally substituted), —$CH_2N(Me)_2$, —$CH_2N(Et)_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or N(H)pyrrolidinyl.

In other preferred embodiments, y is 1 and $WR^y$ is an optionally substituted aryl or heteroaryl group. Preferred substituents for the optionally substituted aryl or heteroaryl group include —$VR^V$; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^V$ is independently selected from R', halogen, $NO_2$, or CN, or $QR^X$ is =O, =S, or =NR'. In still other embodiments, y is 1 and $WR^y$ is —$CH_2N(R')_2$, —$N(R')_2$, or —$CON(R')_2$. Most preferred $WR^y$ groups and substituents thereof include those shown below in Tables 1-8. In certain embodiments, y is 0.

In still other preferred embodiments, compounds have the general formula III-H, III-L, III-M, IV-H, IV-L, IV-M, V-H, V-L, V-M, IX-H, IX-L, or IX-M, and one occurrence of $WR^y$ is an optionally substituted aryl or heteroaryl group, denoted by $Ar^1$ in one of formulae III-H-i, III-L-i, III-M-i, IV-H-i, IV-L-i, IV-M-i, V-H-i, V-L-i, V-M-i, IX-H-i, IX-L-i, or IX-M-i below:

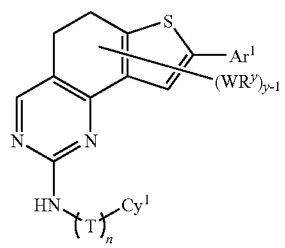

III-H-i

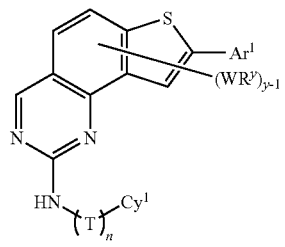

IV-H-i

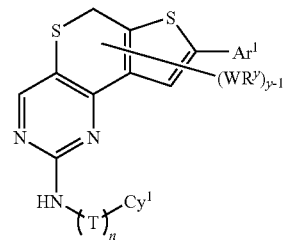

V-H-i

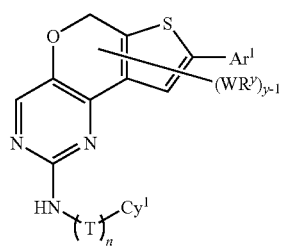

IX-H-i

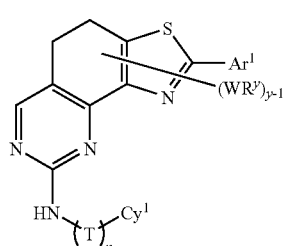

III-L-i

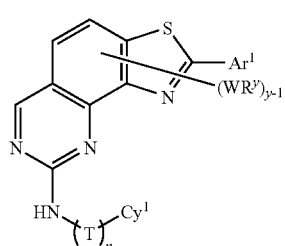

IV-L-i

-continued

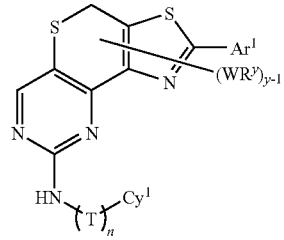

V-L-i

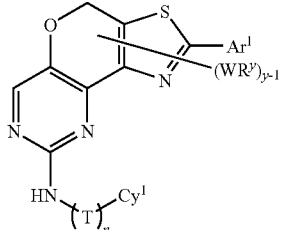

IX-L-i

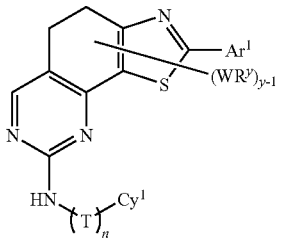

III-M-i

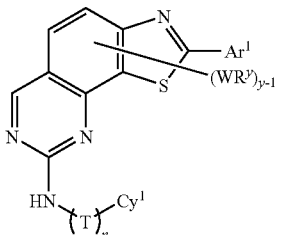

IV-M-i

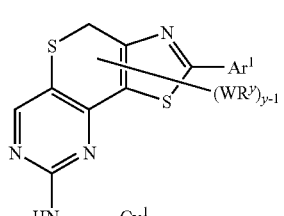

V-M-i

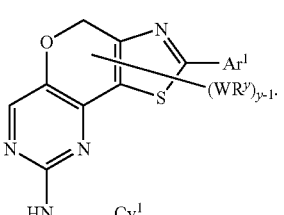

IX-M-i

In still other preferred embodiments, $Ar^1$ is an optionally substituted phenyl, pyridyl, pyrimidinyl, thiophenyl, or furanyl group. Preferred substituents for the optionally substituted aryl or heteroaryl group include —$VR^V$; wherein V is a bond or is a $C_1$-$C_6$ alkylidene chain wherein up to two non-adjacent methylene units of V are independently optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^V$ is independently selected from R', halogen, NO₂, or CN, or -QR$^X$ is =O, =S, or =NR'.

In yet other preferred embodiments, compounds have the general formula III-H, III-L, III-M, IV-H, IV-L, IV-M, V-H, V-L, V-M, IX-H, IX-L, or IX-M and one occurrence of WR$^y$ is —CH₂N(R')₂ and compounds have one of the formulae III-H-ii, III-L-ii, III-M-ii, IV-H-ii, IV-L-ii, IV-M-ii, V-H-ii, V-L-ii, V-M-ii, IX-H-ii, IX-L-ii, or IX-M-ii below:

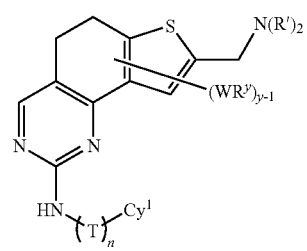

III-H-ii

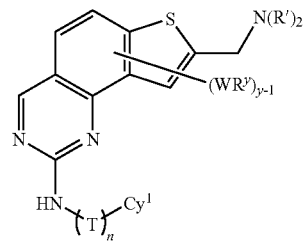

IV-H-ii

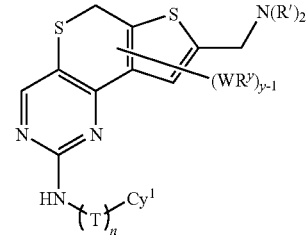

V-H-ii

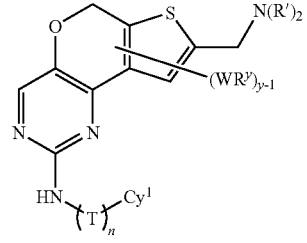

IX-H-ii

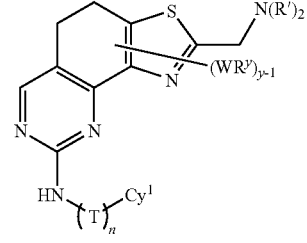

III-L-ii

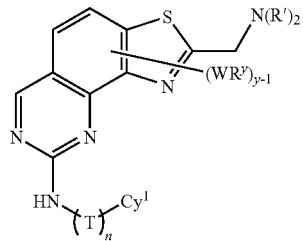

IV-L-ii

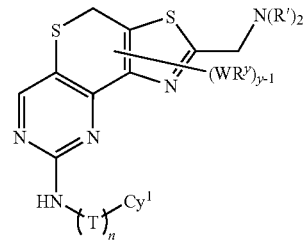

V-L-ii

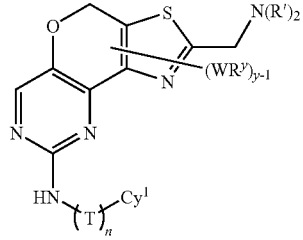

IX-L-ii

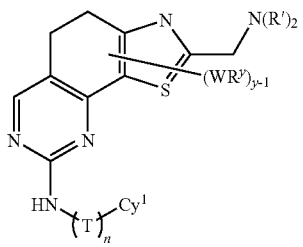

III-M-ii

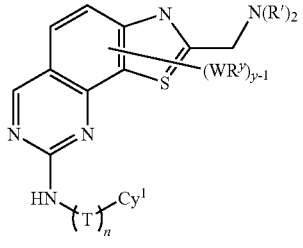

IV-M-ii

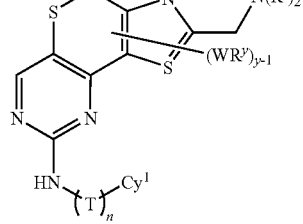

V-M-ii

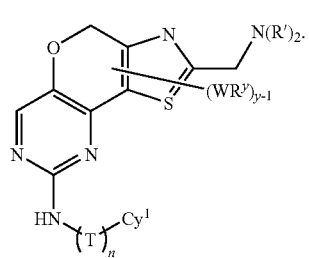

IX-M-ii

In yet other preferred embodiments, compounds have the general formula III-H, III-L, III-M, IV-H, IV-L, IV-M, V-H, V-L, V-M, IX-H, IX-L, or IX-M and one occurrence of WR$^y$ is —N(R')$_2$ and compounds have one of the formulae III-H-iii, III-L-iii, III-M-iii, IV-H-iii, IV-L-iii, IV-M-iii, V-H-iii, V-L-iii, V-M-iii, IX-H-iii, IX-L-iii, or IX-M-iii below:

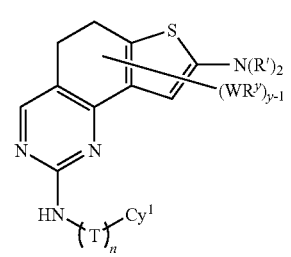

III-H-iii

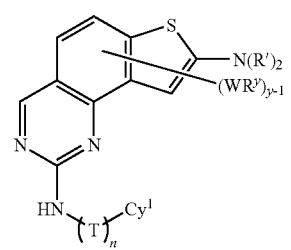

IV-H-iii

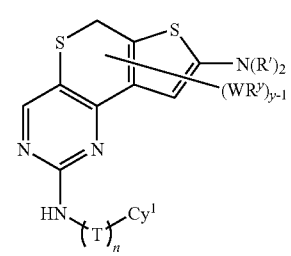

V-H-iii

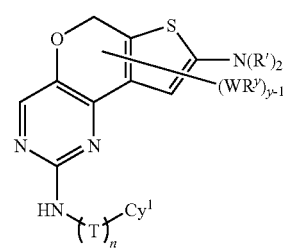

IX-H-iii

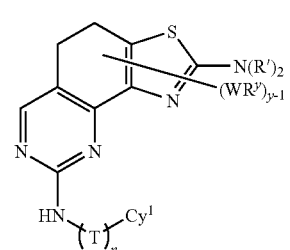

III-L-iii

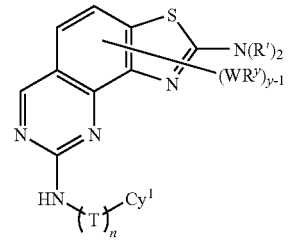

IV-L-iii

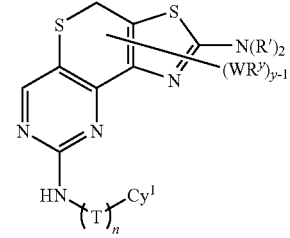

V-L-iii

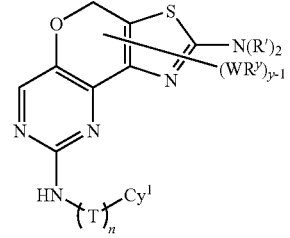

IX-L-iii

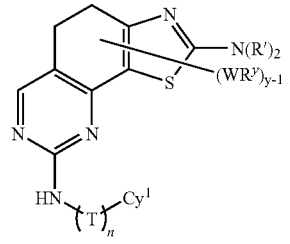

III-M-iii

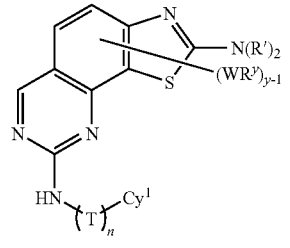

IV-M-iii

-continued

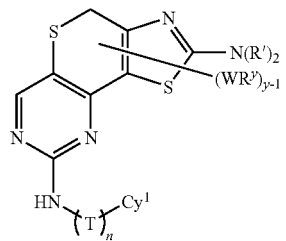
V-M-iii

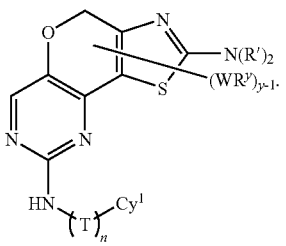
IX-M-iii

In yet other preferred embodiments, compounds have the general formula III-H, III-L, III-M, IV-H, IV-L, IV-M, V-H, V-L, V-M, IX-H, IX-L, or IX-M and one occurrence of $WR^y$ is —$CON(R')_2$ and compounds have one of the formulae III-H-iv, III-L-iv, III-M-iv, IV-H-iv, IV-L-iv, IV-M-iv, V-H-iv, V-L-iv, V-M-iv, IX-H-iv, IX-L-iv, or IX-M-iv below:

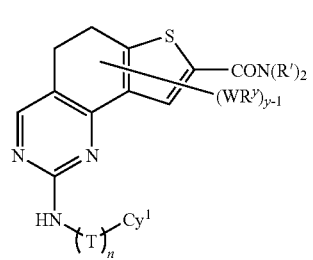
III-H-iv

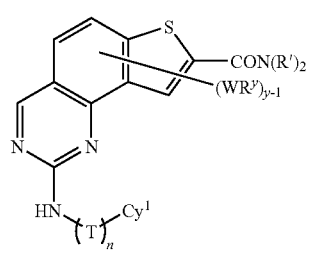
IV-H-iv

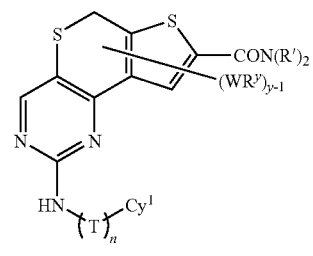
V-H-iv

-continued

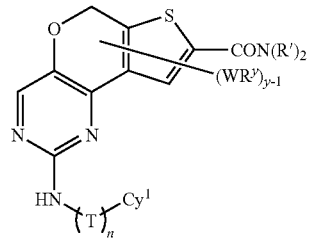
IX-H-iv

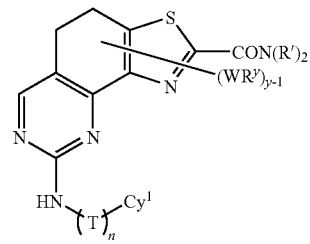
III-L-iv

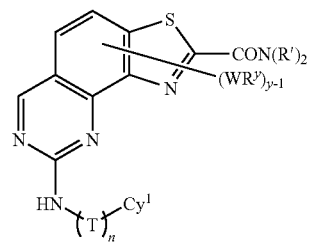
IV-L-iv

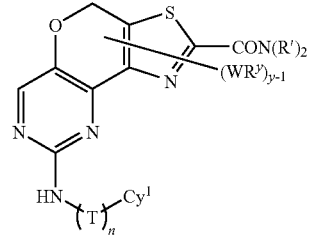
V-L-iv

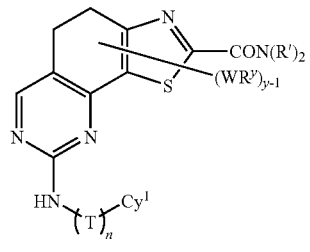
IX-L-iv

III-M-iv tuted group selected from C$_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, —SO$_2$R', NR'SO$_2$R', or —SO$_2$N(R')$_2$. Alternatively, T is —C(H)(CH$_3$)— —C(H)(CH$_3$)CH$_2$—, —CH$_2$C(H)(CH$_3$)—, or —CH$_2$CH$_2$CH$_2$—. In more preferred embodiments, QR$^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optionally substituted group selected from C$_{1-4}$alkoxy, phenyl, phenyloxy, benzyl, or benzyloxy. Most preferred QR$^X$ groups include those shown below in Tables 1-8.

In certain embodiments, preferred compounds are those of formula IV-H (including the subgenerics thereof). In certain other embodiments, preferred compounds are those of formula IV-M (including the subgenerics thereof).

Another class of special interest includes compounds wherein X is an optionally substituted C$_3$ alkylidene moiety and compounds have the general formula X:

As described generally above, in certain preferred embodiments, Cy$^1$ is selected from any one of a through mm depicted above (including certain subsets b-i, c-i, b-ii, b-iii, c-ii, c-iii, g-i, ll, o-i or mm). It will be appreciated, however, that for compounds of formulae III through VI as described above, certain additional compounds are of special interest. For example, in certain exemplary embodiments, for compounds of general formula X above, compounds of special interest include those compounds where Cy$^1$ is optionally substituted phenyl, and compounds have formula X-A:

In certain preferred embodiments, for compounds of formula X, R$^1$ and R$^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), oxadiazolyl (xiv), thiophenyl (iv-1, iv-2, and xviii), or thiazolyl (viii-1 and viii-2). In more preferred embodiments, for compounds of general formula VII, R$^1$ and R$^2$, taken together with the carbon atoms to which they are bound form an optionally substituted 5 or 6-membered aryl or heteroaryl ring selected from phenyl (i), pyridyl (ii-1, ii-2, ii-3, ii-4), pyrazolyl (xiii-2), In still other preferred embodiments, —CH$_2$N(R')$_2$ is preferably —CH$_2$N(CH$_2$)$_3$, —CH$_2$N(CH$_2$CH$_3$)$_2$, —CH$_2$(optionally substituted N-piperazinyl), —CH$_2$(optionally substituted N-piperidinyl), or —CH$_2$(optionally substituted N-morpholinyl); —N(R')$_2$ is preferably —N(CH$_2$)$_3$, —N(CH$_2$CH$_3$)$_2$, -optionally substituted N-piperazinyl, optionally substituted N-piperidinyl, or -optionally substituted N-morpholinyl; and —CON(R')$_2$ is preferably —CON(CH$_2$)$_3$, —CON(CH$_2$CH$_3$)$_2$, —CO(optionally substituted N-piperazinyl), —CO(optionally substituted N-piperidinyl), or —CO(optionally substituted N-morpholinyl). Alternatively, —CH$_2$N(R')$_2$ is preferably, —CH$_2$N(CH$_2$)$_3$, —CH$_2$N(CH$_2$CH$_3$)$_2$, —CH$_2$(optionally substituted N-piperazinyl), —CH$_2$(optionally substituted N-piperidinyl), or —CH$_2$(optionally substituted N-morpholinyl); —N(R')$_2$ is preferably —N(CH$_2$)$_3$, —N(CH$_2$CH$_3$)$_2$, -optionally substituted N-piperazinyl, optionally substituted N-piperidinyl, or -optionally substituted N-morpholinyl; and —CON(R')$_2$ is preferably —CON(CH$_2$)$_3$, —CON(CH$_2$CH$_3$)$_2$, —CO(optionally substituted N-piperazinyl), —CO(optionally substituted N-piperidinyl), —CO(optionally substituted N-morpholinyl), —CO(optionally substituted pyrrolidinyl (including optionally substituted N-pyrrolidinyl), —CO(N(H)optionally substituted pyrrolidinyl), optionally substituted pyrrolidinyl, or —N(H)(optionally substituted pyrrolidinyl).

In certain other embodiments, for compounds described directly above, n is 0, or n is 1 and T is CH$_2$, —CH$_2$CH$_2$—, —CO— or —SO$_2$. Alternatively, T is —C(H)(CH$_3$)——C(H)(CH$_3$)CH$_2$—, —CH$_2$C(H)(CH$_3$)—, or —CH$_2$CH$_2$CH$_2$—.

In certain other embodiments, for compounds described directly above n is 0, or n is 1 and T is CH$_2$, —CH$_2$CH$_2$—, —CO— or —SO$_2$—; x is 0-3; and each occurrence of QR$^X$ is independently halogen, CN, NO$_2$, or an optionally substioxadiazolyl (xiv), thiophenyl (iv-1, iv-2, and xviii), or thiazolyl (viii-1 and viii-2), and compounds have one of the formulae X-B, X-C, X-D, X-E, X-F, X-G, X-H, X-I, X-J, X-K, X-L, or X-M:
X-B
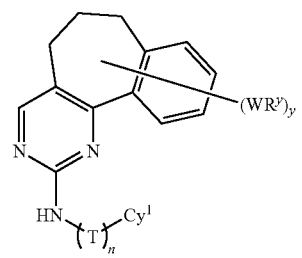
X-C
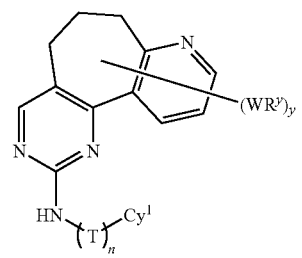
X-D
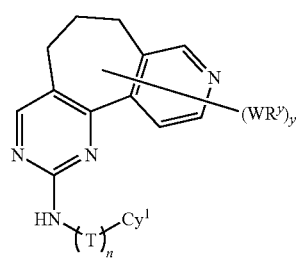
X-E
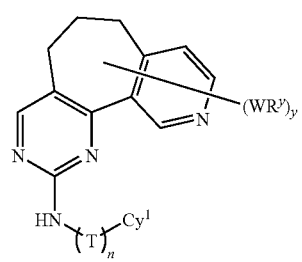
X-F
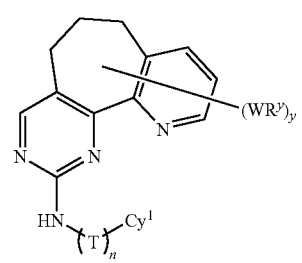
-continued
X-G
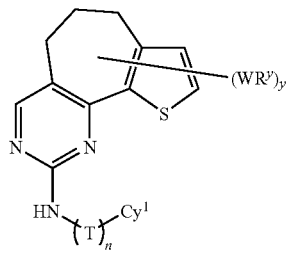
X-H
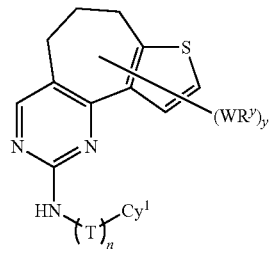
X-I
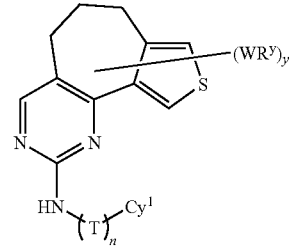
X-J
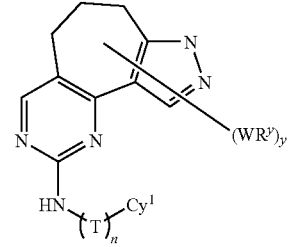
X-K
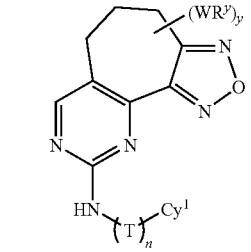
X-L
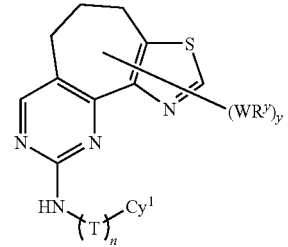

-continued

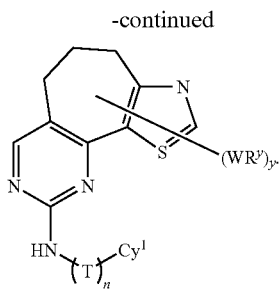

X-M

It will be appreciated that certain subclasses of the foregoing compounds of formulas X-B through X-M are of particular interest.

For example, in certain preferred embodiments, for compounds of formulas X-B through X-M, $Cy^1$ is phenyl, optionally substituted with 0-3 occurrences of $QR^X$. In more preferred embodiments for compounds described above, n is 0, or n is 1 and T is $CH_2$, —$CH_2CH_2$—, —CO— or —$SO_2$—; x is 0-3; and each occurrence of $QR^X$ is independently halogen, CN, $NO_2$, or an optionally substituted group selected from $C_{1-4}$alkyl, aryl, aralkyl, —N(R')$_2$, —$CH_2$N(R')$_2$, —OR', —$CH_2$OR', —SR', —$CH_2$SR', —COOR', —NRCOR', —CON(R')$_2$, —$SO_2$R', NR'$SO_2$R', or —$SO_2$N(R')$_2$. Alternatively, T is —C(H)(CH$_3$)— —C(H)(CH$_3$)CH$_2$—, —CH$_2$C(H)(CH$_3$)—, or —CH$_2$CH$_2$CH$_2$—. In more preferred embodiments, $QR^X$ groups are each independently Cl, Br, F, $CF_3$, methyl, ethyl, isopropyl, n-propyl, n-butyl, tert-butyl, $NO_2$, —OH, —$SO_2NH_2$, $SO_2CH_3$, $NH_2$, $SO_2NHCH_3$, $NHSO_2CH_3$, or an optionally substituted ground selected from $C_{1-4}$alkoxy, phenyl, phenyloxy, benzyl, or benzyloxy.

In certain preferred embodiments, for compounds of formulae X-B through X-M y is 0-3; and each occurrence of $WR^y$ is independently halogen, CN, $NO_2$, or an optionally substituted group selected from $C_{1-4}$alkyl, aryl, heteroaryl, —N(R')$_2$, —$CH_2$N(R')$_2$, —OR', —$CH_2$OR', —SR', —$CH_2$SR', —COOR', —NRCOR', —CON(R')$_2$, or —S(O)$_2$N(R')$_2$. In more preferred embodiments, —$WR^y$ groups are each independently F, Cl, Br, I, Me, Et, —CN, —OMe, —SMe, —NMe$_2$, —NEt$_2$, —COOMe, —COOH, —OH, —$SO_2NH_2$, —CON(CH$_3$)$_2$, —CO(optionally substituted N-piperazinyl), —CO(N-morpholinyl), —CO(N-piperidinyl), —$CH_2$N(Me)$_2$, —$CH_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl. Alternatively, —$WR^y$ groups are each independently $CF_3$, F, Cl, Br, I, Me, Et, —CN, —OMe, —SMe, —NMe$_2$, —NEt$_2$, —COOMe, —COOH, —OH, —$SO_2NH_2$, —CON(CH$_3$)$_2$, —CO(optionally substituted N-piperazinyl), —CO(N-morpholinyl) (including optionally substituted morpholinyl), —CO(N-piperidinyl) (including optionally substituted piperidinyl), —CO(pyrrolidinyl) (including optionally substituted pyrrolidinyl), —CO(N(H)pyrrolidinyl) (including —CO(N-pyrrolidinyl), wherein each pyrrolidinyl is optionally substituted), —$CH_2$N(Me)$_2$, —$CH_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or N(H)pyrrolidinyl.

In other preferred embodiments, y is 1 and $WR^y$ is an optionally substituted aryl or heteroaryl group. Preferred substituents for the optionally substituted aryl or heteroaryl group include —$VR^V$; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2$NR, $NRSO_2$NR, O, S, or NR; and each occurrence of $R_V$ is independently selected from R', halogen, $NO_2$, or CN, or $QR^X$ is =O, =S, or =NR'. In still other embodiments, y is 1 and $WR^y$ is —$CH_2$N(R')$_2$, —N(R')$_2$, or —CON(R')$_2$. Most preferred $WR^y$ groups and substituents thereof include those shown below in Tables 1-8. In certain embodiments, y is 0.

In still other preferred embodiments, compounds have one of the general formulae X-H or X-L and one occurrence of $WR^y$ is an optionally substituted aryl or heteroaryl group, denoted by $Ar^1$ in formula X-H-i and X-L-i below:

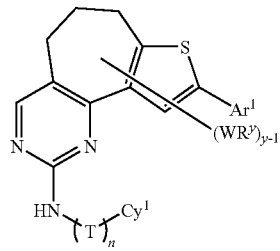

X-H-i

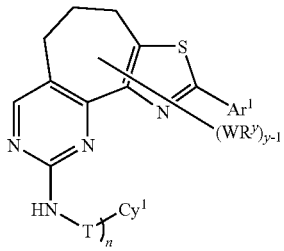

X-L-i

In still other preferred embodiments, $Ar^1$ is an optionally substituted phenyl, pyridyl, pyrimidinyl, thiophenyl, or furanyl group. Preferred substituents for the optionally substituted aryl or heteroaryl group include —$VR^V$; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2$NR, $NRSO_2$NR, O, S, or NR; and each occurrence of $R^V$ is independently selected from R', halogen, $NO_2$, or CN, or -$QR^X$ is =O, =S, or =NR'. In still other embodiments, y is 1 and $WR^y$ is —$CH_2$N(R')$_2$, —N(R')$_2$, or —CON(R')$_2$.

In still other preferred embodiments, compounds have one of the general formulae X-H or X-L and W is —$CH_2$—, a bond, or —CO—, and $R^y$ is —N(R')$_2$ and compounds have one of the formulae X-H-ii and X-L-ii below:

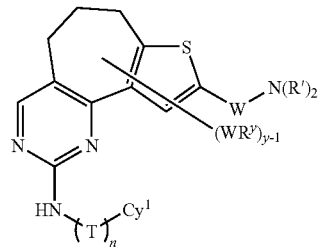

X-H-ii

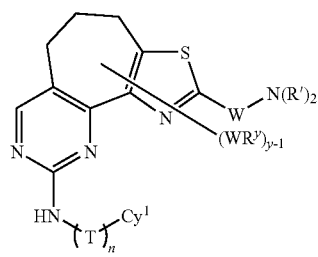

X-L-ii

In certain other embodiments, for compounds described directly above, n is 0, or n is 1 and T is CH$_2$, —CH$_2$CH$_2$—, —CO— or —SO$_2$. Alternatively, T is —C(H)(CH$_3$)— —C(H)(CH$_3$)CH$_2$—, —CH$_2$C(H)(CH$_3$) —, or —CH$_2$CH$_2$CH$_2$—.

In certain other embodiments, for compounds described directly above, n is 0, or n is 1 and T is CH$_2$, —CH$_2$CH$_2$—, —CO— or —SO$_2$—; x is 0-3; and each occurrence of QR$^X$ is independently halogen, CN, NO$_2$, or an optionally substituted group selected from C$_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, —SO$_2$R', NR'SO$_2$R', or —SO$_2$N(R')$_2$. Alternatively, T is —C(H)(CH$_3$)— —C(H)(CH$_3$)CH$_2$—, —CH$_2$C(H)(CH$_3$)—, or —CH$_2$CH$_2$CH$_2$—. In more preferred embodiments, QR$^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optionally substituted group selected from C$_{1-4}$alkoxy, phenyl, phenyloxy, benzyl, or benzyloxy. Most preferred QR$^X$ groups include those shown below in Tables 1-8.

4. General Synthetic Methodology:

The compounds of this invention may be prepared in general by methods known to those skilled in the art for analogous compounds, as illustrated by the general scheme below, and the preparative examples that follow. In these schemes, the variables are as defined in the schemes or may be readily derived from the compounds of this invention.

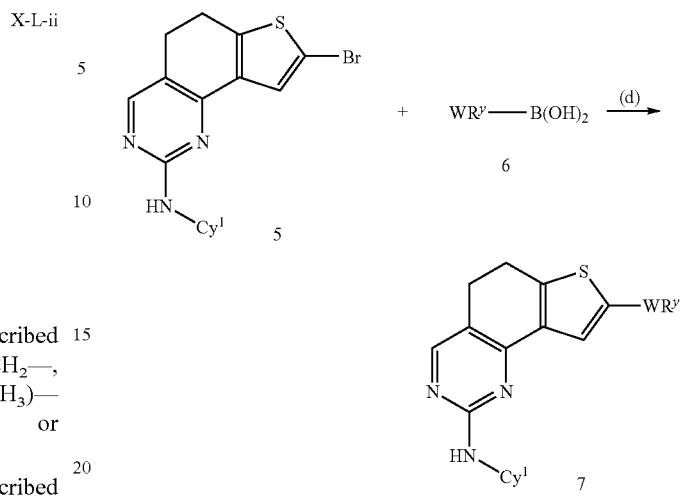

Reagents and conditions: (a) Br$_2$, AcOH, H$_2$O, −5° C., 1 hour; (b) DMF/DMA reflux, 12 hours; (c) IPA, NaOH, reflux, 5 hours; (d) Pd(PPh$_3$)$_4$, Na$_2$CO$_3$, DME, EtOH/H$_2$O, microwave irradiation (120° C.), 2 hours.

Scheme I above shows a general synthetic route that is used for preparing the compounds 7 of this invention when Cy$^1$ and WR$^y$ are as described herein. The bromothiophene 2 may be prepared by methods substantially similar to those described by Pinna, et al, *Eur. J Med. Chem. Chim. Ther.* 1994, 29, 447. Intermediate 3 is prepared according to Scheme I step (b). Compound 3 is treated with N-substituted guanidine 4 according to step (c). Intermediate guanidines of formula 4 may be prepared by reaction of the corresponding amine Cy$^1$NH$_2$ with cyanamide by methods substantially similar to those described by Kaempf, et al, *Chem. Ber.* 1904, 32, 1682. This reaction is amenable to a variety of N-substituted guanidines to form compounds of formula 5.

The formation of the biaryl link derivatives 7 is achieved by treating the bromide 5 with a boronic acid derivatives in the presence of palladium as a catalyst by using the Suzuki coupling methods that are well known in the art. The reaction is amenable to a variety of substituted aryl or heteroaryl boronic acids.

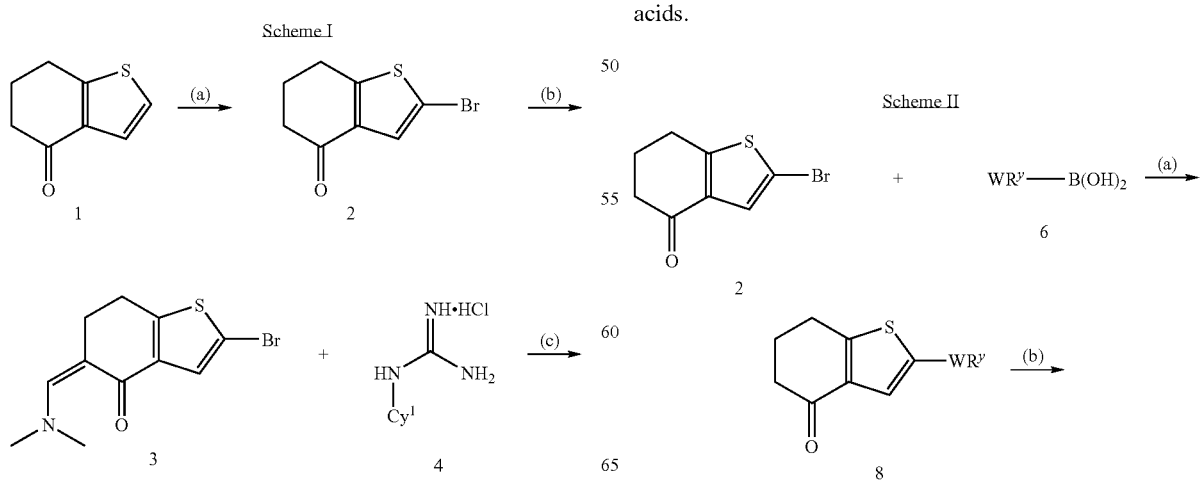

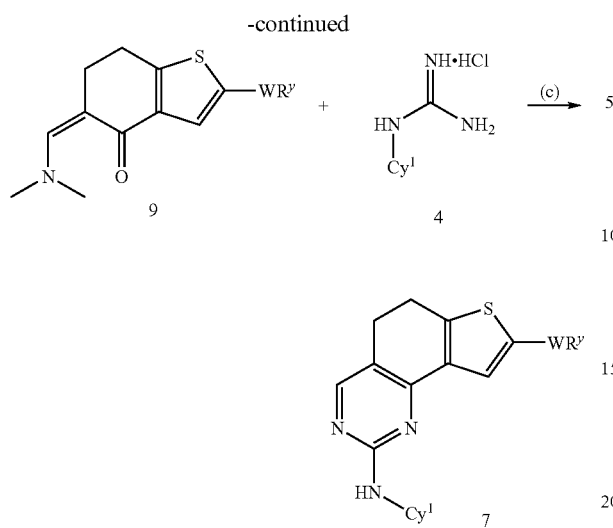

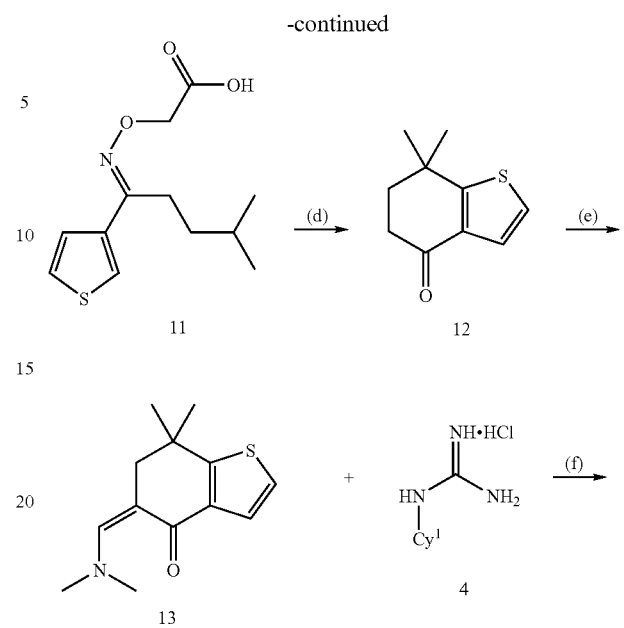

Reagents and conditions: (a) Pd(PPh$_3$)$_4$, Na$_2$CO$_3$, DME, EtOH/H$_2$O, 120° C., 12 hours; (b) DMF/DMA, reflux, 12 hours; (c) K$_2$CO$_3$, DMA, 120° C., 12 hours.

Scheme II above shows another general synthetic route that has been used for preparing the compounds 7 of this invention when Cy$^1$ and WR$^y$ are as described herein. The formation of the biaryl link derivatives 8 is achieved by treating the bromide 2 with a boronic acid derivative in the presence of palladium as a catalyst by using the Suzuki coupling methods that are well known in the art. The reaction is amenable to a variety of substituted aryl or heteroaryl boronic acids. Intermediate 9 is prepared according to Scheme II step (b). Compound 9 is treated with N-substituted guanidine 4 according to step (c). Intermediate guanidines of formula 4 may be prepared by reaction of the corresponding amine Cy$^1$NH$_2$ with cyanamide by methods substantially similar to those described by Kaempf, et al, *Chem. Ber.* 1904, 32, 1682. This reaction is amenable to a variety of N-substituted guanidines to form compounds of formula 7.

Scheme III

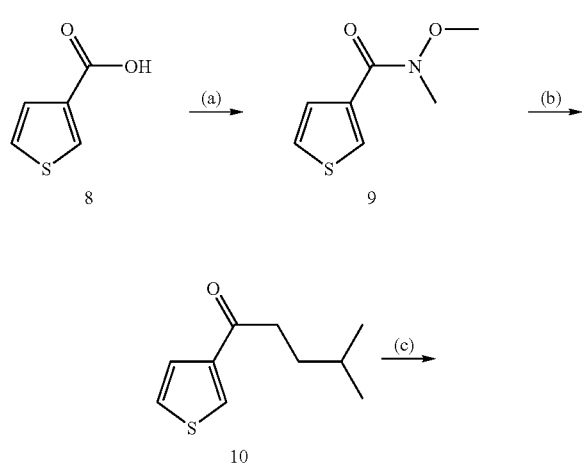

Reagents and conditions: (a) i) SOCl$_2$, CHC$_{1-3}$; ii) MeN-HOMe, Et$_3$N, CHCl$_3$; (b) 1-bromo-3-methylbutane, Mg, I$_2$, Et$_2$O; (c) carboxymethoxylamine hemihydrochloride, NaOH, MeOH; (d) K$_2$S$_2$O$_8$, NaOH$_{aq}$; (e) Brederick's Reagent, DME, reflux, 12 hours; (f) K$_2$CO$_3$, DMA, 120° C., 12 hours.

Scheme III above shows a general synthetic route that is used for preparing compounds of formula 14 of this invention where Cy$^1$ is as described herein. Intermediate 10 is prepared from thiophene-3-carboxylate 8 in a two steps sequence via the Weinreb amide 9. Compound 10 is then treated, in alkali medium, with carboxymethoxylamine hemihydrochloride to form intermediate 11. The cyclisation of 11 is achieved using the method described by Forrester, et al, *J. Chem. Soc., Perkin Trans.* 1 1981, 984. Intermediate 13 is synthesized according to Scheme III step (e). Compound 13 is treated with N-substituted guanidine 4 according to step (f). This reaction is amenable to a variety of N-substituted guanidines to form compounds of formula 14.

Table 1 below depicts exemplary compounds prepared according to the general methods described in Schemes I, II, and III.

TABLE 1
Examples of Compounds of Formula I:
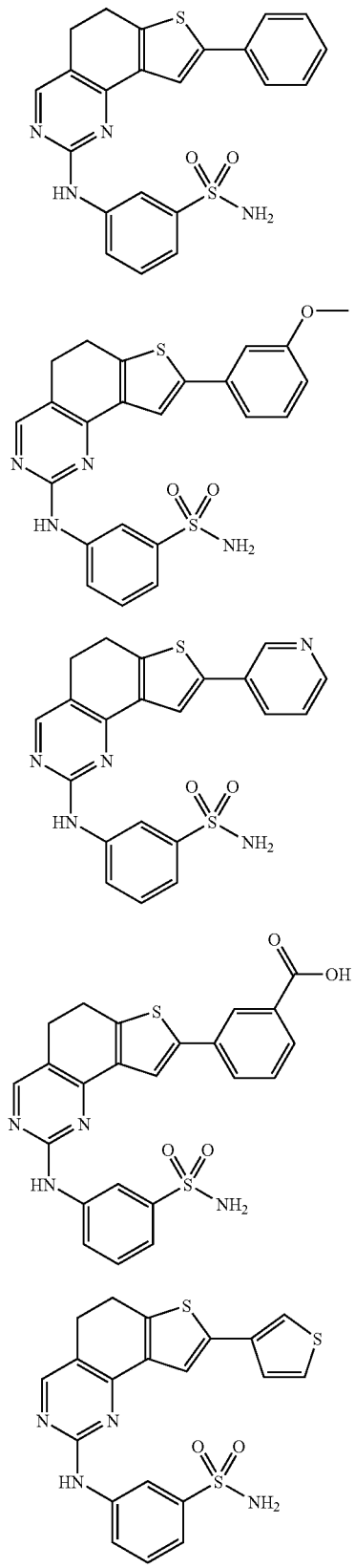
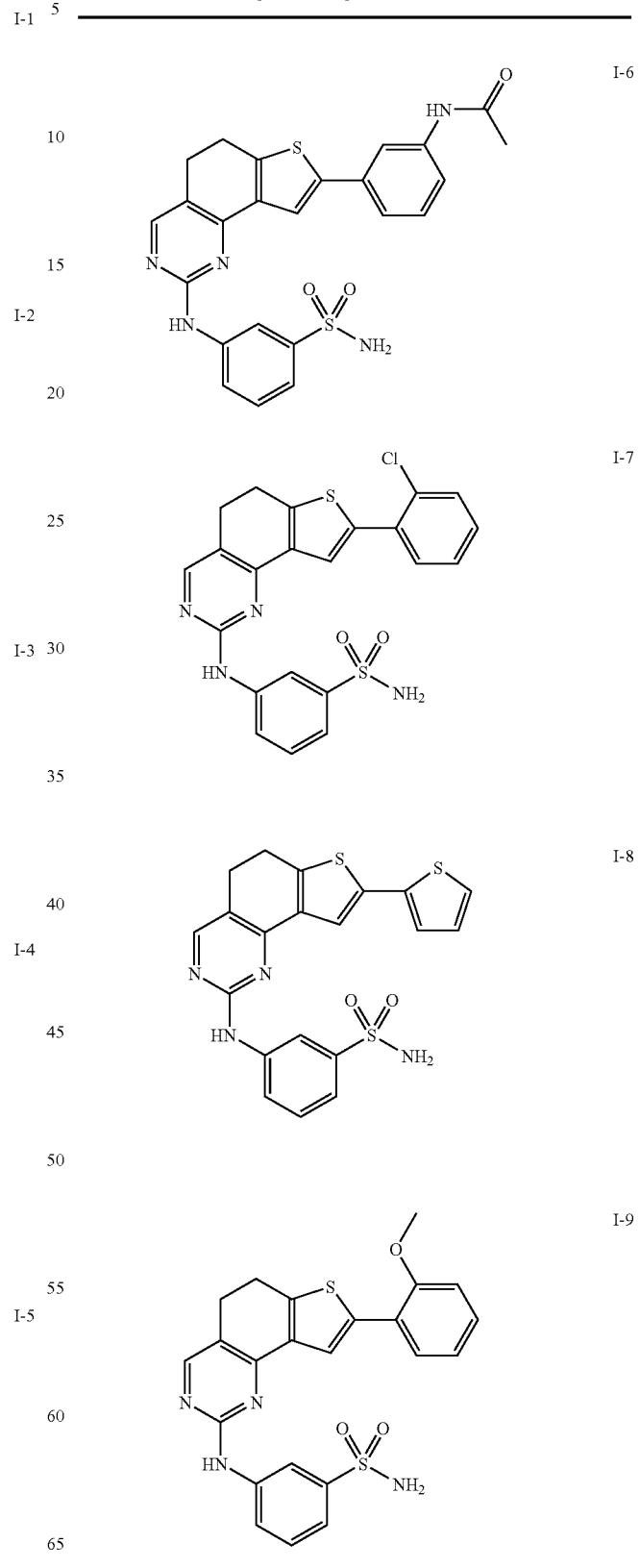

TABLE 1-continued
Examples of Compounds of Formula I:
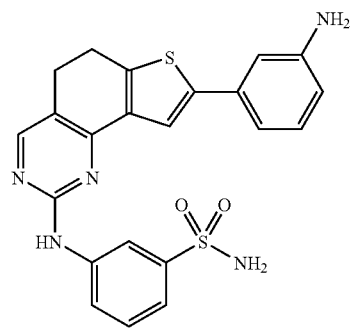
I-10
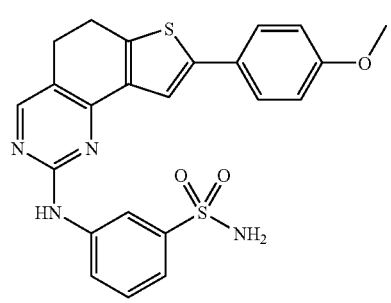
I-11
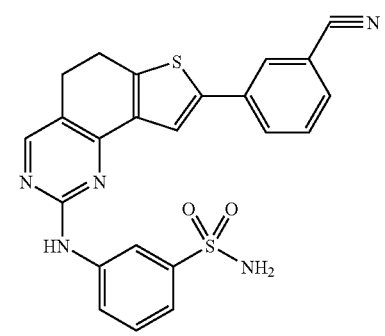
I-12
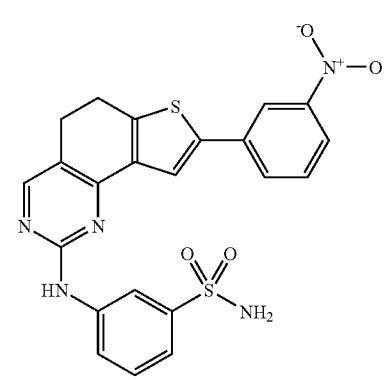
I-13
TABLE 1-continued
Examples of Compounds of Formula I:
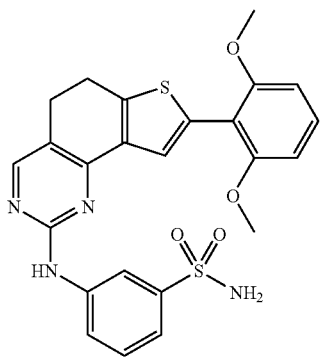
I-14
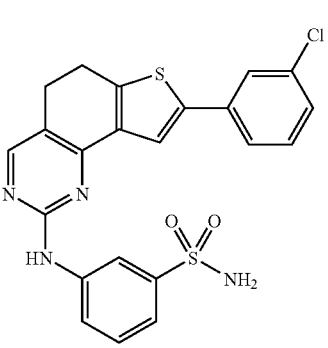
I-15
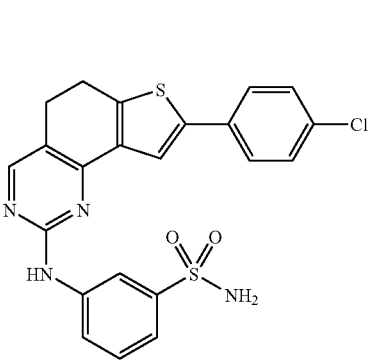
I-16
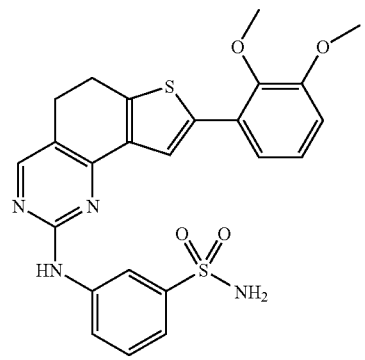
I-17

TABLE 1-continued
Examples of Compounds of Formula I:
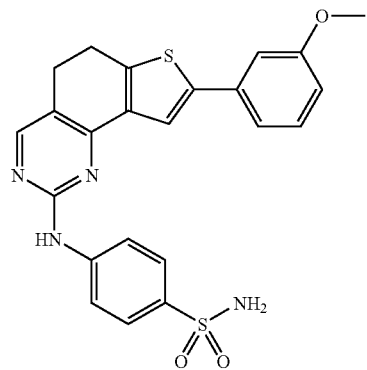
I-18
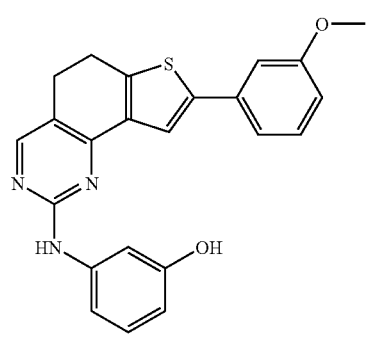
I-19
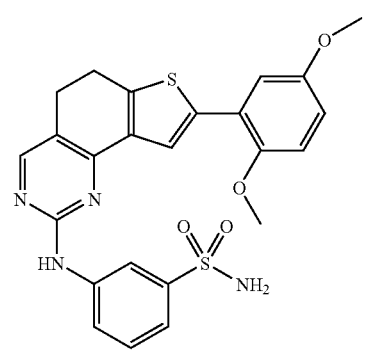
I-20
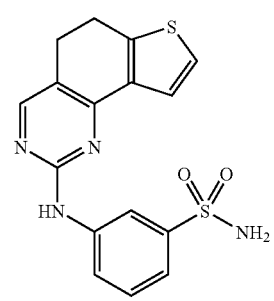
I-21
TABLE 1-continued
Examples of Compounds of Formula I:
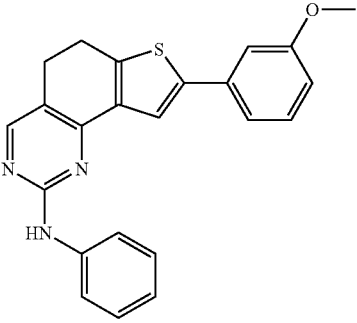
I-22
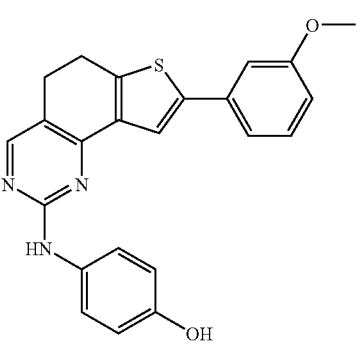
I-23
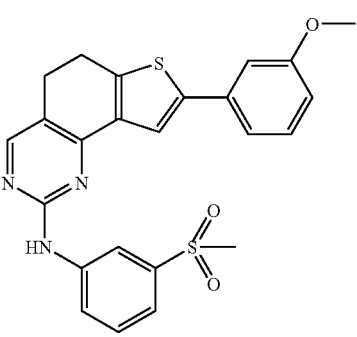
I-24
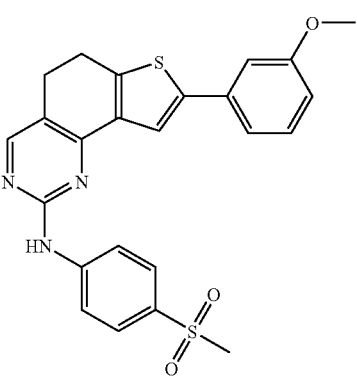
I-25

TABLE 1-continued
Examples of Compounds of Formula I:
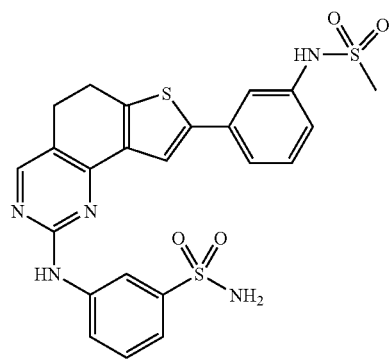 I-26
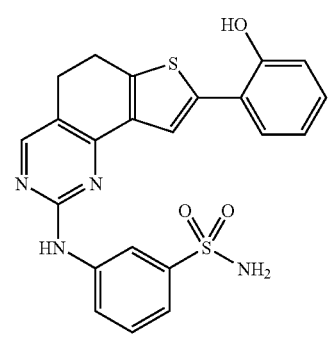 I-27
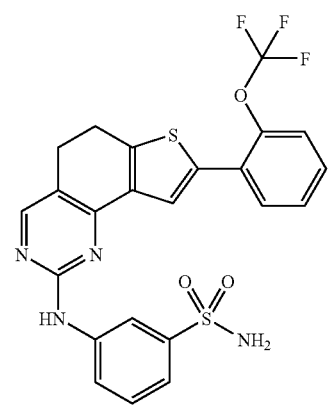 I-28
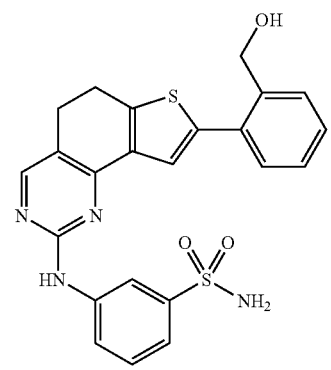 I-29
TABLE 1-continued
Examples of Compounds of Formula I:
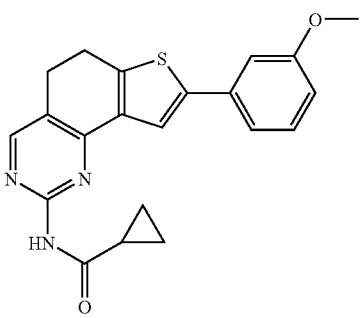 I-30
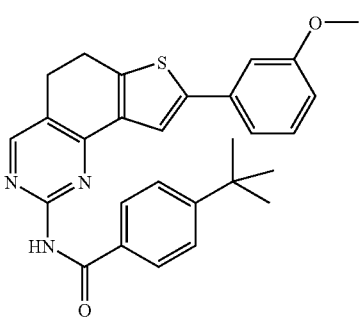 I-31
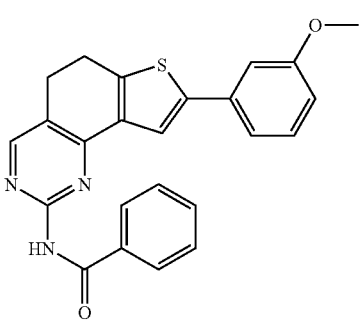 I-32
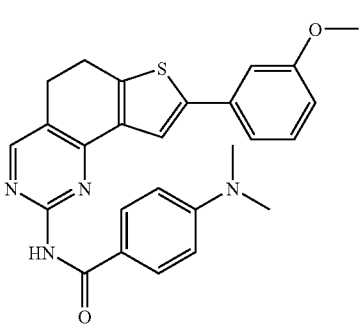 I-33
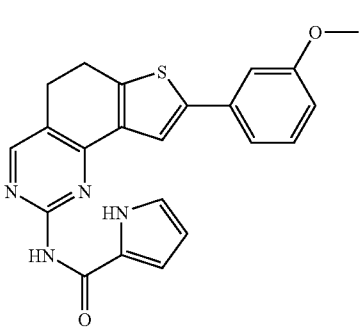 I-34

TABLE 1-continued
Examples of Compounds of Formula I:
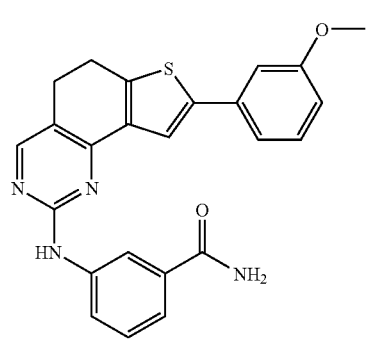 I-35
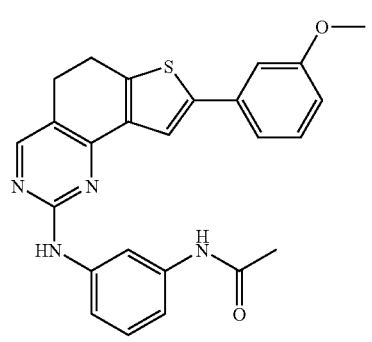 I-36
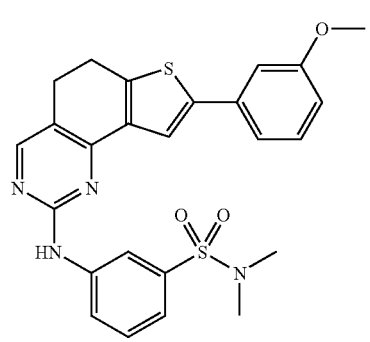 I-37
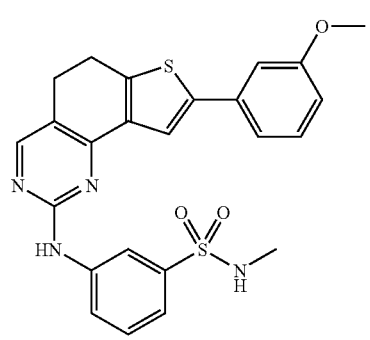 I-38
TABLE 1-continued
Examples of Compounds of Formula I:
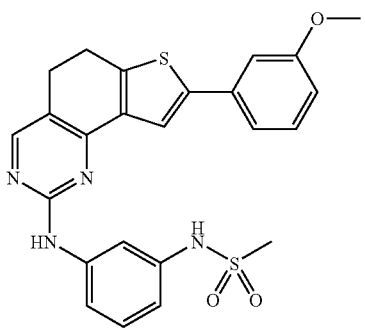 I-39
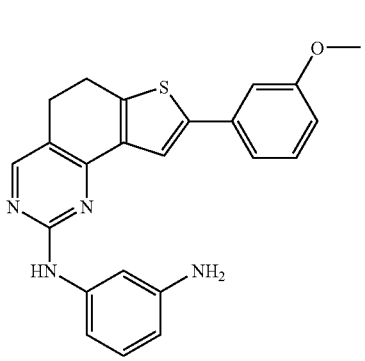 I-40
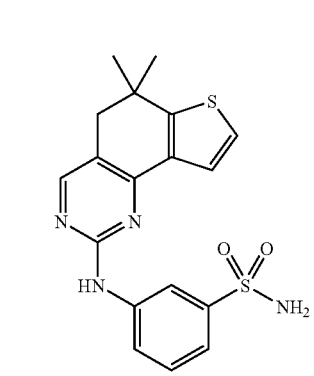 I-41
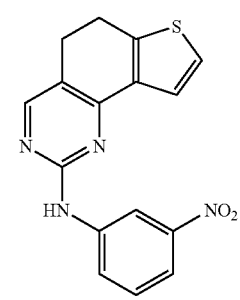 I-42

TABLE 1-continued
Examples of Compounds of Formula I:
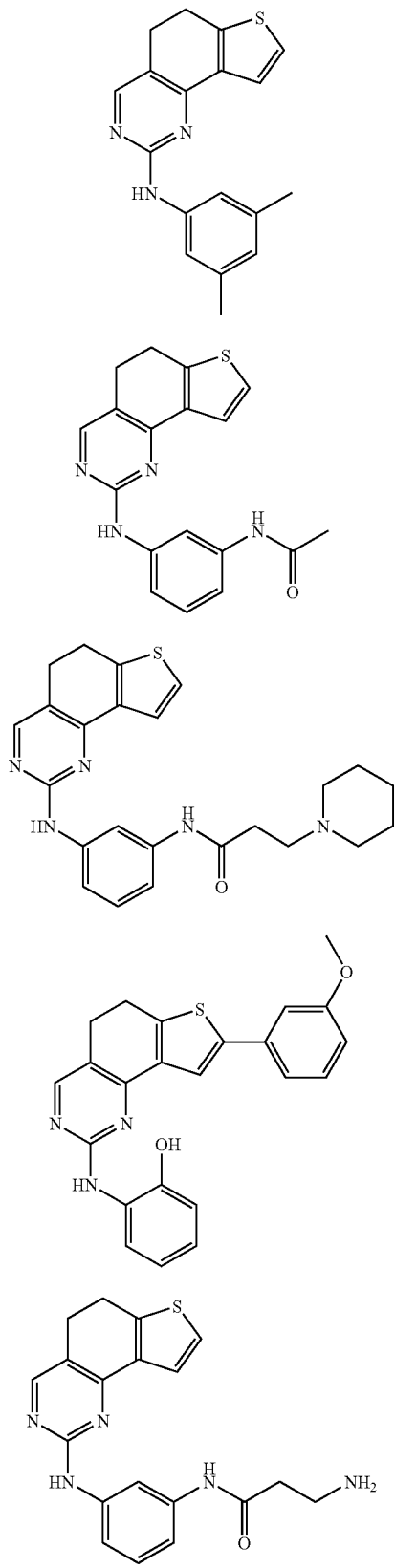
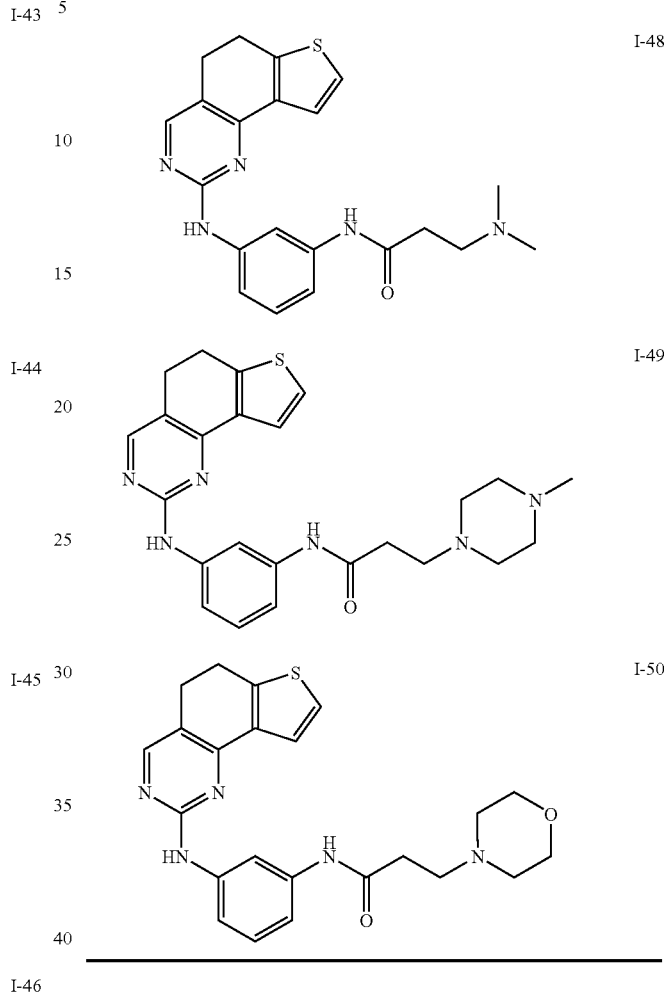
Scheme IV
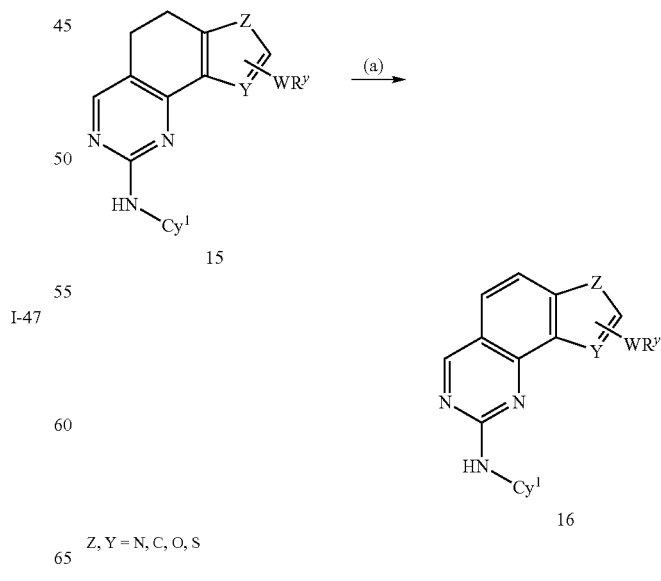
Z, Y = N, C, O, S Reagents and conditions: (a) DDQ, 1,4-dioxane, reflux, 2-3 hours.

Scheme IV above shows a general synthetic route that has been used for preparing compounds 16 of this invention when Cy¹ and WR^y are as described herein. The oxidation of 16 is achieved by treating the tricycle 15 with DDQ according to step (a) of Scheme IV.

Table 2 below depicts exemplary compounds prepared according to the general method described in Scheme IV.

TABLE 2

Examples of Compounds of Formula II:

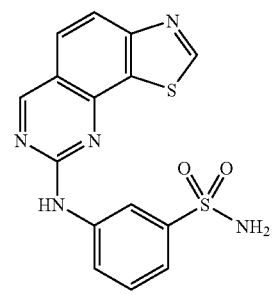
II-1

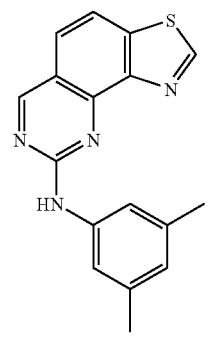
II-2

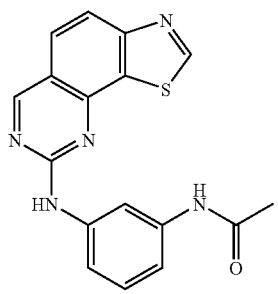
II-3

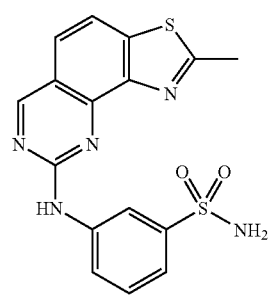
II-4

TABLE 2-continued

Examples of Compounds of Formula II:

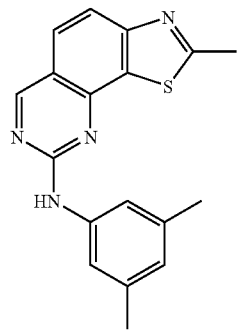
II-5

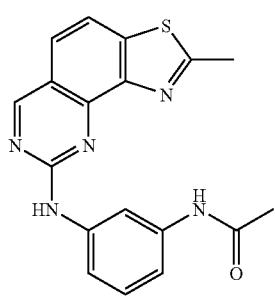
II-6

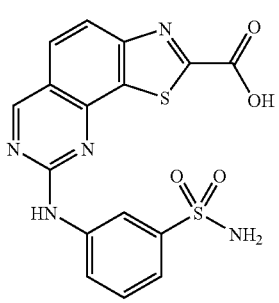
II-7

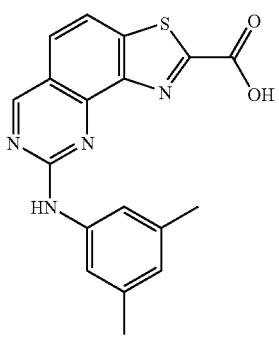
II-8

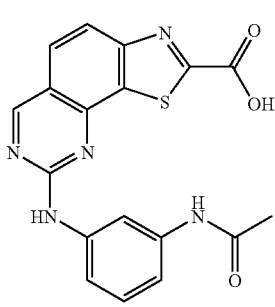
II-9

TABLE 2-continued
Examples of Compounds of Formula II:
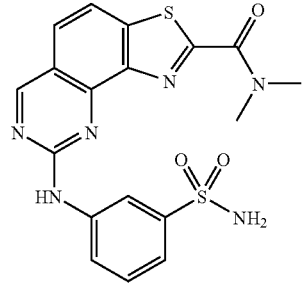
II-10
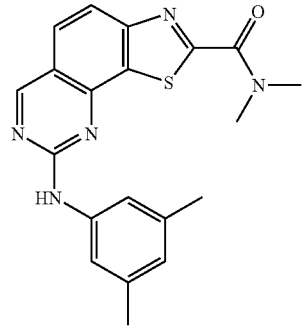
II-11
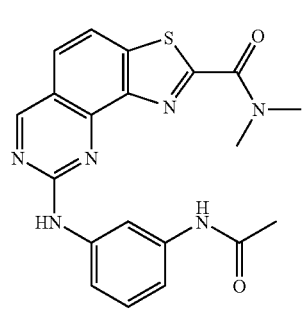
II-12
II-13
II-14
TABLE 2-continued
Examples of Compounds of Formula II:
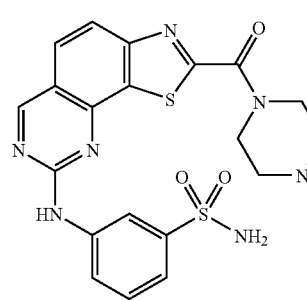
II-15
II-16
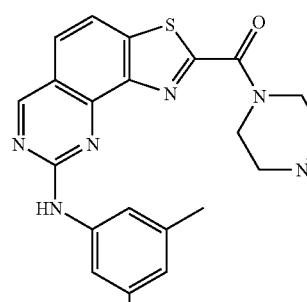
II-17

TABLE 2-continued
Examples of Compounds of Formula II:
II-18
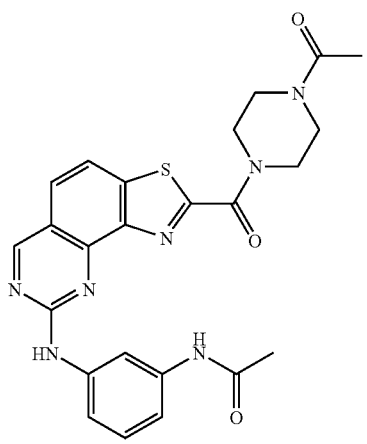
II-19
II-20
II-21
II-22
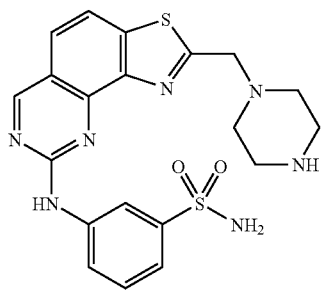
II-23
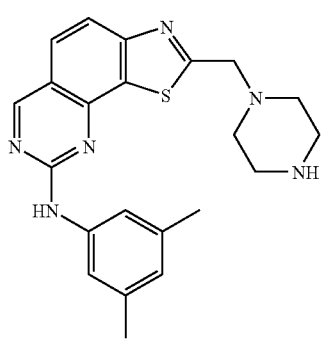
II-24
II-25
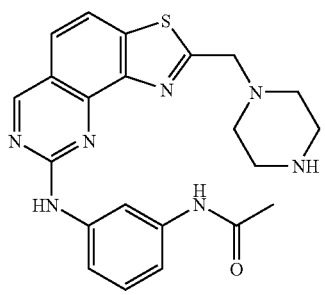
II-26
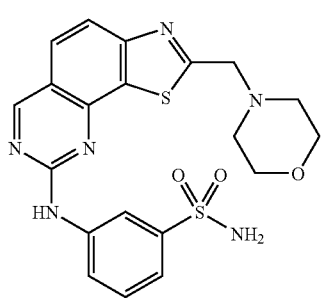
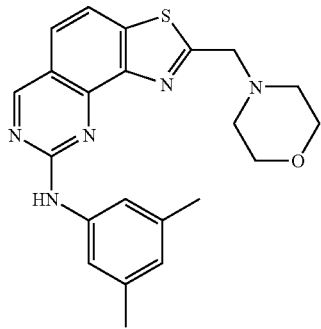

TABLE 2-continued

Examples of Compounds of Formula II:

II-27, II-28, II-29, II-30, II-31, II-32, II-33

TABLE 2-continued

Examples of Compounds of Formula II:

II-34

II-35

II-36

II-37

II-38

II-39

Scheme V

Reagents and conditions: (a) DMF/DMA reflux, 12 hours; (b) $K_2CO_3$, DMA, 120° C., 12 hours.

Scheme V above shows a general synthetic route that is used for preparing the compounds 22 of this invention when $Cy^1$ and $WR^y$ is as described herein. The 2-substituted-5,6-dihydro-4H-benzothiazol-7-ones 20 may be prepared by methods described in the literature by Lehmann, et al, *Z. Chem* 1967, 7, 422. Intermediate 21 is prepared according to Scheme V step (a). Compound 21 is treated with N-substituted guanidine 4 according to step (b). This reaction is amenable to a variety of N-substituted guanidines to form compounds of formula 22.

Table 3 below depicts exemplary compounds prepared according to the general method described in Scheme V.

TABLE 3
Examples of Compounds of Formula III:
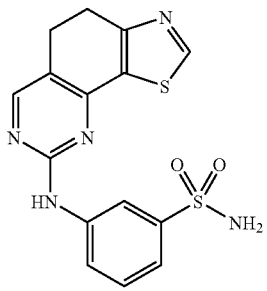
III-1
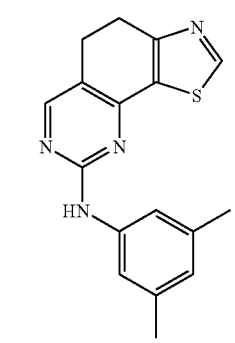
III-2
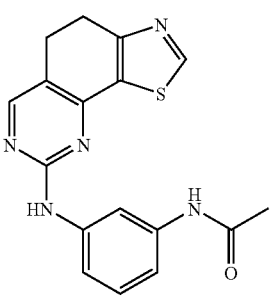
III-3
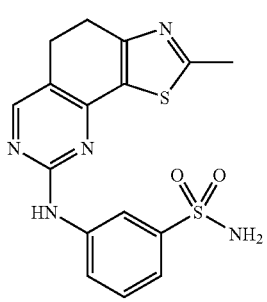
III-4
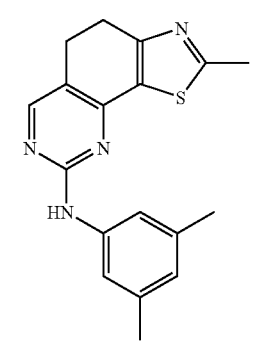
III-5
TABLE 3-continued
Examples of Compounds of Formula III:
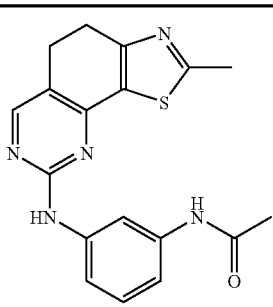
III-6
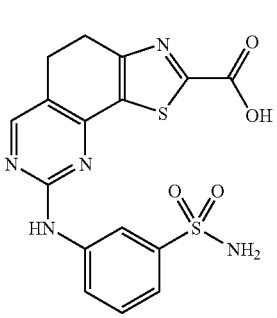
III-7
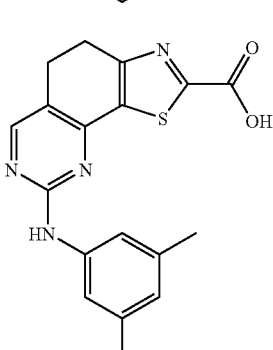
III-8
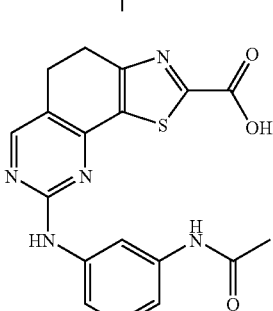
III-9
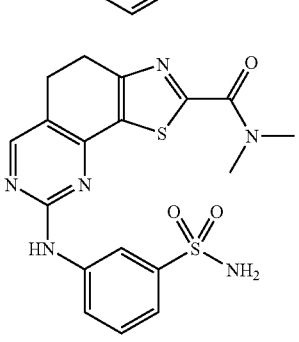
III-10

TABLE 3-continued

Examples of Compounds of Formula III:

III-11

III-12

III-13

III-14

III-15

III-16

III-17

III-18

TABLE 3-continued

Examples of Compounds of Formula III:

TABLE 3-continued

Examples of Compounds of Formula III:

III-28, III-29, III-30, III-31, III-32, III-33, III-34, III-35

TABLE 3-continued

Examples of Compounds of Formula III:

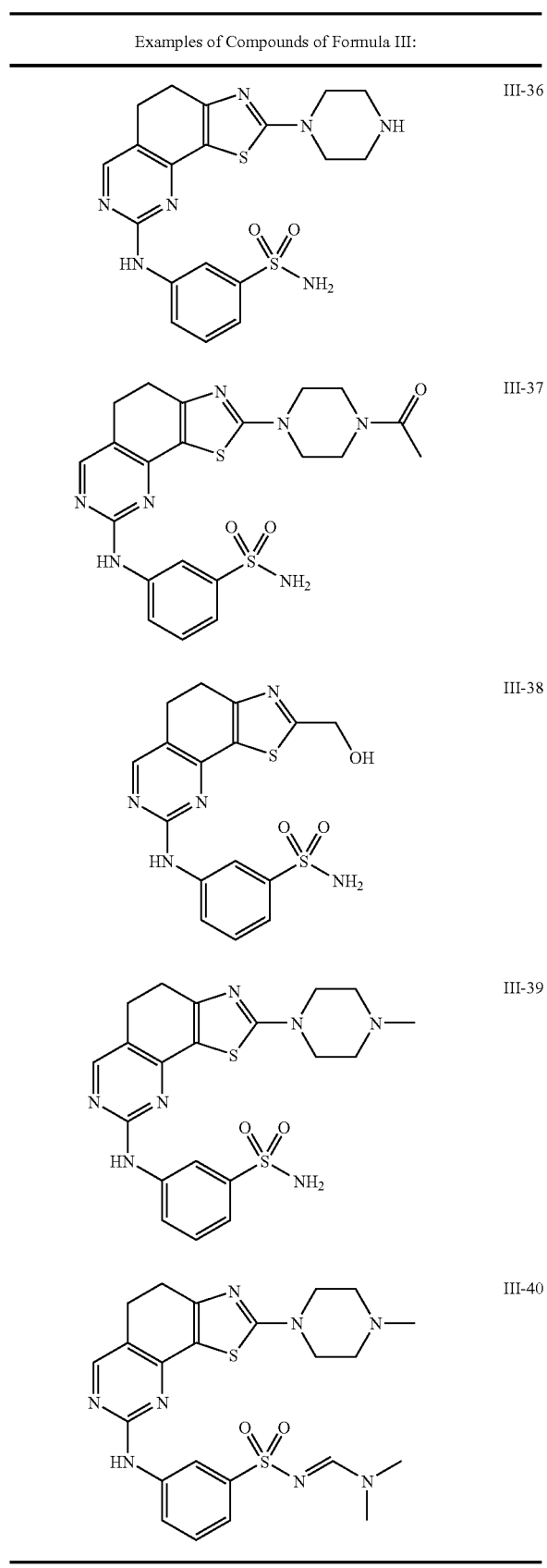

III-36

III-37

III-38

III-39

III-40

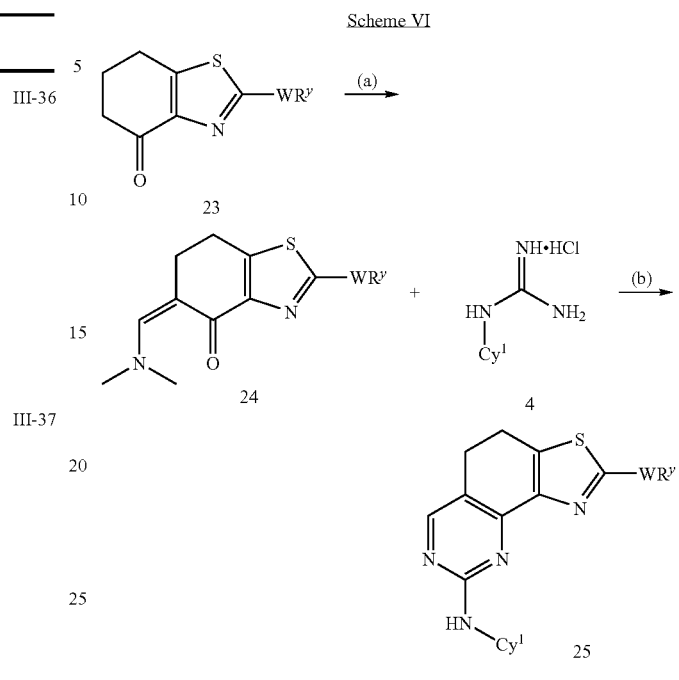

Reagents and conditions: (a) DMF/DMA reflux, 12 hours; (b) $K_2CO_3$, DMA, 120° C., 12 hours.

Scheme VI above shows a general synthetic route that is used for preparing the compounds 25 of this invention when $Cy^1$ and $WR^y$ are as described herein. Compounds of formula 23 may be prepared by methods substantially similar to those described in the literature by Maillard, et al. *Eur. J. Med. Chem. Chim. Ther.* 1984, 19, 451. Intermediate 24 is prepared according to Scheme VI step (a). Compound 24 is treated with N-substituted guanidine 4 according to step (b). This reaction is amenable to a variety of N-substituted guanidines to form compounds of formula 25.

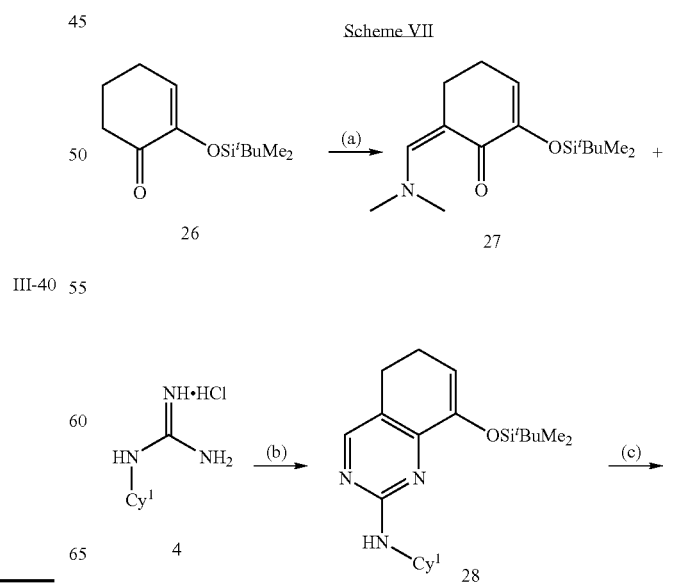

-continued

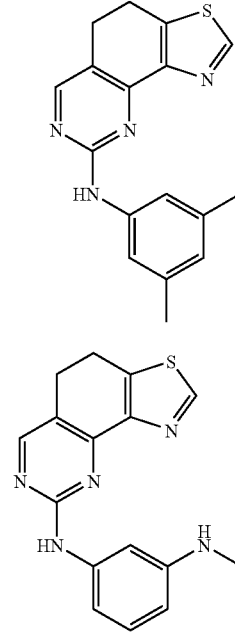

Reagents and conditions: (a) DMF/DMA reflux, 12 hours; (b) K$_2$CO$_3$, DMA, 120° C., 12 hours; (c) KF, TBAFcat, THF; (d) Br$_2$, CHCl$_3$; (e) pyridine 50° C., 3 hours.

Scheme VII above shows another general synthetic route that is used for preparing the compounds 25 of this invention when Cy$^1$ and WR$^y$ are as described herein. The 2-(tert-butyldimethylsilanyloxy)-cyclohex-2-enone 26 is well known in the literature (Crimmins, et al. *Tetrahedron* 1997, 53, 8963). Intermediate 27 is prepared according to Scheme VII step (a). Compound 27 is treated with N-substituted guanidine 4 according to step (b). This reaction is amenable to a variety of N-substituted guanidines to form compounds of formula 28. After a deprotection of 28 to afford 29, this latest is treated with bromine to form compounds of formula 30. Intermediate 30 is treated with thioamide 19 according to Scheme VII step (e). This reaction is amenable to a variety of thioamides to form compounds of structure 25.

Table 4 below depicts exemplary compounds prepared according to the general method described in Schemes VI and VII.

TABLE 4

Examples of Compounds of Formula IV:

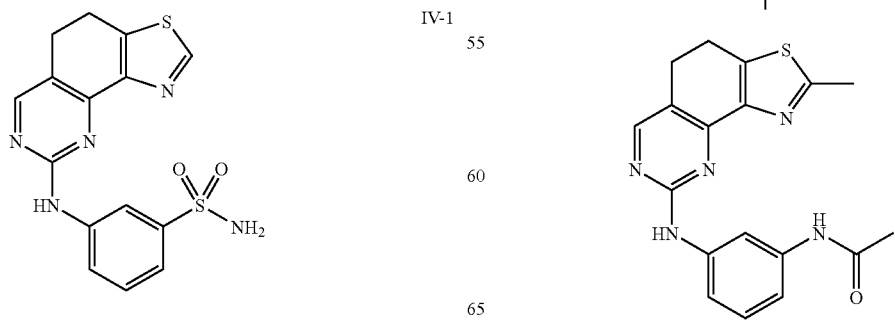
IV-1

TABLE 4-continued

Examples of Compounds of Formula IV:

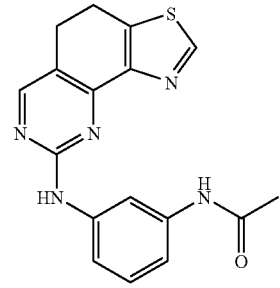
IV-2

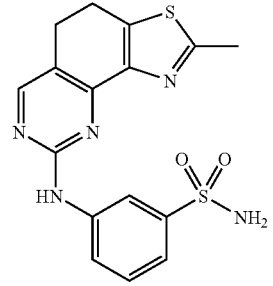
IV-3

IV-4

IV-5

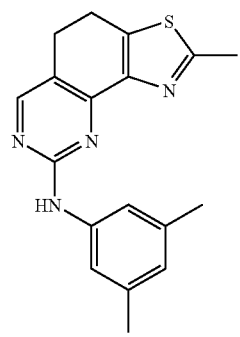

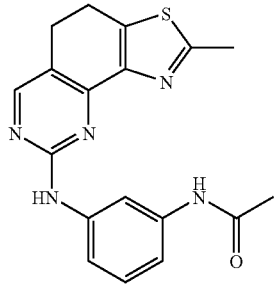
IV-6

TABLE 4-continued

Examples of Compounds of Formula IV:

IV-7, IV-8, IV-9, IV-10, IV-11, IV-12, IV-13, IV-14, IV-15

TABLE 4-continued
Examples of Compounds of Formula IV:
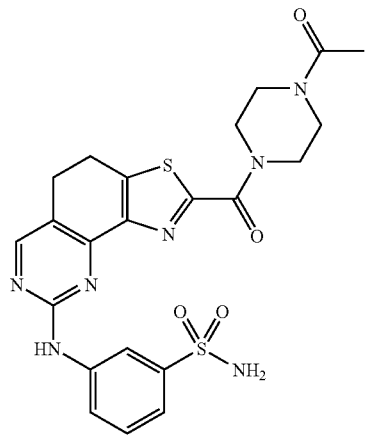
IV-16
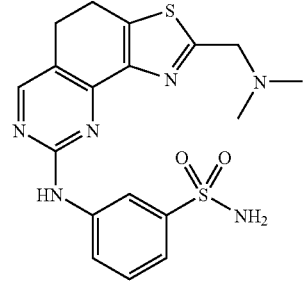
IV-19
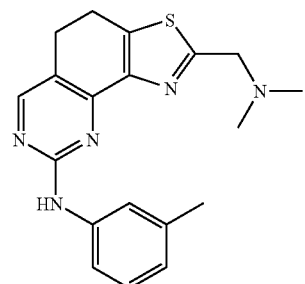
IV-20
IV-17
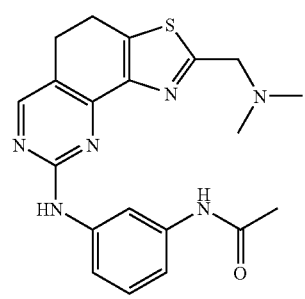
IV-21
IV-18
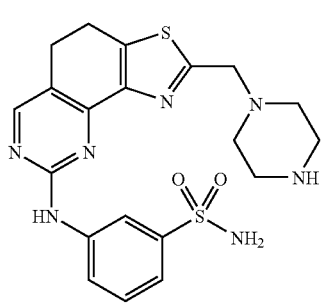
IV-22
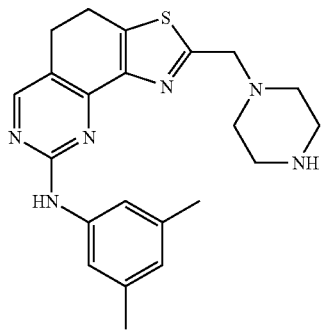
IV-23

TABLE 4-continued
Examples of Compounds of Formula IV:
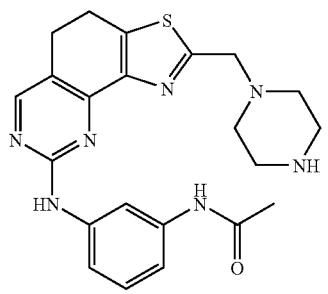
IV-24
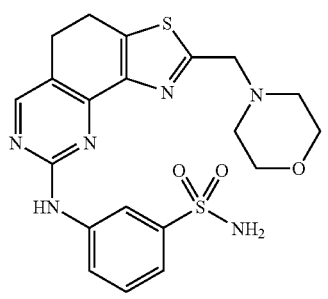
IV-25
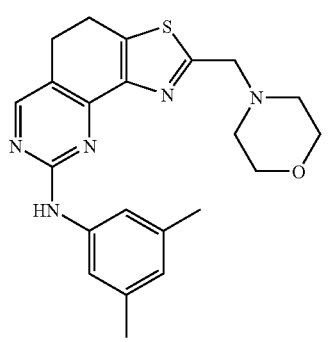
IV-26
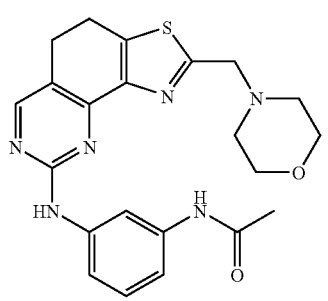
IV-27
TABLE 4-continued
Examples of Compounds of Formula IV:
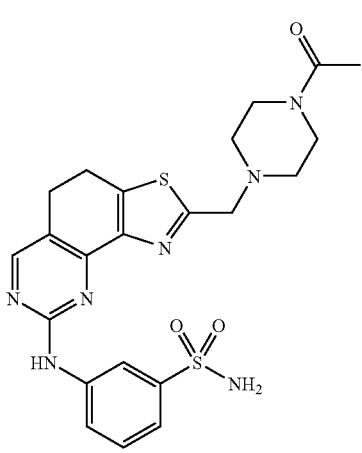
IV-28
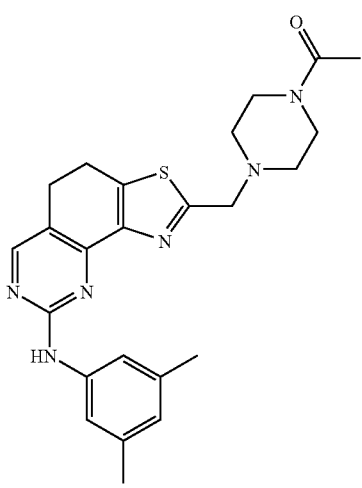
IV-29
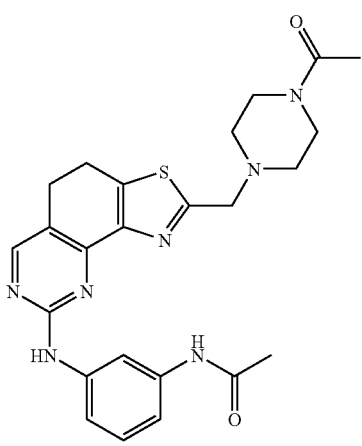
IV-30

TABLE 4-continued

Examples of Compounds of Formula IV:

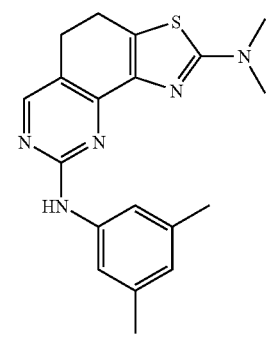
IV-31

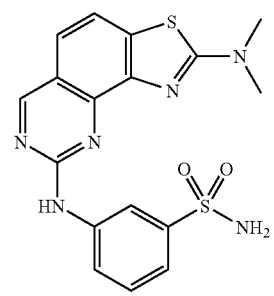
IV-32

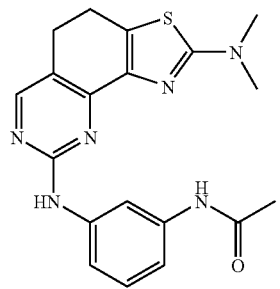
IV-33

Scheme VIII

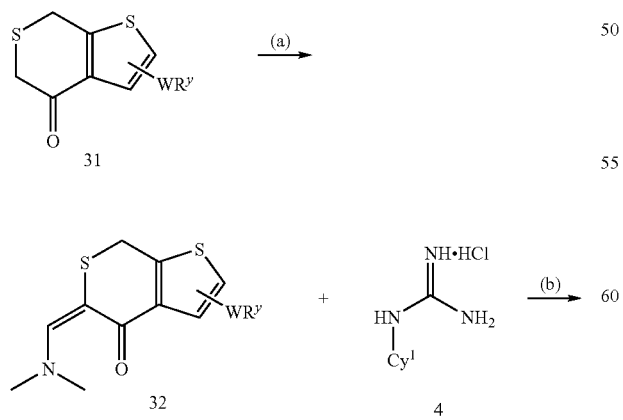

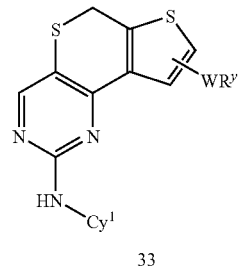
33

Reagents and conditions: (a) Bredereck's reagent, DME, 60° C., 2 hours; (b) IPA, NaOH, reflux, 12 hours.

Scheme VIII above shows a general synthetic route that is used for preparing compounds 33 of this invention when $Cy^1$ is as described herein. The 7H-thieno[2,3-c]thiopyran-4-one 31 ($WR^y$=H) may be prepared by methods described by Mandal, et al, *J. Chem. Soc., Perkin Trans.* 1 1999, 2639. Intermediate 32 is synthesized according the scheme VIII step (a). Compound 32 is treated with N-substituted guanidine 4 according to step (b). This reaction is amenable to a variety of N-substituted guanidines to form compounds of formula 33.

Scheme IX

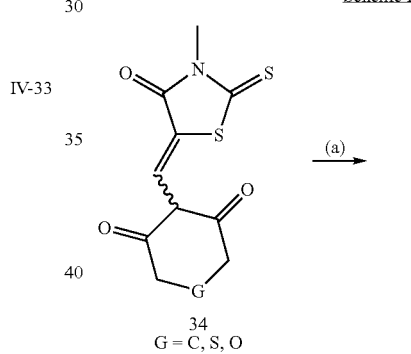
34
G = C, S, O

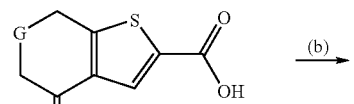
35

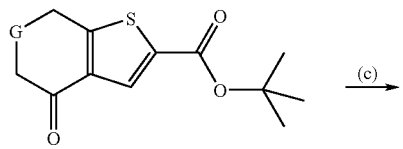
36

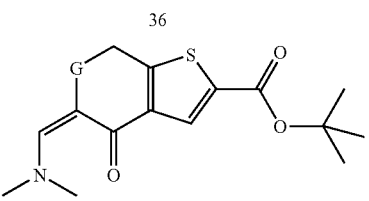
37

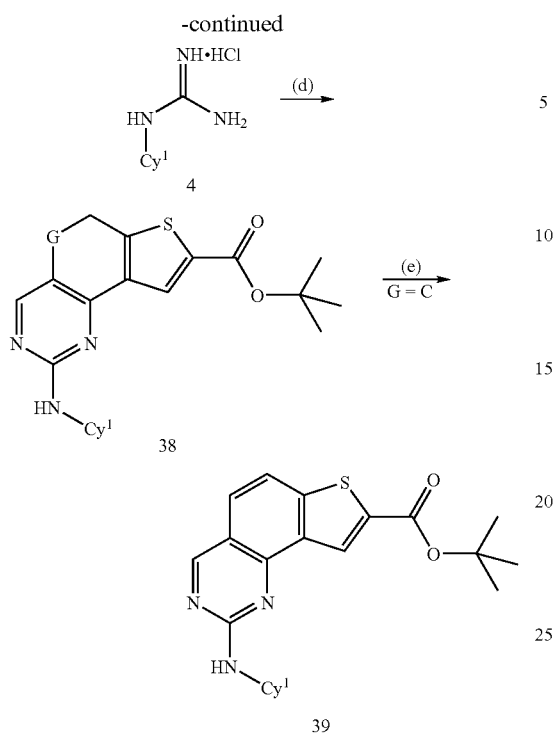

Reagents and conditions: (a) NaOH, Δ, then HCl; (b) 'Bu-trichloroacetimidate, cyclohexane, DCM, F$_3$B:(Et)$_2$O; (c) DMF/DMA, reflux, 12 hours; (d) IPA, NaOH, reflux 12 hours; (e) DDQ, 1,4-dioxane, reflux, 2-3 hours.

Scheme IX above shows a general synthetic approach that is used for preparing compounds 38 and 39 of this invention. The formation of compounds of structure 34 was achieved by methods substantially similar to those described by Lo, et al, *J. Am. Chem. Soc.* 1954, 76, 4166 and by Behringer, et al, *Chem. Ber.* 1966, 3309. Intermediate 35 is prepared according to Scheme IX step (a). The tert-butyl ester 36, prepared by methods well known in the art was treated with N,N-dimethylformamide dimethylacetal complex to form intermediate 37. Compound 37 is treated with N-substituted guanidine 4 according to step (d). This reaction is amenable to a variety of N-substituted guanidines to form compounds of formula 38 of Scheme IX. The aromatization of compound 38 where G is a carbon is achieved in presence of DDQ.

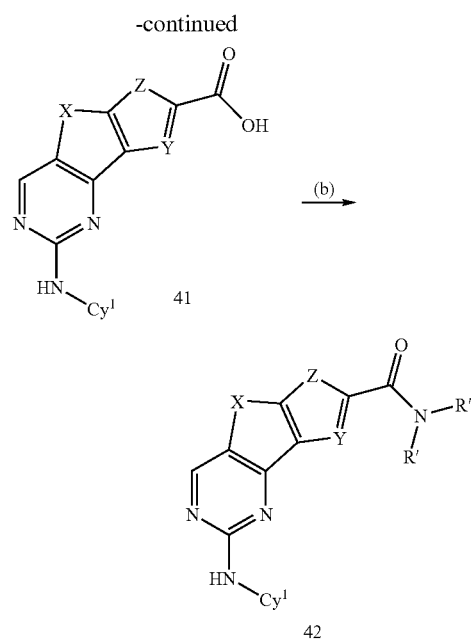

Z, Y = N, C, O, S
R = Et, 'Bu

Reagents and conditions: (a) 1N NaOH, EtOH or TFA, DCM; (b) EDC, HOBt, DCM/DMF, (R')$_2$NH.

Scheme X above shows a general method for preparing compounds of formula 42 of this invention when X and when Cy$^1$ are as described herein. Each of the above steps is well known to one of skill in the art. OK

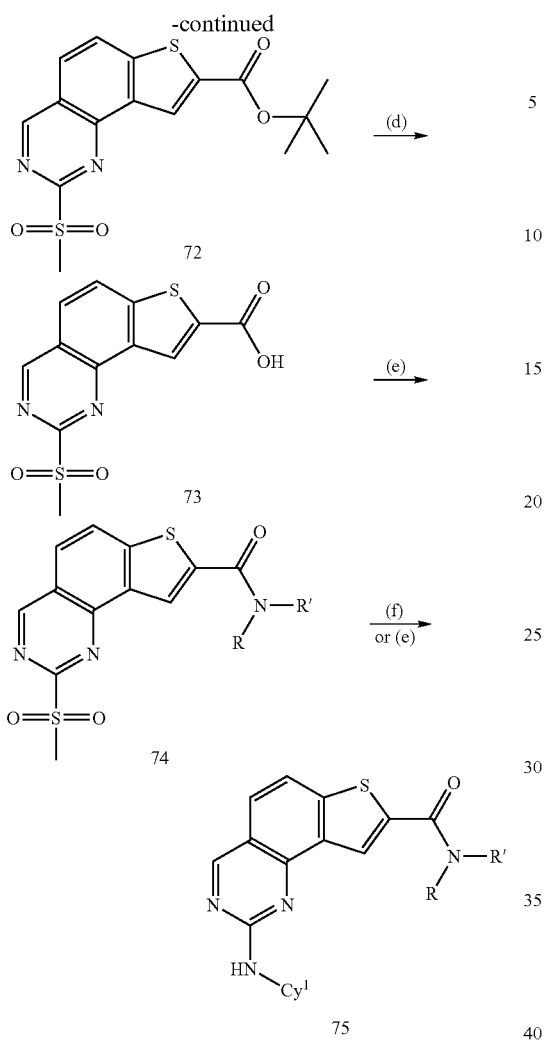

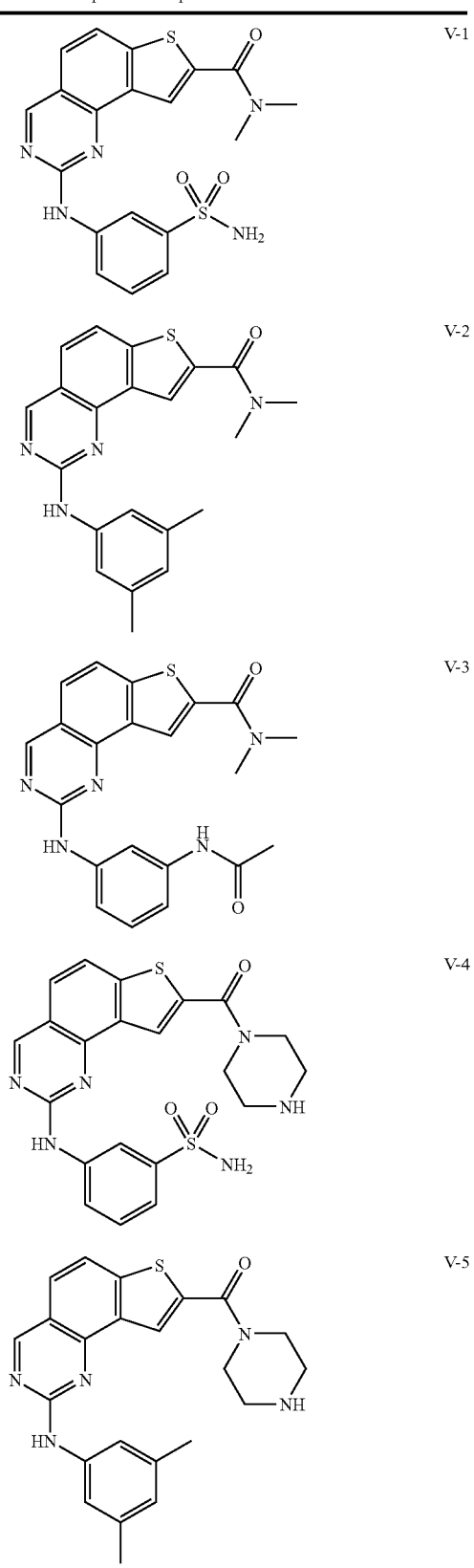

TABLE 5

Examples of Compounds of Formula V:

Reagents and conditions: (a) S-methylisothiouronium sulphate, Na$_2$CO$_3$, DMA, 120° C., 2 hours; (b) DDQ, 1,4-dioxane, reflux, 2-3 hours; (c) $^m$CPBA, DCM, 1 hour; (d) TFA, DCM; (e) EDC, HOBt, DCM/DMF, RR'NH; (f) TFA, Cy$^1$NH$_2$, 1,4-dioxane, 120° C., 16 hours; or (e) i) Cy$^1$NHCHO, THF, NaH; ii) 6N HCl, RT, 3 hours.

Scheme XI above shows a general synthetic approach that is used for preparing compounds 75 of this invention. Intermediate 70, prepared by cyclisation of compound of formula 69 in presence of S-methylisothiouronium sulphate, was aromatized with DDQ according to Scheme XI step (b). The acid 73, obtained by subsequent oxidation to the sulfone 72 and saponification, is treated with an amine RR'NH in a coupling reaction step well known to one of skill in the art. This reaction is amenable to a variety of amine RR'NH to form compounds of formula 74 of Scheme XI. The displacement of the sulfone by an amine Cy$^1$NH$_2$ is achieved according to Scheme XI step (f). This reaction is amenable to a variety of amine Cy$^1$NH$_2$ to form compounds of formula 75 of Scheme XI.

Table 5 below depicts exemplary compounds prepared according to the general method described in Schemes VIII, IX, X and XI.

TABLE 5-continued
Examples of Compounds of Formula V:
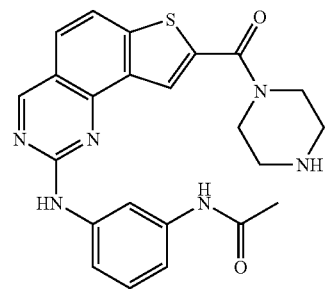
V-6
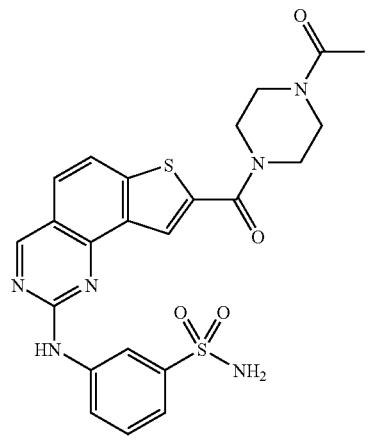
V-7
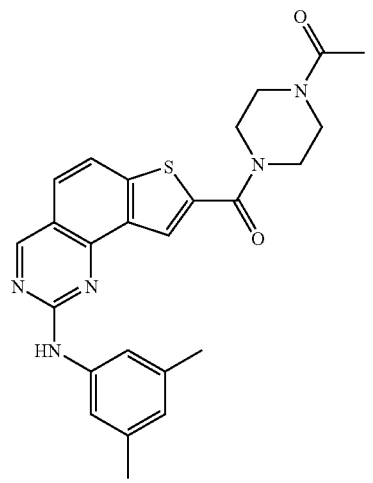
V-8
TABLE 5-continued
Examples of Compounds of Formula V:
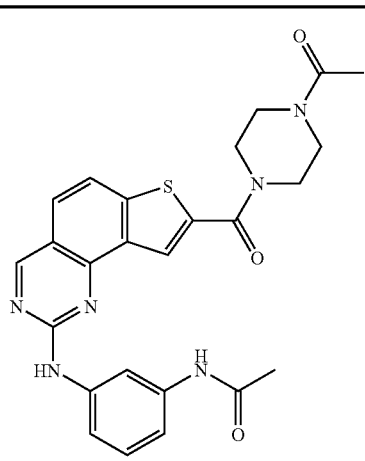
V-9
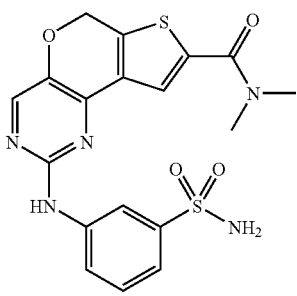
V-10
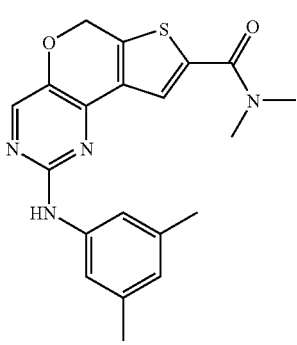
V-11
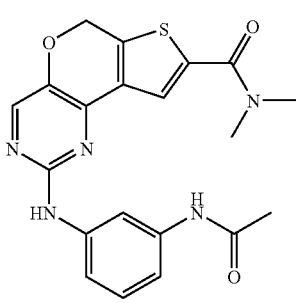
V-12

TABLE 5-continued
Examples of Compounds of Formula V:
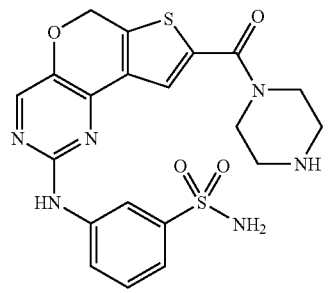
V-13
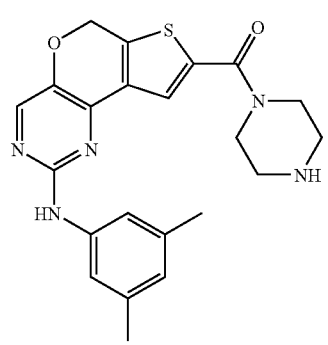
V-14
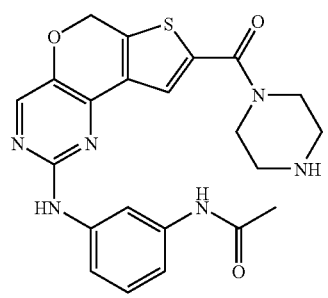
V-15
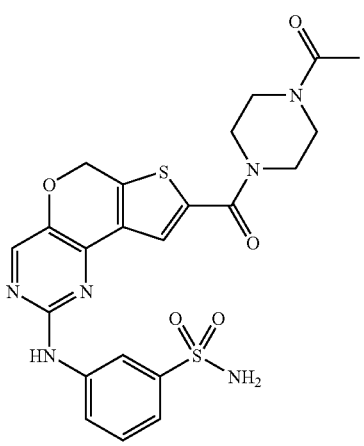
V-16
TABLE 5-continued
Examples of Compounds of Formula V:
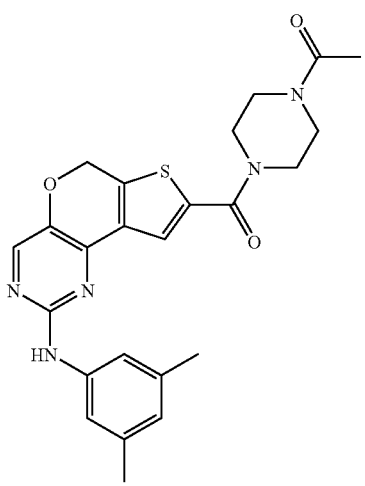
V-17
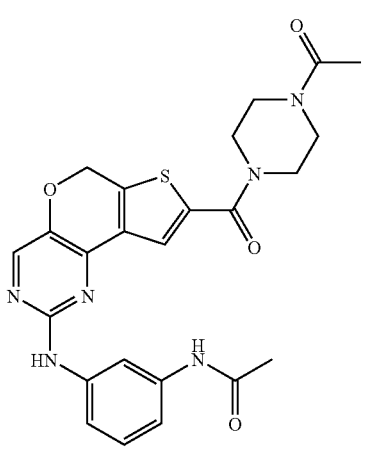
V-18
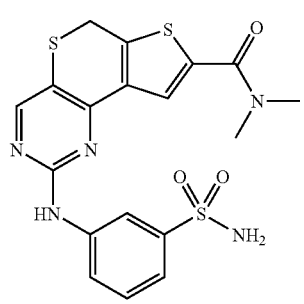
V-19
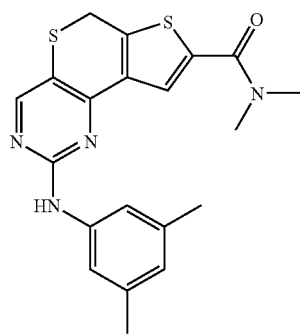
V-20

TABLE 5-continued
Examples of Compounds of Formula V:
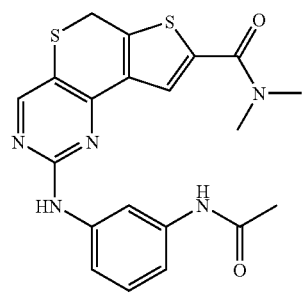
V-21
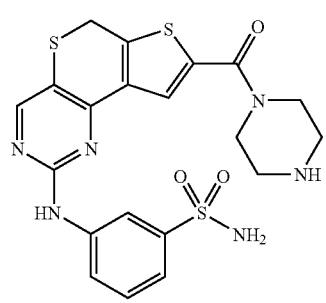
V-22
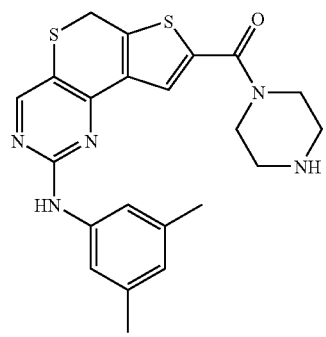
V-23
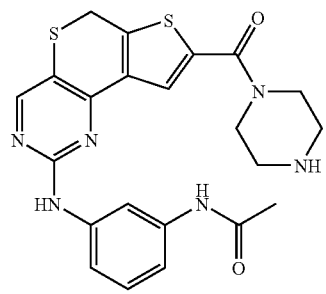
V-24
TABLE 5-continued
Examples of Compounds of Formula V:
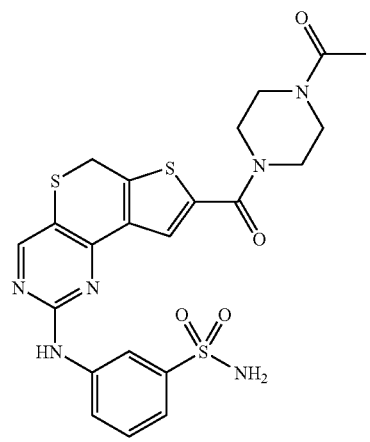
V-25
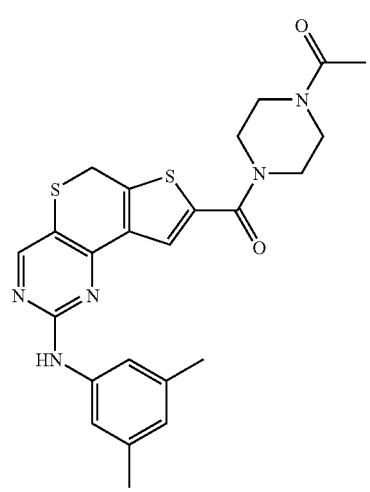
V-26
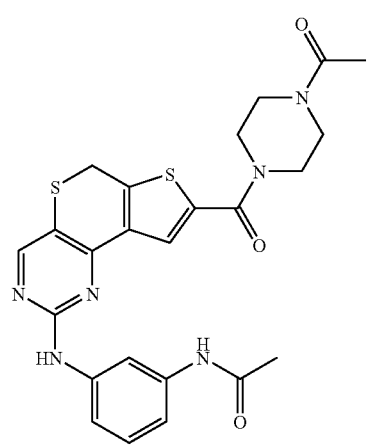
V-27

TABLE 5-continued
Examples of Compounds of Formula V:
V-28
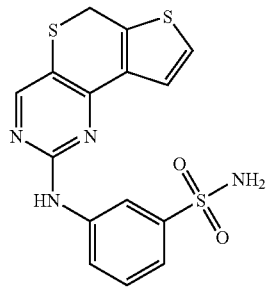
V-29
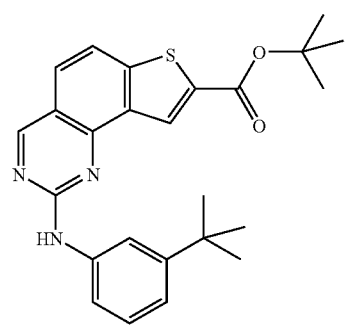
V-30
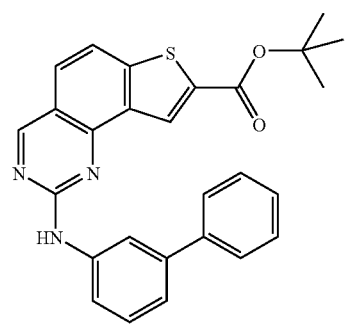
V-31
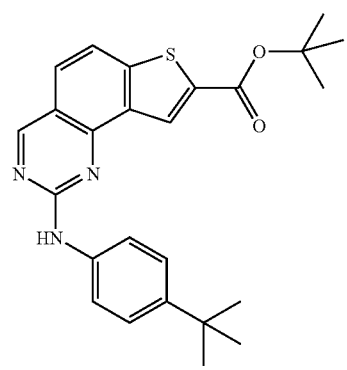
TABLE 5-continued
Examples of Compounds of Formula V:
V-32
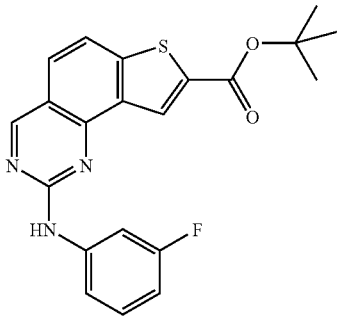
V-33
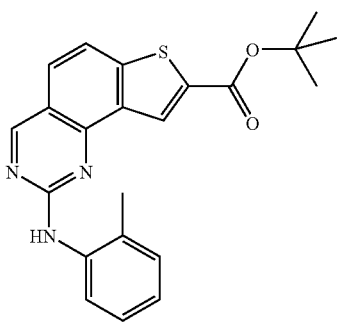
V-34
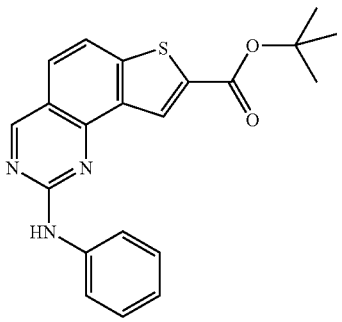
V-35
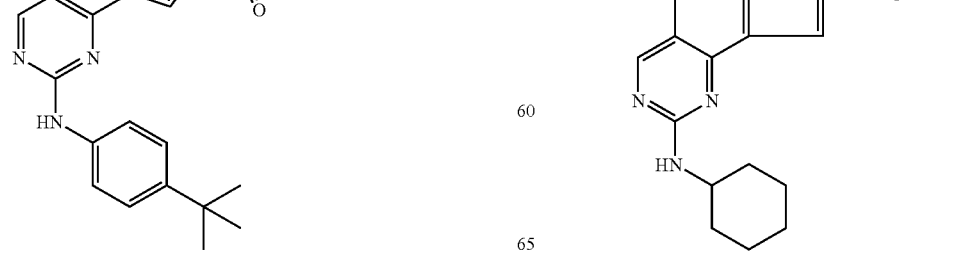

TABLE 5-continued
Examples of Compounds of Formula V:
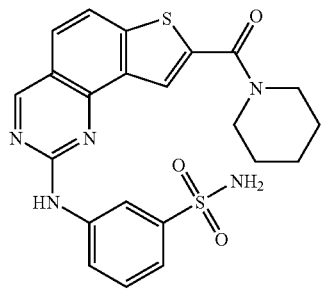 V-36
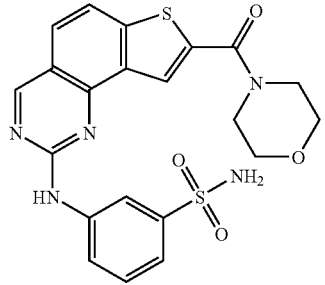 V-37
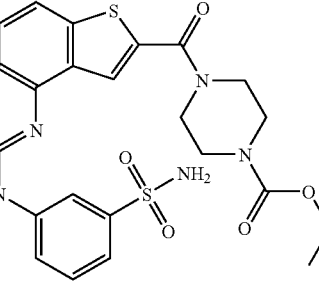 V-38
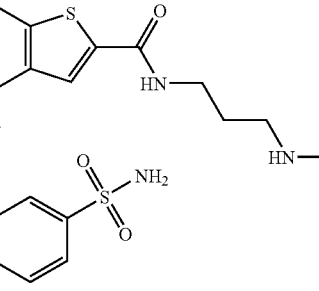 V-39
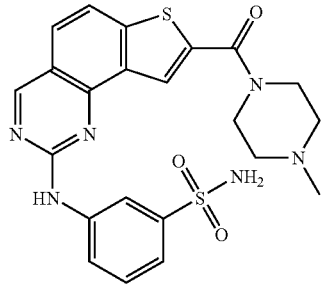 V-40
TABLE 5-continued
Examples of Compounds of Formula V:
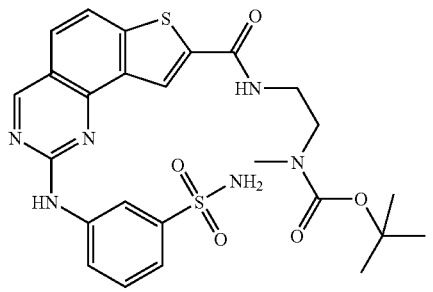 V-41
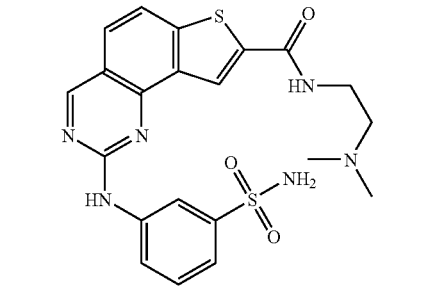 V-42
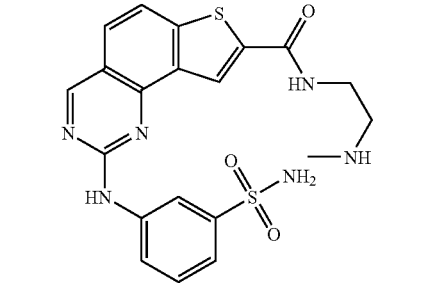 V-43
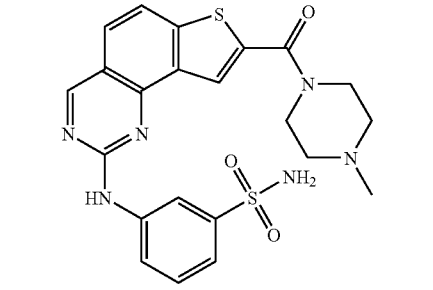 V-44
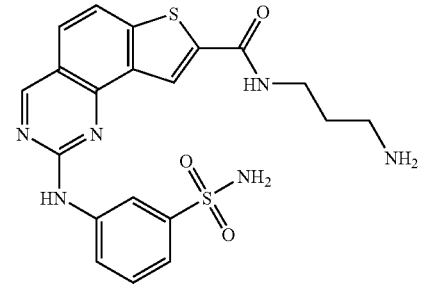 V-45

TABLE 5-continued
Examples of Compounds of Formula V:
V-46
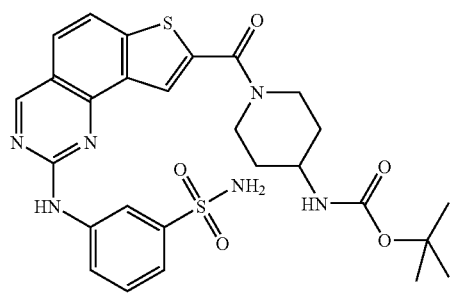
V-47
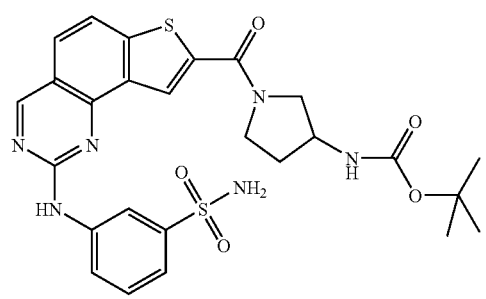
V-48
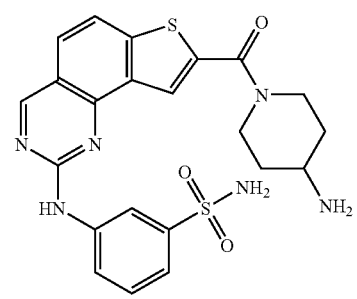
V-49
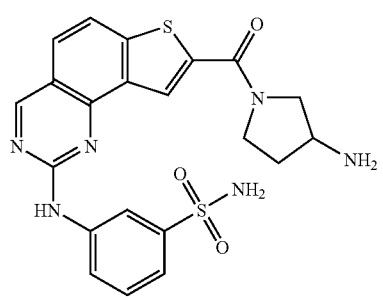
V-50
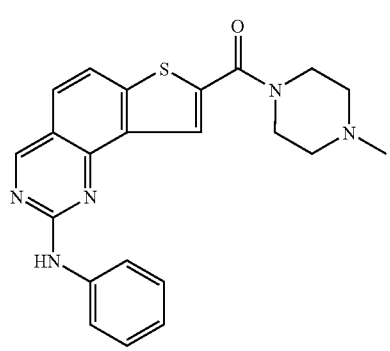
TABLE 5-continued
Examples of Compounds of Formula V:
V-51
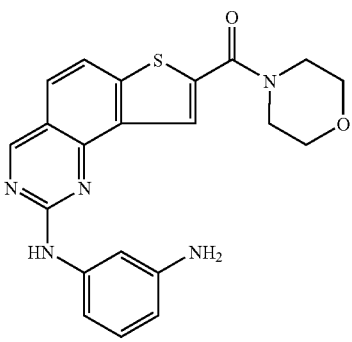
V-52
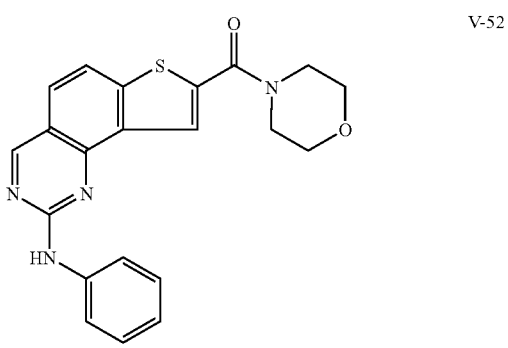
V-53
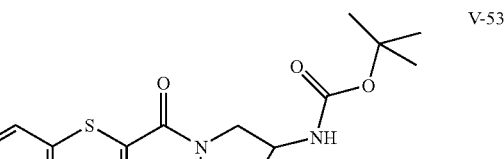
V-54
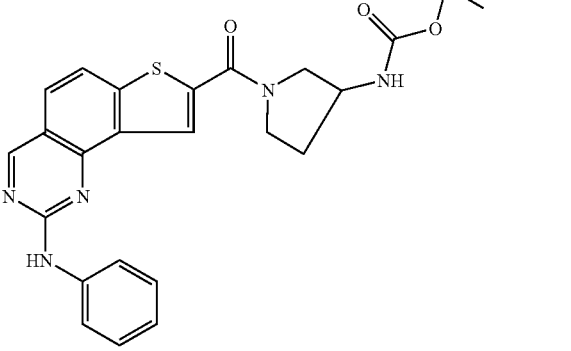

TABLE 5-continued
Examples of Compounds of Formula V:
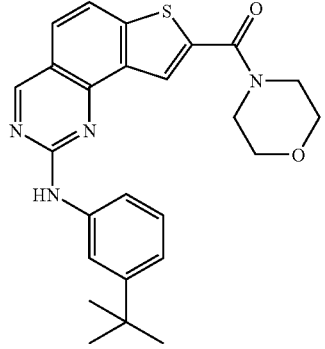 V-55
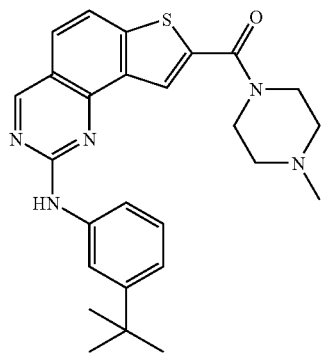 V-56
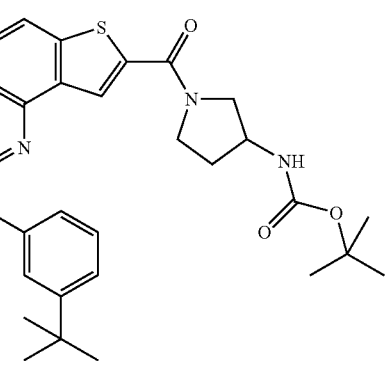 V-57
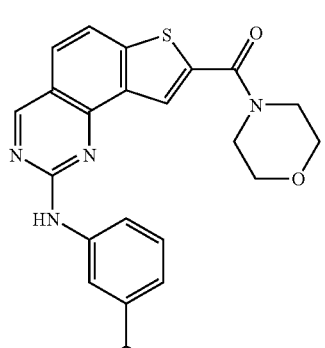 V-58
TABLE 5-continued
Examples of Compounds of Formula V:
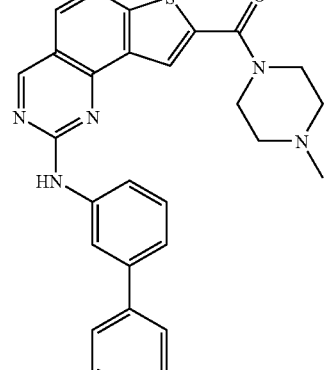 V-59
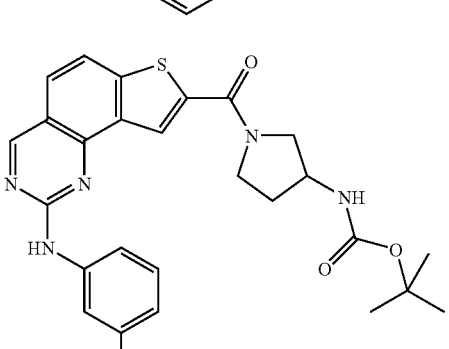 V-60
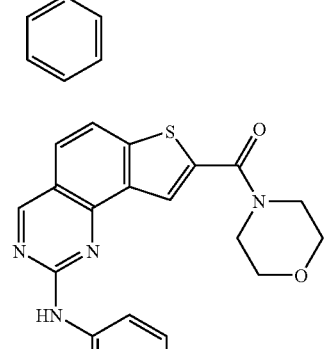 V-61
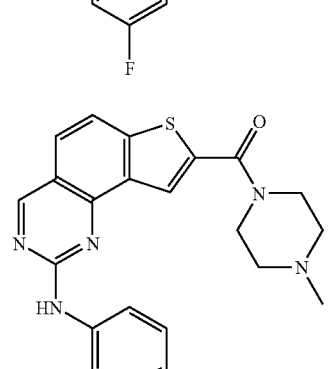 V-62

TABLE 5-continued

Examples of Compounds of Formula V:

V-63

V-64

V-65

V-66

V-67

TABLE 5-continued

Examples of Compounds of Formula V:

V-68

V-69

V-70

V-71

V-72

TABLE 5-continued
Examples of Compounds of Formula V:
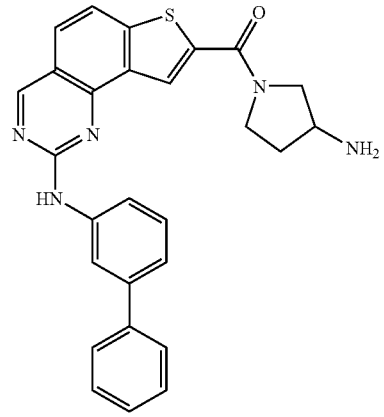
V-73
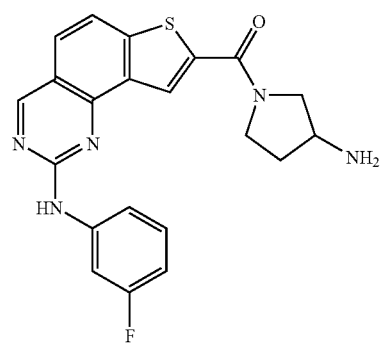
V-74
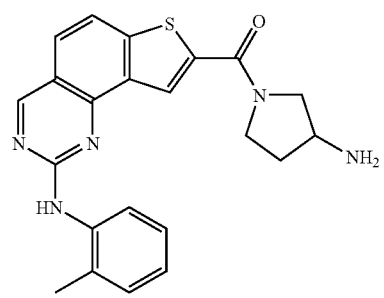
V-75
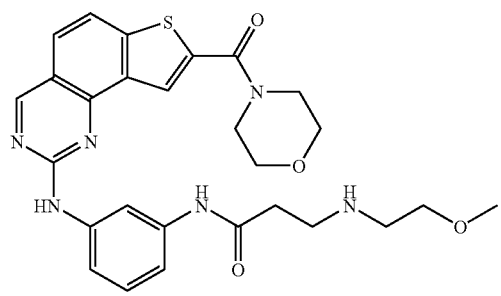
V-76
TABLE 5-continued
Examples of Compounds of Formula V:
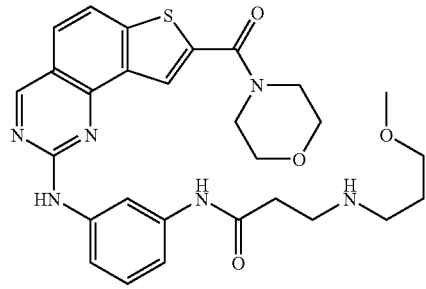
V-77
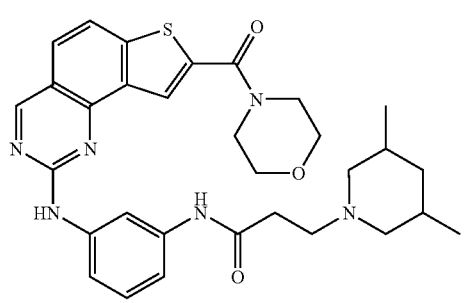
V-78
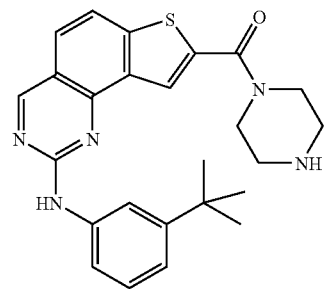
V-79
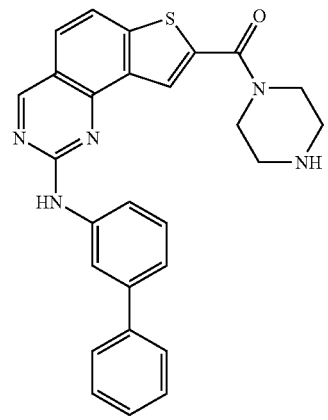
V-80

TABLE 5-continued
Examples of Compounds of Formula V:
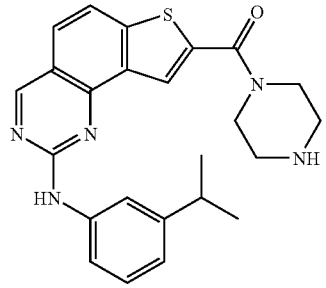
V-81
V-82
V-83
V-84
V-85
TABLE 5-continued
Examples of Compounds of Formula V:
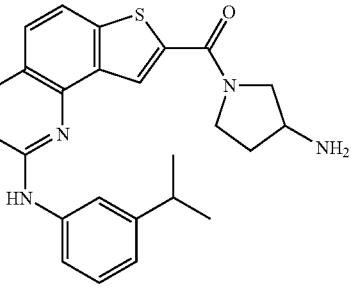
V-86
V-87
V-88
V-89
V-90

TABLE 5-continued
Examples of Compounds of Formula V:
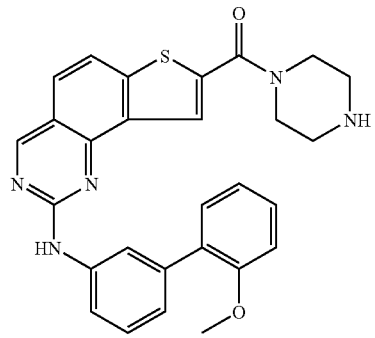
V-91
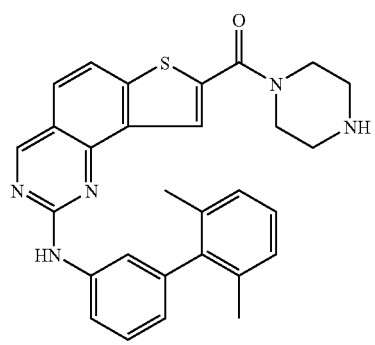
V-92
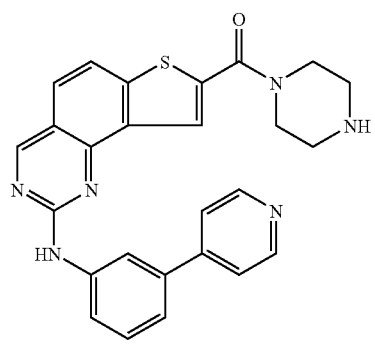
V-93
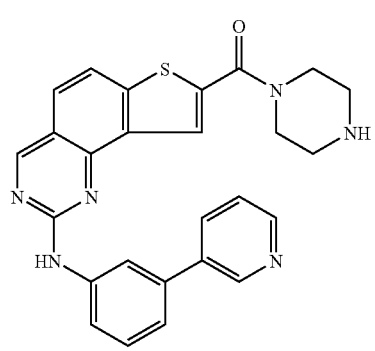
V-94
TABLE 5-continued
Examples of Compounds of Formula V:
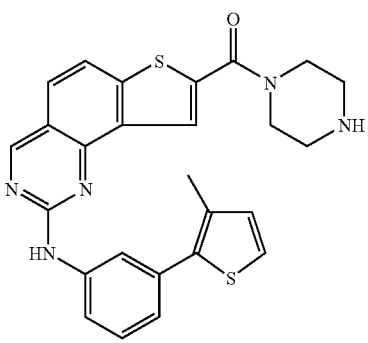
V-95
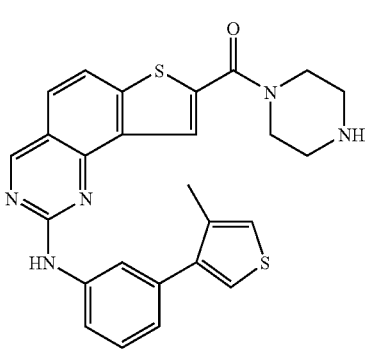
V-96
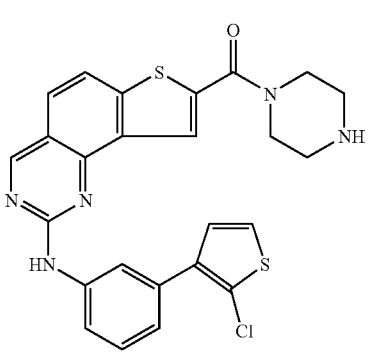
V-97
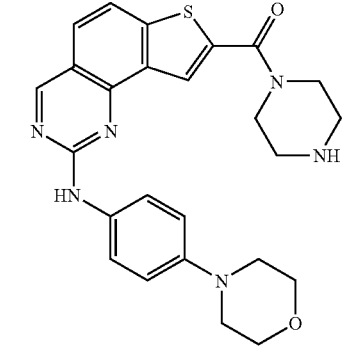
V-98

TABLE 5-continued
Examples of Compounds of Formula V:
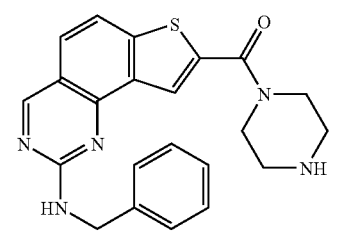
V-99
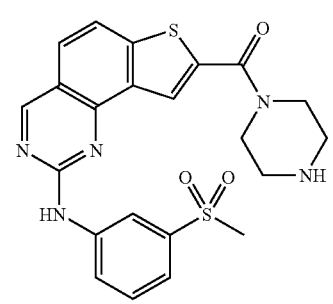
V-100
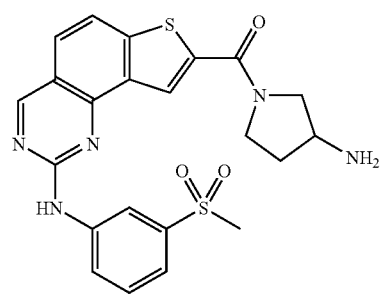
V-101
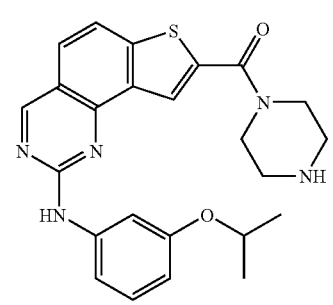
V-102
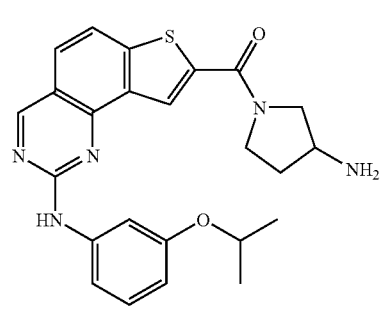
V-103
TABLE 5-continued
Examples of Compounds of Formula V:
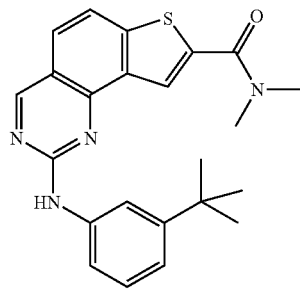
V-104
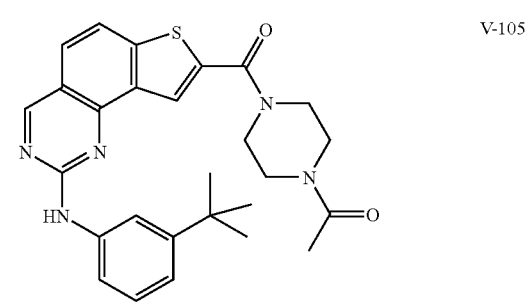
V-105
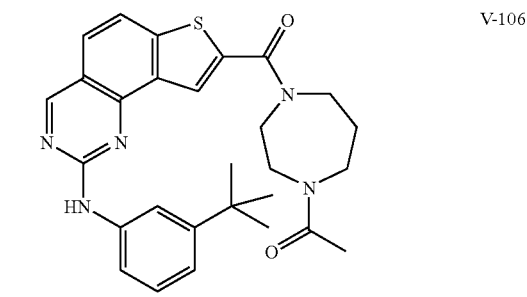
V-106
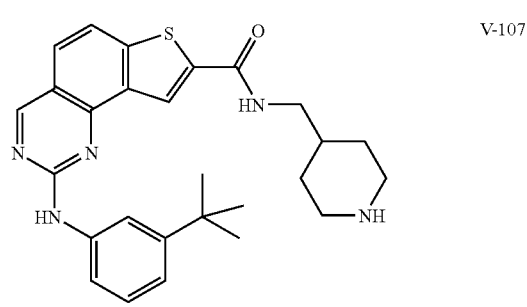
V-107
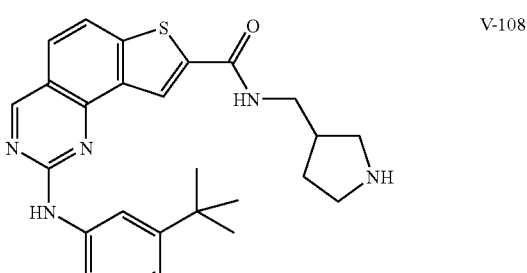
V-108

TABLE 5-continued
Examples of Compounds of Formula V:
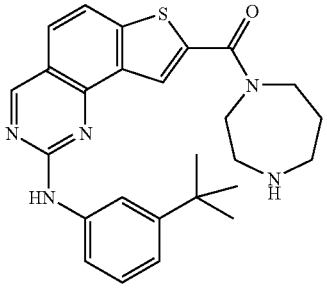
V-109
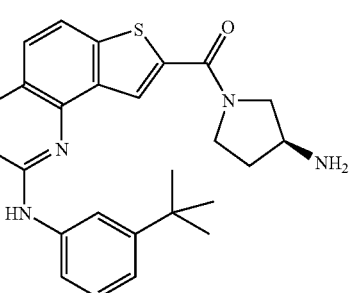
V-110
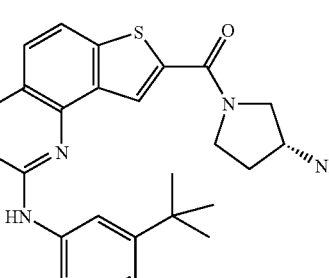
V-111
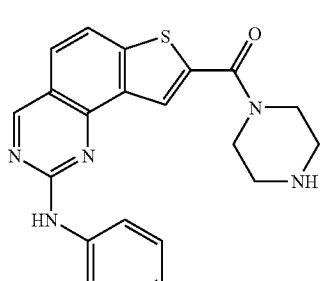
V-112
TABLE 5-continued
Examples of Compounds of Formula V:
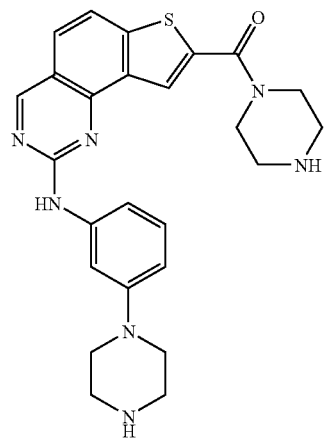
V-113
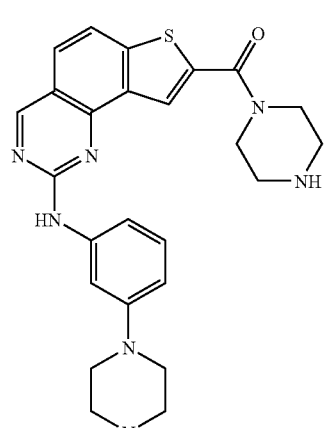
V-114
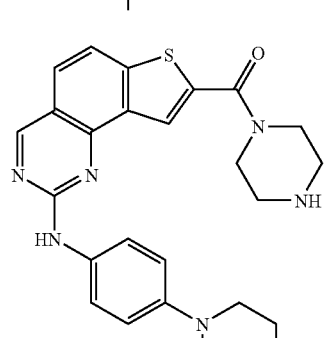
V-115
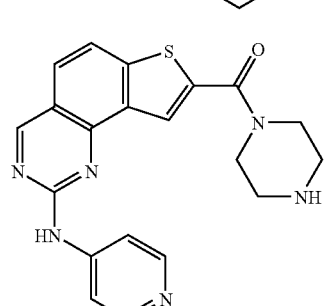
V-116

TABLE 5-continued

Examples of Compounds of Formula V:

TABLE 5-continued

Examples of Compounds of Formula V:

V-126

V-127

V-128

V-129

V-130

V-131

V-132

V-133

V-134

V-135

TABLE 5-continued

Examples of Compounds of Formula V:

V-136
V-137
V-138
V-139
V-140
V-141
V-142
V-143
V-144
V-145

TABLE 5-continued

Examples of Compounds of Formula V:

V-146
V-147
V-148
V-149
V-150
V-151
V-152
V-153
V-154
V-155

TABLE 5-continued
Examples of Compounds of Formula V:
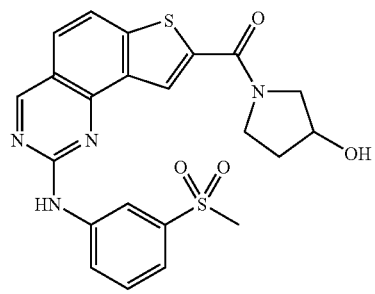 V-156
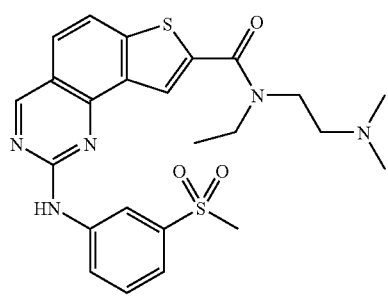 V-157
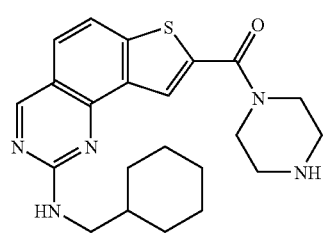 V-158
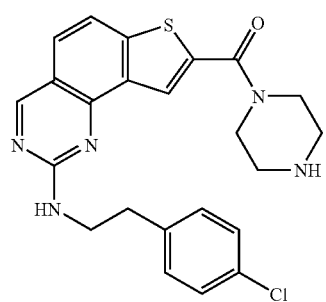 V-159
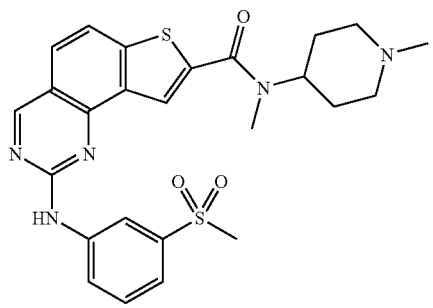 V-160
TABLE 5-continued
Examples of Compounds of Formula V:
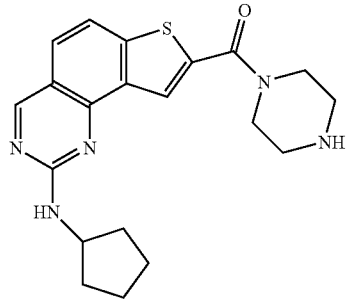 V-161
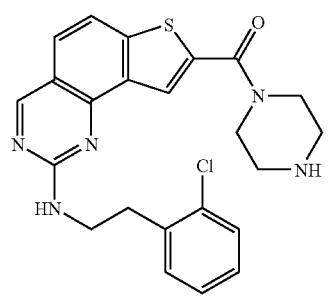 V-162
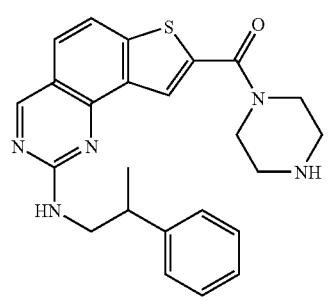 V-163
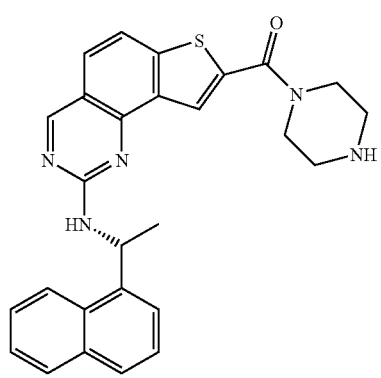 V-164
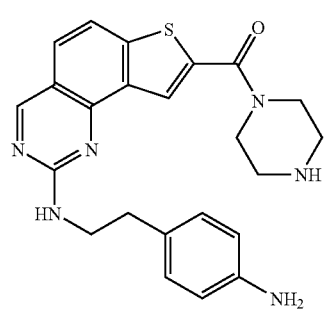 V-165

TABLE 5-continued
Examples of Compounds of Formula V:
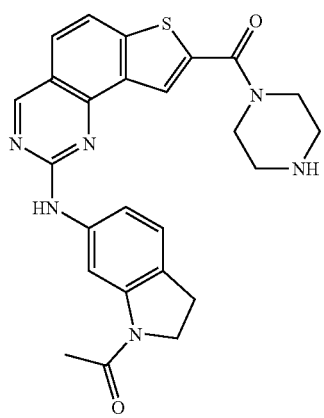
V-166
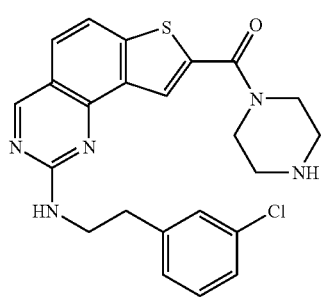
V-167
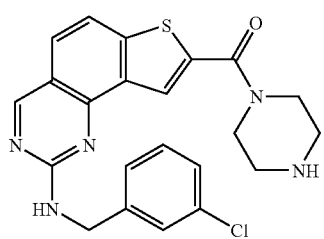
V-168
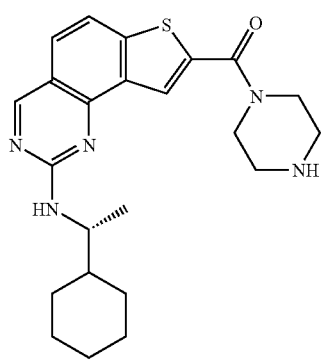
V-169
TABLE 5-continued
Examples of Compounds of Formula V:
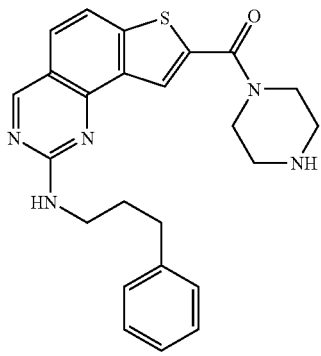
V-170
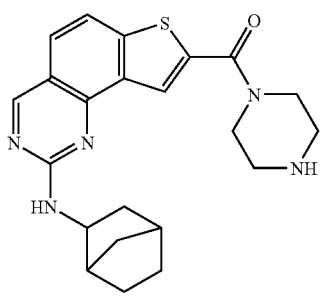
V-171
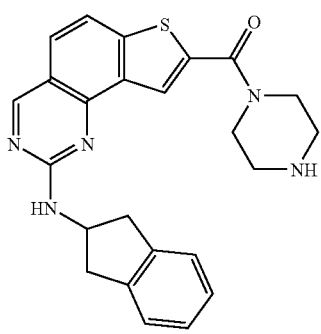
V-172
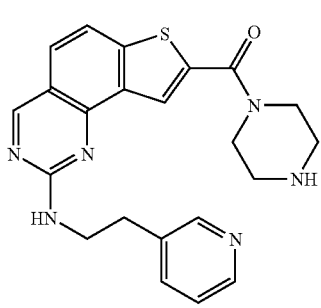
V-173

TABLE 5-continued

Examples of Compounds of Formula V:

Scheme XII

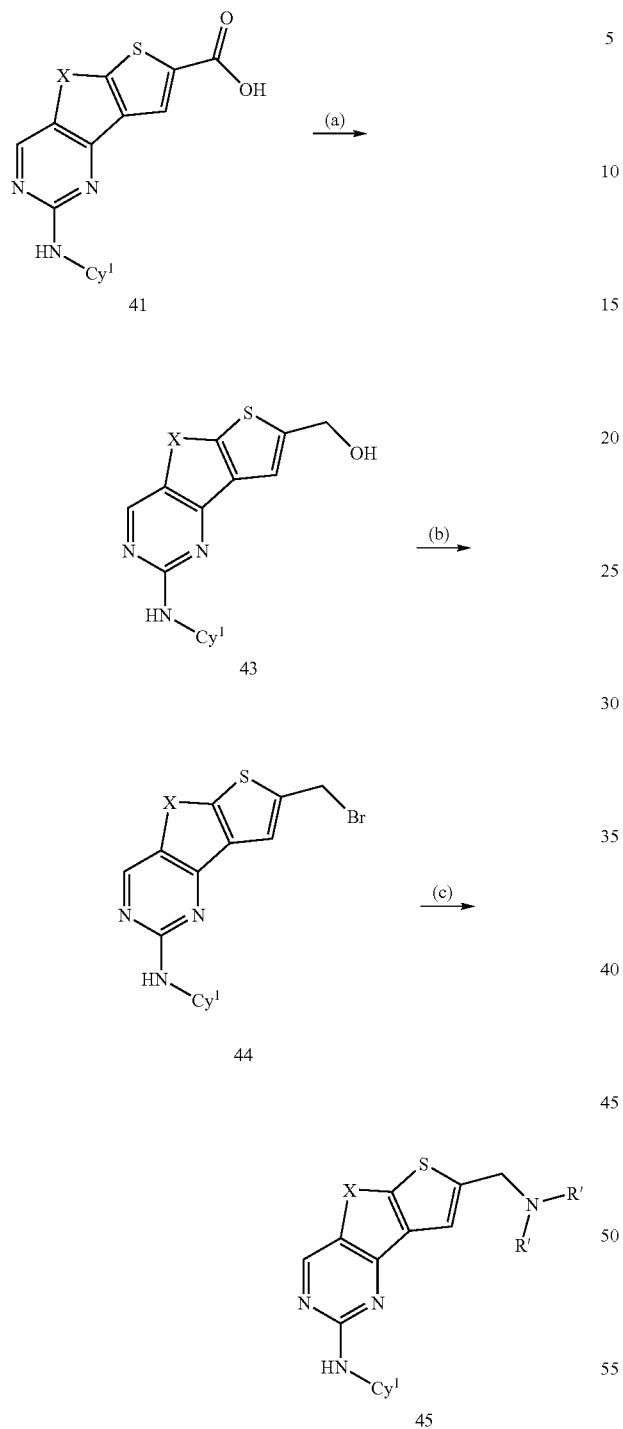

Reagents and conditions: (a) LiAlH₄, THF; (b) CBr₄, PPh₃, Et₂O; (c) R'R'NH, Et₃N, DCM.

Scheme XII above shows a general synthetic route that is used for preparing compounds of formula 45 of this invention where X and Cy¹ are as described above. Each of the above steps is well known to one of skill in the art.

Table 6 below depicts exemplary compounds prepared according to the general method described in Scheme XII.

TABLE 6

Examples of Compounds of Formula VI:

| | |
|---|---|
| 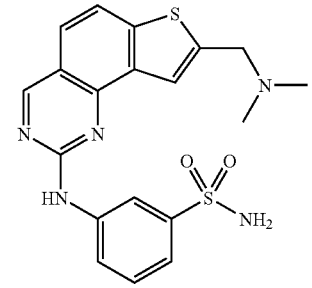 | VI-1 |
| | VI-2 |
| 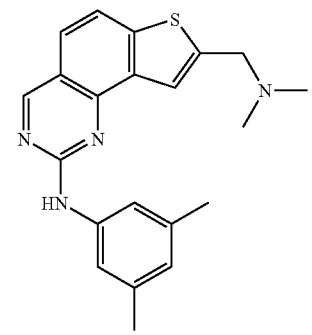 | VI-3 |
| | VI-4 |
| 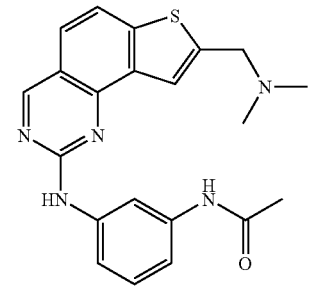 | VI-5 |

TABLE 6-continued
Examples of Compounds of Formula VI:
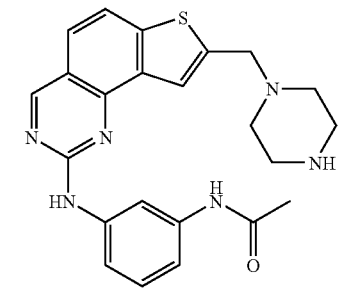
VI-6
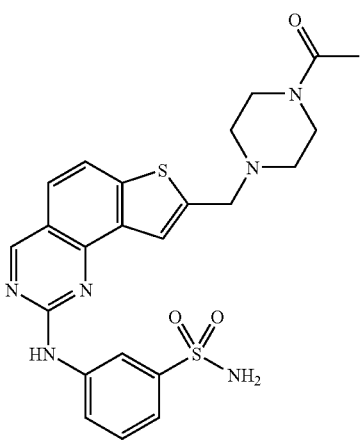
VI-7
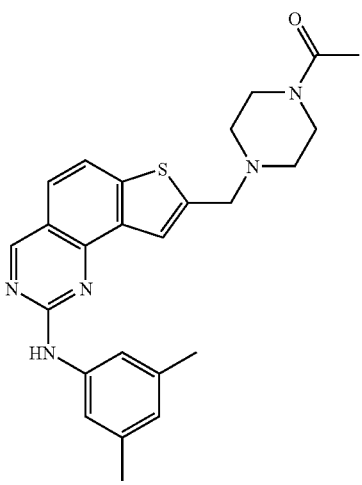
VI-8
TABLE 6-continued
Examples of Compounds of Formula VI:
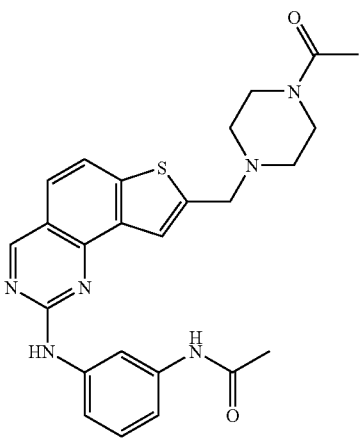
VI-9
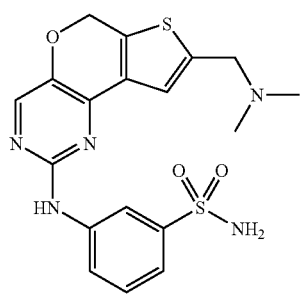
VI-10
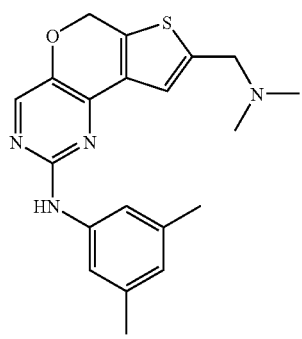
VI-11
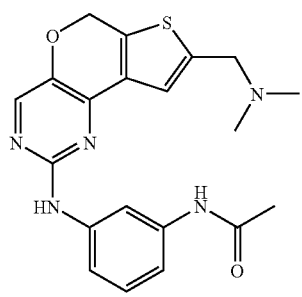
VI-12

TABLE 6-continued
Examples of Compounds of Formula VI:
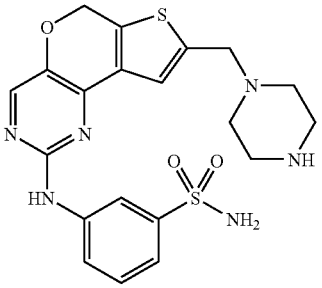 VI-13
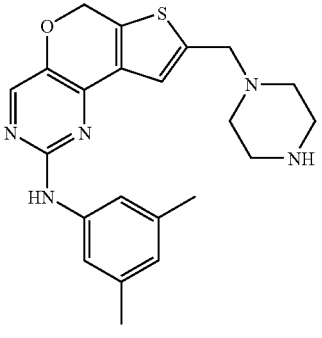 VI-14
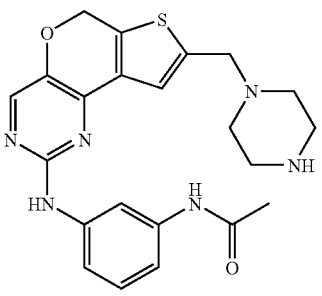 VI-15
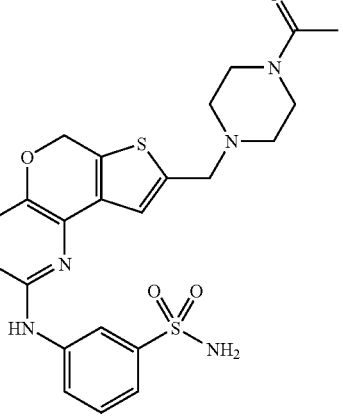 VI-16
TABLE 6-continued
Examples of Compounds of Formula VI:
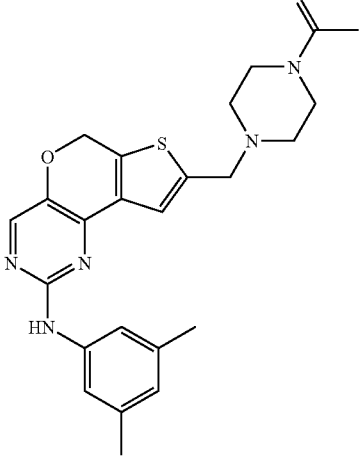 VI-17
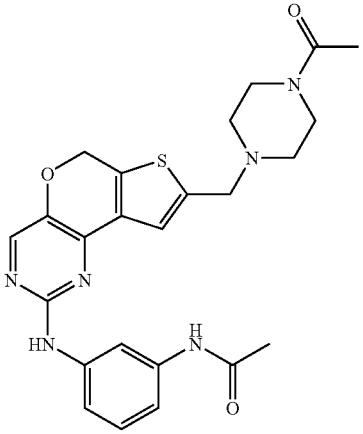 VI-18
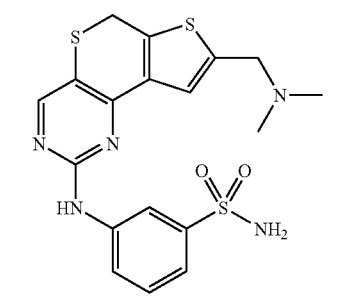 VI-19
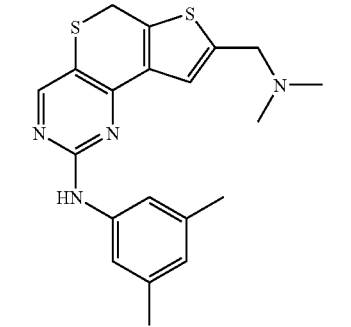 VI-20

TABLE 6-continued
Examples of Compounds of Formula VI:
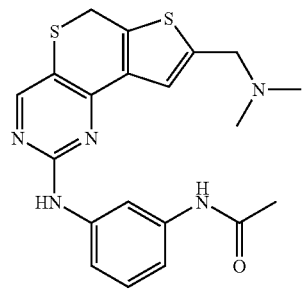 VI-21
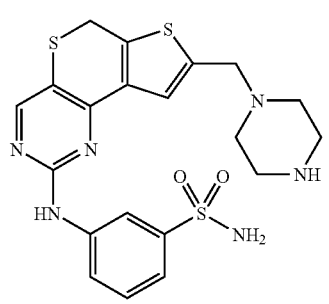 VI-22
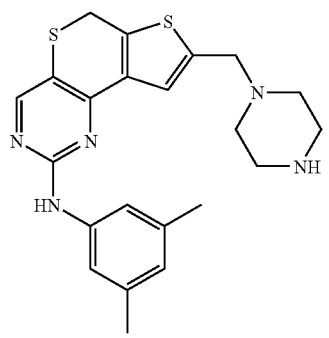 VI-23
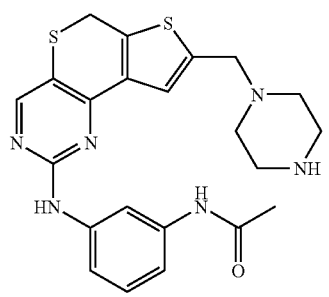 VI-24
TABLE 6-continued
Examples of Compounds of Formula VI:
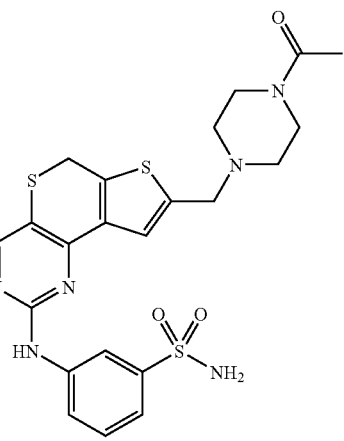 VI-25
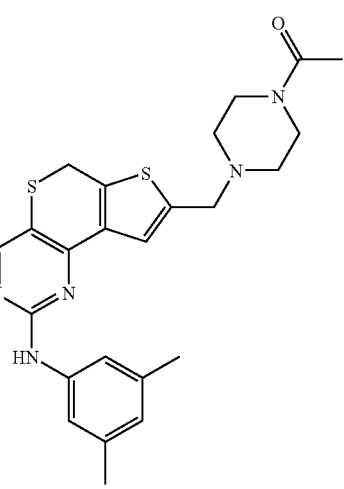 VI-26
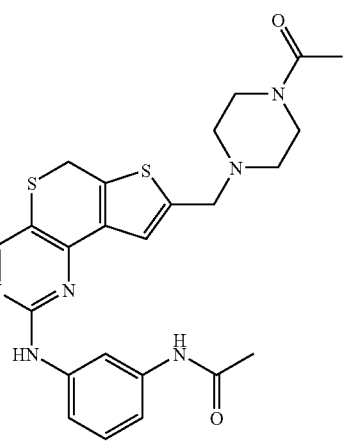 VI-27

Scheme XIII

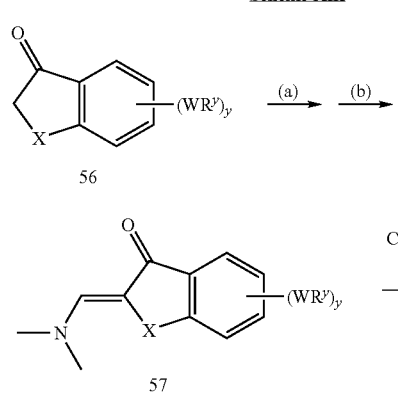

Reagents and conditions: (a) i) 20 eq. DMF-DMA; ii) CH₃CN overnight; (b) 1.2 eq. Bredereck's reagent 80° C. overnight; (c) DMF, 100° C., overnight.

Scheme XIII above shows a general synthetic route that is used for preparing compounds of formula 58 of this invention where X is defined generally herein and where $Cy^1$, $WR^Y$, and y are as described herein. Each of the above steps is well known to one of skill in the art.

Table 7 below depicts exemplary compounds prepared according to the general method described in Scheme XIII.

TABLE 7

Examples of Compounds of Formula VII:

VII-1, VII-2, VII-3, VII-4, VII-5, VII-6, VII-7

TABLE 7-continued
Examples of Compounds of Formula VII:
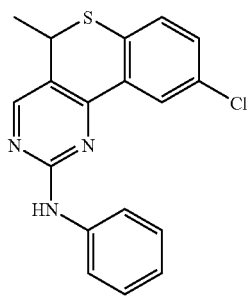 VII-8
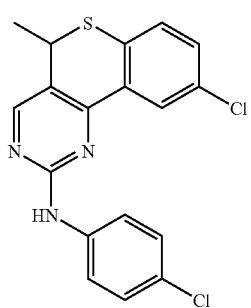 VII-9
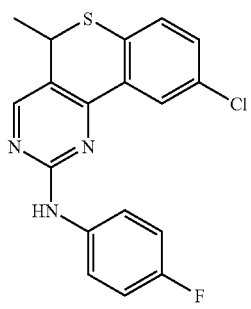 VII-10
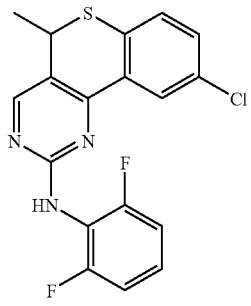 VII-11
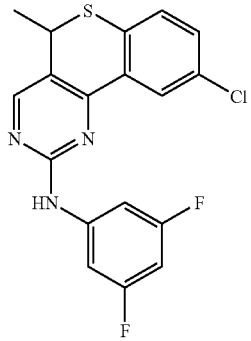 VII-12
TABLE 7-continued
Examples of Compounds of Formula VII:
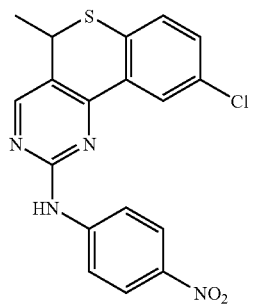 VII-13
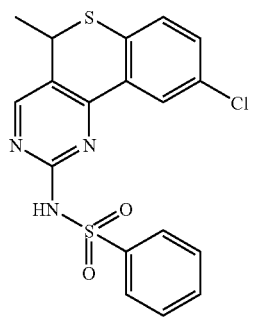 VII-14
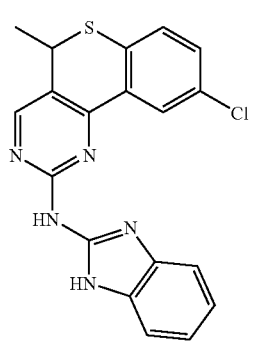 VII-15
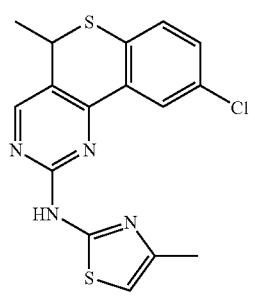 VII-16

TABLE 7-continued
Examples of Compounds of Formula VII:
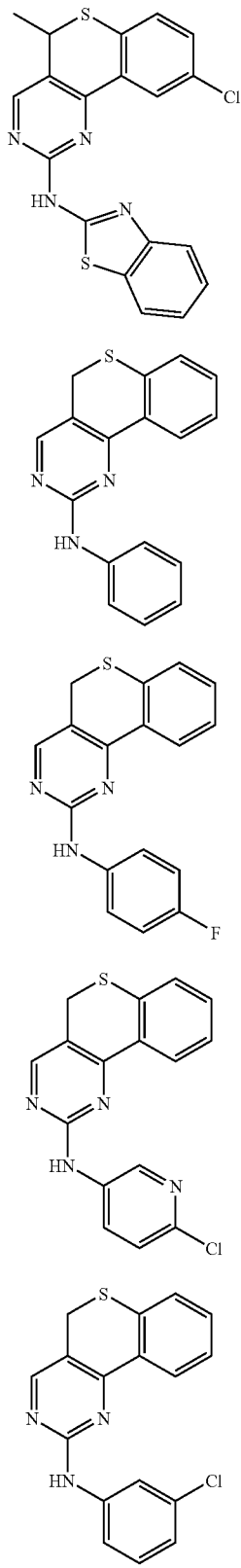
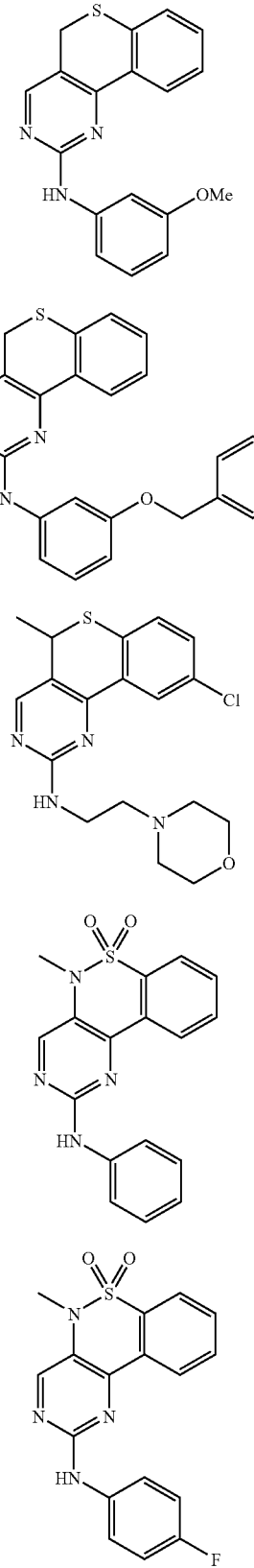

TABLE 7-continued
Examples of Compounds of Formula VII:
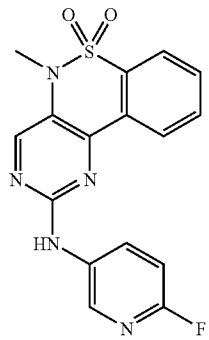
VII-27
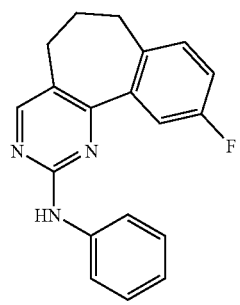
VII-28
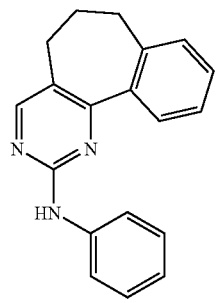
VII-29
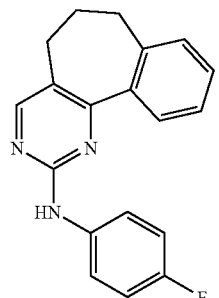
VII-30
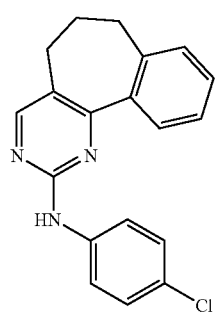
VII-31
TABLE 7-continued
Examples of Compounds of Formula VII:
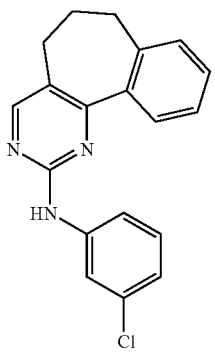
VII-32
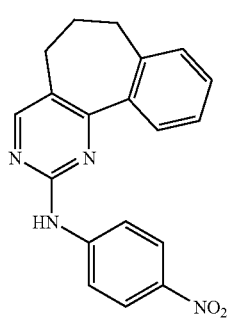
VII-33
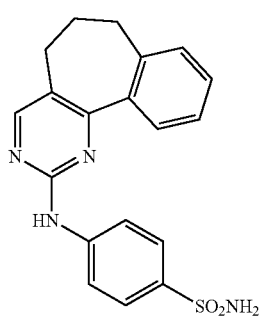
VII-34
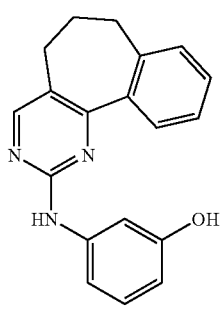
VII-35

TABLE 7-continued

Examples of Compounds of Formula VII:

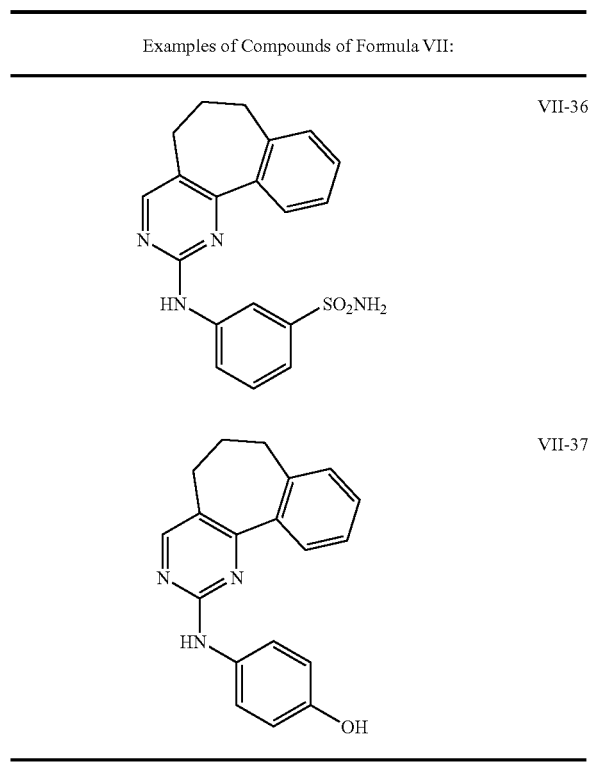

VII-36

VII-37

Scheme XIV

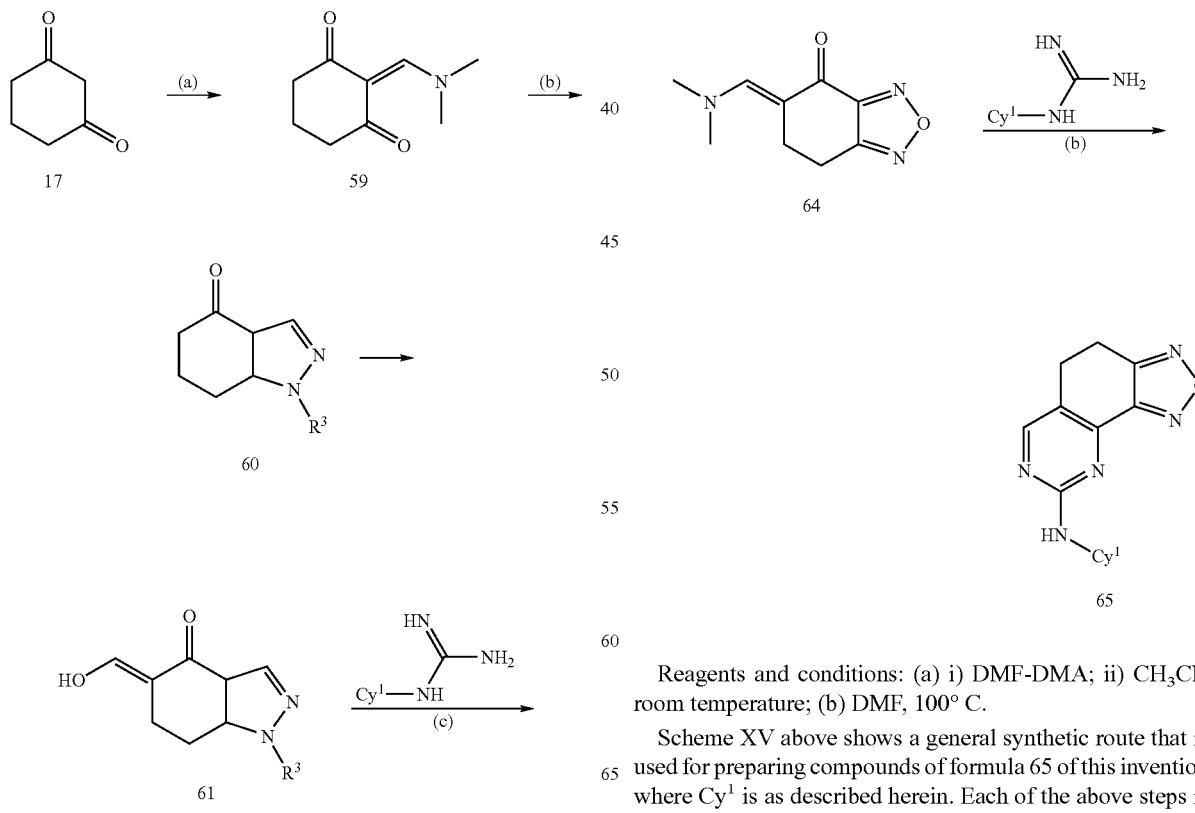

-continued

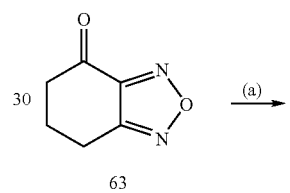

62

Reagents and conditions: (a) i) DMF-DMA; ii) CH$_3$CN room temperature; (b) R$^3$NHNH$_2$, CH$_3$OH; (c) DMF, 100° C.

Scheme XIV above shows a general synthetic route that is used for preparing compounds of formula 62 of this invention where Cy$^1$ and R$^3$ are as described herein. Each of the above steps is well known to one of skill in the art.

Scheme XV

Reagents and conditions: (a) i) DMF-DMA; ii) CH$_3$CN room temperature; (b) DMF, 100° C.

Scheme XV above shows a general synthetic route that is used for preparing compounds of formula 65 of this invention where Cy$^1$ is as described herein. Each of the above steps is well known to one of skill in the art.

Scheme XVI

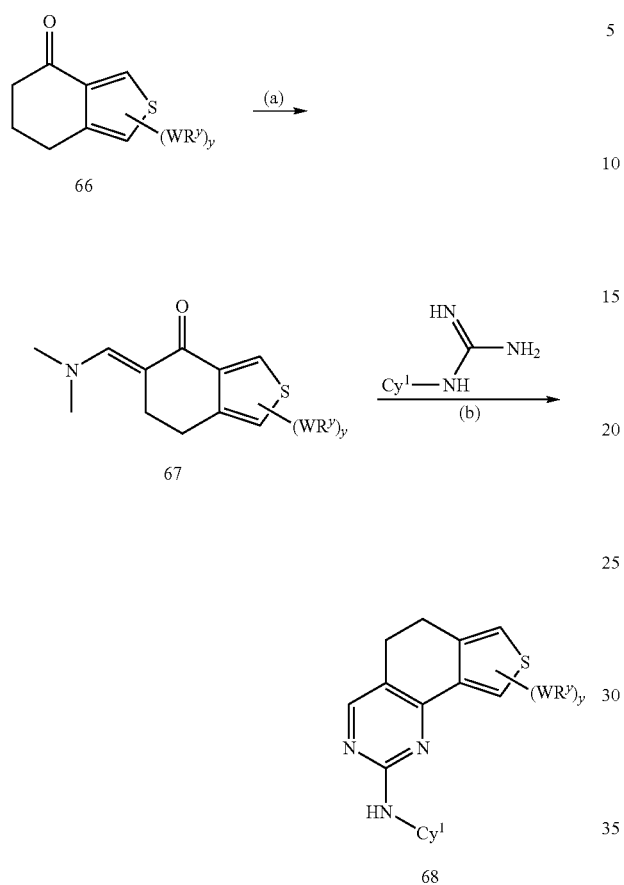

Reagents and conditions: (a) i) DMF-DMA; ii) CH$_3$CN room temperature; (b) DMF, 120° C.

Scheme XVI above shows a general synthetic route that is used for preparing compounds of formula 68 of this invention where Cy$^1$, WR$^Y$, and y are as described herein. Each of the above steps is well known to one of skill in the art.

Table 8 below depicts exemplary compounds prepared according to the general method depicted in Schemes XIV, XV, and XVI.

TABLE 8

Examples of Compounds of Formula VIII:

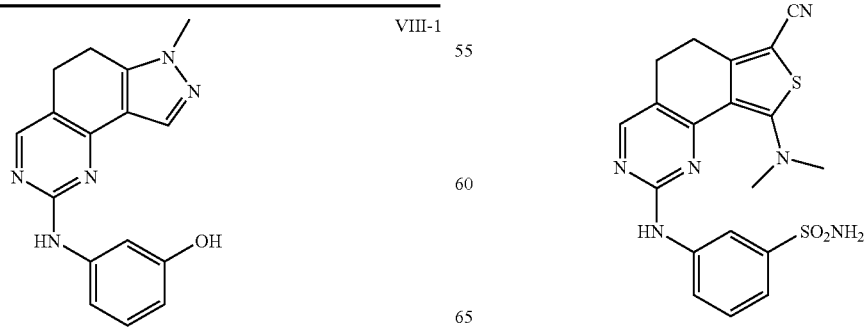

VIII-1

TABLE 8-continued

Examples of Compounds of Formula VIII:

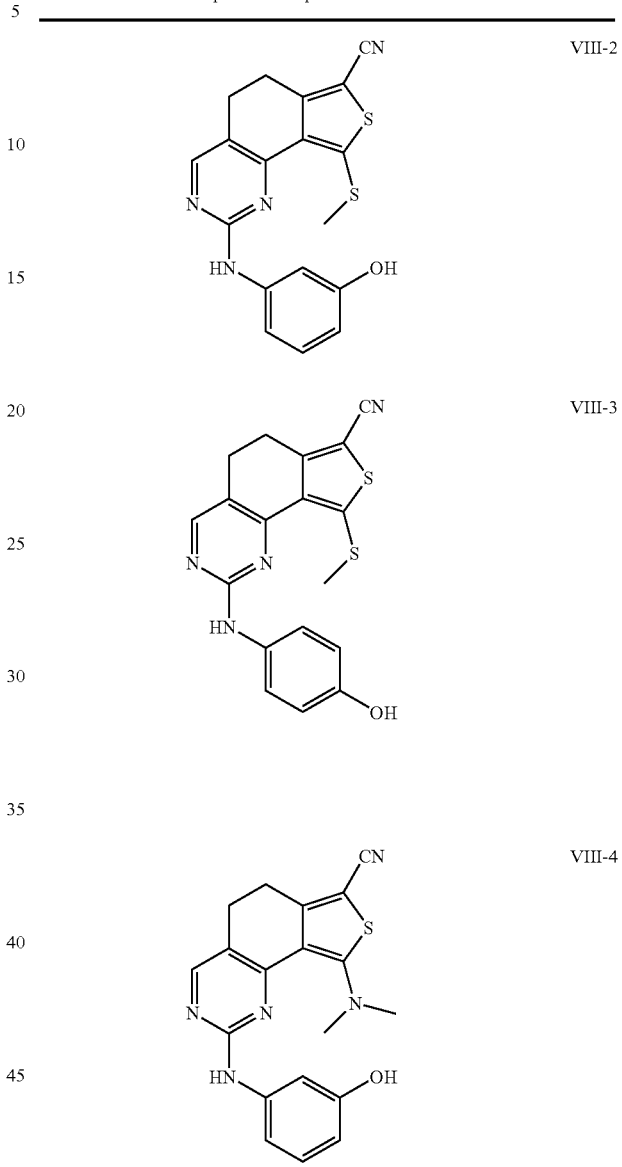

VIII-2

VIII-3

VIII-4

VIII-5

TABLE 8-continued

Examples of Compounds of Formula VIII:

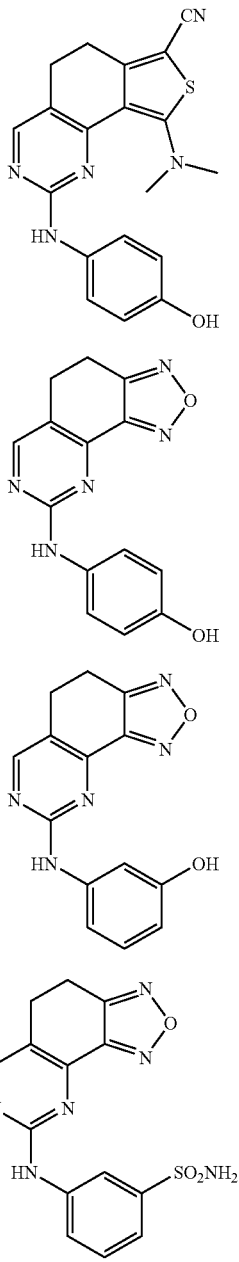

VIII-6

VIII-7

VIII-8

VIII-9

Although certain exemplary embodiments are depicted and described above and herein, it will be appreciated that compounds of the invention can be prepared according to the methods described generally above using appropriate starting materials by methods generally available to one of ordinary skill in the art. Accordingly, another embodiment of this invention provides a process for preparing a compound of this invention according to these methods.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to acute-myelogenous leukemia (AML), acute lymphocytic leukemia (ALL), mastocytosis, gastrointestinal stromal tumor (GIST), cancer including but not limited to colon, breast, hepatic and pancreatic cancer, certain B-cell leukemias and lymphomas, neurodegenerative disorders, diabetes, CNS disorders such as manic depressive disorder and neurodegenerative diseases, cardiomyocyte hypertrophy, immune system dysfunction, bone remodeling diseases, allergic disorders such as asthma, autoimmune diseases such as transplant rejection, rheumatoid arthritis, amyotrophic lateral sclerosis and multiple sclerosis. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a GSK-3, SYK, Aurora-2, CDK-2, JAK-3, LCK, SRC, or Tec family (e.g., Tec, Btk, Itk/Emt/Tsk, Bmx, Txk/Rlk) protein kinases kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a GSK-3, SYK, Aurora-2, CDK-2, JAK-3, LCK, SRC, and/or Tec family (e.g., Tec, Btk, Itk/Emt/Tsk, Bmx, Txk/Rlk)-mediated diseases is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for a GSK-3, SYK, Aurora-2, CDK-2, JAK-3, LCK, SRC, and/or Tec family (e.g., Tec, Btk, Itk/Emt/Tsk, Bmx, Txk/Rlk)-mediated disease. The compounds and compositions, according to the method of the present invention, may be administered using any amount and any route of administration effective for treating or lessening the severity of a GSK-3, SYK, Aurora-2, CDK-2, JAK-3, LCK, SRC, and/or Tec family (e.g., Tec, Btk, Itk/Emt/Tsk, Bmx, Txk/Rlk)-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of GSK-3, SYK, Aurora-2, CDK-2, JAK-3, LCK, SRC, or Tec family (e.g., Tec, Btk, Itk/Emt/Tsk, Bmx, Txk/Rlk) kinase, and thus, without wishing to be bound by any particular theory, the compounds and compositions are particularly useful for treating or lessening the severity of a disease, condition, or disorder where activation of one or more of GSK-3, SYK, Aurora-2, CDK-2, JAK-3, LCK, SRC, and/or Tec family (e.g., Tec, Btk, Itk/Emt/Tsk, Bmx, Txk/Rlk) kinase is implicated in the disease, condition, or disorder. When activation of GSK-3, SYK, Aurora-2, CDK-2, JAK-3, LCK, SRC, and/or Tec family (e.g., Tec, Btk, Itk/Emt/Tsk, Bmx, Txk/Rlk) is implicated in a particular disease, condition, or disorder, the disease, condition, or disorder may also be referred to as a "GSK-3, SYK, Aurora-2, CDK-2, JAK-3, LCK, SRC, and/or Tec family (e.g., Tec, Btk, Itk/Emt/Tsk, Bmx, Txk/Rlk)-mediated disease" or disease symptom.

Accordingly, in another aspect, the present invention provides a method for treating or lessening the severity of a disease, condition, or disorder where activation or one or more of GSK-3, SYK, Aurora-2, CDK-2, JAK-3, LCK, SRC, and/or Tec family (e.g., Tec, Btk, Itk/Emt/Tsk, Bmx, Txk/Rlk) is implicated in the disease state.

The activity of a compound utilized in this invention as an inhibitor of GSK-3, SYK, Aurora-2, CDK-2, JAK-3, LCK, SRC, and/or Tec family (e.g., Tec, Btk, Itk/Emt/Tsk, Bmx, Txk/Rlk), may be assayed in vitro, in vivo or in a cell line. In vitro assays include assays that determine inhibition of either the phosphorylation activity or ATPase activity of activated GSK-3, SYK, Aurora-2, CDK-2, JAK-3, LCK, SRC, and/or Tec family (e.g., Tec, Btk, Itk/Emt/Tsk, Bmx, Txk/Rlk). Alternate in vitro assays quantitate the ability of the inhibitor to bind to GSK-3, SYK, Aurora-2, CDK-2, JAK-3, LCK, SRC, and/or Tec family (e.g., Tec, Btk, Itk/Emt/Tsk, Bmx, Txk/Rlk). Inhibitor binding may be measured by radiolabelling the inhibitor prior to binding, isolating the inhibitor/GSK-3, SYK, Aurora-2, CDK-2, JAK-3, LCK, SRC, and/or Tec family (e.g., Tec, Btk, Itk/Emt/Tsk, Bmx, Txk/Rlk), complex and determining the amount of radiolabel bound. Alternatively, inhibitor binding may be determined by running a competition experiment where new inhibitors are incubated with GSK-3, SYK, Aurora-2, CDK-2, JAK-3, LCK, SRC, and/or Tec family (e.g., Tec, Btk, Itk/Emt/Tsk, Bmx, Txk/Rlk) bound to known radioligands.

The term "measurably inhibit", as used herein means a measurable change in GSK-3, SYK, Aurora-2, CDK-2, JAK-3, LCK, SRC, and/or Tec family (e.g., Tec, Btk, Itk/Emt/Tsk, Bmx, Txk/Rlk) activity between a sample comprising said composition and a GSK-3, SYK, Aurora-2, CDK-2, JAK-3, LCK, SRC, and/or Tec family (e.g., Tec, Btk, Itk/Emt/Tsk, Bmx, Txk/Rlk) kinase and an equivalent sample comprising GSK-3, SYK, Aurora-2, CDK-2, JAK-3, LCK, SRC, and/or Tec family (e.g., Tec, Btk, Itk/Emt/Tsk, Bmx, Txk/Rlk) kinase in the absence of said composition.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer. The term "Aurora-2-mediated disease", as used herein, means any disease or other deleterious condition or disease in which Aurora-2 is known to play a role. Such diseases or conditions include, without limitation, cancers such as colon and breast cancer.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P. *Current Medicinal Chemistry,* 2000, 7, 1213-1245; Mani, S., Wang, C., Wu, K., Francis, R. and Pestell, R. *Exp. Opin. Invest. Drugs* 2000, 9, 1849; Fry, D. W. and Garrett, M. D. *Current Opinion in Oncologic, Endocrine & Metabolic Investigational Drugs* 2000, 2, 40-59.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described [Molina et al., *Nature,* 1992, 357, 161].

The terms "Src-mediated disease" or "Src-mediated condition", as used herein mean any disease or other deleterious condition in which one or more Src-family kinases is known to play a role. The terms "Src-mediated disease" or "Src-mediated condition" also mean those diseases or conditions that are alleviated by treatment with an inhibitor of a Src family kinase. Such diseases or conditions include hypercalcemia, restenosis, osteoporosis, osteoartliritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Src protein kinase and its implication in various diseases has been described [Soriano, *Cell,* 1992, 69, 551; Soriano et al., *Cell* 1991, 64, 693; Takayanagi, *J. Clin. Invest.* 1999, 104, 137; Boschelli, *Drugs of the Future* 2000, 25 (7), 717; Talamonti, *J. Clin. Invest.* 1993, 91, 53; Lutz, *Biochem. Biophys. Res.* 1998, 243, 503; Rosen, *J. Biol. Chem.,* 1986, 261, 13754; Bolen, *Proc. Natl. Acad. Sci. USA* 1987, 84, 2251; Masaki, *Hepatology* 1998, 27, 1257; Biscardi, *Adv. Cancer Res.* 1999, 76, 61; Lynch, *Leukemia* 1993, 7, 1416; Wiener, *Clin. Cancer Res.* 1999, 5, 2164; Staley, *Cell Growth Diff.,* 1997, 8, 269]. Diseases that are affected by Src activity, in particular, include hypercalcemia, osteoporosis, osteoarthritis, cancer, symptomatic treatment of bone metastasis, and Paget's disease.

The term "SYK-mediated disease" or "SYK-mediated condition", as used herein, means any disease or other deleterious condition in which SYK protein kinase is known to play a role. Such conditions include, without limitation, allergic disorders, especially asthma.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, Tec family tyrosine kinases -mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, Tec family tyrosine kinases diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases -mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Tec family tyrosine kinases-mediated conditions also include those diseases and disorders of other tissues and systemic disease, including, without limitation, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine;

agents for treating Multiple Sclerosis (MS) such as beta interferon (e.g., Avonexe and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting GSK-3, SYK, Aurora-2, CDK-2, JAK-3, LCK, SRC, and/or Tec family (e.g., Tec, Btk, Itk/Emt/Tsk, Bmx, Txk/Rlk) activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3, SYK, Aurora-2, CDK-2, JAK-3, LCK, SRC, and/or Tec family (e.g., Tec, Btk, Itk/Emt/Tsk, Bmx, Txk/Rlk) kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, The term "Rt(min)" refers to the HPLC retention time, in minutes, associated with the compound. Unless otherwise indicated, the HPLC method utilized to obtain the reported retention time is as follows:

Column: Ace 5 C8, 15 cm×4.6 mm id
Gradient: 0-100% acetonitrile+methanol (50:50) (20 mM Tris phosphate at pH 7.0)
Flow rate: 1.5 ml/min
Detection: 225 nm Example 1

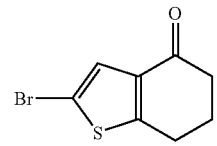

2-Bromo-6,7-dihydro-5H-benzo[b]thiophen-4-one

To a solution of 6,7-Dihydro-5H-benzo[b]thiophen-4-one (10.0 g, 65.8 mmol) in 50% acetic acid (100 mL) at −5 deg C. was added dropwise a solution of bromine (3.4 mL, 65.8 mmol) in acetic acid (61.5 mL). The mixture was stirred at −5 deg C. for 1 hour.

A solution of 1M NaOAc$_{(aq)}$ was added and the resulting precipitate removed by filtration. This was further washed with water to give the titled compound as a grey powder (10.8 g). MS (ES$^+$) 232. δH (d$^6$ DMSO) 2.10 (2H, m), 2.47 (2H, t), 2.96 (2H, t) and 7.33 (1H, s).

Example 2

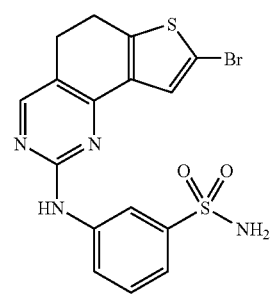

3-(8-Bromo-5,6-dihydro-thieno[2,3-h]quinazolin-2-ylamino)-benzenesulfonamide To the 2-Bromo-6,7-dihydro-5H-benzo[b]thiophen-4-one (7.8 g, 34.2 mmol) in anhydrous toluene (10 mL) was added DMF/DMA solution (9.2 mL, 68.4 mmol) and the mixture was refluxed under nitrogen for 18 hours. The reaction mixture was concentrated in vacuo and the resulting crude deep red product (2-Bromo-5-dimethylaminomethylene-6,7-dihydro-5H-benzo[b]thiophen-4-one) was taken through to the next step without further purification.

The above was dissolved in anhydrous propan-2-ol (30 mL) and treated with 3-Guanidino-benzenesulfonamide hydrogen chloride (10.5 g, 42.0 mmol) and powdered sodium hydroxide (1.5 g, 37.6 mmol). The mixture was refluxed with vigorous stirring for 5 hours. A yellow precipitate formed during the reaction and further alcohol was added to maintain the slurry.

The mixture was cooled to room temperature and concentrated in vacuo. The resulting solid was slurried in hot EtOAc (500 mL) and after cooling the dark green solid product (6.5 g) was removed by filtration. MS (ES+) 439, (ES−) 437. δH (d$^6$ DMSO) 2.91 (2H, m), 3.00 (2H, m), 7.30 (2H, br m), 7.37 (1H, m), 7.46 (2H, m), 7.70 (1H, s), 8.39 (1H, s), 8.80 (1H, s) and 9.91 (1H, s).

Example 3

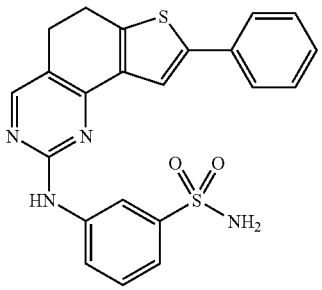

3-(8-Phenyl-5,6-dihydro-thieno[2,3-h]quinazolin-2-ylamino)-benzenesulfonamide To the 3-(8-Bromo-5,6-dihydro-thieno[2,3-h]quinazolin-2-ylamino)-benzenesulfonamide (200 mg, 0.46 mmol) in a 10 mL microwave reaction tube was added Phenyl boronic acid (56 mg, 0.46 mmol), 2M Na$_2$CO$_{3(aq)}$ (920 µL, 1.84 mmol), Pd(PPh$_3$)$_4$ (5.3 mg, 0.0046 mmol), 3:4 EtOH/H$_2$O (1.5 mL) and DME (2.5 mL).

The tube was capped and subjected to microwave irradiation at 120 deg C. for 2 hours. On cooling the organic layer was separated from the reaction mixture and purified by preparative liquid chromatography. The desired compound (67 mg) was obtained as a yellow powder following the freeze-drying of product fractions. MS (ES$^+$) 435, (ES$^−$) 433. δH (d$^6$ DMSO) 2.94 (2H, m), 3.05 (2H, m), 7.30 (3H, m), 7.40 (4H, m), 7.60 (1H, d), 7.80 (2H, d), 8.01 (1H, s), 8.40 (1H, s), 9.10 (1H, s) and 9.90 (1H, s).

A variety of other compounds of formula I have been prepared by methods substantially similar to those described in Example 3. The characterization data for these compounds is summarized in Table 9 below and includes HPLC, LC/MS (observed) and $^1$H NMR data.

$^1$H NMR data is summarized in Table 9 below wherein $^1$H NMR data was obtained at 400 MHz in deuterated DMSO, unless otherwise indicated, and was found to be consistent with structure. Compound numbers correspond to the compound numbers listed in Table 1.

TABLE 9

Characterization Data for Selected Compounds of Formula I

| Compound No. | M + 1 (obs) | Rt (min) | $^1$H-NHR |
|---|---|---|---|
| I-2 | 465 | 9.92 | 2.95(2H, m), 3.07(2H, m), 3.90(3H, s), 6.90(1H, d), 7.31(5H, m), 7.40(1H, m), 7.46(1H, t), 7.69(1H, d), 8.06(1H, s), 8.40(1H, s), 9.20(1H, s), 9.95((1H, s). |
| I-3 | 436 | 8.84 | 2.98(2H, m), 3.12(2H, m), 6.90(1H, d), 7.35(2H, s), 7.40(1H, d), 7.48(1H, t), 7.60(2H, m), 8.20(1H, s), 8.29(1H, d), 8.41(1H, s), 8.59(1H, m), 8.85(1H, d), 9.90(1H, s), 9.98((1H, s). |
| I-4 | 479 | 7.46 | 2.98(2H, m), 3.09(2H, m), 7.30(1H, t), 7.39(1H, s), 7.48(3H, m), 7.77(2H, d), 7.80(1H, d), 8.00(1H, s), 8.19(1H, s), 8.40(1H, s), 8.90(1H, br s), 9.95((1H, s). |
| I-5 | 441 | 9.72 | 2.97(2H, m), 3.07(2H, m), 7.35(2H, s), 7.40(1H, d), 7.48(1H, t), 7.61(2H, m), 7.70(1H, m), 7.81(1H, s), 8.93(1H, s), 8.39(1H, s), 9.18(1H, s), 9.91(1H, s). |
| I-6 | 492 | 8.93 | 2.07(3H, s), 2.97(2H, m), 3.11(2H, m), 7.32(2H, s), 7.39(2H, m), 7.49(2H, d), 7.51(1H, m), 7.70(1H, m), 7.98(1H, s), 8.03(1H, s), 8.39(1H, s), 8.89(1H, s), 9.93(1H, s), 10.03(1H, s). |
| I-7 | 469 | 10.12 | 2.98(2H, m), 3.09(2H, m), 7.29(2H, s), 7.50(4H, br m), 7.60(1H, d), 7.65(2H, m), 7.96(1H, s), 8.40(1H, s), 8.79(1H, s), 9.90(1H, s). |
| I-8 | 441 | 9.67 | 2.95(2H, m), 3.17(2H, m), 7.10(1H, m), 7.22(2H, s), 7.28(1H, d), 7.34(2H, m), 7.55(2H, d), 7.68(1H, d), 7.85(1H, s), 8.40(1H, s), 8.95(1H, s), 9.91(1H, s). |
| I-9 | 465 | 9.72 | 2.95(2H, m), 3.07(2H, m), 3.95(3H, s), 7.11(1H, t), 7.15(1H, d), 7.29(2H, s), 7.31(1H, m), 7.40(1H, d), 7.48(1H, t), 7.70(1H, d), 7.91(1H, d), 8.09(1H, s), 8.38(1H, s), 8.91(1H, s), 9.86(1H, s). |
| I-10 | 450 | 8.93 | 2.95(2H, m), 3.09(2H, m), 6.81(1H, m), 7.20(1H, m), 7.25(1H, m), 7.34(3H, s), 7.35(1H, d), 7.44(1H, m), 7.68(1H, m), 7.95(1H, s), 8.40(1H, s), 8.98(1H, s), 8.91(1H, s). |
| I-11 | 465 | 9.78 | 2.92(2H, m), 3.05(2H, m), 3.80(3H, s), 6.95(2H, d), 7.31(1H, m), 7.39(1H, d), 7.46(1H, t), 7.48(1H, t), 7.61(1H, m), 7.70(2H, d), 7.99(1H, s), 8.39(1H, s), 9.06(1H, br s), 9.89(1H, s). |
| I-12 | 460 | 9.38 | 2.98(2H, m), 3.10(2H, m), 7.20(2H, br s), 7.40(1H, m), 7.43(1H, m), 7.60(2H, br m), 7.80(1H, d), 8.09(1H, d), 8.20(1H, s), 8.26(1H, s), 8.41(1H, s), 9.15(1H, s), 9.93(1H, s). |
| I-13 | 480 | 9.67 | 2.98(2H, m), 3.11(2H, m), 7.31(2H, s), 7.38(1H, d), 7.47(1H, t), 7.62(1H, d), 7.83(1H, t), 8.20(2H, br m), 8.30(1H, br m), 8.41(2H, m), 9.09(1H, s), 9.95(1H, s). |
| I-14 | 495 | 9.52 | 2.95(2H, m), 3.05(2H, m), 6.80(2H, d), 7.28(2H, s), 7.31(1H, t), 7.39(1H, m), 7.45(1H, t), 7.81(1H, s), 7.99(1H, s), 8.39(1H, s), 8.46(1H, s), 9.80(1H, s). |
| I-15 | 469 | 10.12 | 2.96(2H, m), 3.09(2H, m), 7.27(2H, s), 7.39(2H, m), 7.48(2H, t), 7.61(1H, d), 7.75(1H, d), 7.90(1H, s), 8.11(1H, s), 8.40(1H, s), 9.15(1H, s), 9.90(1H, s). |
| I-16 | 469 | 9.99 | 2.95(2H, m), 3.15(2H, m), 7.31(2H, s), 7.40(1H, d), 7.45(3H, m), 7.63(1H, d), |

TABLE 9-continued

Characterization Data for Selected Compounds of Formula I

| Compound No. | M + 1 (obs) | Rt (min) | 1H-NHR |
|---|---|---|---|
| I-17 | 495 | 9.20 | 7.79(1H, d), 8.08(1H, s), 8.40(1H, s), 9.06(1H, s), 9.89(1H, s). 2.98(2H, m), 3.09(2H, m), 3.81(3H, s), 3.87(3H, s), 7.01(1H, d), 7.15(1H, t), 7.31(1H, d), 7.481(1H, t), 7.60(1H, d), 7.70(1H, d), 8.09(1H, s), 8.39(1H, s), 8.91(1H, s) and 9.83(1H, s). |
| I-20 | 495 | 9.20 | 2.92(2H, m), 3.05(2H, m), 3.85(3H, s), 3.87(3H, s), 6.88(1H, m), 7.09(1H, d), 7.27(1H, br s), 7.37(1H, m), 7.44(1H, t), 7.70(1H, m), 8.07(1H, s), 8.39(1H, s), 8.98(1H, br s) and 9.82(1H, s). |
| I-26 | 528 | 8.97 | 2.99(2H, m), 3.10(2H, m), 6.88(1H, m), 7.17(1H, d), 7.30(2H, br s), 7.40(1H, d), 7.46(1H, m), 7.50(1H, m), 7.59(1H, d), 7.71(1H, d), 7.99(1H, s), 8.40(1H, s), 8.90(1H, s), 9.81(1H, s) and 9.89(1H, s). |
| I-27 | 451 | 8.97 | 2.95(2H, m), 3.05(2H, m), 6.85(1H, t), 6.95(1H, m), 7.13(1H, t), 7.29(2H, br s), 7.40(1H, d), 7.46(1H, t), 7.78(1H, d), 7.81(1H, d), 8.09(1H, s), 8.36(1H, s), 8.83(1H, s), 9.83(1H, s) and 10.29(1H, br s). |
| I-28 | 519 | 10.28 | 2.99(2H, m), 3.13(2H, m), 7.29(2H, br s), 7.36(1H, d), 7.40-7.51(4H, br m), 7.75(1H, d), 8.06(2H, s), 8.42(1H, s), 8.86(1H, s) and 10.29(1H, br s). |
| I-29 | 465 | 9.12 | 2.97(2H, m), 3.09(2H, m), 4.63(2H, d), 5.26(1H, m), 7.23(2H, br s), 7.37(2H, m), 7.43(3H, br m), 7.63(1H, d), 7.75(1H, d), 7.91(1H, d), 8.39(1H, s), 8.60(1H, s) and 9.82(1H, s). |

Example 4

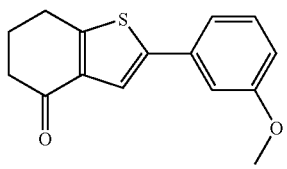

2-(3-Methoxyphenyl)-6,7-dihydro-5H-benzo[b]thiophen-4-one

To 2-bromo-6,7-dihydro-5H-benzo[b]thiophen-4-one (5 g, 21.74 mmol) was successively added 3-methoxyphenol boronic acid (3.63 g, 23.92 mmol), 2M $Na_2CO_{3(aq)}$ (43.5 mL, 86.98 mmol), Pd(PPh$_3$)$_4$ (251mg, 0.22 mmol), 3:4 EtOH/H$_2$O (37.5 mL) and DME (62.5 mL). The reaction mixture was degassed and heated to reflux for 12 hours. EtOAc (250 mL) was added and the crude reaction mixture was washed with water (2×100 mL). The organic layer was dried over magnesium sulphate, filtered and concentrated in vacuo. The residue was purified by silica gel chromatography eluting with EtOAc:hexanes (20:80) to give the title compound as an off-white solid in 95% yield. MS (ES$^+$) 259. δH (d$^6$ DMSO) 2.13 (2H, quint.), 2.50 (2H, m), 3.05 (2H, t), 3.81 (3H, s), 6.91 (1H, m), 7.20-7.22 (2H, m), 7.34 (1H, m), 7.67 (1H, s).

Example 5

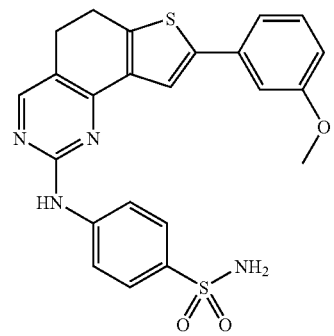

4-[8-(3-Methoxyphenyl)-5,6-dihydro-thieno[2,3-h]quinazolin-2-ylamino)-benzenesulfonamide To 2-(3-methoxyphenyl)-6,7-dihydro-5H-benzo[b]thiophen-4-one (0.3 g, 1.16 mmol) was added DMF/DMA solution (2 mL) and the mixture was refluxed under nitrogen for 12 hours. The reaction mixture was concentrated in vacuo and the resulting crude product (5-dimethylaminomethylene-2-(3-methoxyphenyl)-6,7-dihydro-5H-benzo[b]thiophen-4-one) was taken through to the next step without further purification.

The above was dissolved in anhydrous DMA (3 mL) and treated with 4-Guanidino-benzenesulfonamide hydrogen chloride (297mg, 1.18 mmol) and powdered potassium carbonate (82 mg, 0.59 mmol). The mixture was heated to 120° C. with vigorous stirring for 12 hours. The mixture was cooled down to room temperature and purified by reverse phase preparative HPLC [Waters Delta-Pak C18, 15 uM, 100 A column, gradient 10%-100% B (solvent A: 0.05% TFA in water; solvent B: CH$_3$CN) over 10 minutes at 25 mL/min] to afford the title compound (17 mg) as a yellow powder. MS (ES$^+$) 465, (ES$^-$) 463. δH (d$^6$ DMSO) 2.99 (2H, t), 3.10 (2H, t), 3.85 (3H, s), 6.95 (1H, dd), 7.13 (2H, br s), 7.21 (1H, m), 7.27 (1H, d), 7.40 (1H, t), 7.76 (2H, d), 7.87 (1H, s), 8.01 (2H, d), 8.42 (1H, s), 9.90 (1H, s).

Other compounds of formula I have been prepared by methods substantially similar to those described in Example 5. The characterization data for these compounds is summarized in Table 10 below and includes HPLC, LC/MS (observed) and $^1$H NMR data.

$^1$H NMR data is summarized in Table 10 below wherein $^1$H NMR data was obtained at 400 MHz in deuterated DMSO, unless otherwise indicated, and was found to be consistent with structure. Compound numbers correspond to the compound numbers listed in Table 1.

TABLE 10

Characterization Data for Selected Compounds of Formula I

| Compound No. | M + 1 (obs) | Rt (min) | 1H-NMR |
|---|---|---|---|
| I-19 | 402 | 10.23 | 2.96(2H, t), 3.08(2H, t), 3.84(3H, s), 6.36(1H, dd), 6.94(1H, dd), 7.06(1H, t), 7.14(1H, d), 7.21(1H, |

TABLE 10-continued

Characterization Data for Selected Compounds of Formula I

| Compound No. | M + 1 (obs) | Rt (min) | $^1$H-NMR |
|---|---|---|---|
| | | | t), 7.24(1H, d), 7.38(1H, t), 7.50(1H, t), 7.87(1H, s), 8.33(1H, s), 9.37(1H, s) |
| I-22 | 386 | 10.94 | 2.96(2H, t), 3.08(2H, t), 3.84(3H, s), 6.90-6.97(2H, m), 7.19(1H, t), 7.24(1H, d), 7.30(2H, t), 7.39(1H, t), 7.80-7.86(3H, m), 8.35(1H, s), 9.44(1H, s) |
| I-23 | 402 | 10.14 | 2.93(2H, t), 3.07(2H, t), 3.84(3H, s), 6.74(2H, d), 6.94(1H, dd), 7.18(1H, t), 7.23(1H, d), 7.38(1H, t), 7.54(2H, d), 7.78(1H, s), 8.25(1H, s), 9.27(1H, br s) |
| I-24 | 464 | 10.30 | 2.97-3.02(2H, m), 3.05-3.10(2H, m), 3.22(3H, s), 3.88(3H, s), 6.91(1H, d), 7.27-7.37(3H, m), 7.45(1H, d), 7.55(1H, t), 7.70(1H, d), 8.02(1H, s), 8.41(1H, s), 9.21(1H, s), 10.00(1H, s) |
| I-25 | 464 | 10.30 | 2.96-3.03(2H, m), 3.05-3.15(2H, m), 3.15(3H, s), 3.85(3H, s), 6.96(1H, d), 7.20, (1H, s), 7.26(1H, d), 7.40(1H, t), 7.83-7.90(3H, m), 8.10(2H, d), 8.41(1H, s), 10.05(1H, s) |
| I-35 | 429 | 10.04 | 2.97(2H, t), 3.09(2H, t), 3.88(3H, s), 6.93(1H, dd), 7.21(1H, br s), 7.26(1H, t), 7.30-7.40(3H, m), 7.44(1H, d), 7.72(1H, dd), 7.89(1H, br s), 8.02(1H, s), 8.37(1H, s), 8.82(1H, s), 9.62(1H, s) |
| I-36 | 443 | 10.04 | 2.13(3H, s), 2.96(2H, t), 3.07(2H, t), 3.83(3H, s), 6.92-6.96(2H, m), 7.14-7.17(2H, m), 7.34-7.43(3H, m), 8.27(1H, s), 8.33(1H, s), 8.89(1H, s), 9.44(1H, s), 9.90(1H, s) |
| I-37 | 493 | 10.62 | 2.63(6H, s), 2.99(2H, t), 3.10(2H, t), 3.87(3H, s), 6.93(1H, d), 7.26-7.39(4H, m), 7.55(1H, t), 7.74(1H, dd), 8.01(1H, s), 8.42(1H, s), 9.14(1H, s), 9.99(1H, s) |
| I-38 | 479 | 10.42 | 2.46(3H, d), 2.99(2H, t), 3.10(2H, t), 3.88(3H, s), 6.92(1H, dd), 7.28-7.38(5H, m), 7.50(1H, t), 7.66(1H, dd), 8.04(1H, s), 8.41(1H, s), 9.16(1H, s), 9.92(1H, s) |
| I-39 | 479 | 15.58 | 2.93-3.10(7H, m), 3.85(3H, s), 6.76(1H, d), 6.93(1H, dd), 7.19-7.45(5H, m), 8.01(1H, s), 8.14(1H, s), 8.35(1H, s), 9.52(1H, s), 9.67(1H, br s) |
| I-40 | 401 | 10.29 | 2.94(2H, t), 3.07(2H, t), 3.84(3H, s), 4.96(2H, s), 6.17(1H, m), 6.88-6.95(3H, m), 7.22-7.26(3H, m), 7.37(1H, t), 7.87(1H, s), 8.30(1H, s), 9.11(1H, s) |
| I-46 | 402 | 10.65 | 2.97(2H, t), 3.09(2H, t), 3.85(3H, s), 6.80-6.96(4H, m), 7.20-7.28(3H, m), 7.37(2H, t), 7.88(1H, s), 8.15-8.20(2H, m), 8.34(1H, s) |

Example 6

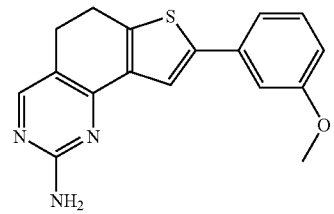

8-(3-Methoxyphenyl)-5,6-dihydro-thieno[2,3-h]quinazolin-2-ylamine

To 2-(3-methoxyphenyl)-6,7-dihydro-5H-benzo[b]thiophen-4-one (1.78 g, 6.89 mmol) was added DMF/DMA solution (12 mL) and the mixture was refluxed under nitrogen for 12 hours. The reaction mixture was concentrated in vacuo and the resulting crude product (5-dimethylaminomethylene-2-(3-methoxyphenyl)-6,7-dihydro-5H-benzo[b]thiophen-4-one) was taken through to the next step without further purification.

The above was dissolved in anhydrous DMA (18 mL) and treated with guanidine hydrogen chloride (724 mg, 7.58 mmol) and powdered potassium carbonate (524 mg, 3.79 mmol). The mixture was heated to 120° C. with vigorous stirring for 12 hours. The mixture was cooled down to room temperature. Water was added and the solid was filtered and rinsed with more to afford the title compound. MS (ES$^+$) 310.

Example 7

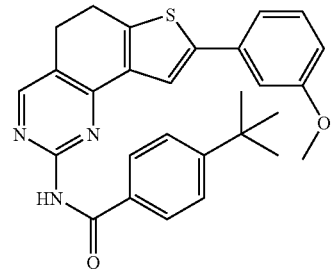

4-tert-Butyl-N-[8-(3-methoxyphenyl)-(5,6-dihydrothieno[2,3-h]quinazolin-2-yl)-benzamide 4-tert-Butylbenzoyl chloride (0.171 mL, 0.88 mmol) was added to 8-(3-methoxyphenyl)-(5,6-dihydrothieno[2,3-h]quinazolin-2-ylamine (0.129 g, 0.42 mmol) in pyridine (1 mL). The reaction mixture was stirred at room temperature overnight. The reaction mixture was concentrated in vacuo. The residue was taken up in dichloromethane (20 mL), washed with water (20 mL×2) and saturated sodium bicarbonate solution (20 mL×2), dried (MgSO$_4$) and concentrated in vacuo. The resulting crude mixture was purified by silica gel chromatography to afford the title compound as a beige solid (75 mg, 30% yield). MS (ES$^+$) 470, (ES$^-$) 468. δH (d$^6$ DMSO) 1.32 (9H, s), 3.02-3.15 (4H, m), 3.83 (3H, s), 6.93 (1H, dd), 7.17 (1H, t), 7.22 (1H, d), 7.36 (1H, t), 7.54 (2H, d), 7.78 (1H, s), 7.94 (2H, d), 8.56 (1H, s), 10.74 (1H, s).

A variety of other compounds of formula I have been prepared by methods substantially similar to those described in Example 7. The characterization data for these compounds is summarized in Table 11 below and includes HPLC, LC/MS (observed) and ¹H NMR data.

¹H NMR data is summarized in Table 11 below wherein ¹H NMR data was obtained at 400 MHz in deuterated DMSO, unless otherwise indicated, and was found to be consistent with structure. Compound numbers correspond to the compound numbers listed in Table 1.

TABLE 11

Characterization Data for Selected Compounds of Formula I

| Compound No. | M + 1 (obs) | Rt (min) | ¹H-NMR |
|---|---|---|---|
| I-30 | 378 | 9.71 | 0.78-0.87(4H, m), 2.14-2.21(1H, m), 2.98-3.12(4H, m), 3.84(3H, s), 6.94(1H, dd), 7.17(1H, t), 7.22(1H, d), 7.37(1H, t), 7.78(1H, s), 8.48(1H, s), 10.65(1H, s) |
| I-32 | 414 | 9.96 | 3.03-3.16(4H, m), 3.83(3H, s), 6.93(1H, dd), 7.17(1H, t), 7.23(1H, d), 7.37(1H, t), 7.52(2H, t), 7.61(1H, t), 7.76(1H, s), 7.98(2H, d), 8.57(1H, s),10.84(1H, s) |
| I-33 | 457 | 10.18 | 3.02(6H, s), 3.02-3.15(4H, m), 3.83(3H, s), 6.75(2H, d), 6.93(1H, dd), 7.18(1H, t), 7.23(1H, d), 7.36(1H, t), 7.81(1H, s), 7.90(2H, d), 8.54(1H, s), 10.40(1H, s) |
| I-34 | 403 | 9.72 | 3.02-3.15(4H, m), 3.84(3H, s), 6.17(1H, m), 6.93(1H, dd), 7.00(1H, m), 7.18-7.20(2H, m), 7.23(1H, d), 7.37(1H, t), 7.85(1H, s), 8.54(1H, s), 10.35(1H, s), 11.68(1H, br s) |

Example 8

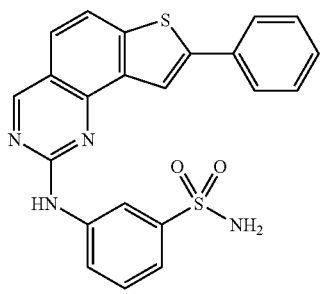

3-(8-Phenyl-thieno[2,3-h]quinazolin-2-ylamino)-benzenesulfonamide

To a dark solution of 3-(8-Phenyl-5,6-dihydro-thieno[2,3-h]quinazolin-2-ylamino)-benzenesulfonamide (130 mg, 0.30 mmol) in anhydrous 1,4-dioxane (7 mL) was added DDQ (75 mg, 0.33 mmol) and the mixture was refluxed under nitrogen for 2-3 hours. The reaction mixture was concentrated in vacuo and the resulting crude residue was triturated in a mixture of 2M NaOH (25 mL) and DCM (25 mL). The resulting solid was filtered and washed with DCM and water to afford 50 mg (39% yield) of the title compound as a pale yellow/green powder. MS (ES⁺) 433, (ES⁻) 431. δH (d⁶ DMSO) 7.39 (2H, br s), 7.41 (1H, m), 7.51 (4H, br m), 7.72 (1H, d), 7.83 (1H, d), 7.96 (3H, m), 8.68 (1H, s), 9.40 (1H, s), 9.61 (1H, br s) and 10.41 (1H, s).

A variety of other compounds of formula II have been prepared by methods substantially similar to those described in Example 8. The characterization data for these compounds is summarized in Table 12 below and includes HPLC, LC/MS (observed) and ¹H NMR data.

¹H NMR data is summarized in Table 12 below wherein ¹H NMR data was obtained at 400 MHz in deuterated DMSO, unless otherwise indicated, and was found to be consistent with structure. Compound numbers correspond to the compound numbers listed in Table 2.

TABLE 12

Characterization Data for Selected Compounds of Formula II

| Compound No. | M + 1 (obs) | Rt (min) | ¹H-NMR |
|---|---|---|---|
| II-31 | 357 | 8.55 | 7.37(2H, s), 7.48(1H, d), 7.55(1H, t), 7.84(1H, d), 7.90(1H, dd), 7.98-8.03(2H, m), 8.29(1H, d), 9.24(1H, s), 9.40(1H, s), 10.39(1H, s) |
| II-32 | 306 | 10.52 | 2.32(6H, s), 6.67(1H, s), 7.72(2H, s), 7.79(1H, d), 7.95(1H, d), 7.98(1H, d), 8.06(1H, d), 9.33(1H, s), 9.87(1H, s) |
| II-33 | 335 | 8.77 | 2.11(3H, s), 7.11(1H, d), 7.25(1H, t), 7.53(1H, d), 7.80(1H, d), 7.92-7.97(2H, m), 8.44(1H, d), 8.72(1H, s), 9.34(1H, s), 9.96(1H, s), 9.99(1H, s) |
| II-34 | 293 | 8.75 | 6.91(1H, d), 7.43(1H, t), 7.73(1H, d), 7.84(1H, d), 7.98-8.03(2H, m), 8.32(1H, d), 8.38(1H, d), 9.40(1H, s), 10.30(1H, s) |
| II-35 | 372 | 7.60 | 2.92(3H, s), 7.37(2H, s), 7.49(1H, d), 7.56(1H, t), 7.89(1H, d), 7.97(1H, d), 8.09(1H, d), 8.68(1H, s), 9.44(1H, s), 10.45(1H, s). |
| II-36 | 472 | 9.0 | 1.28(9H, s), 5.62(2H, s), 7.47-7.55(2H, m), 7.98(2H, d), 8.04(1H, d), 8.79(1H, s), 9.50(1H, s), 10.50(1H, s) |
| II-37 | 443 | 7.6 | 3.67(4H, t), 3.79(4H, t), 7.35(2H, s), 7.46(1H, m), 7.51-7.56(2H, m), 7.84(1H, d), 8.12(1H, d), 8.62(1H, t), 9.27(1H, s), 10.30(1H, s) |
| II-38 | 429 | 8.5 | 1.26(6H, t), 3.63(4H, m), 7.35(2H, s), 7.40-7.60(3H, m), 7.78(1H, d), 8.11(1H, d), 8.63(1H, s), 9.22(1H, s), 10.24(1H, s) |
| II-39 | 441 | 8.8 | 1.68(6H, s), 3.69(4H, s), 7.35(2H, s), 7.45(1H, d), 7.50(1H, d), 7.54(1H, t), 7.80(1H, d), 8.11(1H, dd), 8.64(1H, t), 9.24(1H, s), 10.26(1H, s) |

Example 9

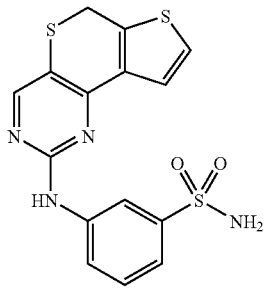

3-(4H-3,5-Dithia-7,9-diazacyclopenta[α]-naphthalen-8-ylamino)-benzenesulfonamide To 7H-thieno[2,3-c]thiopyran-4-one (495 mg, 2.91 mmol) dissolved in anhydrous DME (5 mL), was added Bredereck's reagent (0.9 mL, 4.36 mmol) and the reaction mixture was heated to 60° C. for 2 hours. The reaction mixture was cooled down and concentrated in vacuo. The resulting residue was purified by silica gel chromatography eluting with a gradient of EtOAc:hexanes to give the enaminone as a yellow solid in 58% yield.

The above (100 mg, 0.44 mmol) was dissolved in anhydrous propan-2-ol (5 mL) and treated with 3-Guanidino-benzenesulfonamide hydrogen chloride (172 mg, 0.66 mmol) and powdered sodium hydroxide (20 mg, 0.49 mmol). The mixture was refluxed with vigorous stirring for 12 hours. The mixture was cooled down to room temperature and concentrated in vacuo. The resulting residue was purified by silica gel chromatography eluting with EtOAc:hexanes (50:50) to afford the title compound (25 mg) as a yellow solid. MS (ES+) 377. δH (CDCl$_3$) 4.20 (2H, d), 4.80 (2H, br s), 7.20-7.35 (2H, m), 7.45-7.80 (4H, m), 8.40 (1H, s), 8.80 (1H, s).

Example 10

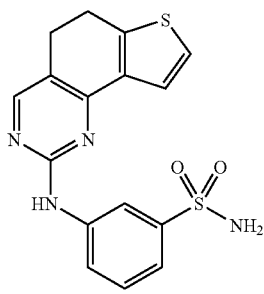

3-(5,6-Dihydrothieno[2,3-h]quinazolin-2-ylamino)-benzenesulfonamide

To 6,7-dihydro-5H-benzo[b]thiophen-4-one (0.5 g, 3.29 mmol) was added DMF/DMA solution (2 mL) and the mixture was refluxed under nitrogen for 12 hours. The reaction mixture was concentrated in vacuo and the resulting crude product (5-dimethylaminomethylene-6,7-dihydro-5H-benzo[b]thiophen-4-one) was taken through to the next step without further purification.

The above was dissolved in anhydrous DMA (3 mL) and treated with 4-guanidino-benzenesulfonamide hydrogen chloride (1.23 g, 4.93 mmol) and powdered potassium carbonate (341 mg, 2.47 mmol). The mixture was heated to 120° C. with vigorous stirring for 12 hours. The mixture was cooled down to room temperature and concentrated in vacuo. The residue was triturated with hot ethyl acetate (30 ml) and 1M HCl (30 ml), filtered and washed with water and ethyl acetate to afford the title compound (546 mg) as a pale green powder in 46% yield. MS (ES+) 359, (ES−) 357. δH (d$^6$ DMSO) 2.93 (2H, m), 3.04 (2H, m), 6.88 (1H, m), 7.29 (1H, br s), 7.40 (1H, m), 7.45 (1H, t), 7.65 (1H, d), 7.77 (1H, d), 8.40 (1H, s), 8.70 (1H, br s) and 10.05 (1H, br s).

A variety of other compounds of formula I have been prepared by methods substantially similar to those described in Example 10. The characterization data for these compounds is summarized in Table 13 below and includes HPLC, LC/MS (observed) and $^1$H NMR data.

$^1$H NMR data is summarized in Table 13 below wherein $^1$H NMR data was obtained at 400 MHz in deuterated DMSO, unless otherwise indicated, and was found to be consistent with structure. Compound numbers correspond to the compound numbers listed in Table 1.

TABLE 13

Characterization Data for Selected Compounds of Formula I

| Compound No. | M + 1 (obs) | Rt (min) | $^1$H-NMR |
|---|---|---|---|
| I-42 | 325 | 10.32 | 2.98(2H, t), 3.10(2H, t), 7.5-7.6(2H, m), 7.65(1H, d), 7.76(1H, d), 8.04(1H, d), 8.43(1H, s), 9.20(1H, s), 10.09(1H, s) |
| I-43 | 308 | 10.59 | 2.25(6H, s), 2.91(2H, t), 3.04(2H, t), 6.57(1H, s), 7.45-7.54(4H, m), 8.32(1H, s), 9.32(1H, s) |
| I-44 | 337 | 8.69 | 2.06(3H, s), 2.93(2H, t), 3.05(2H, t), 7.11-7.21(2H, m), 7.39(1H, d), 7.49(1H, d), 7.71(1H, d), 8.18(1H, s), 8.31(1H, s), 9.59(1H, s), 9.90(1H, s) |
| I-45 | 434 | 8.85 | 1.40-1.55(6H, m), 2.45-2.67(8H, m), 2.92(2H, t), 3.05(2H, t), 7.14-7.20(2H, m), 7.35-7.41(1H, m), 7.47(1H, d), 7.71(1H, d), 8.20(1H, s), 8.31(1H, s), 9.48(1H, s), 10.23(1H, s) |
| I-47 | 366 | 7.80 | 2.72(2H, t), 2.93(2H, t), 3.02-3.14(4H, m), 7.20(2H, d), 7.41(1H, m), 7.48(1H, d), 7.71(1H, d), 7.76(3H, br s), 8.21(1H, s), 8.32(1H, s), 9.54(1H, s), 10.11(1H, s) |
| I-48 | 394 | 8.33 | 2.21(6H, s), 2.46(2H, t), 2.60(2H, t), 2.92(2H, t), 3.05(2H, t), 7.11-7.19(2H, m), 7.37(1H, d), 7.47(1H, d), 7.72(1H, d), 8.24(1H, s), 8.32(1H, s), 9.46(1H, s), 9.99(1H, s) |
| I-49 | 449 | 8.88 | 2.14(3H, s), 2.20-2.52(10H, t), 2.63(2H, t), 2.92(2H, t), 3.05(2H, t), 7.12-7.20(2H, m), 7.38(1H, d), 7.47(1H, d), 7.72(1H, d), 8.22(1H, s), 8.32(1H, s), 9.47(1H, s), 10.07(1H, s) |
| I-50 | 436 | 8.81 | 2.43(4H, m), 2.64(2H, t), 2.92(2H, t), 3.05(2H, t), 3.60(4H, t), 7.15-7.20(2H, m), 7.39(1H, m), 7.47(1H, d), 7.71(1H, d), 8.20(1H, s), 8.31(1H, s), 9.47(1H, s), 10.06(1H, s) |

Example 11

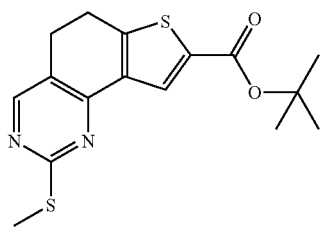

2-Methylsulfanyl-5,6-dihydro-thieno[2,3-h]quinazoline-8-carboxylic acid tert-butyl ester 5-[1-Dimethylamino-methylidene]-4-oxo-4,5,6,7-tetrahydro-benzo[b]thiophene-2-carboxylic acid tert-butyl ester (14.36 g, 46.72 mmol), $Na_2CO_3$ (8.17 g, 77.09 mmol) and S-methylisothiouronium sulphate (19.51 g, 70.08 mmol) were suspended/dissolved in dry DMA (140 mL) and stirred at 120° C. for 1.5 hours. The solvent was removed under reduced pressure and the resultant brown solid mass was partitioned between hot EtOAc and brine using sonication. The aqueous layer was further extracted with EtOAc (3×200 mL) and the combined organics were washed sequentially with dilute $NaHSO_4$ (1×100 mL) [It took 15 minutes for the emulsified mixture to separate fully.], saturated $Na_2CO_3$ (1×100 mL) and brine (1×100 mL), dried over $Na_2SO_4$, filtered and concentrated under reduced pressure to give an ochre-brown solid. This solid was redissolved in DCM, silica (~100 mL) was added and the resulting suspension was concentrated under reduced pressure. The solid obtained was subjected to column chromatography (gradient elution, 20-40% EtOAc in hexanes, ~1 L silica) giving a light yellow solid (8.78 g, 56% yield). MS (ES$^+$) 335, (ES$^-$) 332. δH (CDCl$_3$) 1.6 (9H, s), 2.6 (3H, s), 3.0-3.2 (4H, m), 8.2 (1H, s), 8.3 (1H, s).

Example 12

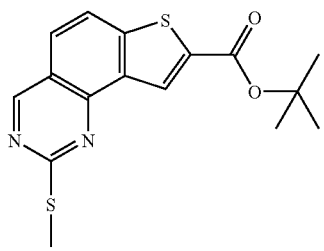

2-Methylsulfanyl-thieno[2,3-h]quinazoline-8-carboxylic acid tert-butyl ester

2-Methylsulfanyl-5,6-dihydro-thieno[2,3-h]quinazoline-8-carboxylic acid tert-butyl ester (9.0 g, 26.91 mmol) and DDQ (12.22 g, 53.82 mmol) were suspended/dissolved in dry dioxane (100 mL) and heated at reflux for 1 hour. Further DDQ (12.22 g, 53.82 mmol) was added and the resulting suspension was heated at reflux for 1.5 hours. After cooling to room temperature the mixture was concentrated under reduced pressure and then partitioned between EtOAc and saturated $Na_2CO_3$. The aqueous layer was further extracted with EtOAc (3×200 mL) and the combined organics were washed with saturated $Na_2CO_3$ (2×250 mL) and brine (1×200 mL), dried over $Na_2SO_4$, filtered and concentrated under reduced pressure. The deep brown gum obtained was redissolved in hot acetone, silica (~60 mL) was added and the resultant suspension was concentrated under reduced pressure. The solid obtained was subjected to column chromatography (gradient elution, 20-30% acetone in hexanes, ~600 mL silica) giving a light brown solid (6.50 g, 73% yield). ). MS (ES$^+$) 333. δH (CDCl$_3$) 1.7 (9H, s), 2.8 (3H, s), 7.8 (1H, d), 7.9 (1H, d), 8.8 (1H, s), 9.2 (1H, s)

Example 13

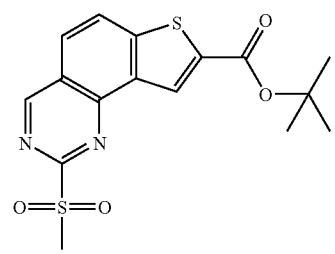

2-Methanesulfonyl-thieno[2,3-h]quinazoline-8-carboxylic acid tert-butyl ester

2-Methylsulfanyl-thieno[2,3-h]quinazoline-8-carboxylic acid tert-butyl ester (6.50 g, 19.55 mmol) was suspended/dissolved in DCM (150 mL) and cooled in an ice-bath. 3-chloroperbenzoic acid (22.49 g, 97.76 mmol, 75% pure) was added in one portion and the resultant suspension was stirred at 0° C. for 5 minutes and at room temperature for a further 55 minutes. This mixture was then carefully added to a 1:1:1 mixture of saturated $Na_2CO_3$, saturated $Na_2S_2O_3$ and brine (~500 mL). The organic layer was separated and the aqueous layer was further extracted with DCM (3×200 mL). The combined organics were washed with brine (1×100 mL), dried over $Na_2SO_4$, filtered and concentrated under reduced pressure. The yellow solid obtained was redissolved in acetone, silica (~80 mL) was added and the suspension was concentrated under reduced pressure. The solid obtained was subjected to column chromatography (gradient elution, 5-10% EtOAc in DCM, ~600 mL silica) to give a yellow solid (6.25 g, 88% yield). MS (ES$^+$) 365. δH (CDCl$_3$) 1.7 (9H, s), 3.5-3.6 (3H, s), 8.0 (1H, d), 8,2 (1H, d), 8,9 (1H, s), 9.6 (1H, s)

Example 14

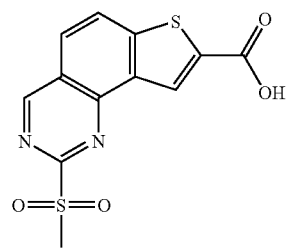

2-Methanesulfonyl-thieno[2,3-h]quinazoline-8-carboxylic acid

2-Methanesulfonyl-thieno[2,3-h]quinazoline-8-carboxylic acid tert-butyl ester (4.20 g, 11.52 mmol) was placed in a 500 mL Florentine and cooled in an ice-bath. Pre-mixed TFA:DCM:water (1:1:0.025, 4.5 mL) was added in one portion and the resultant solution was stirred at 0° C. for 0.75 hours and a further 0.75 hours at room temperature. The reaction mixture was concentrated under reduced pressure and azeotroped with portions of DCM (5×50 mL) and Et$_2$O (5×50 mL). The solid obtained was triturated with Et$_2$O, filtered and washed with Et$_2$O (3×5mL) to give a light yellow powder (3.51 g, 99% yield). δH (d$^6$ DMSO) 3.6-3.7(3H, s), 8.3(1H, d), 8.6(1H, d), 8.8(1H, s), 9.9-10.0(1H, s), 13.8-14.0 (1H, br s)

Example 15

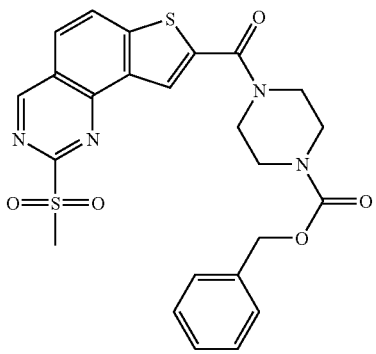

4-(2-Methanesulfonyl-thieno[2,3-h]quinazoline-8-carbonyl)-piperazine-1-carboxylic acid benzyl ester 2-Methanesulfonyl-thieno[2,3-h]quinazoline-8-carboxylic acid (3.51 g, 11.38 mmol), 1-hydroxyazatriazole (1.70 g, 12.52 mmol), 1-benzylpiperazine carboxylate (2.76 g, 12.52 mmol) and diisopropylethylamine (1.62 g, 12.52 mmol) were dissolved in dry DMF (35 mL) and cooled in an ice-bath. EDC (2.40 g, 12.52 mmol) was added in one portion and the resulting suspension was stirred at 0° C. for 20 minutes and for a further 16 hours at room temperature. The reaction was concentrated under reduced pressure and partitioned between hot DCM and brine. The aqueous layer was extracted with DCM (3×50 mL) and the combined organics were washed sequentially with dilute HCl (1×50 mL), saturated Na$_2$CO$_3$ (1×50 mL) and brine (1×50 mL), dried over Na$_2$SO$_4$, filtered and concentrated under reduced pressure. The yellow wax obtained was subjected to column chromatography (50% EtOAc in DCM, loaded in DCM, ~350 mL silica) giving a cream solid which was immediately triturated with EtOAc, filtered and washed with pentane (3×20 mL) to give a cream powder (4.33 g, 75% yield). The filtration liquors were concentrated under reduced pressure and the solid obtained was triturated with EtOAc, filtered and washed with pentane (3×5 mL) to give a second crop of cream powder (0.58 g, 10% yield). MS (ES$^+$) 511. δH (CDCl$_3$) 3.5 (3H, s), 3.7 (4H, br m), 3.9 (4H, br m), 7.3-7.4 (5H, m), 8.0 (1H, d), 8.2-8.3 (1H, d), 8.5 (1H, s), 9.6 (1H, s).

Example 16

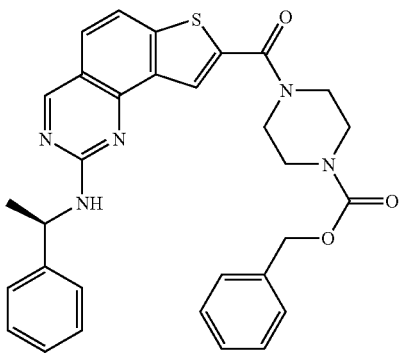

4-[2-((R)-1-Phenyl-ethylamino)-thieno[2,3-h]quinazoline-8-carbonyl]-piperazine-1-carboxylic acid benzyl ester 4-(2-Methanesulfonyl-thieno[2,3-h]quinazoline-8-carbonyl)-piperazine-1-carboxylic acid benzyl ester (0.2 g, 0.39 mmol), TFA (4.5 mg, 0.04 mmol) and (R)-(α-methyl)benzylamine (0.47 g, 3.92 mmol) was suspended/dissolved in dry dioxane (2 mL) and stirred at 120° C. for 16 hours. The reaction mixture was concentrated under reduced pressure and partitioned between DCM and dilute HCl. The organic layer was washed with saturated Na$_2$CO$_3$ (1×10 mL) and brine (1×10 mL), dried over Na$_2$SO$_4$, filtered and concentrated under reduced pressure. The brown gum obtained was redissolved in DCM, silica (~5 mL) was added and the suspension was concentrated under reduced pressure. The solid obtained was subjected to column chromatography (25% EtOAc in DCM, ~75 mL silica) to give a light yellow gum (198.4 mg, 92% yield). MS (ES$^+$) 552, (ES$^-$) 551. δH (CDCl$_3$) 1.7 (3H, d), 3.6-3.7 (4H, br m), 3.8-4.0 (4H, br m), 5.2 (2H, s), 5.4 (1H, m), 5.7-5.8 (1H, br d), 7.2-7.5 (10 H, m), 7.6 (2H, s), 8.1-8.2 (1H, s), 9.0 (1H, s)

Example 17

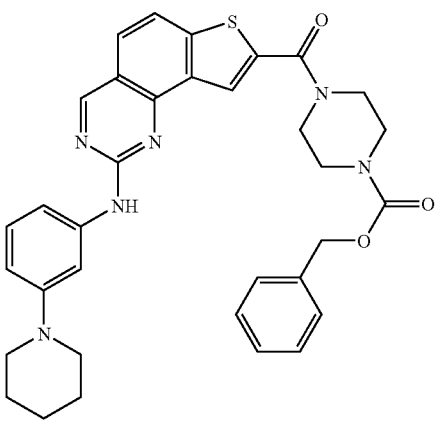

4-[2-(3-Piperidin-1-yl-phenylamino)-thieno[2,3-h]quinazoline-8-carbonyl]-piperazine-1-carboxylic acid benzyl ester Formyl [(3-piperadinyl)-aniline] (0.14 g, 0.71 mmol) was dissolved in dry THF (5 mL) and sodium hydride (35 mg, 0.88 mmol, 60wt % in oil) was added in one portion. The resultant suspension was stirred at room temperature for 1 hour and cooled in an ice-bath. 4-(2-Methanesulfonyl-thieno[2,3-h]quinazoline-8-carbonyl)-piperazine-1-carboxylic acid benzyl ester (0.3 g, 0.59 mmol) was added in one portion and the suspension obtained was stirred at 0° C. for 1.5 hours. HCl (1 mL, 6M) was added and the homogeneous reaction was allowed to stir at room temperature for 3 hours. After concentration under reduced pressure the reaction mixture was partitioned between DCM and dilute HCl. The organic layer was washed with very dilute $Na_2CO_3$ (High dilution reduced emulsion problems), brine (1×10 mL), dried over $Na_2SO_4$, filtered and concentrated under reduced pressure. The yellow gum obtained was subjected to column chromatography (5% MeOH in DCM, loaded in DCM, ~50 mL silica) and gave a bright yellow powder (212 mg, 59% yield). MS (ES$^+$) 607, (ES$^-$) 605. δH (CDCl$_3$) 1.6 (2H, m), 1.8 (4H, m), 3.3 (4H m), 3.6-3.7 (4H, br m), 3.8-4.0 (4H, br m), 5.2 (2H, s), 6.7 (1H, m), 7.3 (3H, m), 7.4 (6H, m), 7.6 (1H, m), 7.7 (2H, m), 8.3 (1H, s), 9.1 (1H, s).

Example 18

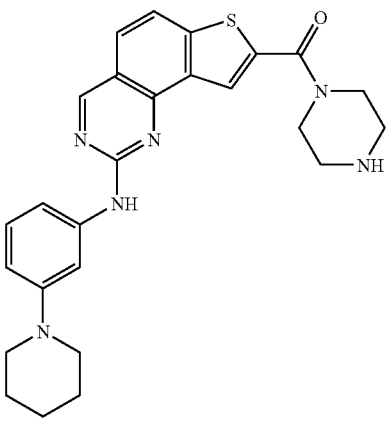

Piperazin-1-yl-[2-(3-piperidin-1-yl-phenylamino)-thieno[2,3-h]quinazolin-8-yl]-methanone 4-[2-(3-Piperidin-1-yl-phenylamino)-thieno[2,3-h]quinazoline-8-carbonyl]-piperazine-1-carboxylic acid benzyl ester (205 mg, 0.34 mmol) was dissolved in dry DCM (4 mL) and HBr (2 mL, 33 wt % solution in AcOH) added. The resultant mixture was stirred at room temperature for 0.5 hours and concentrated under reduced pressure. The yellow gum obtained was partitioned between Et$_2$O and dilute HCl. The aqueous layer was extracted with Et$_2$O (1×10 mL). The aqueous layer was then basified with saturated Na$_2$CO$_3$ and extracted with DCM (3×10 mL). The DCM organics were dried over Na$_2$SO$_4$, filtered and concentrated under reduced pressure. The brown gum obtained was redissolved in DCM, silica (~5 mL) added and concentrated under reduced pressure. The solid obtained was subjected to column chromatography (10% MeOH in DCM, ~100 mL silica) to give a bright yellow solid. This solid was triturated with Et$_2$O, filtered and washed with Et$_2$O (3×5 mL) and pentane (3×5 mL) to give a yellow powder (96.4 mg, 60% yield). MS (ES$^+$) 473, (ES$^-$) 472. δH (CDCl$_3$) 1.5-1.9 (6H, m), 2.9-3.1 (4H, m), 3.2-3.3 (4H, m), 3.8-3.9 (4H, m), 6.7 (1H m), 7.2-7.3 (3H, m), 7.4 (1H, s), 7.6-7.7 (3H, m), 8.2-8.3 (1H, s), 9.1 (1H, s)

Example 19

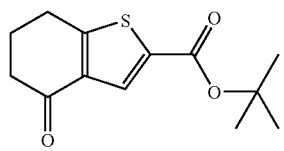

4-Oxo-4,5,6,7-tetrahydro-benzo[b]thiophene-2-carboxylic acid tert-butyl ester 4-Oxo-4,5,6,7-tetrahydro-benzo[b]thiophene-2-carboxylic acid (Behringer, H.; Falkenberg, K. *Chem. Ber.*, 1966, 99, 3309) (7.69 g, 39.19 mmol) was suspended in 120 mL 2:1 cyclohexane: dichloromethane. Tert-butyl 2,2,2-trichloroacetimidate (17.13 g, 78.38 mmol) was added in one portion, followed by boron trifluoride diethyl etherate (87.8 mg, 6.19 µmol, 0.16 mol %). The resultant slurry was stirred vigorously for 1.5 hours and a further portion of tert-butyl 2,2,2-trichloroacetimidate (8.57 g, 39.19 mmol) was added. Stirring was continued overnight. Further portions of tert-butyl 2,2,2-trichloroacetimidate (8.57 g, 39.19 mmol) were added at 1.5 hours and 3 hours and after a further 3 hours the reaction was quenched by cautious addition of solid NaHCO$_3$ (~1 g). Silica was added (~80 mL) and the resulting suspension was concentrated under reduced pressure. The resulting crude mixture was purified by silica gel chromatography (20% EtOAc in hexanes on 1 L of silica) to afford the title compound as a light yellow solid (8.81 g, 89% yield). ). MS (ES$^+$) 253. δH (CDCl$_3$) 1.5-1.6 (9H, s), 2.2-2.3 (2H, m), 2.5-2.6 (2H, m), 3.0-3.1 (2H, m), 7.9 (1H, s).

Example 20

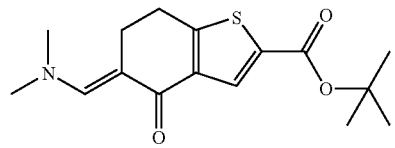

5-Dimethylaminomethylene-4-oxo-4,5,6,7-tetrahydro-benzo[b]thiophene-2-carboxylic acid tert-butyl ester 4-Oxo-4,5,6,7-tetrahydro-benzo[b]thiophene-2-carboxylic acid tert-butyl ester (8.75 g, 34.68 mmol) was suspended in dry toluene (40 mL) and Bredereck's reagent (6.65 g, 38.14 mmol) was added. The resulting suspension was heated at reflux for 2 hours, during which time all starting material dissolved, allowed to cool to room temperature and concentrated under reduced pressure. The resulting oil was purified by silica gel chromatography (50% EtOAc in hexanes on 1 L silica, loaded as a solution in dichloromethane) to afford the title compound as a brown solid (6.21 g, 58% yield). MS (ES+) 308. δH (CDCl₃) 1.5-1.6 (9H, s), 2.9-3.0 (2H, m), 3.0-3.1 (2H, m), 3.1 (6H, s), 7.6 (1H, s), 8.0 (1H, s).

Example 21

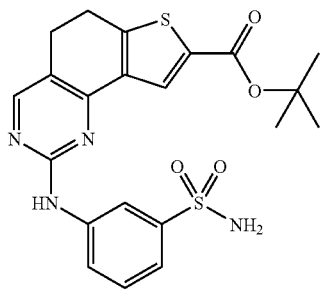

2-(3-Sulfamoyl-phenylamino)-5,6-dihydro-thieno[2,3-h]quinazoline-8-carboxylic acid tert-butyl ester 5-Dimethylaminomethylene-4-oxo-4,5,6,7-tetrahydro-benzo[b]thiophene-2-carboxylic acid tert-butyl ester (6.21 g, 20.20 mmol), 3-guanidinophenylsulphonamide hydrochloride (5.07 g, 20.20 mmol) and sodium hydroxide (0.81 g, 20.20 mmol) were suspended in isopropanol (250 mL) and stirred at reflux overnight. The reaction was allowed to cool to room temperature and diluted with water (~200 mL). The resulting precipitate was isolated by filtration and the solid obtained was washed with water (1×100 mL), isopropanol (1×50 mL), diethyl ether (2×50 mL) and pentane (3×100 mL). Air drying gave an ochre powder (4.92 g, 53% yield). MS (ES+)459. δH (d⁶ DMSO) 1.5-1.6 (9H, s), 2.9-3.0 (2H, m), 3.1-3.2 (2H, m), 7.2-7.3 (2H, br s), 7.3-7.5 (2H, m), 7.7-7.8 (1H, m), 8.1 (1H, s), 8.4 (1H, s), 8.6 (1H, s), 9.9 (1H, s).

Example 22

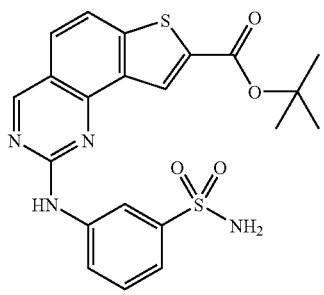

2-(3-Sulfamoyl-phenylamino)-thieno[2,3-h]quinazoline-8-carboxylic acid tert-butyl ester 2-(3-Sulfamoyl-phenylamino)-5,6-dihydro-thieno[2,3-h]quinazoline-8-carboxylic acid tert-butyl ester (4.90 g, 10.69 mmol) and 2,3-dichloro-5,6-dicyano-1,4-benzoquinone (4.85 g, 21.37 mmol) were suspended in dry 1,4-dioxane (300 mL) and heated at reflux overnight. After allowing the reaction to cool to room temperature the mixture was concentrated under reduced pressure and partitioned between ethyl acetate and 1:1 saturated Na₂CO₃:brine. The organic layer was washed with further portions of 1:1 saturated Na₂CO₃:brine (2×200 mL), dried over Na₂SO₄, and filtered. Silica (~60 mL) was added to the filtrate and the resulting suspension was concentrated under reduced pressure. The resulting solid was purified by silica gel chromatography (80-90% EtOAc in hexanes on ~800 mL of silica) to afford the title compound as a yellow solid (1.84 g, 38% yield) and further impure material (~2 g). MS (ES+) 457. δH (d⁶ DMSO) 1.6 (9H, s), 7.3 (2H, br s), 7.4-7.6 (2H, m), 7.8-7.9 (1H, m), 8.0 (2H, m), 8.7 (1H, s), 9.1 (1H, br s), 9.4 (1H, s), 10.4-10.5 (1H, s).

A variety of other compounds of formula V have been prepared by methods substantially similar to those described in Example 22. The characterization data for these compounds is summarized in Table 14 below and includes HPLC, LC/MS (observed) and ¹H NMR data.

¹H NMR data is summarized in Table 14 below wherein ¹H NMR data was obtained at 400 MHz in CDCl₃, unless otherwise indicated, and was found to be consistent with structure. Compound numbers correspond to the compound numbers listed in Table 5.

TABLE 14

Characterization Data for Selected Compounds of Formula V

| Compound No. | M + 1 (obs) | Rt (min) | ¹H-NMR |
|---|---|---|---|
| V-29 | 434 | 11.7 | (CDCl₃)1.5(9H, s), 1.6-1.7(9H, s), 7.2(1H, m), 7.3-7.4(1H, m), 7.4(1H, s), 7.5-7.6(1H, m), 7.6-7.7(1H, m), 8.0-8.1(1H, s), 8.7-8.8(1H, s), 9.1(1H, s) |
| V-30 | 454 | 11.6 | 1.6-1.7(9H, s), 7.4(2H, m), 7.5(4H, m), 7.6-7.7(4H, m), 7.8-7.9(1H, m), 8.1-8.2(1H, s), 8.7-8.8(1H, s), 9.1(1H, s) |
| V-31 | 434 | 11.6 | 1.4(9H, s), 1.7(9H, s), 7.4(1H, m), 7.4-7.5(2H, m), 7.7(2H, s), 7.8(2H, m), 8.7-8.8(1H, s), 9.1(1H, s) |
| V-32 | 396 | 11.2 | 1.7(9H, s), 6.8(1H, m), 7.3-7.4(2H, m), 7.5(1H, s), 7.7(2H, m), 8.0-8.1(1H, m), 8.7-8.8(1H, s), 9.1(1H, s) |
| V-33 | 392 | 11.1 | 1.7(9H, s), 2.4-2.5(3H, s), 7.1(1H, m), 7.2(1H, s), 7.3(1H, m), 7.3-7.4(1H, m), 7.7(2H, s), 8.4-8.5(1H, m), 8.7(1H, s), 9.1(1H, s) |
| V-34 | 378 | 11.0 | (DMSO-d6) 1.70(9H, s), 7.05(1H, t), 7.40(2H, t), 8.00(1H, s), 8.05(2H, d), 8.60(1H, d), 9.40(1H, s), 10.15(1H, s) |
| V-35 | / | 9.5 | 1.10-1.90(17H, m), 2.00(2H, m), 3.75(1H, m), 6.95(1H, d), 7.25(1H, d), 8.05(1H, s), 8.60(1H, d) |

Example 23

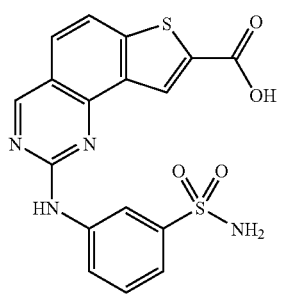

2-(3-Sulfamoyl-phenylamino)-thieno[2,3-h]quinazoline-8-carboxylic acid 2-(3-Sulfamoyl-phenylamino)-thieno[2,3-h]quinazoline-8-carboxylic acid tert-butyl ester (1.84 g, 4.02 mmol) was placed in a 100 mL florentine and cooled in an ice-bath. Premixed TFA/dichloromethane/water (1:4:0.1, 9 mL TFA) was added in one portion and the resultant suspension was stirred at 0° C. for 10 minutes. After a further 2.5 hours at room temperature and 1.5 hours at 40° C. the reaction was concentrated under reduced pressure. The solid obtained was azeotroped with dry dichloromethane (3×10 mL), triturated with diethyl ether and isolated by filtration. The solid obtained was washed with diethyl ether (4×5 mL) and dried in a drying pistol at 40° C. overnight to afford the title compound as a yellow powder (1.44 g, 86% yield containing 1.24 eq. TFA). MS (ES⁺) 400. δH (d⁶ DMSO) 7.2-7.4 (2H, br s), 7.5 (1H, m), 7.6 (1H, m), 8.0 (3H, m), 8.7 (1H, s), 8.8-8.9 (1H, s), 9.4 (1H, s), 10.4-10.5 (1H, s), 13.4-13.8 (1H, br s).

Example 24

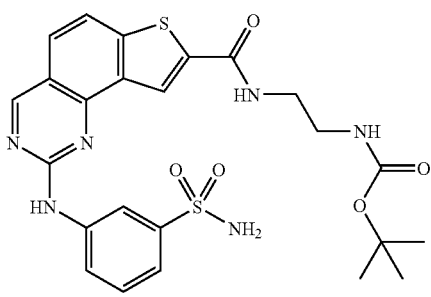

(2-{[2-(3-Sulfamoyl-phenylamino)-thieno[2,3-h]quinazoline-8-carbonyl]-amino}-ethyl)-carbamic acid tert-butyl ester 2-(3-Sulfamoyl-phenylamino)-thieno[2,3-h]quinazoline-8-carboxylic acid (150 mg, 0.37 mmol), 1-hydroxy-7-azabenzotriazole (56 mg, 0.41 mmol), N,N-diisopropylethylamine (73 mg, 0.56 mmol) and BOC-ethylenediamine (66 mg, 0.41 mmol) were dissolved in dry DMF (2 mL) and cooled in an ice-bath. EDC (79 mg, 0.41 mmol) was added in one portion and the resultant suspension was stirred overnight allowing the ice-bath to melt. The reaction was concentrated under reduced pressure, redissolved in isopropanol (~10 mL) and water was added (~5 mL). The precipitate formed was isolated by filtration and washed with water (1×5 mL), dilute NaHSO₄ (1×5 mL), water (1×5mL), saturated Na₂CO₃ (1×5 mL), water (1×5mL), isopropanol (1×5 mL), diethyl ether (2×5 mL) and pentane (2×5 mL) giving an ochre powder (102 mg, 51% yield). MS (ES⁺) 543. δH (d⁶ DMSO) 1.2-1.5 (9H, s), 3.3-3.5 (4H, br m), 6.6 (0.1 H, br s), 7.0 (0.9H, br s), 7.1-7.4 (2H, br s), 7.4-7.6 (2H, m), 7.8-8.0 (2H, m), 8.2 (1H, m), 8.6-9.0 (3H, br m), 9.4 (1H, s), 10.3-10.6 (1H, br s).

Example 25

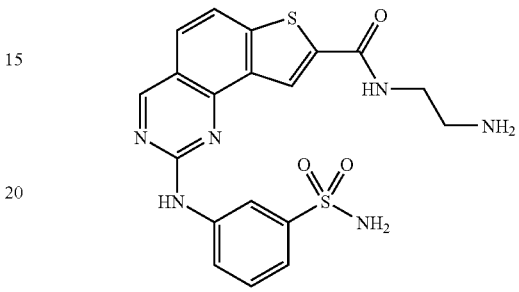

2-(3-Sulfamoyl-phenylamino)-thieno[2,3-h]quinazoline-8-carboxylic acid (2-amino-ethyl)-amide (2-{[2-(3-Sulfamoyl-phenylamino)-thieno[2,3-h]quinazoline-8-carbonyl]-amino}-ethyl)-carbamic acid tert-butyl ester (138.1 mg, 0.25 mmol) was placed in a 50 mL florentine and cooled in an ice-bath. Premixed TFA/dichloromethane/water (1:4:0.1, 0.5 mL TFA) was added in one portion and the resultant suspension was stirred at 0° C. for 35 minutes. After a further 1.75 hours at room temperature the solution was concentrated under reduced pressure to give a yellow solid. This solid was azeotroped with dichloromethane (3×10 mL), triturated with diethyl ether and isolated by filtration. The solid collected was washed with diethyl ether (3×5 mL) and pentane (3×5 mL) and placed in a drying pistol at 40° C. overnight giving a yellow powder (145.5 mg, 95% yield containing ~1.5 eq. TFA). MS (ES⁺) 442. δH (d⁶ DMSO) 3.0-3.1 (2H, m), 3.5-3.7 (2H, m), 7.3-7.4 (2H, br s), 7.5 (1H, m), 7.6 (1H, m), 7.8-8.1 (5H, m), 8.2-8.3 (1H, m), 8.7-8.9 (3H, m), 9.4 (1H, s), 10.5 (1H, s).

A variety of other compounds of formula V have been prepared by methods substantially similar to those described in Example 18 or 25. The characterization data for these compounds is summarized in Table 15 below and includes HPLC, LC/MS (observed) and ¹H NMR data.

¹H NMR data is summarized in Table 15 below wherein ¹H NMR data was obtained at 400 MHz in deuterated DMSO, unless otherwise indicated, and was found to be consistent with structure. Compound numbers correspond to the compound numbers listed in Table 5.

TABLE 15

Characterization Data for Selected Compounds of Formula V

| Compound No. | M + 1 (obs) | Rt (min) | ¹H-NMR |
|---|---|---|---|
| V-36 | 468.0 | 8.5 | 1.5-1.8(6H, br m), 3.5-3.9(4H, br m), 7.1-7.4(2H, br s), 7.4-7.6(2H, m), 7.8-8.0(3H, m), 8.3(1H, s), 9.2(1H, s), 9.4(1H, s), 10.3-10.6(1H, br s) |

TABLE 15-continued

Characterization Data for Selected Compounds of Formula V

| Compound No. | M + 1 (obs) | Rt (min) | $^1$H-NMR |
|---|---|---|---|
| V-37 | 470.0 | 7.5 | 3.5-4.0(8H, br m), 7.2-7.4(2H, br s), 7.4-7.5(2H, m), 7.7(1H, m), 7.9(1H, m), 8.0(1H, m), 8.4(1H, s), 9.3-9.4(2H, m), 10.3-10.6(1H, br s) |
| V-38 | 569.0 | 8.9 | 1.4-1.5(9H, s), 3.4-3.6(4H, br m), 3.6-4.0(4H, br m), 7.3(2H, s), 7.4-7.6(2H, m), 7.7-7.8(1H, m), 7.9(1H, m), 8.0(1H, m), 8.4(1H, s), 9.3(1H, s), 9.4(1H, s), 10.4-10.5(1H, s) |
| V-39 | 557.0 | 8.7 | 1.2-1.5(9H, s), 1.6-1.8(2H, m), 3.0-3.1(2H, m), 3.2-3.5(2H, m), 6.5(0.1H, br s), 6.8-6.9(0.9H, br s), 7.1-7.4(2H, br s), 7.4-7.6(2H, m), 7.8-8.0(2H, m), 8.0-8.2(1H, m), 8.6-8.8(1H, br s), 8.8(1H, s), 9.0(1H, br s), 9.3-9.5(1H, br s), 10.3-10.6(1H, br s) |
| V-40 | 483.0 | 7.5 | 2.6-2.8(3H, br m), 2.9-4.8(8H, br m), 7.4(2H, br s), 7.5(2H, m), 7.7-7.8(1H, m), 7.9-8.1(2H, m), 8.4(1H, s), 9.4(2H, m), 10.5(1H, s) |
| V-41 | 557.0 | 8.8 | 1.3(9H, s), 2.8-2.9(3H, m), 3.3-3.5(4H, m), 7.2-7.4(2H, br s), 7.5-7.6(2H, m), 7.8-8.0(2H, m), 8.1-8.3(1H, m), 8.7-8.9(3H, m), 9.4(1H, s), 10.4(1H, s) |
| V-42 | 471.0 | 7.3 | 2.1-2.3(6H, m), 3.2-3.6(4H, m), 7.0-7.3(2H, br s), 7.4-7.6(2H, m), 7.8-8.1(3H, m), 8.5-8.7(1H, br s), 8.8-8.9(1H, s), 9.1(1H, s), 9.4(1H, s), 10.2-10.6(1H, br s) |
| V-4 | 468.9 | 6.8 | 2.7-2.9(4H, br m), 3.5-4.0(4H, br m), 7.2-7.4(2H, br s), 7.4-7.6(2H, m), 7.7-7.8(1H, m), 7.8-8.0(2H, m), 8.3-8.4(1H, br s), 9.2-9.3(1H, br s), 9.3-9.5(1H, br s), 10.3-10.5(1H, s) |
| V-43 | 457.0 | 6.8 | 2.3-2.4(3H, s), 2.7-2.8(2H, m), 3.4-3.5(2H, m), 5.4-6.2(2H, br s), 7.5(1H, m), 7.5-7.6(1H, m), 7.9(1H, m), 8.0(1H, m), 8.1(1H, m), 8.5(1H, m), 8.7-8.8(1H, s), 9.0-9.1(1H, s), 9.4-9.5(1H, s), 10.5(1H, s) |
| V-44 | 444.0 | 6.6 | 3.0-3.1(2H, m), 3.5-3.7(2H, m), 7.3-7.4(2H, br s), 7.5(1H, m), 7.6(1H, m), 7.8-8.1(5H, m), 8.2-8.3(1H, m), 8.7-8.9(3H, m), 9.4(1H, m), 10.5(1H, s) |
| V-45= | 458.0 | 6.8 | 1.8-2.0(2H, m), 2.8-3.0(2H, m), 3.3-3.5(2H, m), 7.3-7.4(2H, br s), 7.5(1H, m), 7.5-7.6(1H, m), 7.6-7.8(3H, br s), 7.8-8.0(2H, m), 8.1-8.2(1H, m), 8.7-8.8(2H, m), 8.9(1H, s), 9.4(1H, s), 10.4-1.5(1H, s) |
| V-46 | 583.0 | 8.7 | 1.2-1.5(9H, s), 1.8-2.0(2H, m), 2.8-3.7(5H, m), 4.1-4.5(2H, m), 6.5-7.0(1H, m), 7.1-7.4(2H, br s), 7.4-7.6(2H, m), 7.8-8.0(3H, m), 8.3-8.4(1H, s), 9.2(1H, s), 9.4(1H, s), 10.4-10.5(1H, br s) |
| V-47 | 568.9 | 8.5 | 1.2-1.5(9H, s), 1.8-2.3(2H, m), 3.4-3.9(2H, m), 4.0-4.3(3H, m), 6.8-7.4(3H, br m), 7.4-7.6(2H, m), 7.7-8.0(3H, m), 8.4-8.6(1H, m), 9.0-9.3(1H, m), 9.4(1H, s), 10.3-10.6(1H, br s) |
| V-48 | 484.0 | 6.4 | 1.4-1.6(2H, m), 1.9-2.1(2H, m), 2.8-3.8(3H, m), 4.2-4.7(2H, m), 7.2-7.4(2H, br s), 7.4-7.6(2H, m), 7.7-8.1(6H, m), 8.4(1H, s), 9.2(1H, s), 9.4(1H, s), 10.4-10.5(1H, br s) |
| V-49 | 470.0 | 6.6 | 2.0-2.5(3H, m), 3.6-4.6(4H, m), 7.3-7.9(5H, m), 7.9-8.3(5H, m), 8.4-8.6(1H, m), 9.2-9.3(1H, m), 9.4(1H, s), 10.5(1H, br s) |
| V-50 | 404 | 9.0 | 2.25(3H, s), 2.40(2H, t), 3.80(2H, m), 7.05(1H, t), 7.40(2H, t), 7.85-8.15(4H, m), 8.25(1H, s), 9.40(1H, s), 10.10(1H, s) |
| V-51 | 406 | 7.9 | 3.69(2H, m), 3.76(2H, m), 5.12(2H, s), 6.23(1H, m), 6.96(2H, m), 7.52(1H, s), 7.84(1H, d), 7.90(1H, d), 8.36(1H, s), 9.31(1H, s) and 9.80(1H, s) |
| V-52 | 391 | 9.0 | 3.65-3.90(8H, 2 x m), 7.05(1H, t), 7.40(2H, t), 7.80-8.10(4H, dd and d), 8.30(1H, s), 9.40(1H, s), 10.10(1H, s) |
| V-53 | 490 | 9.8 | 1.30-1.50(9H, m), 1.80-2.25(2H, m), 3.40-3.80(3H, m), 4.10-4.30(2H, m), 7.05(1H, q), 7.40(2H, m), 7.85-8.15(4H, dd and d), 8.40-8.55(1H, m), 9.40(1H, s), 10.15(1H, s) |
| V-54 | 390 | 8.2 | 2.00-2.80(2H, m), 3.60-4.50(5H, m), 7.05(1H, q), 7.45(2H, m), 7.90-8.30(6H, m), 8.40-8.55(1H, m), 9.40(1H, s), 10.15(1H, s) |
| V-55 | 447 | 10.2 | 1.3-1.4(9H, s), 3.6-3.8(8H, br m), 7.0-7.1(1H, m), 7.3(1H, m), 7.7-7.8(1H, m), 7.8-7.9(1H, m), 7.9-8.0(1H, m), 8.1-8.3(2H, m), 9.3-9.4(1H, s), 10.0(1H, s) |
| V-56 | 460 | 10.3 | 1.3(9H, s), 2.2(3H, s), 2.3-2.4(4H, m), 3.6-3.8(4H, m), 7.0-7.1(1H, m), 7.3(1H, m), 7.7(1H, m), 7.8-7.9(1H, m), 7.9-8.0(1H, m), 8.2-8.3(2H, m), 9.3-9.4(1H, m), 10.0(1H, s) |
| V-57 | 546 | 10.6 | 1.3-1.5(18H, m), 1.8-2.3(2H, m), 3.4-4.3(5H, m), 7.0-7.1(1H, m), 7.2-7.4(2H, m), 7.6-7.8(1H, m), 7.8-8.0(2H, m), 8.0-8.2(1H, m), 8.3-8.5(1H, m), 9.3-9.4(1H, s), 10.0(1H, s) |
| V-58 | 467 | 10.0 | 3.4-3.8(8H, br m), 7.3(1H, m), 7.4-7.6(4H, m), 7.7(2H, m), 7.8-8.0(3H, m), 8.2(1H, s), 8.6(1H, br s), 9.4(1H, s), 10.2(1H, s) |
| V-59 | 480 | 10.1 | 2.2(3H, s), 2.2-2.4(4H, br s), 3.6-3.7(4H, br m), 7.3(1H, m), 7.3-7.6(4H, m), 7.7(2H, m), 7.8-8.0(3H, m), 8.1-8.2(1H, s), 8.6-8.7(1H, m), 9.4(1H, s), 10.2(1H, s) |
| V-60 | 566 | 10.5 | 1.2-1.5(9H, m), 1.7-2.1(2H, m), 3.3-4.2(5H, m), 7.2-7.3(2H, m), 7.4-7.5(2H, m), 7.7(2H, m), 7.8-8.0(3H, m), 8.3-8.4(1H, m), 8.4-8.6(1H, m), 9.4(1H, s), 10.2-10.3(1H, m) |
| V-61 | 409 | 9.2 | 3.6-3.9(8H, br m), 6.8-6.9(1H, m), 7.4(1H, m), 7.7-7.8(1H, m), 7.9(1H, m), 8.0(1H, m), 8.1(1H, m), 8.2(1H, s), 9.4(1H, s), 10.3-10.4(1H, s) |
| V-62 | 422 | 9.4 | 2.2-2.3(3H, br s), 2.4(4H, m), 3.7-3.8(4H, br m), 6.8(1H, m), 7.3-7.4(1H, m), 7.7(1H, m), 7.9(1H, m), 8.0(1H, m), 8.2(2H, m), 9.4(1H, s), 10.3-10.4(1H, s) |

TABLE 15-continued

Characterization Data for Selected Compounds of Formula V

| Compound No. | M + 1 (obs) | Rt (min) | ¹H-NMR |
|---|---|---|---|
| V-63 | 508 | 9.9 | 1.3-1.5(9H, br m), 1.8-2.3(2H, m), 3.4-4.2(5H, m), 6.8(1H, m), 7.3-7.5(2H, m), 7.7-7.9(1H, m), 7.9(1H, m), 8.0(1H, m), 8.0-8.2(1H, m), 8.4-8.5(1H, m), 9.4(1H, s), 10.3-10.4(1H, s) |
| V-64 | 405 | 9.1 | 2.3(3H, s), 3.6-3.8(8H, br m), 7.1(1H, m), 7.2-7.3(2H, m), 7.7-7.8(1H, m), 7.8-7.9(2H, m), 8.0-8.1(1H, s), 9.2(1H, s), 9.3(1H, s) |
| V-65 | 418 | 9.2 | 2.2-2.3(3H, br s), 2.3(3H, br s), 2.3-2.4(4H, br m), 3.5-3.8(4H, br m), 7.1(1H, m), 7.2-7.3(1H, m), 7.7-7.8(1H, m), 7.8-7.9(2H, m), 8.0-8.1(1H, s), 9.2(1H, s), 9.3(1H, s) |
| V-66 | 504 | 9.9 | 1.3-1.5(9H, br m), 1.8-2.3(2H, m), 2.3-2.4(3H, s), 3.4-4.3(5H, m), 7.1(1H, m), 7.2-7.4(3H, m), 7.7-7.8(1H, m), 7.8-7.9(2H, m), 8.2-8.4(1H, m), 9.2-9.3(2H, m) |
| V-67 | 545 | 8.4 | 1.39(2H, m), 1.50(4H, m), 2.37(4H, m), 2.53(2H, m), 2.63(2H, m), 3.69(4H, m), 3.80(4H, m), 7.00(1H, d), 7.23(1H, t), 7.33(1H, d), 7.89(1H, d), 7.98(1H, d), 8.73(1H, s), 9.07(1H, br s), 9.37(1H, s), 10.07(1H, s) and 10.29(1H, s) |
| V-68 | 448 | 8.0 | 2.10(3H, s), 3.69(4H, m), 3.81(4H, m), 7.00(1H, d), 7.20(1H, t), 7.28(1H, d), 7.85(1H, d), 7.93(1H, d), 8.73(1H, s), 9.10(1H, br s), 9.25(1H, s), 10.04(1H, s) and 10.07(1H, s) |
| V-69 | 547 | 8.1 | 2.37(4H, m), 2.50(2H, m), 2.66(2H, m), 3.56(4H, m), 3.65(4H, m), 3.80(4H, m), 7.03(1H, d), 7.23(1H, t), 7.30(1H, d), 7.88(1H, d), 7.95(1H, d), 8.71(1H, s), 9.03(1H, br s), 9.37(1H, s), 10.08(1H, s) and 10.14(1H, s) |
| V-70 | 560 | 8.0 | 2.12(3H, s), 2.20-2.60(10H, br m), 2.69(2H, m), 3.67(4H, m), 3.79(4H, m), 7.02(1H, d), 7.23(1H, t), 7.32(1H, d), 7.88(1H, d), 7.96(1H, d), 8.73(1H, s), 9.09(1H, br s), 9.35(1H, s), 10.07(1H, s) and 10.18(1H, s) |
| V-71 | 505 | 8.0 | 2.84(6H, s), 2.89(2H, m), 3.45(2H, m), 3.70(4H, m), 3.77(4H, m), 7.21(1H, d), 7.28(1H, t), 7.47(1H, d), 7.89(1H, d), 7.97(1H, d), 8.63(1H, s), 8.77(1H, br s), 9.37(1H, s), 9.40(1H, br s), 10.13(1H, s) and 10.29(1H, s) |
| V-72 | 446 | 9.8 | 1.3-1.4(9H, s), 2.0-2.7(2H, m), 3.6-4.3(5H, m), 7.0-7.1(1H, m), 7.3(1H, m), 7.7-8.2(6H, m), 8.3-8.5(1H, m), 9.3-9.4(1H, s), 10.0(1H, s) |
| V-73 | 466 | 9.6 | 2.0-2.4(2H, m), 3.5-4.1(5H, m), 7.3(1H, m), 7.4-7.6(4H, m), 7.7(1H, m), 7.8-8.2(6H, m), 8.3-8.5(2H, m), 9.4(1H, s), 10.2-10.3(1H, m) |
| V-74 | 408 | 8.6 | 2.0-2.6(2H, m), 3.6-4.4(5H, m), 6.8(1H, m), 7.4(1H, m), 7.6-8.3(6H, m), 8.3-8.5(1H, m), 9.4(1H, s), 10.4(1H, s) |
| V-75 | 404 | 8.4 | 2.0-2.4(2H, m), 2.3(3H, s), 3.6-4.2(5H, m), 7.1(1H, m), 7.2-7.3(2H, m), 7.7-8.3(7H, m), 9.2-9.4(2H, m) |
| V-76 | 535 | 7.8 | 2.83(2H, s), 3.20(2H, m), 3.29(5H, m), 3.60(2H, m), 3.69(4H, m), 3.77(4H, m), 7.19(1H, d), 7.29(1H, t), 7.50(1H, d), 7.89(1H, d), 7.97(1H, d), 8.55(2H, br s), 8.62(1H, s), 8.74(1H, s), 9.36(1H, s), 10.11(1H, s) and 10.23(1H, s) |
| V-77 | 549 | 7.9 | 1.80(2H, m), 2.80(2H, m), 3.03(2H, m), 3.23(3H, s), 3.29(2H, m), 3.39(2H, m), 3.69(4H, m), 3.77(4H, m), 7.20(1H, d), 7.30(1H, t), 7.49(1H, d), 7.89(1H, d), 7.97(1H, d), 8.40(2H, br s), 8.62(1H, s), 8.78(1H, s), 9.36(1H, s), 10.11(1H, s) and 10.25(1H, s) |
| V-78 | 573 | 9.5 | 0.70-0.92(10H, br m), 1.70(2H, m), 1.83(2H, m), 3.41(4H, m), 3.67(4H, m), 3.79(4H, m), 7.19(1H, d), 7.30(1H, t), 7.47(1H, d), 7.89(1H, d), 7.97(1H, d), 8.63(1H, s), 8.78(1H, s), 9.27(1H, br s), 9.36(1H, s), 10.11(1H, s) and 10.25(1H, s) |
| V-79 | 446 | 9.8 | 1.4(9H, s), 3.2(4H, br s), 3.9-4.0(4H, br s), 7.0-7.1(1H, m), 7.3(1H, m), 7.8-8.0(3H, m), 8.1(1H, s), 8.3(1H, s), 8.8-9.0(2H, br s), 9.3-9.4(1H, s), 10.0(1H, s) |
| V-80 | 466 | 9.7 | 3.1-3.3(4H, br s), 3.8-4.0(4H, br m), 7.3-7.5(5H, m), 7.7(2H, m), 7.9-8.0(2H, m), 8.1-8.2(1H, m), 8.2-8.4(2H, m), 8.8-9.0(2H, br s), 9.4(1H, s), 10.2(1H, s) |
| V-81 | 432 | 9.6 | 1.30(6H, d), 2.95(1H, m), 3.30(4H, br s), 4.00(4H, br s), 6.95(1H, d), 7.35(1H, t), 7.85-8.05(4H, m), 8.30(1H, s), 8.90(2H, br s), 9.40(1H, s), 10.10(1H, s) |
| V-82 | 432 | 9.4 | 1.30(6H, d), 2.00-2.50(2H, m), 2.95(1H, m), 3.60-4.40(5H, m), 6.95(1H, d), 7.35(1H, m), 7.70-8.60(8H, m), 9.40(1H, s), 10.05(1H, s) |
| V-83 | 496 | 10.0 | 2.15(3H, m), 2.40(4H, br s), 3.75(4H, br s), 6.65(1H, d), 7.15(3H, m), 7.45(3H, m), 7.70(1H, d), 7.85-8.10(4H, m), 9.45(1H, s), 10.25(1H, s) |
| V-84 | 482 | 9.6 | 3.25(4H, br s), 4.00(4H, br s), 6.70(1H, d), 7.15(3H, m), 7.45(3H, m), 7.80-8.10(4H, m), 8.95(2H, br s), 9.45(1H, s), 10.25(1H, s) |
| V-85 | 482 | 9.5 | 2.00-2.50(2H, m), 3.65-4.30(5H, m), 6.65(1H, m), 7.15(2H, m), 7.45(2H, m), 7.75-8.40(6H, m), 9.40(1H, s), 10.30(1H, s) |
| V-86 | 494 | 10.2 | 2.45(4H, br s), 3.35(3H, s), 3.75(4H, br s), 4.05(2H, s), 6.90(1H, d), 7.10- |

TABLE 15-continued

Characterization Data for Selected Compounds of Formula V

| Compound No. | M + 1 (obs) | Rt (min) | ¹H-NMR |
|---|---|---|---|
| V-87 | 480 | 9.8 | 7.50(6H, m), 7.85-8.25(5H, m), 9.35(1H, s), 10.10(1H, s) 3.25(4H, br s), 3.95(4H, br s), 4.00(2H, s), 6.90(1H, d), 7.00-7.50(6H, m), 7.80-8.30(5H, m), 8.95(1H, s), 9.35(1H, s), 10.10(1H, s) |
| V-88 | 480 | 9.7 | 1.90-2.40(2H, m), 3.65-4.35(7H, m), 6.85(1H, m), 7.15-7.40(5H, m), 7.75-8.50(8H, m), 9.35(1H, s), 10.15(1H, s) |
| V-89 | 470 | 9.4 | 3.40(4H, br s), 4.05(4H, br s), 7.20(1H, m), 7.35(1H, t), 7.90-8.10(3H, m), 8.30(1H, s), 8.55(1H, s), 8.95(2H, br s), 9.40(1H, s), 10.35(1H, s) |
| V-90 | 478 | 10.1 | 2.30(3H, s), 3.35(4H, br s), 3.95(4H, br s), 7.05(1H, d), 7.20-7.55(4H, m), 7.90-8.10(3H, m), 8.25-8.40(2H, m), 8.95(2H, br s), 9.45(1H, s), 10.25(1H, s) |
| V-91 | 494 | 9.6 | 3.30(4H, br s), 3.85(3H, s), 3.95(4H, br s), 7.05(1H, t), 7.20(2H, m), 7.30-7.55(3H, m), 7.90-8.30(4H, m), 8.95(2H, br s), 9.45(1H, s), 10.20(1H, s) |
| V-92 | 494 | 10.4 | 2.10(6H, s), 3.30(4H, br s), 3.95(4H, br s), 6.85(1H, d), 7.20(3H, m), 7.55(1H, t), 7.90-8.10(2H, dd), 8.20(1H, s), 8.35(1H, d), 9.00(2H, br s), 9.45(1H, s), 10.25(1H, s) |
| V-93 | 468 | 9.4 | 3.35(4H, br s), 4.10(4H, br s), 7.20(1H, d), 7.35(1H, t), 7.90-8.10(4H, m), 8.35(1H, s), 8.60(1H, s), 8.95(2H, br s), 9.45(1H, s), 10.35(1H, s) |
| V-94 | 467 | 9.0 | 3.25(4H, br s), 4.00(4H, br s), 7.40(1H, d), 7.60(1H, t), 7.70(1H, m), 7.90-8.10(2H, m), 8.20-8.50(4H, m), 8.70(1H, d), 8.85-9.10(3H, m), 9.45(1H, s), 10.35(1H, s) |
| V-95 | 486 | 10.0 | 2.30(3H, s), 3.25(4H, br s), 4.05(4H, br s), 6.95-7.25(2H, m), 7.55(2H, m), 7.90-8.15(3H, m), 8.30-8.45(2H, m), 8.90(2H, br s),9.40(1H, s), 10.30(1H, s) |
| V-96 | 486 | 9.9 | 2.35(3H, s), 3.25(4H, br s), 4.05(4H, br s), 6.95-7.40(4H, m), 7.45(2H, m), 7.90-8.10(3H, m), 8.90(2H, br s), 9.40(1H, s), 10.30(1H, s) |
| V-97 | 506 | 10.1 | 3.25(4H, br s), 4.00(4H, br s), 7.25-7.40(2H, m), 7.50-7.70(2H, m), 7.85-8.10(2H, m), 8.20-8.40(3H, m), 8.90(2H, br s), 9.45(1H, s), 10.30(1H, s) |
| V-98 | 475 | 8.0 | 2.7-2.9(4H, br m), 3.0-3.1(4H, br m), 3.6-3.8(8H, br m), 7.0(2H, m), 7.7-7.9(4H, m), 8.1-8.2(1H, m), 9.2-9.3(1H, s), 9.8-9.9(1H, s) |
| V-99 | 404 | 8.5 | 2.7-2.8(4H, br m), 3.5-3.7(4H, br m), 4.6-4.7(2H, m), 7.1-7.2(1H, m), 7.2-7.5(4H, m), 7.7-7.8(2H, m), 8.0-8.3(2H, m), 9.1-9.2(1H, s) |
| V-100 | 468 | 7.6 | 3.27(4H, br s), 3.32(3H, s), 4.03(4H, br s), 7.58(1H, d), 7.65(1H, t), 7.89(1H, d), 7.97(1H, d), 8.05(1H, d), 8.45(1H, s), 8.90(2H, br s), 9.46(1H, s), 9.52(1H, br s), 10.62(1H, s) |
| V-101 | 468 | 7.5 | 2.00-2.50(2H, m), 3.28-3.32(3H, m), 3.65-4.43(5H, m), 7.58-7.67(2H, m), 7.82-8.10(6H, m), 8.50-8.58(1H, m), 9.34(1H, br s), 9.45(1H, s), 10.60(1H, s) |
| V-102 | 448 | 9.3 | 1.33(6H, d), 3.27(4H, br s), 3.95(4H, br s), 4.63(1H, quint.), 6.59(1H, d), 7.28(1H, t), 7.54(1H, s), 7.80(1H, d), 7.92(1H, d), 7.98(1H, d), 8.29(1H, s), 8.88(2H, br s), 9.38(1H, s), 10.06(1H, s) |
| V-103 | 448 | 9.2 | 1.33(6H, d), 2.00-2.50(2H, m), 3.60-4.25(5H, m), 4.63(1H, quint.), 6.60(1H, m), 7.20-7.33(1H, m), 7.54-7.78(2H, m), 7.90-8.07(5H, m), 8.39-8.48(1H, m), 9.38(1H, s), 10.08(1H, s) |
| V-104 | 405 | 10.4 | 1.36(9H, s), 3.34(6H, s), 7.07(1H, d), 7.30(1H, t), 7.71(1H, m), 7.89(1H, d), 7.94(1H, d), 8.23(1H, br s), 8.31(1H, s), 9.35(1H, s), 9.99 (1H, s) |
| V-105 | 488 | 9.8 | 1.35(9H, s), 2.05(3H, s), 3.58(4H, t), 3.70-3.82(4H, m), 7.07(1H, d), 7.31(1H, t), 7.82(1H, m), 7.90(1H, d), 7.96(1H, d), 8.14(1H, t), 8.27(1H, s), 9.36(1H, s), 10.00(1H, s) |
| V-106 | 502 | 9.8 | 1.34(9H, s), 1.75-2.10(5H, m), 3.55-3.95(8H, m), 7.05-7.10(1H, m), 7.32(1H, m), 7.86-8.10(4H, m), 8.27(1H, d), 9.35(1H, s), 9.97-10.00(1H, m) |
| V-107 | 474 | 10.1 | 1.30-1.40(11H, m), 1.83-1.89(3H, m), 2.80-2.95(2H, m), 3.20-3.45(4H, m), 7.10(1H, d), 7.34(1H, t), 7.85-8.20(5H, m), 8.44(1H, m), 8.70(1H, s), 9.10(1H, t), 9.34(1H, s), 9.95(1H, s) |
| V-108 | 460 | 10.2 | 1.35(9H, s), 1.71(1H, m), 2.08(1H, m), 2.40-2.62(1H, m), 2.92-3.50(6H, m), 7.11(1H, d), 7.34(1H, t), 7.86-8.01(4H, m), 8.55-8.70(3H, m), 9.17(1H, t), 9.35(1H, s), 9.96(1H, s) |
| V-109 | 460 | 10.3 | 1.34(9H, m), 2.00-2.20(2H, m), 3.20-4.20(8H, m), 7.09(1H, d), 7.33(1H, t), 7.88-8.04(4H, m), 8.32(1H, br s), 8.75(2H, s), 9.36(1H, s), 10.00(1H, s) |
| V-110 | 446 | 9.9 | 1.35(9H, s), 2.00-2.50(2H, m), 3.40-4.30(5H, m), 7.08(1H, d), 7.28-7.36(1H, m), 7.77-8.10(7H, m), 8.40-8.48(1H, m), 9.36(1H, s), 10.02(1H, s) |
| V-111 | 446 | 9.9 | 1.35(9H, s), 2.00-2.50(2H, m), 3.30-4.30(5H, m), 7.08(1H, d), 7.28-7.36(1H, m), 7.76-8.10(7H, m), 8.40-8.47(1H, m), 9.36(1H, s), 10.02(1H, s) |
| V-112 | 475 | 8.4 | (CDCl₃) 3.0(4H, m), 3.2-3.3(4H, m), 3.8-4.0(8H, m), 6.7(1H, m), 7.2-7.5(4H, m), 7.6(1H, s), 7.7-7.8(2H, m), 8.3(1H, s), 9.1-9.2(1H, s) |

TABLE 15-continued

Characterization Data for Selected Compounds of Formula V

| Compound No. | M + 1 (obs) | Rt (min) | ¹H-NMR |
|---|---|---|---|
| V-113 | 474 | / | 2.8(4H, m), 3.0(4H, m), 3.2(4H, m), 3.7(4H, m), 6.4(1H, m), 7.1-7.2(1H, m), 7.3-7.4(1H, m), 7.8-8.0(3H, m), 8.1-8.2(1H, s), 9.3-9.4 (1H, s), 9.9-10.0(1H, s) |
| V-114 | 488 | / | 2.2(3H, s), 2.8(4H, m), 3.0-3.2(4H, m), 3.2-3.6(4H, br m), 3.6-3.8(4H, m), 7.0(1H, m), 7.8-7.9(4H, m), 8.2(1H, s), 9.2-9.3(1H, s), 9.8-9.9(1H, s) |
| V-115 | 474 | / | 2.8(4H, m), 2.9(4H, m), 3.1(4H, m), 3.7(4H, m), 6.9-7.0(2H, m), 7.8-7.9(4H, m), 8.2(1H, s), 9.2-9.3(1H, s), 9.8-9.9(1H, s) |
| V-116 | 391 | 7.8 | 2.9(4H, m), 3.8-3.9(4H, m), 7.9-8.1(4H, m), 8.3(1H, m), 8.4-8.5(2H, m), 9.4-9.5(1H, s), 10.5(1H, s) |
| V-117 | 391 | 7.5 | 2.8(4H, m), 3.6-3.8(4H, m), 7.4-7.5(1H, m), 7.9-8.1(2H, m), 8.2(2H, m), 8.5-8.6(1H, m), 9.0-9.1(1H, s), 9.4(1H, s), 10.2-10.3(1H, s) |
| V-118 | 516 | 10.0 | 1.00-1.20(2H, m), 1.35(9H, s), 1.70-1.85(3H, m), 1.99(3H, s), 2.40-2.55(1H, m), 2.97-3.04(1H, m), 3.10-3.30(2H, m), 3.80-3.84(1H, m), 4.36-4.40(1H, s), 7.10(1H, d), 7.33(1H, t), 7.85-7.94(3H, m), 8.00(1H, t), 8.69(1H, s), 9.04(1H, t), 9.34(1H, s), 9.94(1H, s) |
| V-119 | 502 | 9.9 | 1.34(9H, s), 1.63-1.77(1H, m), 1.93-2.05(4H, m), 2.43-2.55(1H, m), 3.04-3.57(6H, m), 7.10(1H, d), 7.34(1H, dt), 7.86-7.98(4H, m), 8.69(1H, s), 9.10-9.13(1H, m), 9.34(1H, s), 9.94(1H, s) |
| V-120 | 503 | 7.4 | 3.20-4.05(16H, m) 7.50(2H, d), 7.85-8.45(5H, m), 8.95(2H, br s), 9.45(1H, s), 10.40(1H, s) |
| V-121 | 461 | 7.5 | 3.05(6H, s), 3.25(4H, br s), 4.00(4H, br s), 7.50(2H, d), 7.90-8.45(5H, m), 8.95(2H, br s), 9.45(1H, s), 10.40(1H, s) |
| V-122 | 516 | 7.8 | 2.90(3H, s), 3.00-4.00(16H, m) 7.55(2H, d), 7.90-8.40(5H, m), 9.00(2H, br s), 9.45(1H, s), 10.45(1H, s) |
| V-123 | 418 | 8.8 | (CDCl₃)1.6-1.7(3H, d), 3.0(4H, m), 3.8-3.9(4H, m), 5.3-5.4(1H, m), 5.7-5.8(1H, m), 7.2-7.4(3H, m), 7.4-7.6(4H, m), 8.1-8.2(1H, s), 9.0 (1H, s) |
| V-124 | 418 | 8.8 | (CDCl₃)1.6-1.7(3H, d), 3.0(4H, m), 3.8-3.9(4H, m), 5.3-5.4(1H, m), 5.7-5.8(1H, m), 7.2-7.4(3H, m), 7.4-7.6(4H, m), 8.1-8.2(1H, s), 9.0(1H, s) |
| V-125 | 418 | 9.0 | (CDCl₃)2.9-3.2(6H, m), 3.8-4.0(6H, m), 5.4-5.5(1H, m), 7.2-7.4(5H, m), 7.6(2H, m), 8.2-8.3(1H, s), 9.0(1H, s) |
| V-126 | 430 | 9.4 | (CDCl₃)1.9-2.1(1H, m), 2.7-2.8(1H, m), 2.9-3.2(6H, m), 3.7-3.9(4H, m), 5.5-5.7(1H, m), 5.8-6.0(1H, m), 7.2-7.5(4H, m), 7.6(2H, m), 8.1-8.3(1H, br s), 8.9-9.2(1H, br s) |
| V-127 | 430 | 9.0 | (CDCl₃)1.3-1.5(2H, m), 2.1-2.2(1H, m), 2.6-3.1(4H, br m), 3.1-3.2(1H, m), 3.5-3.9(4H, br m), 5.7(1H, s), 7.2-7.4(5H, m), 7.6(2H, m), 8.0(1H, s), 9.0(1H, s) |
| V-128 | 475 | / | 3.29(3H, s), 7.15(1H, t), 7.41(2H, t), 7.59(1H, d), 7.70(1H, t), 7.83(2H, d), 7.96(1H, d), 8.04(1H, d), 8.34(1H, d), 8.95(1H, s), 9.00(1H, s), 9.44(1H, s), 10.50(1H, s), 10.54(1H, s) |
| V-129 | 489 | / | 3.18(3H, s), 4.55(2H, d), 7.27(1H, t), 7.32-7.47(4H, m), 7.56(1H, d), 7.66(1H, t), 7.92(1H, d), 8.00(1H, d), 8.32(1H, d), 8.82(1H, s), 8.88(1H, s), 9.21(1H, t), 9.41(1H, s), 10.49(1H, s) |
| V-130 | 453 | / | 1.83-1.95(2H, m), 1.96-2.11(2H, m), 3.26(3H, s), 3.57(2H, t), 4.02(2H, t), 7.53-7.67(2H, m), 7.84(1H, d), 7.90(1H, d), 7.97(1H, d), 8.51(1H, s), 9.32(1H, s), 9.40(1H, s), 10.53(1H, s) |
| V-131 | 482 | / | 3.26(3H, s), 3.36(2H, s), 3.97(2H, s), 4.31(2H, s), 7.56(1H, d), 7.63(1H, t), 7.88-7.98(2H, m), 8.02(1H, d), 8.25(1H, s), 8.46(1H, s), 9.37(1H, s), 9.43(1H, s), 10.57(1H, s) |
| V-132 | 497 | / | 1.52-1.66(2H, m), 1.67-1.88(4H, m), 2.00-2.14(2H, m), 3.29(3H, s), 3.65(2H, d), 4.89(1H, t), 7.58(1H, d), 7.65(1H, t), 7.82-7.86(1H, m), 7.90(1H, d), 7.98(1H, d), 8.10(1H, d), 8.79(1H, s), 9.33(1H, s), 9.41(1H, s), 10.55(1H, s) |
| V-133 | 443 | / | 3.37-3.45(2H, m), 3.52-3.65(2H, m), 4.82(1H, t), 7.58(1H, d), 7.68(1H, t), 7.91(1H, d), 7.98(1H, d), 8.34(1H, dd), 8.60(1H, t), 8.78(1H, s), 8.94(1H, t), 9.40(1H, s), 10.50(1H, s) |
| V-134 | 457 | / | 3.29(3H, s), 3.30(3H, s), 3.45-3.58(4H, m), 7.58(1H, d), 7.68(1H, t), 7.91(1H, d), 7.98(1H, d), 8.33(1H, dd), 8.65(1H, t), 8.77(1H, s), 8.93(1H, s), 9.40(1H, s), 10.50(1H, s) |
| V-135 | 484 | / | 1.83(3H, s), 3.22-3.32(5H, m), 3.32-3.42(2H, m), 7.56-7.62(1H, m), 7.70(1H, t), 7.91(1H, d), 7.98(1H, d), 8.05(1H, t), 8.41(1H, dd), 8.72(1H, t), 8.75(1H, s), 8.84(1H, t), 9.41(1H, s), 10.50(1H, s) |
| V-136 | 482 | / | 1.95-2.24(2H, m), 3.27(3H, s), 3.54-4.68(8H, m), 7.57(1H, d), 7.64(1H, t), 7.91-7.99(2H, m), 8.02(1H, d), 8.44(1H, s), 8.80(1H, s), 9.28(1H, s), 9.43(1H, s), 10.56(1H, s) |
| V-137 | 496 | / | 0.80-1.23(6H, m), 2.72-2.93(2H, m), 3.25(3H, s), 3.82-4.61(2H, m), 7.56(1H, d), 7.62(1H, t), 7.92(1H, d), 7.96(1H, dd), 8.01(1H, d), |

TABLE 15-continued

Characterization Data for Selected Compounds of Formula V

| Compound No. | M + 1 (obs) | Rt (min) | ¹H-NMR |
|---|---|---|---|
| V-138 | 524 | / | 8.34(1H, s), 9.35(1H, s), 9.42(1H, s), 10.55(1H, s) 1.70-1.81(1H, m), 1.81-1.95(2H, m), 1.94-2.12(2H, m), 3.25(3H, s), 3.48-3.62(2H, m), 3.62-3.92(5H, m), 3.92-4.07(1H, m), 7.51-7.60(1H, m), 7.63(1H, t), 7.86-7.96(1H, m), 7.96-8.07(2H, m), 8.39(1H, s), 9.04-9.34(1H, m), 9.41(1H, d), 10.53(1H, s) |
| V-139 | 471 | / | 3.25(6H, s), 3.38-3.53(2H, m), 3.59(2H, t), 3.64-4.06(3H, m), 7.56(1H, dt), 7.62(1H, t), 7.77-7.94(2H, m), 7.98(1H, d), 8.43(1H, s), 9.40(2H, s), 10.53(1H, s) |
| V-140 | 455 | / | 1.22(3H, s), 1.23(3H, s), 3.06-3.29(3H, m), 3.23(3H, s), 4.71(1H, m), 7.56(1H, d), 7.62(1H, t), 7.74-7.95(1H, m), 7.91(1H, d), 7.99(1H, d), 8.28-8.55(1H, m), 9.41(1H, s), 9.42-9.71(1H, m), 10.54(1H, s) |
| V-141 | 427 | / | 2.97-3.21(3H, m), 3.26(3H, s), 3.37-3.54(3H, m), 7.56(1H, dt), 7.62(1H, t), 7.86(1H, ddd), 7.92(1H, d), 7.99(1H, d), 8.45(1H, s), 9.41(2H, s), 10.55(1H, s) |
| V-142 | 483 | / | 1.84-2.19(4H, m), 3.25(3H, s), 3.41-3.55(1H, m), 3.58-3.71(1H, m), 3.89-4.01(1H, m), 4.02-4.14(1H, m), 4.17-4.32(1H, m), 7.54-7.59(1H, m), 7.62(1H, t), 7.82-7.89(1H, m), 7.92(1H, d), 7.99(1H, d), 8.52(1H, s), 9.30(1H, s), 9.41(1H, s), 10.54(1H, s) |
| V-143 | 497 | / | 1.03-1.29(6H, m), 3.25(3H, s), 3.47-3.75(2H, m), 3.97-4.63(2H, m), 7.54-7.59(1H, m), 7.62(1H, t), 7.88-7.96(2H, m), 8.01(1H, d), 8.37(1H, s), 9.39(1H, s), 9.42(1H, s), 10.56(1H, s) |
| V-144 | 510 | / | 0.78-0.87(1H, m), 1.14-1.31(2H, m), 1.50-1.69(2H, m), 1.74-1.90(2H, m), 3.26(3H, s), 6.86(1H, s), 7.35(1H, s), 7.55(1H, d), 7.63(1H, t), 7.91(1H, d), 7.94-8.04(2H, m), 8.35(1H, s), 9.30(1H, s), 9.41(1H, s), 10.54(1H, s), |
| V-145 | 511 | / | 3.23(2H, t), 3.26-3.32(2H, m), 3.30(3H, s), 3.40-3.51(4H, m), 6.32(1H, s), 7.58(1H, ddd), 7.69(1H, t), 7.91(1H, d), 7.98(1H, d), 8.38(1H, dd), 8.67-8.76(2H, m), 8.84(1H, s), 9.40(1H, s), 10.49(1H, s) |
| V-146 | 482 | / | 1.66-1.80(1H, m), 2.01-2.19(1H, m), 2.54-2.65(1H, m), 2.89-3.03(1H, m), 3.09-3.23(1H, m), 3.22-3.55(4H, m), 3.30(3H, s), 7.59(1H, d), 7.67(1H, t), 7.92(1H, d), 7.99(1H, d), 8.21(1H, dd), 8.71-8.91(3H, m), 9.04(1H, s), 9.42(1H, s), 10.53(1H, s) |
| V-147 | 510 | / | 2.05(3H, s), 3.25(3H, s), 3.51-3.67(4H, m), 3.68-3.98(4H, m), 7.57(1H, d), 7.63(1H, t), 7.89(1H, d), 7.93(1H, d), 8.01(1H, d), 8.41(1H, s), 9.39(1H, s), 9.42(1H, s), 10.56(1H, s) |
| V-148 | 510 | / | 1.84(3H, s), 1.86-2.06(2H, m), 2.07-2.28(2H, m), 3.25(3H, s), 3.26(3H, s), 3.41-3.52(1H, m), 3.57-3.86(4H, m), 4.05-4.19(2H, m), 4.23-4.33(2H, m), 4.33-4.43(1H, m), 7.54-7.59(2H, m), 7.59-7.67(2H, m), 7.81-7.96(2H, m), 7.91(2H, d), 7.98(2H, d), 8.19(2H, t), 8.45(1H, s), 8.54(1H, s), 9.25(1H, s), 9.30(1H, s), 9.40(2H, s), 10.54(2H, s) |
| V-149 | 496 | / | 1.26-1.49(2H, m), 1.84-2.00(3H, m), 2.76-2.96(2H, m), 3.14-3.39(5H, m), 7.56(1H, d), 7.66(1H, t), 7.89(1H, d), 7.94(1H, d), 8.08(1H, dd), 8.62(1H, t), 8.73(1H, s), 9.14(1H, s), 9.35(1H, s) |
| V-150 | 483 | / | 1.54-1.70(2H, m), 1.86(2H, dd), 3.31(3H, s), 3.39-3.46(2H, m), 3.86-3.96(2H, m), 3.96-4.11(1H, m), 7.59(1H, d), 7.66(1H, t), 7.90(1H, d), 7.98(1H, d), 8.11(1H, dd), 8.38(1H, d), 8.77(1H, s), 9.18(1H, s), 9.40(1H, s), 10.52(1H, s) |
| V-151 | 497 | / | 1.19-1.34(2H, m), 1.34-1.52(2H, m), 1.82-1.98(4H, m), 3.30(3H, s), 3.39-3.51(1H, m), 3.63-3.85(1H, m), 4.56-4.64(1H, m), 7.59(1H, d), 7.66(1H, t), 7.91(1H, d), 7.98(1H, d), 8.12(1H, d), 8.24(1H, d), 8.75(1H, s), 9.18(1H, s), 9.41(1H, s), 10.53(1H, s) |
| V-152 | 457 | / | 2.99-3.12(1H, m), 3.22(3H, s), 3.39-3.51(1H, m), 3.56-3.60(1H, m), 3.61-3.69(3H, m), 3.69-3.86(1H, m), 7.54(1H, d), 7.58-7.70(1H, m), 7.81-7.88(1H, m), 7.89(1H, d), 7.96(1H, d), 8.36-8.58(1H, m), 9.29-9.37(1H, m), 9.38(1H, s) |
| V-153 | 471 | / | 1.22(3H, d), 3.30(3H, s), 3.31(3H, s), 3.33-3.40(1H, m), 3.47(1H, dd), 4.14-4.30(1H, m), 7.56-7.61(1H, m), 7.66(1H, t), 7.91(1H, d), 7.98(1H, d), 8.12(1H, ddd), 8.26(1H, d), 8.78(1H, s), 9.21(1H, s), 9.40(1H, s), 10.53(1H, s) |
| V-154 | 483 | / | 1.36-1.55(2H, m), 1.75-1.95(2H, m), 3.25(3H, s), 3.41-3.60(2H, m), 3.72-3.89(1H, m), 3.95-4.13(2H, m), 4.73-4.98(1H, m), 7.56(1H, td), 7.63(1H, t), 7.91(1H, d), 7.93-7.98(1H, m), 8.00(1H, d), 8.35(1H, s), 9.32(1H, s), 9.41(1H, s), 10.54(1H, s) |
| V-155 | 497 | / | 1.84-2.02(2H, m), 2.02-2.16(1H, m), 3.25(3H, s), 3.29(3H, s), 3.37-3.49(2H, m), 3.50-3.67(1H, m), 3.86-4.01(1H, m), 4.01-4.18(1H, m), 4.28-4.46(1H, m), 7.54-7.59(1H, m), 7.62(1H, t), 7.78-7.88(1H, m), 7.91(1H, d), 7.98(1H, d), 8.51(1H, s), 9.28-9.36(1H, m), 9.40(1H, s), 10.53(1H, s), |
| V-156 | 469 | / | 1.87-2.02(1H, m), 2.02-2.18(1H, m), 3.60-3.74(1H, m), 3.21(3H, s), 3.76-4.14(2H, m), 4.34-4.51(1H, m), 4.52-4.97(1H, m), 7.49-7.66(2H, m), 7.80-7.95(2H, m), 8.00(1H, d), 8.51(1H, s), 9.13(1H, s), 9.35(1H, s), 9.89-10.28(1H, m) |
| V-157 | 498 | / | 1.27(3H, t), 2.88(6H, s), 3.25(3H, s), 3.31-3.48(2H, m), 3.61-3.80(2H, m), 3.74-4.18(2H, m), 7.57(1H, td), 7.62(1H, t), 7.93(1H, d), 8.01(1H, d), 8.04-8.15(1H, m), 8.42(1H, s), 9.04-9.26(0.5H, m), 9.43(1H, s), 9.48-9.69(0.5H, m), 10.54(1H, s) |

TABLE 15-continued

Characterization Data for Selected Compounds of Formula V

| Compound No. | M + 1 (obs) | Rt (min) | ¹H-NMR |
|---|---|---|---|
| V-158 | 410 | / | (CDCl₃) 0.98-1.11(2H, m), 1.13-1.34(3H, m), 1.60-1.79(2H, m), 1.80-1.89(2H, m), 1.89-2.03(2H, m), 2.97(4H, t), 3.44(2H, t), 3.83(4H, t), 5.47(1H, t), 7.55(2H, s), 8.21(1H, s), 8.95(1H, s) |
| V-159 | 452 | / | (CDCl₃) 2.88-3.05(6H, m), 3.75-3.89(6H, m), 5.48(1H, t), 7.19(2H, d), 7.27(2H, d), 7.56(1H, d), 7.59(1H, d), 8.21(1H, s), 8.95(1H, s) |
| V-160 | 510 | / | 1.90-2.03(2H, m), 2.03-2.20(2H, m), 2.78(2H, s), 3.03-3.31(6H, m), 3.26(3H, s), 3.43-3.62(2H, m), 4.41-4.69(1H, m), 7.54-7.59(1H, m), 7.62(1H, t), 7.77-7.90(1H, m), 7.93(1H, d), 8.01(1H, d), 8.47(1H, s), 9.43(1H, s), 9.44-9.65(1H, m), 10.58(1H, s) |
| V-161 | 382 | / | (CDCl₃) 1.50-1.62(2H, m), 1.62-1.83(4H, m), 2.08-2.21(2H, m), 2.90-3.00(4H, m), 3.77-3.84(4H, m), 4.40-4.52(1H, m), 5.40(1H, d, 7.3Hz), 7.55(2H, s), 8.21(1H, s), 8.95(1H, s) |
| V-162 | 452 | / | (CDCl₃) 2.91-3.03(4H, m), 3.17(2H, t), 3.81-3.87(4H, m), 3.90(2H, td), 5.56(1H, t), 7.12-7.22(2H, m), 7.28(1H, dd), 7.37(1H, dd), 7.57(1H, d), 7.60(1H, d), 8.26(1H, s), 8.96(1H, s) |
| V-163 | 432 | / | (CDCl₃) 1.40(3H, d), 2.89-3.03(4H, m), 3.08-3.30(1H, m), 3.63-3.74(1H, m), 3.79-3.86(4H, m), 3.86-3.96(1H, m), 5.37(1H, t), 7.20-7.40(5H, m), 7.56(1H, d), 7.59(1H, d), 8.24(1H, s), 8.94(1H, s) |
| V-164 | 468 | / | (CDCl₃) 1.78(3H, d), 2.83(4H, s), 3.67(4H, s), 5.91(1H, s), 6.12-6.24(1H, m), 7.42(1H, dd), 7.48-7.60(4H, m), 7.65(1H, d), 7.74(1H, d), 7.78-7.92(1H, m), 7.89(1H, d), 8.32(1H, d), 8.95(1H, s) |
| V-165 | 433 | / | (MeOD) 2.86(2H, t), 2.94-3.06(4H, m), 3.67-3.74(2H, m), 3.81-3.91(4H, m), 6.69(2H, d), 7.05(2H, d), 7.65(1H, d), 7.68(1H, d), 8.25(1H, s), 8.99(1H, s) |
| V-166 | 473 | / | 2.26(3H, s), 2.74(4H, s), 3.10(2H, t), 3.70(4H, s), 4.14(2H, t), 7.14(2H, s), 7.84(1H, d), 7.92(1H, d), 8.75(1H, s), 9.30(1H, s), 9.67(1H, s), 10.03(1H, s) |
| V-167 | 452 | / | 2.96(2H, s), 3.23(4H, s), 3.70(2H, t), 3.93(4H, s), 7.45-7.08(4H, m), 7.77(2H, s), 8.24(1H, s), 9.10(2H, s) |
| V-168 | 438 | / | 3.24(4H, s), 3.93(4H, s), 4.67(2H, d), 7.23-7.29(1H, m), 7.33(1H, t), 7.44(1H, s), 7.53(1H, s), 7.78(2H, d), 8.16-8.36(1H, m), 9.03(1H, s), 9.16(1H, s) |
| V-169 | 424 | / | 0.92-1.27(7H, m), 1.43-1.87(6H, m), 3.24(4H, s), 3.90(4H, s), 4.03-4.26(1H, m), 7.49(1H, d), 7.74(2H, s), 8.19(1H, s), 8.91(1H, s), 9.03-9.24(1H, m) |
| V-170 | 432 | / | 1.93(2H, s), 2.69(2H, t), 3.23(4H, s), 3.49(2H, t), 3.92(4H, s), 7.05-7.39(5H, m), 7.77(2H, s), 8.16(1H, s), 9.09(2H, s) |
| V-171 | 407 | / | (CDCl₃) 0.82-0.96(1H, m), 1.17-1.34(1H, m), 1.34-1.47(1H, m), 1.50-1.76(2H, m), 2.14-2.34(2H, m), 2.62-2.86(3H, m), 2.90-3.03(4H, m), 3.74-3.90(4H, m), 4.23-4.42(1H, m), 5.68(2H, d), 7.54(2H, s), 8.22(1H, s), 8.93(1H, s) |
| V-172 | 430 | / | 2.68-2.85(5H, m), 3.00(2H, dd), 3.64(4H, s), 4.76-4.96(1H, m), 7.15(2H, dd), 7.18-7.30(2H, m), 7.76(2H, s), 7.96(1H, s), 8.11(1H, s), 9.15(1H, s) |
| V-173 | 419 | / | 2.85(4H, s), 2.97(2H, s), 3.62-3.78(6H, m), 7.19-7.38(1H, m), 7.64-7.82(4H, m), 8.16(1H, s), 8.37(1H, dd), 8.51(1H, s), 9.11(1H, s) |
| V-174 | 482 | / | 2.75-2.90(4H, m), 3.14(3H, s), 3.62-3.79(4H, m), 4.74(2H, d), 7.59-7.80(4H, m), 7.85(2H, d), 8.09(1H, s), 8.36(1H, s), 9.16(1H, s) |
| V-175 | 448 | / | 2.88(6H, s), 3.54-3.67(3H, m), 3.68-3.78(6H, m), 6.85(2H, d), 7.21(2H, d), 7.69(1H, s), 7.75(2H, s), 8.17(1H, s), 9.12(1H, s) |
| V-5 | 418 | / | 2.32(6H, s), 3.26(4H, s), 3.99(4H, s), 6.68(1H, s), 7.69(2H, s), 7.89(1H, d), 7.95(1H, d), 8.27(1H, s), 8.93(1H, s), 9.34(1H, s), 9.95(1H, s) |
| V-178 | 408 | / | (CD₃OD) 2.65(1H, s), 3.16(2H, t), 3.42-3.33(4H, m), 3.98(2H, t), 4.18-4.05(4H, m), 7.38(1H, s), 7.83(2H, s), 8.47(1H, s), 8.76(1H, s), 9.21(1H, s) |
| V-179 | 419 | / | (CD₃OD) 3.03(4H, d), 3.22-3.10(2H, m), 3.97-3.80(6H, m), 7.25-7.13(1H, m), 7.36(1H, d), 7.79-7.51(3H, m), 8.27-8.17(1H, m), 8.44(1H, d), 8.95(1H, d) |
| V-180 | 436 | / | (CD₃OD) 3.00(2H, t), 3.44-3.33(4H, m), 3.84(2H, s), 4.18-4.00(4H, m), 6.99(2H, t), 7.29(2H, dd), 7.75(2H, s), 8.38(1H, s), 9.18(1H, s) |
| V-181 | 394 | / | (CD₃OD) 3.43-3.33(4H, m), 4.14-3.93(6H, m), 5.96(1H, s), 6.39(2H, d), 7.22(1H, d), 7.70(2H, d), 8.07(1H s) |
| V-182 | 434 | / | (CD₃OD) 2.90(2H, t), 3.43-3.32(4H, m), 3.77(2H, s), 4.15-4.02(4H, m), 6.70(2H, d), 7.10(2H, d), 7.70(2H, s), 8.32(1H, s), 9.08(1H, s) |

Example 26

Thiophene-3-carboxylic acid methoxymethyl amide

Thiophene-3-carboxylate (10 g, 78 mmol) was dissolved in chloroform (500 ml), treated with thionyl chloride (6.83 ml, 93.6 mmol) and heated to reflux for 2 hours. This solution was then added by cannulation to a solution of Weinreb Amine (11.4 g, 117 mmol) and triethylamine (30 ml, 210.6 mmol) in chloroform (100 ml). The reaction was then stirred at room temperature overnight. The solvent was reduced in vacuo to 100 ml, washed with water (150 ml), dried ($Na_2SO_4$) and concentrated. The resulting orange oil was purified by vacuum distillation (150° C. at 5 mbar) to give the title compound as a pale yellow oil (8.50 g, 64%). MS ($ES^+$) 172. δH ($d^6$ DMSO): 3.25 (3H, s), 3.64 (3H, s), 7.43 (1H, d), 7.56 (1H, d), 8.25 (1H, s).

Example 27

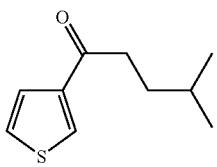

4-Methyl-1-thiophen-3-yl-pentan-1-one

Magnesium powder (1.49 g, 61.3 mmol) was added to dry diethyl ether (100 ml) under nitrogen atmosphere. One iodine crystal (catalytic) was added, followed by 1-bromo-3-methylbutane (6.3 ml, 52.6 mmol). The reaction was initiated by sonication at 30° C. and was allowed to spontaneously reflux. Once the exothermic reaction had subsided, the mixture was added by cannulation to a solution of thiophene-3-carboxylic acid methoxy-methyl-amide (7.50 g, 43.8 mmol) in dry diethyl ether (10 ml). Once addition was complete, the mixture was stirred at room temperature for 2 hours. The reaction mixture was then washed with saturated ammonium chloride (2×150 ml), dried ($Na_2SO_4$) and concentrated in vacuo. The crude yellow oil was purified by silica gel chromatography to yield the title compound as a colourless oil (1.55 g, 19%). δH ($d^6$ DMSO): 0.88 (6H, d), 1.49 (2H, q), 1.56 (1H, m), 2.90 (2H, t), 7.49 (1H, d), 7.59 (1H, d), 8.50 (1H, s).

Example 28

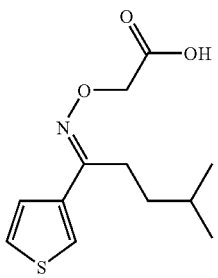

(4-Methyl-1-thiophen-3-yl-pentylideneaminooxy)-acetic acid

4-Methyl-1-thiophen-3-yl-pentan-1-one (324 mg, 1.78 mmol) was dissolved in dry methanol (20 ml) under nitrogen atmosphere, treated with carboxymethoxylamine hemihydrochloride (194 mg, 1.78 mmol) and sodium hydroxide (35 mg, 0.89 mmol) and stirred at room temperature for 4 hours. The solvent is then removed in vacuo and the resulting oil was triturated with hexane to give the title compound as a white solid (307 mg, 67%). MS ($ES^+$) 25. δH ($d^6$ DMSO): 1.00 (6H, d), 1.45 (2H, q), 1.63 (1H, m), 2.75 (2H, t), 4.65 (2H, s), 7.39 (1H, d), 7.60 (1H, d), 7.86 (1H, s), 12.70 (1H, s).

Example 29

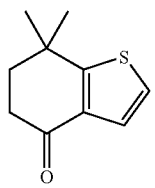

7,7-Dimethyl-6,7-dihydro-5H-benzo[b]thiophen-4-one (4-Methyl-1-thiophen-3-yl-pentylideneaminooxy)-acetic acid (2.17 g, 8.5 mmol) was added to a 0.1 M sodium hydroxide solution (93.5 ml) and heated to reflux. A solution of potassium persulfate (3.45 g, 12.75 mmol) in water (10 ml) was added dropwise and heating continued. After 2 hours, the reaction mixture was extracted with dry diethyl ether (100 ml). The organic layer was then washed with saturate sodium bicarbonate, water and brine, dried ($Na_2SO_4$) and concentrated in vacuo. The resulting oil was purified by silica gel chromatography to afford the title compound as a colourless oil (196 mg, 13%). MS ($ES^+$) 18. δH ($d^6$DMSO): 1.42 (6H, s), 2.03 (2H, t), 2.60 (2H, t), 7.22 (1H, d), 7.42 (1H, d).

Example 30

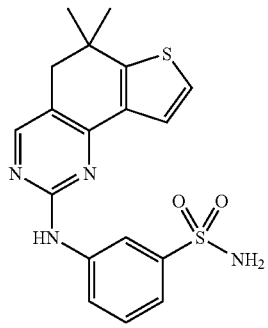

3-(6,6-Dimethyl-5,6-dihydrothieon[2,3-h]quinazolin-2-ylamino)-benzenesulfonamide 7,7-Dimethyl-6,7-dihydro-5H-benzo[b]thiophen-4-one (196 mg, 1.09 mmol) was dissolved in DME (5 ml), treated with Brederick's reagent (336 µl, 1.63 mmol) and heated to reflux for 12 hours. The solvent was then removed in vacuo to give an orange solid which was triturated with pentane to afford the enaminone as a yellow solid (141 mg, 55%). MS ($ES^+$) 236.2. δH ($d^6$ DMSO): 0.80-0.88 (6H, m), 2.87 (2H, s), 3.08 (6H, s), 7.19 (1H, d), 7.28 (1H, d), 7.48 (1H, s).

3-Guanidino-benzenesulfonamide hydrochloride (225 mg, 0.9 mmol) was dissolved in DMA (10 ml), treated with potassium carbonate (62 mg, 0.45 mmol) and heated to 50° C. for 10 minutes. 5-Dimethylaminomethylene-7,7-dimethyl-6,7-dihydro-5H-benzo[b]thiophen-4-one (141 mg, 0.6 mmol) was the added and the reaction mixture heated to reflux for 12 hours. The mixture was extracted in ethyl acetate (100 ml) and washed with water (2×100 ml), dried (Na$_2$SO$_4$) and concentrated to give an orange oil. This was initially purified by flash chromatography and then by reverse phase preparative HPLC [Waters Delta-Pak C18, 15 uM, 100 A column, gradient 10%-100% B (solvent A: water; solvent B: CH$_3$CN) over 10 minutes at 25 mL/min] to afford the title compound as a white solid (22 mg, 9%). MS (ES$^+$) 385.2. δH (d$^6$ DMSO): 1.30 (6H, s), 2.85 (2H, s), 7.30 (2H, s), 7.36 (1H, d), 7.45 (1H, t), 7.53 (1H, d), 7.66 (1H, d), 7.77 (1H, d), 8.39 (1H, s), 8.78 (1H, s), 9.90 (1H, s).

Example 31

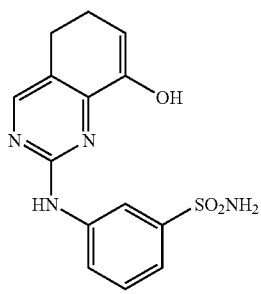

3-(8-Hydroxy-5,6-dihydro-quinazolin-2-ylamino)benzenesulfonamide

A mixture of 2-(tert-butyl-dimethyl-silanyloxy)-cyclohex-2-enone (6.9 g, 30.48 mmol) in dry toluene (50 mL) was treated with Bredereck's reagent (9.44 ml, 45.72 mmol) was stirred at 115° C. for 24 hours. The mixture was concentrated under reduced pressure to give 2-(tert-butyl-dimethyl-silanyloxy)-6-dimethylaminomethylene-cyclohex-2-enone as a semi-solid brown residue which was used as such in the next step.

The crude 2-(tert-butyl-dimethyl-silanyloxy)-6-dimethylaminomethylene-cyclohex-2-enone in DMA (75 mL) was treated with 3-guanidino-benzenesulfonamide as the hydrochloride salt (7.79 g, 31.09 mmol) and potassium carbonate (2.13, g, 15.54 mmol) and the mixture stirred at 110° C. for 20 hours. The mixture was evaporated under high vacuum and triturated with dichloromethane (100 mL) to give a buff coloured precipitate. The precipitate was filtered, the mother liquors concentrated in vacuo and purified by flash chromatography on silica gel eluting with ethyl acetate to give 3-(8-hydroxy-5,6-dihydro-quinazolin-2-ylamino)benzenesulfonamide as a yellow solid (0.63 g, 6.5%). MS (ES$^+$) 319, (ES$^-$) 317. δH (d$^6$ DMSO) 2.04-2.12 (2H, m), 2.66-2.74 (2H, m), 2.84-2.90 (2H, m), 7.33 (2H, s), 7.43 (1H, d), 7.48 (1H, t), 8.16 (1H, d), 8.25 (1H, s), 8.78 (1H, s), 10.25 (1H, s).

Example 32

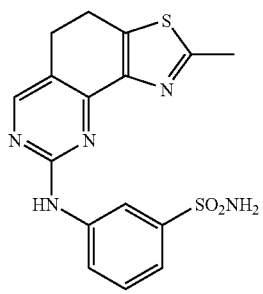

3-(2-Methyl-4,5-dihydro-3-thia-1,7,9-triaza-cyclopenta[a]naphthalen-8-ylamino)-benzenesulfonamide A solution of 3-(8-hydroxy-5,6-dihydro-quinazolin-2-ylamino)benzenesulfonamide (100 mg, 0.314 mmol) in chloroform (1 mL) was treated with a solution of bromine (32 μl, 0.628 mmol) in chloroform (1 mL) and the mixture stirred at room temperature for 2 hours giving an insoluble black residue. The solvent was decanted and the residue treated with thioacetamide (47 mg, 0.6 mmol) in ethanol (3 mL). The mixture was stirred at 80° C. for 3 hours and filtered to give a black solid (75 mg). The solid was dissolved in DMSO and purified by reverse phase preparative HPLC [Waters Delta-Pak C18, 15 uM, 100 A column, gradient 10%-100% B (solvent A: 0.05% TFA in water; solvent B: CH$_3$CN) over 10 minutes at 25 mL/min] to give a yellow solid (6.9 mg) which was further purified by flash chromatography on silica gel eluting with ethyl acetate to afford the title compound (1.9 mg) as a pale yellow solid. MS (ES$^+$) 374, (ES$^-$) 372. δH (CD$_3$OD) 2.78 (3H, s), 3.01-3.07 (2H, m), 3.10-3.16 (2H, m), 7.46 (1H, t), 7.53 (1H, d), 7.65 (2H, s, partially exchanged), 7.83 (1H, d), 8.27 (1H, s), 8.48 (1H, s).

Example 33

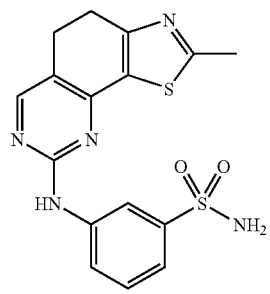

3-(2-Methyl-4,5-dihydro-thiazolo[4,5-h]quinazolin-8-ylamino)-benzenesulfonamide

Sodium (76 mg, 3.33 mmol) in diethylether (6 mL) was treated with ethyl formate (0.146 mL, 1.80 mmol) and 2-methyl-5,6-dihydro-4H-benzothiazol-7-one (0.251 g, 1.50 mmol). The reaction mixture was cooled down to 0° C. and ethanol (0.193 mL, 3.30 mmol) was added. The cooling bath was removed and the reaction mixture was stirred at room temperature for 4 hours. The solvent was then removed in vacuo and the resulting crude product was taken through to the next step without further purification.

The above was dissolved in anhydrous DMA (5 mL) and treated with 3-guanidino-benzenesulfonamide hydrogen chloride (384 mg, 1.53 mmol) and powdered potassium carbonate (106 mg, 0.77 mmol). The mixture was heated to 120° C. with vigorous stirring for 12 hours. The mixture was cooled down to room temperature, extracted in ethyl acetate (20 ml) and washed with water (2×20 ml), dried (MgSO$_4$) and concentrated in vacuo. This was initially purified by flash chromatography and then by reverse phase preparative HPLC [Waters Delta-Pak C18, 15 uM, 100 A column, gradient 10% -100% B (solvent A: 0.05% TFA in water; solvent B: CH$_3$CN) over 10 minutes at 25 mL/min] to afford the title compound (20 mg) as a yellow powder. MS (ES$^+$) 374, (ES$^-$) 372. δH (d$^6$ DMSO) 2.73 (3H, s), 3.00 (4H, m), 7.31 (2H, s), 7.38 (1H, s), 7.46 (1H, t), 7.89 (1H, d), 8.36 (1H, s), 8.41 (1H, s), 9.91 (1H, s).

A variety of other compounds of formula III have been prepared by methods substantially similar to those described in Example 33. The characterization data for these compounds is summarized in Table 16 below and includes HPLC, LC/MS (observed) and $^1$H NMR data.

$^1$H NMR data is summarized in Table 16 below wherein $^1$H NMR data was obtained at 400 MHz in deuterated DMSO, unless otherwise indicated, and was found to be consistent with structure. Compound numbers correspond to the compound numbers listed in Table 3.

TABLE 16

Characterization Data for Selected Compounds of Formula III

| Compound No. | M + 1 (obs) | Rt (min) | $^1$H-NMR |
|---|---|---|---|
| III-31 | 474 | 8.9 | 1.22(9H, s), 2.99(2H, d), 3.05(2H, d), 5.42(2H, s), 7.28(2H, s), 7.37(1H, d), 7.44(1H, t), 7.83(1H, d), 8.39(1H, s), 8.43(1H, s), 9.93(1H, s) |
| III-32 | 445 | 7.5 | 2.87(4H, m), 3.54(4H, t), 3.74(4H, t), 7.29(2H, s), 7.35(1H, m), 7.43(1H, t), 7.89(1H, m), 8.16(1H, s), 8.41(1H, t), 9.73(1H, s) |
| III-33 | 431 | 8.4 | 1.21(6H, t), 2.85(4H, m), 3.54(4H, q), 7.28(2H, s), 7.35(1H, m), 7.43(1H, t), 7.87(1H, m), 8.12(1H, s), 8.42(1H, t), 9.66(1H, s) |
| III-34 | 443 | 8.7 | 1.63(6H, s), 2.84(4H, m), 3.56(4H, s), 7.29(2H, s), 7.35(1H, d), 7.43 (1H, t), 7.89(1H, d), 8.13(1H, s), 8.42(1H, s), 9.69(1H, s) |
| III-35 | 472 | 7.1 | 1.44-1.54(2H, m), 1.89-2.10(4H, m), 2.16(3H, s), 2.67-2.74(2H, m), 2.76-2.88(4H, m), 3.58(1H, br s), 7.27(2H, s), 7.35(1H, m), 7.42(1H, t), 7.89(1H, m), 8.10(1H, s), 8.37-8.40(2H, m), 9.64(1H, s) |
| III-36 | 444 | 7.0 | 2.75-2.90(8H, m), 3.47(4H, t), 7.29(2H, s), 7.35(1H, d), 7.43(1H, t), 7.89(1H, d), 8.14(1H, s), 8.41(1H, s), 9.71(1H, s) |
| III-37 | 486 | 7.1 | 2.06(3H, s), 2.80-2.93(4H, m), 3.50-3.78(8H, m), 7.29(2H, s), 7.36(1H, d), 7.44(1H, t), 7.89(1H, d), 8.16(1H, s), 8.40(1H, t), 9.72(1H, s) |
| III-38 | 390 | 6.4 | 2.95-3.05(4H, m), 4.76(2H, d), 6.22(1H, t), 7.29(2H, s), 7.39(1H, d), 7.48(1H, t), 7.94(1H, d), 8.39(2H, s), 9.90(1H, s) |
| III-39 | 458 | 7.7 | 2.24(3H, s), 2.44(4H, t), 2.86(4H, m), 3.55(4H, t), 7.29(2H, s), 7.35(1H, m), 7.43(1H, t), 7.89(1H, m), 8.15(1H, s), 8.40(1H, t), 9.72(1H, s) |
| III-40 | 513 | 8.1 | 2.24(3H, s), 2.44(4H, t), 2.86(4H, m), 2.92(3H, s), 3.15(3H, s), 3.55(4H, t), 7.26(1H, m), 7.39(1H, t), 7.92(1H, dd), 8.15(1H, s), 8.20(1H, s), 8.30(1H, t), 9.68(1H, s) |

Example 34

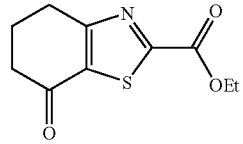

7-Oxo-4,5,6,7-tetrahydro-benzothiazole-2-carboxylic acid ethyl ester

A mixture of 2-bromo-cyclohexane-1,3-dione (3.84 g, 20.10 mmol) and ethyl thiooxamate (1.339 g, 10.05 mmol) in pyridine (20 mL) was heated overnight at 50° C. The crude reaction mixture was concentrated in vacuo, taken up in dichloromethane and washed with water and brine. The organic extract was dried over magnesium sulfate, filtered and concentrated in vacuo. The residue was purified by silica gel chromatography eluting with EtOAc:hexanes (30:70) to give the title compound in 20% yield (0.45 g). MS (ES+) 226. δH (CDCl₃) 1.47(3H, t), 2.28 (2H, quint.), 2.71 (2H, t), 3.18 (2H, t), 4.53 (2H, q).

Example 35

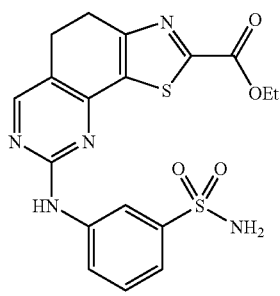

8-(3-Sulfamoyl-phenylamino)-4,5-dihydro-thiazolo[4,5-h]quinazoline-2-carboxylic acid ethyl ester To 7-oxo-4,5,6,7-tetrahydro-benzothiazole-2-carboxylic acid ethyl ester (0.1128 g, 0.50 mmol) was added DMF/DMA solution (3 mL) and the mixture was refluxed under nitrogen for 1 hour. The reaction mixture was concentrated in vacuo and the resulting crude product (6-dimethylaminomethylene-7-oxo-4,5,6,7-tetrahydro-benzothiazole-2-carboxylic acid ethyl ester) was taken through to the next step without further purification. The above was dissolved in anhydrous DMA (3 mL) and treated with 3-guanidino-benzenesulfonamide hydrogen chloride (128 mg, 0.51 mmol) and powdered potassium carbonate (35 mg, 0.26 mmol). The mixture was heated to 120° C. with vigorous stirring for 12 hours. The mixture was cooled down to room temperature, and diluted with water. The resulting solid was filtered, rinsed with more water, a little bit of ⁱPrOH and Et₂O. The crude solid was purified by silica gel to give the title compound as a brown solid in 24% yield (52mg). MS (ES+) 432, (ES−) 430. δH (d⁶ DMSO) 1.36 (3H, t), 3.05 (2H, t), 3.17 (2H, t), 4.42 (2H, q), 7.33 (2H, s), 7.41 (1H, d), 7.50 (1H, t), 7.89 (1H, d), 8.43 (1H, t), 8.52 (1H, s), 10.04 (1H, s).

Example 36

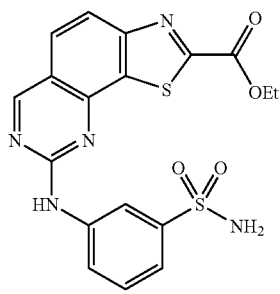

8-(3-Sulfamoyl-phenylamino)-thiazolo[4,5-h]quinazoline-2-carboxylic acid ethyl ester A suspension of 8-(3-Sulfamoyl-phenylamino)-4,5-dihydro-thiazolo[4,5-h]quinazoline-2-carboxylic acid ethyl ester (609 mg, 1.41 mmol) and 2,3-dichloro-5,6-dicyano-1,4-benzoquinone (480 mg, 2.12 mmol) in anhydrous 1,4-dioxane (30 mL) was refluxed under nitrogen for 2 hours. The reaction mixture was cooled down to room temperature and the DDQ residues were filtered. The mother liquor was concentrated in vacuo and the resulting crude residue was triturated in a mixture of EtOAc, MeOH and DCM. The resulting solid was filtered to afford 523 mg (86% yield) of the title compound as a yellow solid. MS (ES+) 430, (ES−) 428. δH (d⁶ DMSO) 1.42 (3H, t), 4.51 (2H, q), 7.37 (2H, s), 7.52 (1H, d), 7.60 (1H, t), 8.09 (1H, d), 8.14 (2H, s), 8.70 (1H, s), 9.55 (1H, s), 10.59 (1H, s).

Example 37

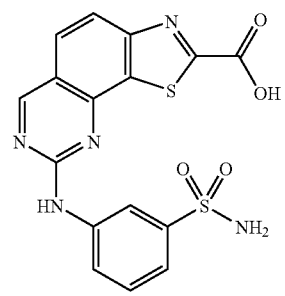

8-(3-Sulfamoyl-phenylamino)-thiazolo[4,5-h]quinazoline-2-carboxylic acid 8-(3-Sulfamoyl-phenylamino)-thiazolo[4,5-h]quinazoline-2-carboxylic acid ethyl ester (494 mg, 1.15mmol) was suspended in a mixture of EtOH (30 ml) and 1N sodium hydroxide (20 ml). The mixture was stirred at room temperature for 12 h. EtOH was removed in vacuo and the residual crude mixture was neutralised with 1N HCl (20 ml). The resulting solid was filtered and dried under vacuo to afford 0.473 g of a brownish solid. MS (ES+) 402, (ES−) 400. δH (d⁶ DMSO) 7.37 (2H, s), 7.50 (1H, d), 7.60 (1H, t), 8.06 (2H, s), 8.16 (1H, d), 8.62 (1H, s), 9.50 (1H, s), 10.52 (1H, s), 14.80 (1H, br s).

Example 38

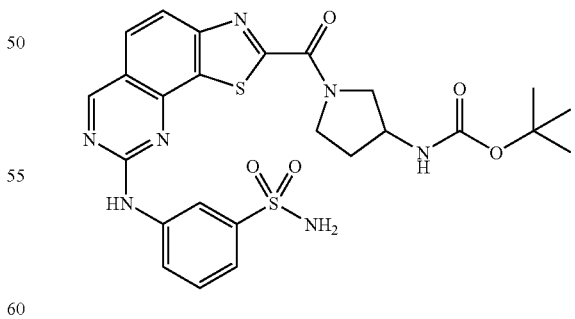

{1-[8-(3-Sulfamoyl-phenylamino)-thiazolo[4,5-h]quinazoline-2-carbonyl]-pyrrolidin-3-yl}-carbamic acid tert-butyl ester Diisopropylethylamine (68 μl, 0.39 mmol) was added to a mixture of 8-(3-Sulfamoyl-phenylamino)-thiazolo[4,5-h]

quinazoline-2-carboxylic acid (78 mg, 0.19 mmol), 3-(tert-butoxycarbonylamino)pyrrolidine (36.2 mg, 0.19 mmol) and PyBrop (91 mg, 0.19 mmol) in dimethylformamide (1 ml). The reaction mixture was stirred at room temperature for 12 h. The reaction was concentrated under reduced pressure, redissolved in isopropanol (10 mL) and water was added (5 mL). The precipitate formed was isolated by filtration and washed with water (1×5 mL), dilute NaHSO$_4$ (1×5 mL), water (1×5 mL), saturated Na$_2$CO$_3$ (1×5 mL), water (1×5 mL), isopropanol (1×5 mL), diethyl ether (4×5 mL) giving a yellow powder (87 mg, 80% yield). MS (ES$^+$) 570, (ES$^-$) 568.

Example 39

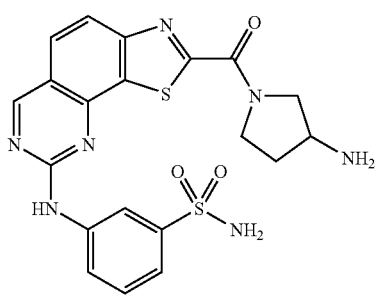

3-[2-(3-aminopyrrolidine-1-carbonyl)-thiazolo[4,5-h]quinazolin-8-ylamino]-benzenesulfonamide Trifluoroacetic acid (1 ml) was added to a suspension of {1-[8-(3-Sulfamoyl-phenylamino)-thiazolo[4,5-h]quinazoline-2-carbonyl]-pyrrolidin-3-yl}-carbamic acid tert-butyl ester (87 mg, 0.15 mmol) in dichloromethane (1 ml). The reaction mixture was stirred at room temperature for 1 hour. The solution was concentrated under reduced pressure and the residue was purified by reverse phase preparative HPLC [Waters Delta-Pak C18, 15 uM, 100 A column, gradient 10%-100% B (solvent A: 0.05% TFA in water; solvent B: CH$_3$CN) over 10 minutes at 25 mL/min] to afford the title compound as a yellow solid. MS (ES$^+$) 470, (ES$^-$) 468. δH (d$^6$ DMSO) 2.0-2.5 (4H, m), 3.70-4.05 (3H, m), 4.31-4.44 (2H, m), 7.37 (2H, s), 7.52 (1H, d), 7.60 (1H, t), 8.02-8.13 (6H, m), 8.69 (1H, s), 9.55 (1H, d), 10.57 (1H, s).

A variety of other compounds of formula V have been prepared by methods substantially similar to those described in Example 38 and 39. The characterization data for these compounds is summarized in Table 17 below and includes HPLC, LC/MS (observed) and $^1$H NMR data.

$^1$H NMR data is summarized in Table 17 below wherein $^1$H NMR data was obtained at 400 MHz in deuterated DMSO, unless otherwise indicated, and was found to be consistent with structure. Compound numbers correspond to the compound numbers listed in Table 5.

TABLE 17

Characterization Data for Selected Compounds of Formula V

| Compound No. | M + 1 (obs) | Rt (min) | $^1$H-NMR |
|---|---|---|---|
| V-177 | 484 | 6.4 | 1.50-1.67(2H, m), 2.00-2.15(2H, m), 3.00-3.13(1H, m), 3.30-3.50(2H, m), 4.52-4.58(1H, m), 5.09-5.15(1H, m), 7.37(2H, s), 7.51 (1H, d), 7.59(1H, t), 7.92(3H, br s), 8.02-8.13(3H, m), 8.74(1H, s), 9.55(1H, s), 10.58(1H, s) |
| V-178 A | 470 | / | 3.25-3.35(4H, m), 3.94(2H, s), 4.56(2H, s), 7.34(2H, s), 7.49(1H, d), 7.58(1H, t), 8.02-8.13(3H, m), 8.73(1H, s), 8.92(2H, s), 9.56(1H, s), 10.59(1H, s) |

Example 40

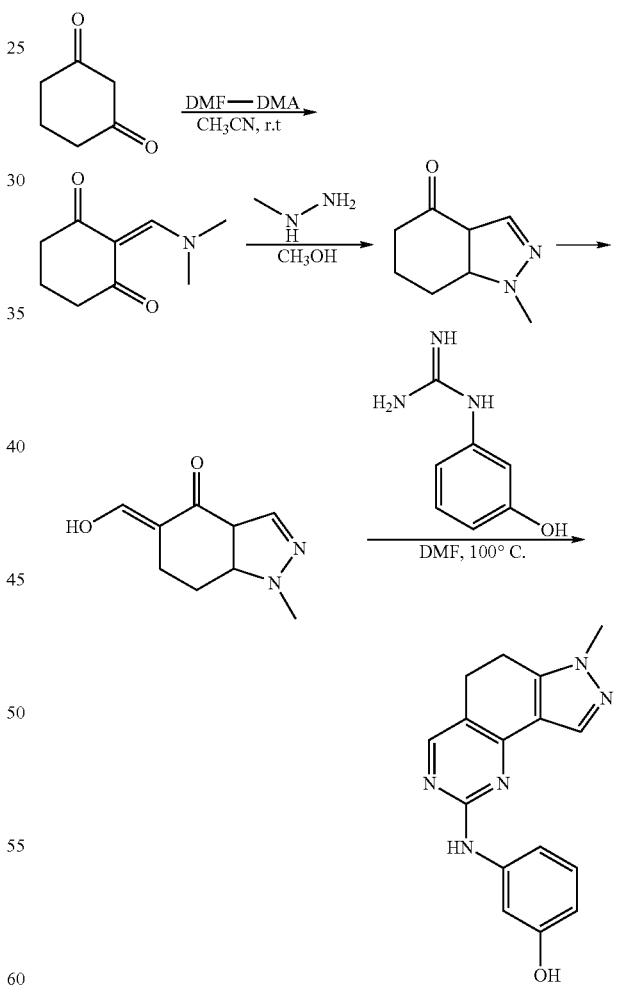

2-Dimethylaminomethylene-cyclohexane-1,3-dione

A MeCN solution of cyclohexane-1,3-dione 2.24 g (0.02 mol) i and DMF-DMA 11.9 g (0.1 mol) was stirred at room temperature for 4 h. The solvent was removed under reduced pressure and the product was used for the next step with no purification.

1-Methyl-1,3a,5,6,7,7a-hexahydro-indazol-4-one

A MeOH solution of methylhydrazine 0.046 g (0.01 mol) and 2-dimethylaminomethylene-cyclohexane-1,3-dione 1.67 g (0.01 mol) was stirred at room temperature for 1 h, and then was stirred at 50° C. for 1 h. NMR of crude material indicated the reaction was completed. Work up: The reaction mixture was diluted with ethyl acetate and washed with brine. The organic phase was dried with $MgSO_4$, and the solvent was rotary evaporated. The crude product was filtered through silica gel, and 1.03 g pure product was obtained, the yield is 69%.

5-Hydroxymethylene-1-methyl-1,3a,5,6,7,7α-hexahydro-indazol-4-one

To a MeCN solution of 1-methyl-1,3a,5,6,7,7a-hexahydro-indazol-4-one 1.03 g (0.00686 mol) was added Bredereck's reagent 1.79 g (0.010 mol) and the mixture was stirred at 75° C. for 2 h. Thin layer chromatography indicated starting material to be the major component, hence 3 equivalents of DMF-DMA were added and the reaction mixture was stirred at 80° C. overnight. The solvent was evaporated and the crude material was used for next step.

3-(7-Methyl-5,7-dihydro-6H-pyrazolo[3,4-h]quinazolin-2-ylamino)-phenol

To the DMF solution of crude 5-hydroxymethylene-1-methyl-1,3a,5,6,7,7a-hexahydro-indazol-4-one was added 10 eq of N-(3-hydroxy-phenyl)-guanidine, the reaction mixture was stirred at 100° C. for overnight, LC/MS indicated one of the two peaks is the desired product. The DMF solution of reaction mixture was directly injected into prep HPLC, only a portion of the product mixture was purified.

Example 41

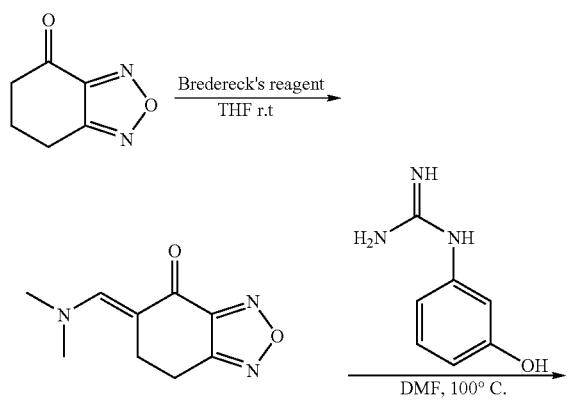

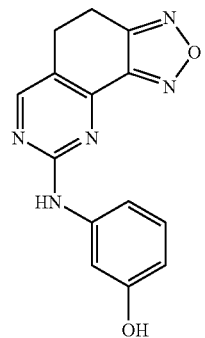

5-Dimethylaminomethylene-6,7-dihydro-5H-benzo[1,2,5]oxadiazol-4-one

A THF solution of 4,5,6,7-tetrahydro-2,1,3-benzoxadiazole-4-one 1 g (0.00725 mol) and Bredereck's reagent 1.89 g (0.0109 mol) was stirred at room temperature for 2 days. The crystalline precipitate was filtered, washed with THF and dried, 0.8 g desired product was obtained, the yield is 57%.

3-(4,5-dihydro-2-oxa-1,3,7,9-tetraaza-cyclopenta[a]naphthalen-8-ylamino)-phenol The DMF solution of 5-dimethylaminomethylene-6,7-dihydro-5H-benzo[1,2,5]oxadiazol-4-one 0.1 g (0.00052 mol) and 3 equivalents of N-(3-hydroxy-phenyl)-guanidine was stirred at 110° C. for overnight, the final product was purified by directly injecting the DMF reaction solution into prep HPLC.

Example 42

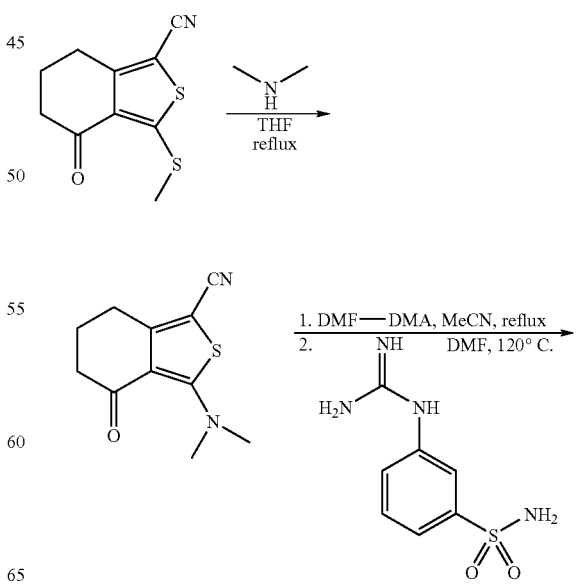

-continued

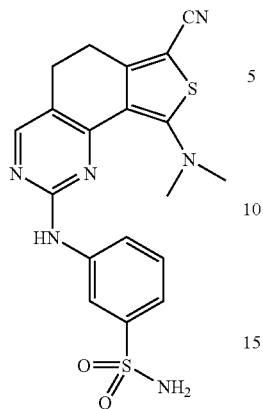

3-Dimethylamino-4-oxo-4,5,6,7-tetrahydro-benzo[c]thiophene-1-carbonitrile

A solution of 3-methylsulfanyl-4-oxo-4,5,6,7-tetrahydro-benzo[c]thiophene-1-carbonitrile (0.446 g) and dimethylamine (excess) in THF were heated in a sealed tube at 80° C. for 10 days. Aqueous work up and chromatographic purification afforded 0.2 g of 3-dimethylamino-4-oxo-4,5,6,7-tetrahydro-benzo[c]thiophene-1-carbonitrile (45%).

3-(3-Cyano-1-dimethylamino-4,5-dihydro-2-thia-7,9-diaza-cyclopenta-[a]naphthalen-8-ylamino)-benzene sulfonamide 1. A solution of 3-dimethylamino-4-oxo-4,5,6,7-tetrahydro-benzo[c]thiophene-1-carbonitrile 0.2 g (0.9 mmol) and excess of DMF-DMA in MeCN was refluxed overnight. The solvent was evaporated and the crude material was used for the next step without purification.
2. The crude enaminone was heated together with 3-guanidino-benzenesulfonamide in DMF at 120° C. overnight. Following aqueous work up, the product was purified by preparative HPLC.

Example 43

Exemplary Synthesis of Compounds where X is —CH$_2$CH$_2$—, n is 0 and Cy$^1$ is Optionally Substituted Phenyl

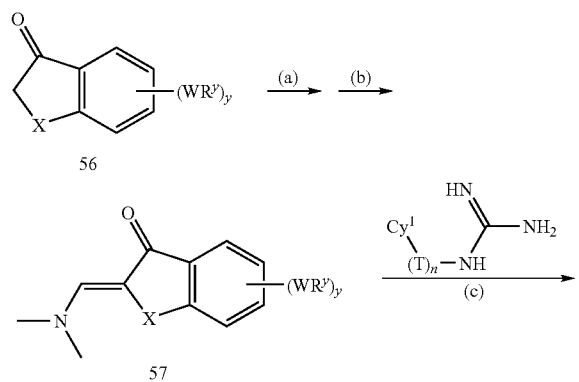

-continued

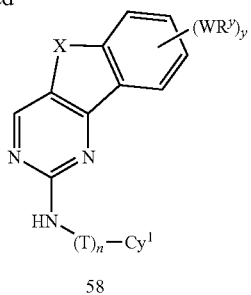

2-Dimethylaminomethylene-3,4-dihydro-2H-naphthalen-1-one (57)

A solution of 3,4-dihydro-2H-naphthalen-1-one in MeCN and 20 eq. of DMF-DMA were stirred at 90° C. overnight. Thin layer chromatography indicated there is almost no desired product, hence 1.2 equivalents of Bredereck's reagent was added, and the reaction mixture stirred at 80° C. overnight. The solvent was removed under reduced pressure and the crude material was used for the next step with no further purification.

(5,6-Dihydro-benzo[h]quinazolin-2-yl)-phenyl-amine (58)

A solution of 2-dimethylaminomethylene-3,4-dihydro-2H-naphthalen-1-one 100 mg in 5 ml DMF and 3 eq. of N-phenyl-guanidine was stirred at 110° C. for overnight, the product was purified by directly injecting the DMF reaction solution into prep HPLC.

BIOLOGICAL EXAMPLES

Example 1

Aurora-2 Inhibition Assay

Compounds were screened for their ability to inhibit Aurora-2 using a standard coupled enzyme assay (Fox et al., Protein Sci., (1998) 7, 2249). Assays were carried out in a mixture of 100 mM Hepes (pH 7.5), 10 mM MgCl$_2$, 1 mM DTT, 25 mM NaCl, 2.5mM phosphoenolpyruvate, 300 μM NADH, 30 μg/ml pyruvate kinase and 10 μg/ml lactate dehydrogenase. Final substrate concentrations in the assay were 400 μM ATP (Sigma Chemicals) and 570 μM peptide (Kemptide, American Peptide, Sunnyvale, Calif.). Assays were carried out at 30° C. and in the presence of 40 nM Aurora-2.

An assay stock buffer solution was prepared containing all of the reagents listed above, with the exception of Aurora-2 and the test compound of interest. 55 μl of the stock solution was placed in a 96 well plate followed by addition of 2 μl of DMSO stock containing serial dilutions of the test compound (typically starting from a final concentration of 7.5 μM). The plate was preincubated for 10 minutes at 30° C. and the reaction initiated by addition of 10 μl of Aurora-2. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Compounds of the present invention were shown to inhibit Aurora-2 using the assay methods described above. In general, compounds of the invention are effective for the inhibition of Aurora-2.

Example 2

CDK-2 Inhibition Assay

Compounds were screened for their ability to inhibit Cdk2/cyclin A using a standard coupled enzyme assay (Fox et al., Protein Sci., (1998) 7, 2249). Assays were carried out in a mixture of 25 mM Hepes (pH 7.5), 10 mM $MgCl_2$, 0.5 mM DTT, 2.5 mM phosphoenolpyruvate, 300 µM NADH, 30 µg/ml pyruvate kinase and 10 µg/ml lactate dehydrogenase. Final substrate concentrations in the assay were 500 µM ATP (Sigma Chemicals) and 150 µM peptide (Histone H1, Upstate Biotechnology, UK). Assays were carried out at 30° C. and in the presence of 9 nM Cdk2/cyclin A.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Compounds of the present invention were shown to inhibit CDK-2 using the assay methods described above. In general, compounds of the invention are effective for the inhibition of CDK-2.

Example 3

Inhibition of c-KIT

Compounds were screened for their ability to inhibit c-KIT activity using a radiometric filter-binding assay. This assay monitors the $^{33}P$ incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 700 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 1.4 mM ATP(containing 0.5 µCi of $[\gamma-^{33}P]$ ATP for each reaction). Solution 2 contains 100 mM HEPES (pH 7.5), 10 mM $MgCl_2$, 25 mM NaCl, 2 mM DTT, 0.02% BSA and 25 nM c-KIT. The assay was run on a 96 well plate by mixing 33 µL of Solution 1 and 1.65 µL of the test compounds. The reaction was initiated with 33 µL of Solution 2. After incubation for 20 minutes at room temperature, the reaction was stopped with 50 µL of 10% TCA containing 0.2 mM of ATP. All of the reaction volume was then transferred to a filter plate and washed with 5% TCA by a Harvester 9600 from TOMTEC (Hamden, Conn.). The amount of $^{33}P$ incorporation into pE4y was analyzed by a Packard TopCount Microplate Scintillation Counter (Meriden, Conn.). The data was fitted using Prism software to get an $IC_{50}$ or $K_i$.

In general, compounds of the invention are effective for the inhibition of c-KIT.

Example 4 cMET Inhibition Assay

Compounds were screened for their ability to inhibit cMet kinase activity using a standard coupled enzyme system (Fox et al., Protein Sci. 1998, 7, 2249). Reactions were carried out in a solution containing 100 mM HEPES (pH 7.5), 10 mM $MgCl_2$, 25 mM NaCl, 300 µM NADH, 1 mM DTT, and 1.5% DMSO. Final substrate concentrations in the assay were 200 µM ATP (Sigma Chemicals, St Louis, Mo.) and 10 µM poly-GluTyr (Sigma Chemical Company, St. Louis). Reactions were carried out at 30° C. and 80 nM cMet. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and a test compound of the present invention. The assay stock buffer solution (175 µl) was incubated in a 96 well plate with 5 µl of the test compound of the present invention at final concentrations spanning 0.006 µM to 12.5 µM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 µl of ATP (final concentration 200 µM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the present invention were shown to inhibit cMet using the assay methods described above. In general, compounds of the invention are effective for the inhibition of cMet.

Example 5

ERK Inhibition Assay

Compounds were assayed for the inhibition of ERK2 by a spectrophotometric coupled-enzyme assay (Fox et al. Protein Sci. 1998, 7, 2249). In this assay, a fixed concentration of activated ERK2 (10 nM) was incubated with various concentrations of a compound of the present invention in DMSO (2.5%) for 10 min. at 30° C. in 0.1 M HEPES buffer (pH 7.5), containing 10 mM $MgCl_2$, 2.5 mM phosphoenolpyruvate, 200 µM NADH, 150 µg/ml pyruvate kinase, 50 µg/ml lactate dehydrogenase, and 200 µM erktide peptide. The reaction was initiated by the addition of 65 µM ATP. The rate of decrease of absorbance at 340 nM was monitored. The $K_i$ values were determined from the rate data as a function of inhibitor concentration.

In general, compounds of the invention are effective for the inhibition of ERK-2.

Example 6

FLT-3 Inhibition Assay

Compounds were screened for their ability to inhibit FLT-3 activity using a radiometric filter-binding assay. This assay monitors the $^{33}$P incorporation into a substrate poly(Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 µM ATP and 0.5 mg/ml pE4Y (both from Sigma Chemicals, St Louis, Mo.). The final concentration of a compound of the present invention is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM MgCl$_2$, 25 mM NaCl, 1 mg/ml pE4Y and 180 µM ATP(containing 0.3 µCi of [γ-$^{33}$P] ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay was run on a 96 well plate by mixing 50 µl each of Solution 1 and 2.5 ml of the compounds of the present invention. The reaction was initiated with Solution 2. After incubation for 20 minutes at room temperature, the reaction was stopped with 50 µl of 20% TCA containing 0.4 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard Top Count Microplate Scintillation Counter (Meriden, Conn.). The data was fitted using Prism software to get an IC$_{50}$ or K$_i$.

Compounds of the present invention were shown to inhibit FLT-3 using the assay methods described above. In general, compounds of the invention are effective for the inhibition of FLT-3.

Example 7

GSK-3 Inhibition Assay

Compounds were screened for their ability to inhibit GSK-3β using a standard coupled enzyme assay (Fox et al., Protein Sci., (1998) 7, 2249). Assays were carried out in a mixture of 100 mM Hepes (pH 7.5), 10 mM MgCl$_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay were 60 µM ATP (Sigma Chemicals) and 300 µM peptide (HSSPHQS(PO$_3$H$_2$) EDEEE, American Peptide, Sunnyvale, Calif.). Assays were carried out at 30° C. and in the presence of 35 nM GSK-3β.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of GSK-3.

Example 8

JAK Inhibition Assay

Method A

Compounds of the present invention were screened for their ability to inhibit JAK activity using the method described by G. R. Brown et al., Bioorg. Med. Chem. Lett. 2000, 10, 575-579 in the following manner. Into Maxisorb plates, previously coated at 4° C. with Poly (Glu, Ala, Tyr) 6:3:1 then washed with phosphate buffered saline 0.05% and Tween (PBST), was added 2 µM ATP, 5 mM MgCl$_2$, and a solution of a compound of the present invention in DMSO. The reaction was started with JAK enzyme and the plates incubated for 60 minutes at 30° C. The plates were then washed with PBST, 100 µl HRP-Conjugated 4G10 antibody was added, and the plate incubated for 90 minutes at 30° C. The plate was again washed with PBST, 100 µl TMB solution was added, and the plates were incubated for another 30 minutes at 30° C. Sulfuric acid (100 µl of a 1M solution) was added to stop the reaction and the plate was read at 450 nm to obtain the optical densities for analysis to determine IC$_{50}$ values and K$_i$ values.

Method B

JAK-3 Assay Components:

"kinase buffer": 100 mM HEPES pH 7.4; 1 mM DTT; 10 mM MgCl2; 25 mM NaCl; 0.01%; BSA.

1 nM JAK3 (enzyme)

1 uM poly(Glu)$_4$Tyr (substrate)

5 uM ATP (substrate, 200 uCi/umole ATP)

Procedure:

To each well of a 96 well polycarbonate plate is added 1.5 ul of a candidate JAK3 inhibitor along with 50 ul of kinase buffer containing 2 uM poly(Glu)$_4$Tyr and 10 uM ATP. This is then mixed and 50 ul of kinase buffer containing 2 nM JAK-3 enzyme is added to start the reaction. After 20 minutes at room temperature (25 C), the reaction is stopped with 50 ul of 20% trichloroacetic acid (TCA) that also contains 0.4 mM ATP. The entire content of each well is then transferred to a 96 well glass fiber filter plate using a TomTek Cell Harvester. After washing, 60 ul of scintillation fluid is added and $^{33}$P incorporation detected on a Perkin Elmer TopCount.

JAK-2 Assay:

As above except that final poly(Glu)4Tyr concentration is 15 uM and final ATP concentration is 12 uM.

In general, compounds of the invention are effective for the inhibition of JAK (particularly JAK-3).

Example 9

SRC Inhibition Assay

Compounds were screened for their ability to inhibit Src using a standard coupled enzyme assay (Fox et al., Protein Sci., (1998) 7, 2249). Assays were carried out in a mixture of 25 mM Hepes (pH 7.5), 10 mM MgCl2, 2.2 mM DTT, 2.5 mM phosphoenolpyruvate, 300 µM NADH, 30 µg/ml pyruvate kinase and 10 µg/ml lactate dehydrogenase. Final substrate concentrations in the assay were 100 µM ATP (Sigma Chemicals) and 0.28 mg/ml peptide (poly 4Glu:Tyr, Sigma Chemicals). Assays were carried out at 30° C. and in the presence of 25 nM Src.

An assay stock buffer solution was prepared containing all of the reagents listed above, with the exception of peptide and the test compound of interest. 60 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 5 µl of peptide. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of SRC.

Example 10

LCK Inhibition Assay

The compounds were assayed as inhibitors of lck kinase purified from bovine thymus (from Upstate Biotechnology, cat. no. 14-106). Lck kinase activity was monitored by following the incorporation of $^{33}$P from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 µM ATP (1-2 µCi $^{33}$P-ATP per reaction), 5 mg/ml poly Glu-Tyr, and 1-2 units of lck kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}$P-ATP. After 20 min of reaction, the reactions were quenched with 150 µl of 10% trichloroacetic acid (TCA) containing 20 mM $Na_3PO4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 µl of scintillation fluid was then added to each well. The plates were sealed and the amount of radioactivity associated with the filters was quantified on a TopCount scintillation counter.

In general, compounds of the invention are effective for the inhibition of LCK.

Example 11

SYK Inhibition Assay

Compounds were screened for their ability to inhibit Syk using a standard coupled enzyme assay (Fox et al., Protein Sci., (1998) 7, 2249). Assays were carried out in a mixture of 100 mM Hepes (pH 7.5), 10 mM $MgCl_2$, 2mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay were 100 µM ATP (Sigma Chemicals) and 20 µM peptide (poly 4Glu:Tyr, Sigma Chemicals). Assays were carried out at 30° C. and in the presence of 20 nM Syk.

An assay stock buffer solution was prepared containing all of the reagents listed above, with the exception of Syk enzyme and the test compound of interest. 55 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 10 µl of Syk enzyme. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of SYK.

Example 12

ITK Inhibition Assay

The compounds of the present invention were evaluated as inhibitors of human Itk kinase using either a radioactivity-based, spectrophotometric or alphascreen assay.

Itk Inhibition Assay: Radioactivity-based Assay (Method A)

Assays were carried out in a mixture of 100 mM HEPES (pH 7.5), 10 mM $MgCl_2$, 25 mM NaCl, 0.01% BSA and 1 mM DTT. Final substrate concentrations were 15 µM [γ-$^{33}$P]ATP (400 µCi $^{33}$P ATP/µmol ATP, Amersham Pharmacia Biotech/Sigma Chemicals) and 2 µM peptide (SAM68 protein Δ332-443). Assays were carried out at 25° C. in the presence of 30 nM Itk. An assay stock buffer solution was prepared containing all of the reagents listed above, with the exception of ATP and the test compound of interest. 50 µL of the stock solution was placed in a 96 well plate followed by addition of 1.5 µL of DMSO stock containing serial dilutions of the test compound (typically starting from a final concentration of 15 µM with 2-fold serial dilutions) in duplicate (final DMSO concentration 1.5%). The plate was pre-incubated for 10 minutes at 25° C. and the reaction initiated by addition of 50 µL [γ-$^{33}$P]ATP (final concentration 15 µM).

The reaction was stopped after 10 minutes by the addition of 50 µL of a TCA/ATP mixture (20% TCA, 0.4 mM ATP). A Unifilter GF/C 96 well plate (Perkin Elmer Life Sciences, Cat no. 6005174) was pretreated with 50 µL Milli Q water prior to the addition of the entire reaction mixture (150 µL). The plate was washed with 200 µL Milli Q water followed by 200 µL of a TCA/ATP mixture (5% TCA, 1 mM ATP). This wash cycle was repeated a further 2 times. After drying, 30 µL Optiphase 'SuperMix' liquid scintillation cocktail (Perkin Elmer) was added to the well prior to scintillation counting (1450 Microbeta Liquid Scintillation Counter, Wallac).

IC50 data were calculated from non-linear regression analysis of the initial rate data using the Prism software package (GraphPad Prism version 3.0cx for Macintosh, GraphPad Software, San Diego Calif., USA).

Itk Inhibition Assay: Alphascreen Assay (Method B)

Assays were carried out in a mixture of 20 mM MOPS (pH 7.0), 10 mM $MgCl_2$, 0.1% BSA and 1 mM DTT. Final substrate concentrations in the assay were 100 µM ATP (Sigma Chemicals) and 2 µM peptide (Biotinylated SAM68 Δ332-443). Assays were carried out at 25° C. and in the presence of 10 nM Itk. An assay stock buffer solution was prepared containing all of the reagents listed above, with the exception of ATP and the test compound of interest. 25 µL of the stock solution was placed in each well of a 96 well plate followed by 1 μL of DMSO containing serial dilutions of the test compound (typically starting from a final concentration of 15 μM) in duplicate (final DMSO concentration 2%). The plate was preincubated for 10 minutes at 25° C. and the reaction initiated by addition of 25 μL ATP (final concentration 100 μM). Background counts were determined by the addition of 5 μL 500 mM EDTA to control wells containing assay stock buffer and DMSO prior to initiation with ATP. The reaction was stopped after 30 minutes by diluting the reaction 225-fold into MOPS buffer (20 mM MOPS (pH 7.0), 1 mM DTT, 10 mM $MgCl_2$, 0.1% BSA) containing 50 mM EDTA to bring the final concentration of peptide to 9 nM.

AlphaScreen™ reagents were prepared according to the manufacturers instructions (AlphaScreen™ phosphotyrosine (P-Tyr-100) assay kit, PerkinElmer catalogue number 6760620C). Under subdued lighting, 20 μL of AlphaScreen™ reagents were placed in each well of a white half area 96 well plate (Corning Inc.—COSTAR 3693) with 30 μL of the stopped, diluted kinase reactions. Plates were incubated in the dark for 60 minutes prior to reading on a Fusion Alpha plate reader (PerkinElmer).

After removing mean background values for all of the data points, Ki(app) data were calculated from non-linear regression analysis using the Prism software package (GraphPad Prism version 3.0cx for Macintosh, GraphPad Software, San Diego Calif., USA).

Itk Inhibition Assay: Spectrophotometric Assay (Method C)

Compounds were screened for their ability to inhibit Itk using a standard coupled enzyme assay (Fox et al., Protein Sci., (1998) 7, 2249).

Assays were carried out in a mixture of 20 mM MOPS (pH 7.0), 10 mM $MgCl_2$, 0.1% BSA, 1 mM DTT, 2.5 mM phosphoenolpyruvate, 300 μM NADH, 30 μg/ml pyruvate kinase and 10 μg/ml lactate dehydrogenase. Final substrate concentrations in the assay were 100 μM ATP (Sigma Chemicals) and 3 μM peptide (Biotinylated SAM68 Δ332-443). Assays were carried out at 25° C. and in the presence of 10 nM Itk.

An assay stock buffer solution was prepared containing all of the reagents listed above, with the exception of ATP and the test compound of interest. 60 μl of the stock solution was placed in a 96 well plate followed by addition of 2 μl of DMSO stock containing serial dilutions of the test compound (typically starting from a final concentration of 15 μM). The plate was preincubated for 10 minutes at 25° C. and the reaction initiated by addition of 5 μl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

In general, compounds of the invention are effective for the inhibition of Itk. Preferred compounds showed IC50 below 1 μM in the radioactive incorporation assay (Method A) (I-1, I-2, I-3, I-4, I-5, I-6, I-7, I-8, I-9, I-10, I-11, I-12, I-13, I-14, I-15, I-17, I-18, I-19, I-20, I-21, I-23, I-24, I-25, I-27, I-28, I-29. Preferred compounds showed Ki below 1 μM in the AlphaScreen™ assay (Method B) (I-36, I-41, II-13, II-34, II-35, II-36, II-37, II-38, II-39, III-4, III-31, III-32, III-33, III-34, III-35, III-38, III-39, III-40, IV-4, V-4, V-36, V-37, V-38, V-39, V-40, V-41, V-42, V-43, V-44, V-45, V-46, V-47, V-48, V-49, V-50, V-51, V-52, V-54). Preferred compounds showed Ki below 1 μM in the standard coupled enzyme assay (Method C) (V-55, V-56, V-58, V-59, V-60, V-61, V-63, V-67, V-68, V-69, V-70, V-71, V-72, V-73, V-74, V-76, V-77, V-78, V-79, V-80, V-81, V-82, V-83, V-84, V-85, V-86, V-87, V-88, V-89, V-90, V-91, V-92, V-93, V-94, V-95, V-96, V-97, V-98, V-100, V-101, V-102, V-103, V-104, V-105, V-106, V-107, V-108, V-109, V-110, V-111, V-112, V-113, V-114, V-115, V-116, V-117, V-118, V-119, V-120, V-121, V-122, V-125, V-127, V-129, V-130, V-131, V-132, V-133, V-134, V-135, V-136, V-137, V-138, V-139, V-140, V-141, V-142, V-143, V-144, V-145, V-146, V-147, V-148, V-149, V-150, V-151, V-152, V-153, V-154, V-155, V-156, V-157, V-159, V-162, V-165, V-166, V-167, V-170, V-172, V-173, V-175, V-176, V-177, V-178, V-179, V-180, V-182).

Example 13

BTK Inhibition Assay

The compounds of the present invention were evaluated as inhibitors of human Btk kinase using either a radioactivity-based or alphascreen assay.

Btk Inhibition Assay: Radioactivity-based Assay

Assays were carried out in a mixture of 20 mM MOPS (pH 7.0), 10 mM $MgCl_2$, 0.1% BSA and 1 mM DTT. Final substrate concentrations in the assay were 50 μM [γ-$^{33}$P]ATP (200 μCi $^{33}$P ATP/μmol ATP, Amersham Pharmacia Biotech, Amersham, UK/Sigma Chemicals) and 2 μM peptide (SAM68 Δ332-443). Assays were carried out at 25° C. and in the presence of 25 nM Btk. An assay stock buffer solution was prepared containing all of the reagents listed above, with the exception of the peptide and the test compound of interest. 75 μL of the stock solution was placed in a 96 well plate followed by addition of 2 μL of DMSO stock containing serial dilutions of the test compound (typically starting from a final concentration of 15 μM) in duplicate (final DMSO concentration 2%). The plate was preincubated for 15 minutes at 25° C. and the reaction initiated by addition of 25 μL peptide (final concentration 2 μM). Background counts were determined by the addition of 100 μL 0.2M phosphoric acid+0.01% TWEEN to control wells containing assay stock buffer and DMSO prior to initiation with peptide.

The reaction was stopped after 10 minutes by the addition of 100 μL 0.2M phosphoric acid+0.01% TWEEN. A multiscreen phosphocellulose filter 96-well plate (Millipore, Cat no. MAPHN0B50) was pretreated with 100 μL 0.2M phosphoric acid+0.01% TWEEN 20 prior to the addition of 170 μL of the stopped assay mixture. The plate was washed with 4×200 μL 0.2M phosphoric acid+0.01% TWEEN 20. After drying, 30 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis using the Prism software package (GraphPad Prism version 3.0cx for Macintosh, GraphPad Software, San Diego Calif., USA).

Btk Inhibition Assay: Alphascreen Assay

Assays were carried out in a mixture of 20 mM MOPS (pH 7.0), 10 mM $MgCl_2$, 0.1% BSA and 1 mM DTT. Final substrate concentrations in the assay were 50 μM ATP (Sigma Chemicals) and 2 μM peptide (Biotinylated SAM68 Δ332-443). Assays were carried out at 25° C. and in the presence of 25 nM Btk. An assay stock buffer solution was prepared containing all of the reagents listed above, with the exception of peptide and the test compound of interest. 37.5 μL of the stock solution was placed in each well of a 96 well plate followed by 1 μL of DMSO containing serial dilutions of the test compound (typically starting from a final concentration of 15 μM) in duplicate (final DMSO concentration 2%). The plate was preincubated for 15 minutes at 25° C. and the reaction initiated by addition of 12.5 μL peptide (final concentration 2 μM). Background counts were determined by the addition of 5 μL 500 mM EDTA to control wells containing assay stock buffer and DMSO prior to initiation with Biotin-SAM68.

The reaction was stopped after 30 minutes by diluting the reaction 225-fold into MOPS buffer (20 mM MOPS (pH 7.0), 1 mM DTT, 10 mM $MgCl_2$, 0.1% BSA) containing 50 mM EDTA to bring the final concentration of peptide to 9 nM. AlphaScreen™ reagents were prepared according to the manufacturers instructions (AlphaScreen™ phosphotyrosine (P-Tyr-100) assay kit, PerkinElmer catalogue number 6760620C). Under subdued lighting, 20 μL of AlphaScreen™ reagents were placed in each well of a white half area 96 well plate (Corning Inc.—COSTAR 3693) with 30 μL of the stopped, diluted kinase reactions. Plates were incubated in the dark for 60 minutes prior to reading on a Fusion Alpha plate reader (PerkinElmer).

After removing mean background values for all of the data points, Ki(app) data were calculated from non-linear regression analysis using the Prism software package (GraphPad Prism version 3.0cx for Macintosh, GraphPad Software, San Diego Calif., USA).

In general, compounds of the invention are effective for the inhibition of Btk.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

The invention claimed is:

1. A compound of formula I:

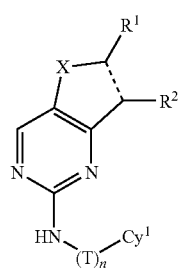

I or a pharmaceutically acceptable salt thereof, wherein:
X is —CH=CH—, —S—$CH_2$—, —$CH_2$—S—, —$CH_2$—O—, —O—$CH_2$—, or —$(CH_2)_3$—, wherein one or more of the hydrogen substituents are optionally and independently replaced with m occurrences of —$WR^y$, wherein m is an integer selected from 0 to 5;
$R^1$ and $R^2$, taken together with the carbon atoms to which they are bound form an optionally substituted 5-membered heteroaryl thiophene ring,
wherein the ring formed by $R^1$ and $R^2$ taken together is optionally and independently substituted at one or more carbon atoms with m occurrences of —$WR^y$, wherein m is an integer selected from 0 to 5;
each occurrence of W is independently a bond or is a $C_1$-$C_6$ alkylidene chain wherein up to two non-adjacent methylene units of W are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^y$ is independently selected from R', halogen, $NO_2$, or CN, or —$WR^y$ is =O, =S, or =NR';
T is CHR', $CH_2CH(R')$, —S(=O)$_2$, or C(=O);
n is 0 or 1;
$Cy^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur, wherein $Cy^1$ is optionally and independently substituted at one or more carbon atoms with k occurrences of -$QR^X$, wherein k is an integer selected from 0 to 5; and at one or more substitutable nitrogen atoms with —$R^4$; wherein Q is a bond or is a $C_1$-$C_6$ alkylidene chain wherein up to two non-adjacent methylene units of Q are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and
each occurrence of $R^X$ is independently selected from R', halogen, $NO_2$, $CF_3$, or CN, or -$QR^X$ is =O, =S, or =NR';
each occurrence of $R^3$ and $R^4$ is independently R', —COR', —$CO_2(C_{1-6}$aliphatic), —$CON(R')_2$, or —$SO_2R'$;
each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form an optionally substituted 3-8 membered cycloalkyl, heterocyclyl, aryl, or heteroaryl ring having 0-3 heteroatoms independently selected from nitrogen, oxygen, or sulfur; and
the dashed bond represents a single or double bond, as valency permits.

2. A compound of formula I:

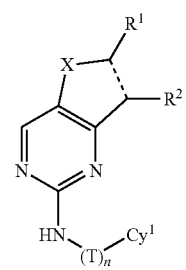

I or a pharmaceutically acceptable salt thereof, wherein:
X is —CH=CH—, —S—$CH_2$—, —$CH_2$—S—, —$CH_2$—O—, —O—$CH_2$—, or —$(CH_2)_3$—, wherein one or more of the hydrogen substituents are optionally and independently replaced with m occurrences of —$WR^y$, wherein m is an integer selected from 0 to 5;
$R^1$ and $R^2$, taken together with the carbon atoms to which they are bound form an optionally substituted 5-membered heteroaryl thiophene ring, wherein the ring formed by R¹ and R² taken together is optionally and independently substituted at one or more carbon atoms with m occurrences of —WR^y, wherein m is an integer selected from 0 to 5;

each occurrence of W is independently a bond or is a $C_1$-$C_6$ alkylidene chain wherein up to two non-adjacent methylene units of W are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of R^y is independently selected from R', halogen, $NO_2$, or CN, or —WR^y is =O, =S, or =NR';

T is CHR', $CH_2CH_2(R')$, —S(=O)$_2$, C(=O), CHR'CH$_2$; $CH_2CH_2CH_2$, or $CH_2CHR'CH_2$;

n is 0 or 1;

$Cy^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur, wherein $Cy^1$ is optionally and independently substituted at one or more carbon atoms with k occurrences of -QR^X, wherein k is an integer selected from 0 to 5; and at one or more substitutable nitrogen atoms with —R⁴; wherein Q is a bond or is a $C_1$-$C_6$ alkylidene chain wherein up to two non-adjacent methylene units of Q are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence R^X is independently selected from R', halogen, $NO_2$, $CF_3$, or CN, or -QR^X is =O, =S, =NR';

each occurrence of R³ and R⁴ is independently R', —COR', —$CO_2$($C_{1-6}$aliphatic), —CON(R')$_2$, or —$SO_2$R';

each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form an optionally substituted 3-8 membered cycloalkyl, heterocyclyl, aryl, or heteroaryl ring having 0-3 heteroatoms independently selected from nitrogen, oxygen, or sulfur; and the dashed bond represents a single or double bond, as valency permits.

3. The compound of claim 1 or claim 2, wherein R¹ and R², taken together with the carbon atoms to which they are bound form an optionally substituted 5-membered heteroaryl ring selected from one of the following groups:

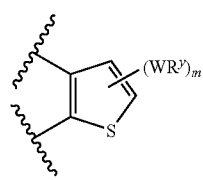

iv-1

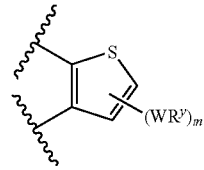

iv-2

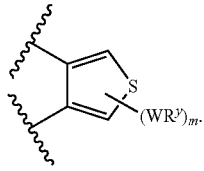

xviii

4. The compound of claim 1 or claim 2, wherein R¹ and R², taken together with the carbon atoms to which they are bound form an optionally substituted 5-membered heteroaryl ring selected from thiophenyl (iv-1, iv-2, and xviii).

5. The compound of claim 1 or claim 2, wherein each occurrence of WR^y, when present, is independently halogen, CN, $NO_2$, —N(R')$_2$, —$CH_2$N(R')$_2$, —OR', —$CH_2$OR', —SR', —$CH_2$SR', —COOR', —NRCOR', —CON(R')$_2$, or —S(O)$_2$N(R')$_2$, or an optionally substituted group selected from $C_{1-4}$alkyl, aryl, heteroaryl.

6. The compound of claim 1 or claim 2, wherein —WR^y groups are each independently F, Cl, Br, I, Me, Et, —CN, —OMe, —SMe, —NMe$_2$, —NEt$_2$, —COOMe, —COOH, —OH, —$SO_2NH_2$, —CON(CH$_3$)$_2$, —CO(optionally substituted N-piperazinyl), —CO(N-morpholinyl), —CO(N-piperidinyl), —$CH_2$N(Me)$_2$, —$CH_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl.

7. The compound of claim 1 or claim 2, wherein —WR^y groups are each independently CF$_3$, F, Cl, Br, I, Me, Et, —CN, —OMe, —SMe, —NMe$_2$, —NEt$_2$, —COOMe, —COOH, —OH, —$SO_2NH_2$, —CON(CH$_3$)$_2$, —CO(optionally substituted N-piperazinyl, —CO(N-morpholinyl), —CO(N-piperidinyl), —CO(pyrrolidinyl), —CO(N(H)pyrrolidinyl), —$CH_2$N(Me)$_2$, —$CH_2$N(Et)$_2$ or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or N(H)pyrrolidinyl.

8. The compound of claim 1 or claim 2, wherein m is 1 and WR^y is an optionally substituted aryl or heteroaryl group, wherein substituents for the optionally substituted aryl or heteroaryl group are independently selected from —VR^V; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of R^V is independently selected from R', halogen, $NO_2$, or CN, or -QR^X is =O, =S, or =NR'.

9. The compound of claim 1 or claim 2, wherein m is 1 and WR^y is —$CH_2$N(R')$_2$, —N(R')$_2$, or —CON(R')$_2$.

10. The compound of claim 1 or claim 2, wherein T groups, when present are —CH$_2$—, —CH$_2$CH$_2$—, —CO—, or —SO$_2$—.

11. The compound of claim 1 or claim 2, wherein T groups, when present are —C(H)(CH$_3$)—, —C(H)(CH$_3$)CH$_2$—, —CH$_2$C(H)(CH$_3$)—, or —CH$_2$CH$_2$CH$_2$—.

12. The compound of claim 1 or claim 2, wherein n is 0 and T is absent.
13. The compound of claim 1 or claim 2, wherein T is absent (n=0) or T is —CO—.
14. The compound of claim 1 or claim 2, wherein $Cy^1$ is selected from one of the following groups:
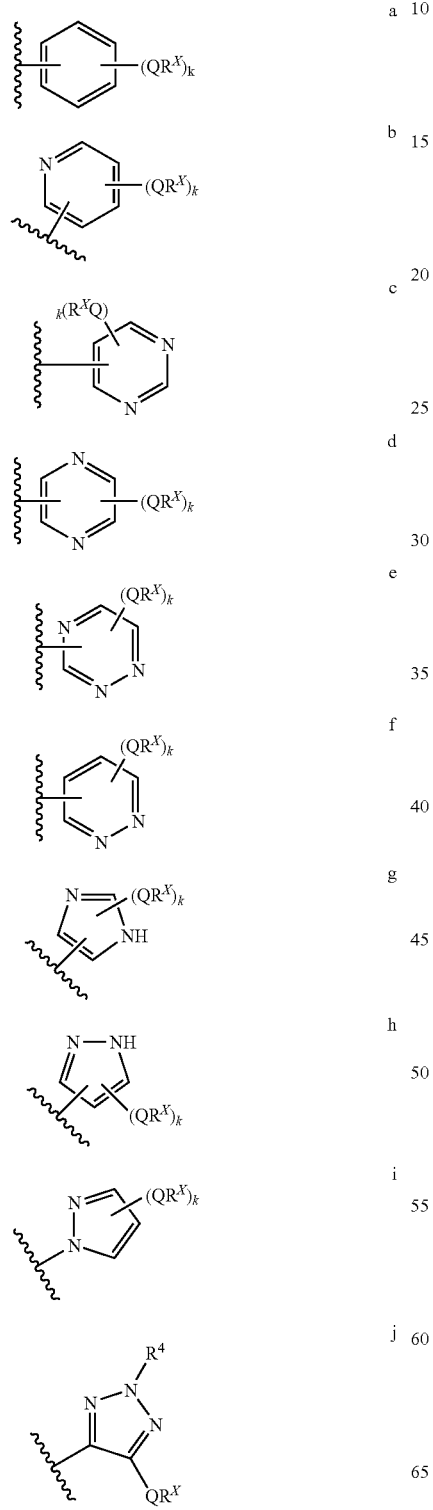
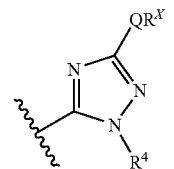
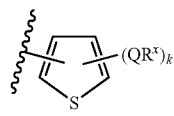
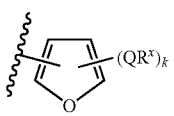
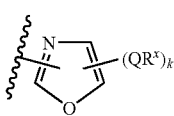
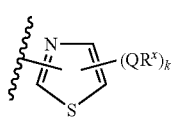
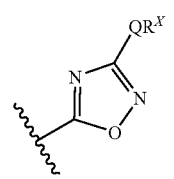
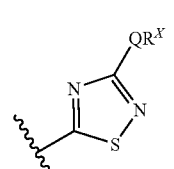
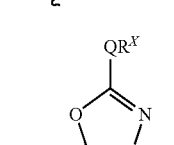
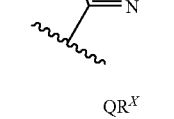
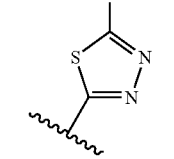
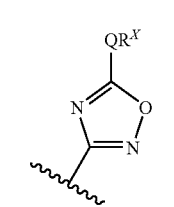

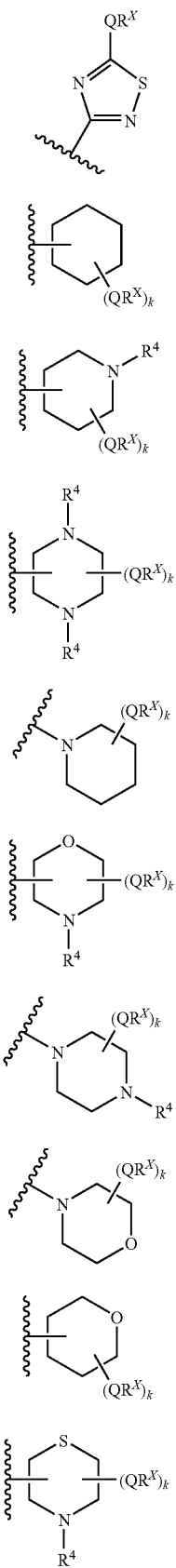
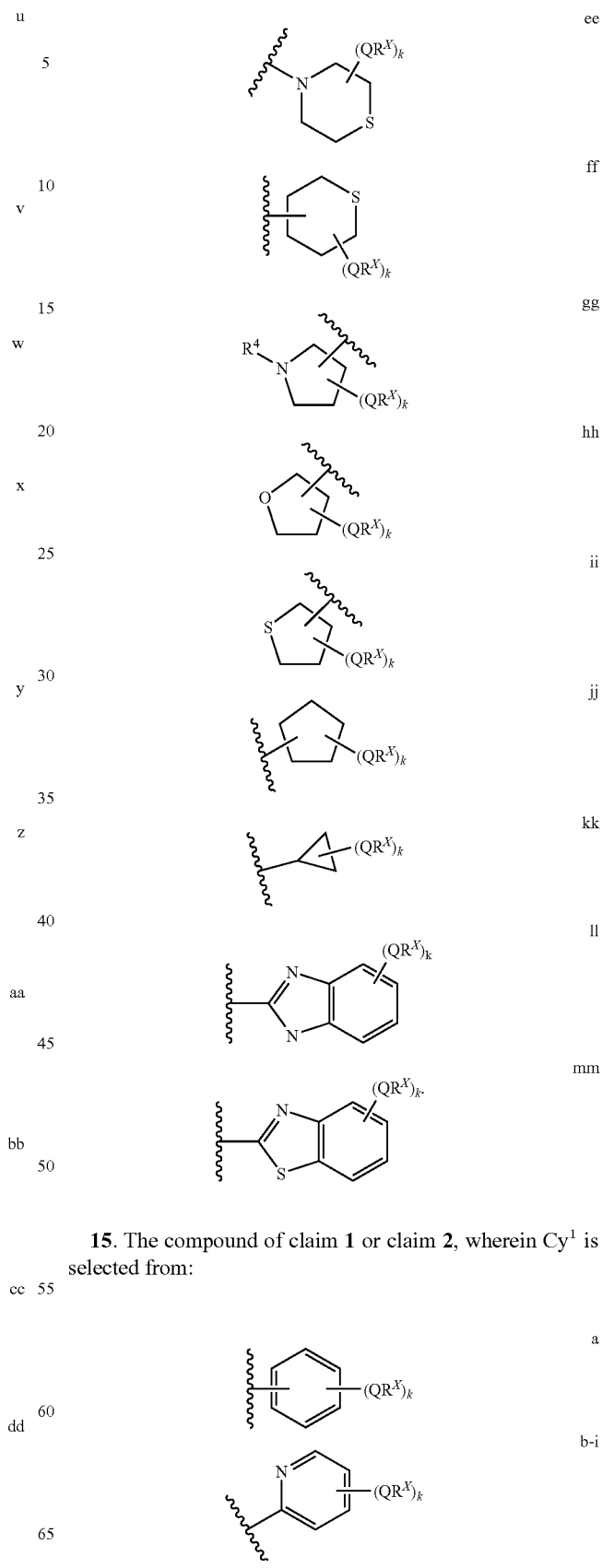
15. The compound of claim 1 or claim 2, wherein Cy$^1$ is selected from:
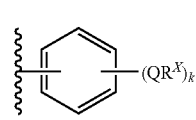
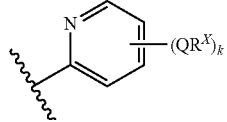

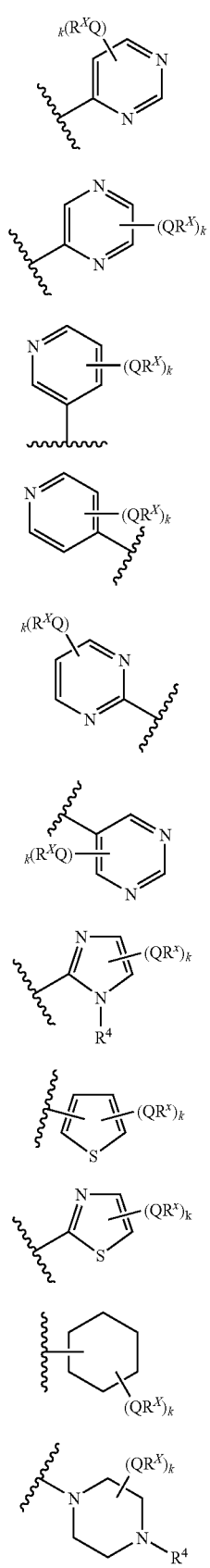
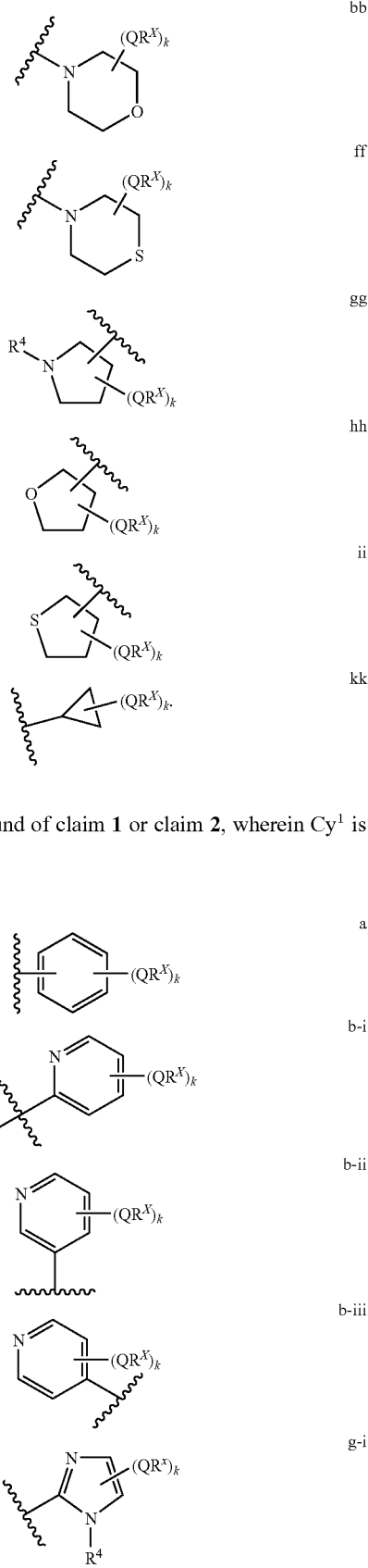
16. The compound of claim 1 or claim 2, wherein Cy¹ is selected from:

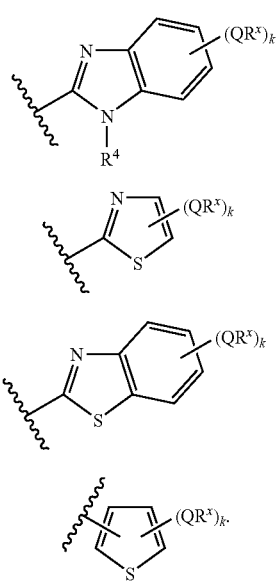

II o-i mm l

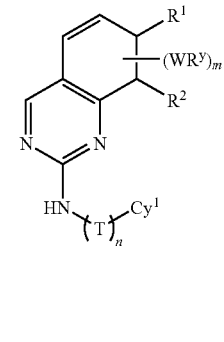

IV

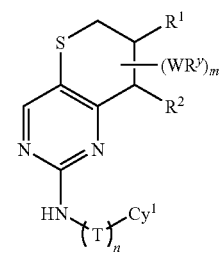

V

17. The compound of claim 1 or claim 2, wherein Cy¹ is phenyl (a), and compounds have the formula I-A:

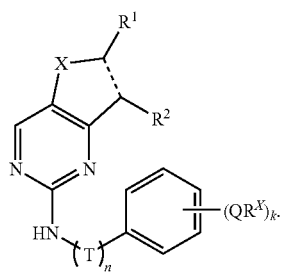

I-A

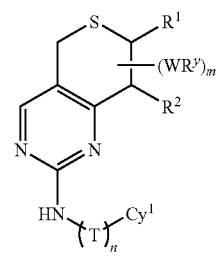

VI

18. The compound of claim 1 or claim 2, wherein QR$^X$ groups, when present, are each independently halogen, CN, NO$_2$, or an optionally substituted group selected from C$_{1-4}$alkyl, aryl, aralkyl, —N(R')$_2$, —CH$_2$N(R')$_2$, —OR', —CH$_2$OR', —SR', —CH$_2$SR', —COOR', —NRCOR', —CON(R')$_2$, —SO$_2$R', NR'SO$_2$R', or —SO$_2$N(R')$_2$.

19. The compound of claim 1 or claim 2, wherein QR$^X$ groups, when present are each independently halogen, CN, NO$_2$, or an optionally substituted group selected from C$_{1-4}$alkyl, —CF$_3$, aryl, heteroaryl, aralkyl, —N(R')$_2$, —CH$_2$N(R')$_2$, —OR', —CH$_2$OR', —SR', —CH$_2$SR', —COOR', —NRCOR', —CON(R')$_2$, —SO$_2$R', NR'SO$_2$R', SO$_2$N=R', or —SO$_2$N(R')$_2$.

20. The compound of claim 1 or claim 2, wherein QR$^X$ groups are each independently Cl, Br, F, CF$_3$, methyl, ethyl, isopropyl, n-propyl, n-butyl, tert-butyl, NO$_2$, —OH, —SO$_2$NH$_2$, SO$_2$CH$_3$, NH$_2$, SO$_2$NHCH$_3$, NHSO$_2$CH$_3$, or an optionally substituted group selected from C$_{1-4}$alkoxy, phenyl, phenyloxy, benzyl, or benzyloxy.

21. The compound of claim 2, wherein X is —CH=CH—, —S—CH$_2$—, —CH$_2$—S—, —CH$_2$—O—, or —O—CH$_2$—, and the compounds have one of the structures IV, V, VI, VII, VIII, or IX:

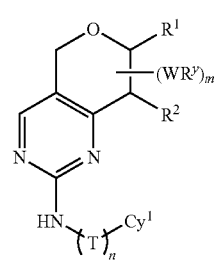

VIII

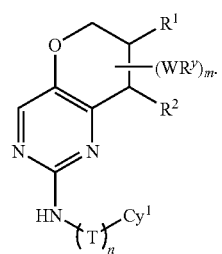

IX

22. The compound of claim 21 wherein Cy¹ is optionally substituted phenyl, and compounds have one of formulae IV-A through IX-A:

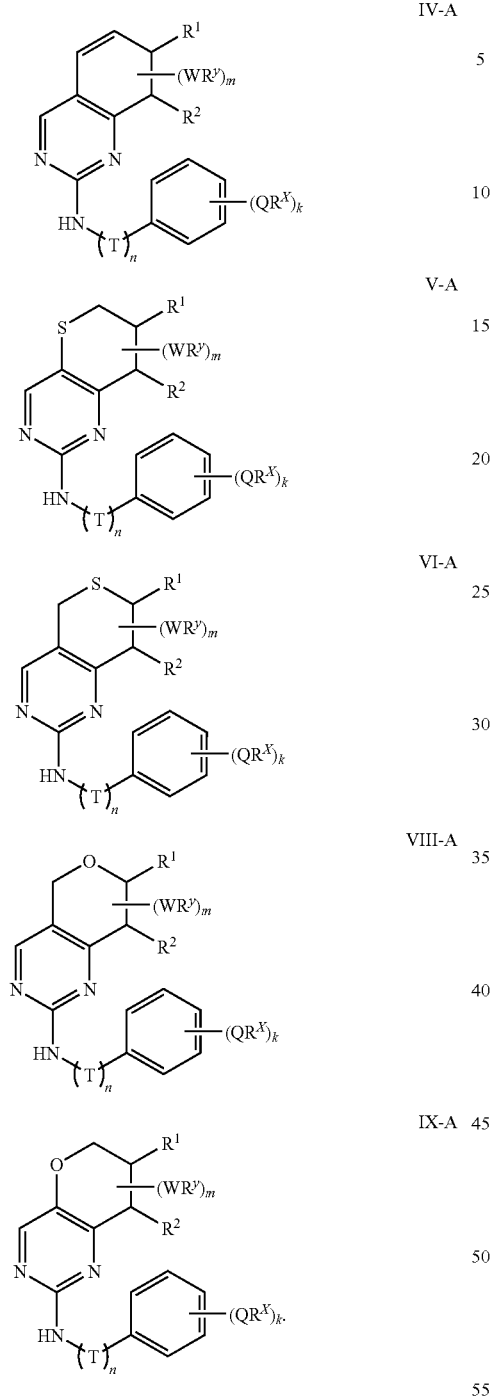

23. The compound of claim 21, wherein $R^1$ and $R^2$, taken together with the carbon atoms to which they are bound form an optionally substituted 5-membered heteroaryl ring selected from thiophenyl (iv-1, iv-2, and xviii).

24. The compound of claim 21, wherein $R^1$ and $R^2$, taken together with the carbon atoms to which they are bound form an optionally substituted 5-membered aryl or heteroaryl ring selected from thiophenyl (iv-1, iv-2, and xviii), and compounds have one of the formulas IV-G, IV-H, or IV-I:

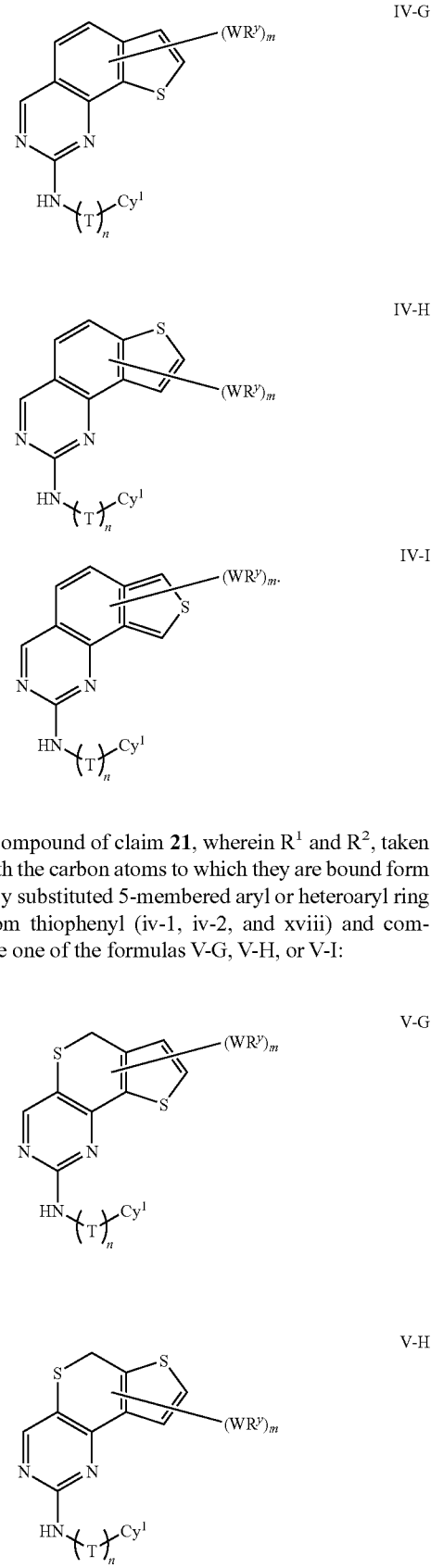

25. The compound of claim 21, wherein $R^1$ and $R^2$, taken together with the carbon atoms to which they are bound form an optionally substituted 5-membered aryl or heteroaryl ring selected from thiophenyl (iv-1, iv-2, and xviii) and compounds have one of the formulas V-G, V-H, or V-I:

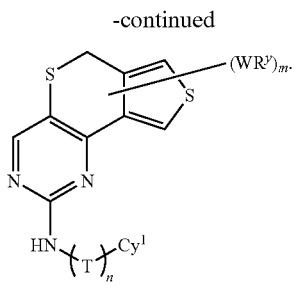

26. The compound of claim 21, wherein $R^1$ and $R^2$, taken together with the carbon atoms to which they are bound form an optionally substituted 5-membered heteroaryl ring selected from thiophenyl (iv-1, iv-2, and xviii)-and compounds have one of the formulas IX-G, IX-H, or IX-I:

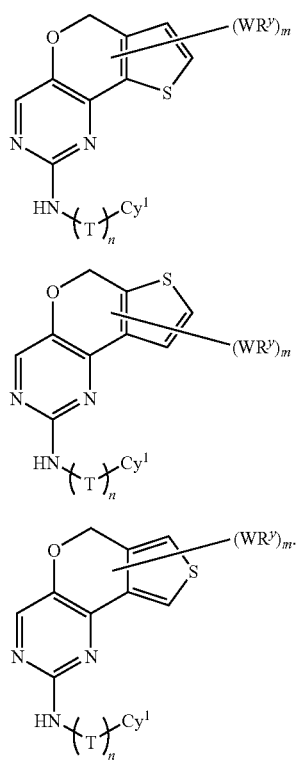

27. The compound of claim 21, wherein $Cy^1$ is phenyl, optionally substituted with 0-3 occurrences of $QR^X$.

28. The compound of claim 27, wherein n is 0, or n is 1 and T is $CH_2$, $-CH_2CH_2-$, $-CO-$ or $-SO_2-$; k is 0-3; and each occurrence of $QR^X$ is independently halogen, CN, $NO_2$, or an optionally substituted group selected from $C_{1-4}$alkyl, aryl, aralkyl, $-N(R')_2$, $-CH_2N(R')_2$, $-OR'$, $-CH_2OR'$, $-SR'$, $-CH_2SR'$, $-COOR'$, $-NRCOR'$, $-CON(R')_2$, $-SO_2R'$, $NR'SO_2R'$, or $-SO_2N(R')_2$.

29. The compound of claim 28, wherein m is 0-3 and each occurrence of $WR^y$ is independently halogen, CN, $NO_2$, or an optionally substituted group selected from $C_{1-4}$alkyl, aryl, heteroaryl, $-N(R')_2$, $-CH_2N(R')_2$, $-OR'$, $-CH_2OR'$, $-SR'$, $-CH_2SR'$, $-COOR'$, $-NRCOR'$, $-CON(R')_2$, or $-S(O)_2N(R')_2$.

30. The compound of claim 28, wherein $-WR^y$ groups are each independently $CF_3$, F, Cl, Br, I, Me, Et, $-CN$, $-OMe$, $-SMe$, $-NMe_2$, $-NEt_2$, $-COOMe$, $-COOH$, $-OH$, $-SO_2NH_2$, $-CON(CH_3)_2$, $-CO$(optionally substituted N-piperazinyl), $-CO$(N-morpholinyl), $-CO$(N-piperidinyl), $-CO$(pyrrolidinyl), $-CO$(N(H)pyrrolidinyl), $-CH_2N(Me)_2$, $-CH_2N(Et)_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, furanyl, pyrrolidinyl, or N(H) pyrrolidinyl.

31. The compound of claim 29, wherein one occurrence of $WR^y$ is an optionally substituted aryl or heteroaryl group, denoted by $Ar^1$ in one of formulae IV-H-i, V-H-i, or IX-H-i below:

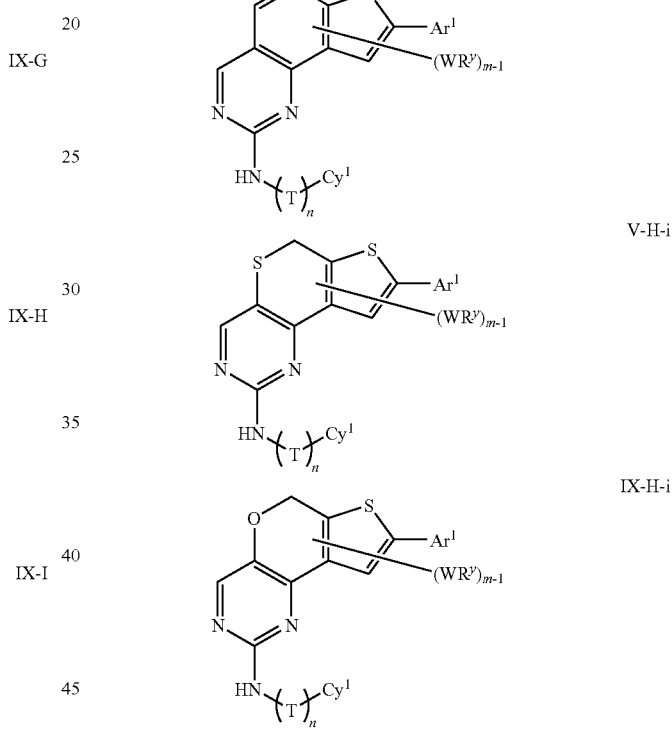

wherein $Ar^1$ is an optionally substituted with one or more occurrences of $-VR^V$; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^V$ is independently selected from R', halogen, $NO_2$, or CN, or $-QR^X$ is $=O$, $=S$, or $=NR'$.

32. The compound of claim 31, wherein m is 1 and $Ar^1$ is a phenyl, pyridyl, pyrimidinyl, thiophenyl, or furanyl group optionally substituted with one or more occurrences of $-VR^V$; wherein V is a bond or is a $C_1$-$C_6$ alkylidene chain wherein up to two non-adjacent methylene units of V are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^V$ is independently selected from R', halogen, $NO_2$, or CN, or $-QR^X$ is $=O$, $=S$, or $=NR'$.

33. The compound of claim 29, wherein one occurrence of WR$^y$ is —CH$_2$N(R')$_2$, and compounds have one of formulae IV-H-ii, V-H-ii, or IX-H-ii below, wherein m is 1-3:

IV-H-ii

V-H-ii

IX-H-ii

34. The compound of claim 29, wherein one occurrence of WR$^y$ is —N(R')$_2$, and compounds have one of formulae IV-H-iii, V-H-iii, or IX-H-iii below, wherein m is 1-3:

IV-H-iii

V-H-iii

IX-H-iii

35. The compound of claim 29, wherein one occurrence of WR$^y$ is —CON(R')$_2$ and compounds have one of the formulae IV-H-iv, V-H-iv, -or IX-H-iv below, wherein m is 1-3:

IV-H-iv

V-H-iv

IX-H-iv

36. The compound of claim 33, 34, or 35, wherein —CH$_2$N(R')$_2$ is —CH$_2$N(CH$_2$)$_3$, —CH$_2$N(CH$_2$CH$_3$)$_2$, —CH$_2$(optionally substituted N-piperazinyl), —CH$_2$(optionally substituted N-piperidinyl), or —CH$_2$(optionally substituted N-morpholinyl); —N(R')$_2$ is —N(CH$_2$)$_3$, —N(CH$_2$CH$_3$)$_2$, -optionally substituted N-piperazinyl, optionally substituted N-piperidinyl, or -optionally substituted N-morpholinyl; and —CON(R')$_2$ is —CON(CH$_2$)$_3$, —CON(CH$_2$CH$_3$)$_2$, —CO(optionally substituted N-piperazinyl), —CO(optionally substituted N-piperidinyl), or —CO(optionally substituted N-morpholinyl).

37. The compound of claim 33, 34, or 35, wherein —CH$_2$N(R')$_2$ is —CH$_2$N(CH$_2$)$_3$, —CH$_2$N(CH$_2$CH$_3$)$_2$, —CH$_2$(optionally substituted N-piperazinyl), —CH$_2$(optionally substituted N-piperidinyl), or —CH$_2$(optionally substituted N-morpholinyl); —N(R')$_2$ is —N(CH$_2$)$_3$, —N(CH$_2$CH$_3$)$_2$, -optionally substituted N-piperazinyl, optionally substituted N-piperidinyl, or -optionally substituted N-morpholinyl; and —CON(R')₂ is —CON(CH₂)₃, —CON(CH₂CH₃)₂, —CO(optionally substituted N-piperazinyl), —CO(optionally substituted N-piperidinyl), —CO(optionally substituted N-morpholinyl), —CO(optionally substituted pyrrolidinyl), —CO(N(H)optionally substituted pyrrolidinyl), optionally substituted pyrrolidinyl, or —N(H)(optionally substituted pyrrolidinyl).

38. The compound of claim 21, wherein n is 0, or n is 1 and T is CH₂, —CH₂CH₂—, —CO— or —SO₂—.

39. The compound of claim 21, wherein n is 0, or n is 1 and T is —C(H)(CH₃)—, —C(H)(CH₃)CH₂—, —CH₂C(H)(CH₃)—, or —CH₂CH₂CH₂—.

40. The compound of claim 22, wherein n is 0, or n is 1 and T is CH₂, —CH₂CH₂—, —CO— or —SO₂—; k is 0-3 and each occurrence of QR$^X$ is independently halogen, CN, NO₂, or an optionally substituted group selected from C₁₋₄alkyl, aryl, aralkyl, —N(R')₂, —CH₂N(R')₂, —OR', —CH₂OR', —SR', —CH₂SR', —COOR', —NRCOR', —CON(R')₂, —SO₂R', NR'SO₂R', or —SO₂N(R')₂.

41. The compound of claim 1 or claim 2, wherein X is —(CH₂)₃— and compounds have the general formula VII:

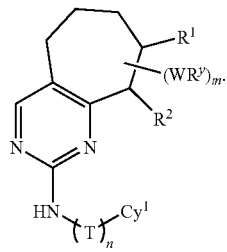

VII

42. The compound of claim 41, wherein Cy¹ is selected from any one of a through mm depicted above (including certain subsets b-i, c-i, b-ii, b-iii, c-ii c-iii, g-i, ll, o-i or mm).

43. The compound of claim 41, wherein Cy¹ is optionally substituted phenyl, and compounds have formula VII-A:

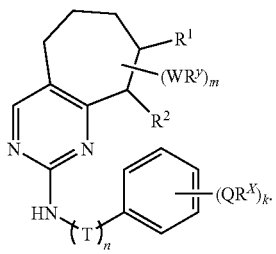

VII-A

44. The compound of claim 41, wherein R¹ and R², taken together with the carbon atoms to which they are bound form an optionally substituted 5-membered heteroaryl ring selected from thiophenyl (iv-1, iv-2, and xviii), and compounds have one of the formulae X-G, X-H, or X-I:

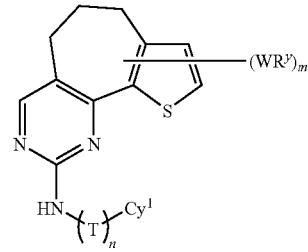

X-G

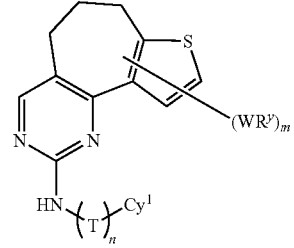

X-H

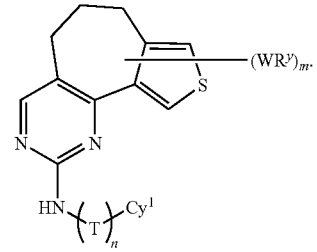

X-I

45. The compound of claim 44, wherein Cy¹ is phenyl, optionally and independently substituted with k occurrences of QR$^X$, wherein k is 0-3.

46. The compound of claim 45, wherein n is 0, or n is 1 and T is CH₂ —CH₂CH₂—, —CO— or —SO₂—; and each occurrence of QR$^X$is independently halogen, CN, NO₂, or an optionally substituted group selected from C₁-4alkyl, aryl, aralkyl, —N(R')₂, —CH₂N(R')₂, —OR', —CH₂OR', —SR', —CH₂SR', —COOR', —NRCOR', —CON(R')₂, —SO₂R', NR'SO₂R', or —SO₂N(R')₂.

47. The compound of claim 44, wherein m is 0-3; and each occurrence of WR$^y$ is independently halogen, CN, NO₂, or an optionally substituted group selected from C₁₋₄alkyl, aryl, heteroaryl, —N(R')₂, —CH₂N(R')₂, —OR', —CH₂OR', —SR', —CH₂SR', —COOR', —NRCOR', —CON(R')₂, or —S(O)₂N(R')₂.

48. The compound of claim 44, wherein m is 1 and WR$^y$ is an aryl or heteroaryl group optionally substituted with one or more occurrences of —VR$^V$; wherein V is a bond or is a C₁-C₆ alkylidene chain wherein up to two non-adjacent methylene units of V are independently optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of R$^V$ is independently selected from R', halogen, NO₂, or CN, or -QR$^X$ is =O, =S, or =NR'.

49. The compound of claim 44, wherein m is 1 and WR$^y$ is a phenyl, pyridyl, pyrimidinyl, thiophenyl, or furanyl group optionally substituted with one or more occurrences of —VR$^V$; wherein V is a bond or is a C₁-C₆ alkylidene chain wherein up to two non-adjacent methylene units of V are independently optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^V$ is independently selected from R', halogen, NO₂, or CN, or -QR$^X$ is =O, =S, or =NR'.

50. The compound of claim 44, wherein m is 1, W is —CH₂—, a bond, or —CO—, and $R^y$ is —N(R')₂ and compounds have the formula X-H-ii below:

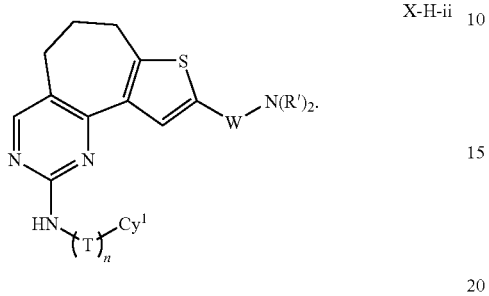

X-H-ii

51. The compound of claim 44, wherein one occurrence of WR$^y$ is an optionally substituted aryl or heteroaryl group, denoted by Ar¹ in formula X-H-i below, wherein m is 1-5:

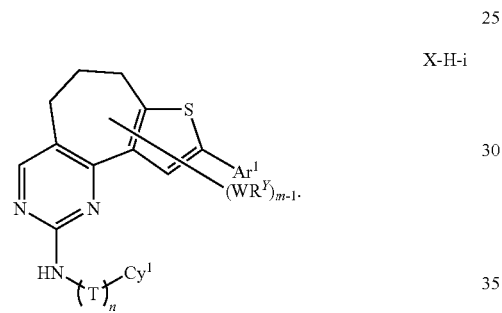

X-H-i

52. The compound of claim 51, wherein Ar¹ is a phenyl, pyridyl, pyrimidinyl, thiophenyl, or furanyl group optionally substituted with one or more occurrences of —VR$^V$; wherein V is a bond or is a C₁-C₆ alkylidene chain wherein up to two non-adjacent methylene units of V are independently optionally replaced by CO, C₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^V$ is independently selected from R', halogen, NO₂, or CN, or -QR$^X$ is =O, =S, or =NR'.

53. The compound of claim 44, wherein n is 0, or n is 1 and T is CH₂, —CH₂CH₂, —CO— or —SO₂.

54. The compound of claim 45, wherein n is 0, or n is 1 and T is CH₂, —CH₂CH₂—, —CO— or —SO₂—; and each occurrence of QR$^X$ is independently halogen, CN, NO₂, or an optionally substituted group selected from C₁-4alkyl, aryl, aralkyl, —N(R')₂, —CH₂N(R')₂, —OR', —CH₂OR', —SR', —CH₂SR', —COOR', —NRCOR', —CON(R')₂, —SO₂R', NR'SO₂R', or —SO₂N(R')₂.

55. The compound of claim 22, wherein X is —CH=CH—.

56. The compound of claim 55 wherein R¹ and R², taken together with the carbon atoms to which they are bound, form an optionally substituted thieno ring.

57. The compound of claim 1, wherein the compound is selected from:

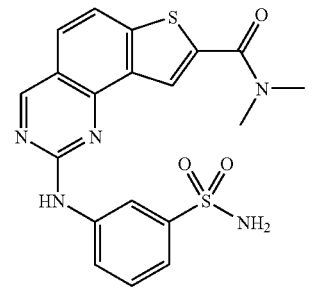

V-1

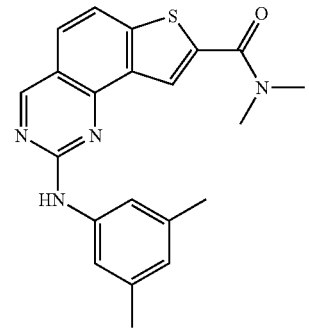

V-2

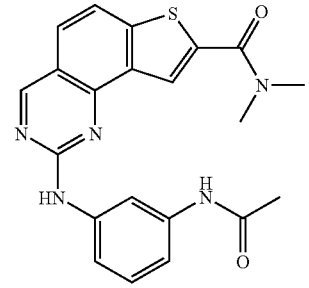

V-3

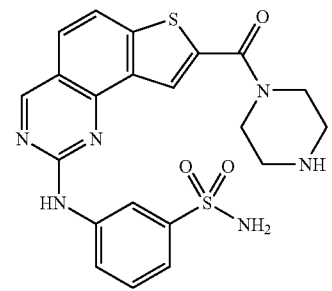

V-4

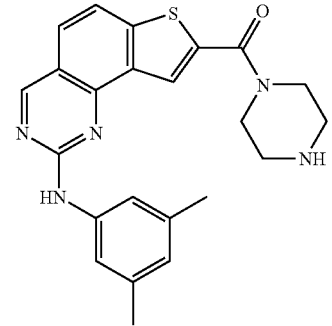

V-5

-continued
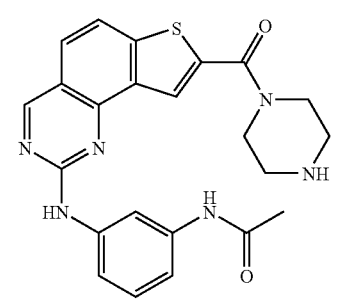
V-6
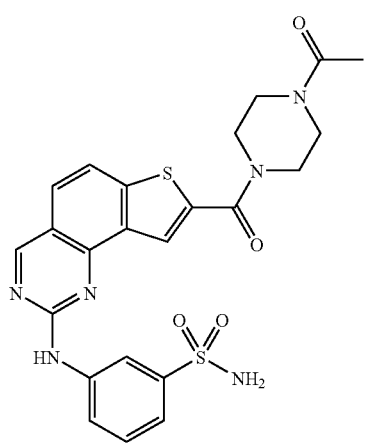
V-7
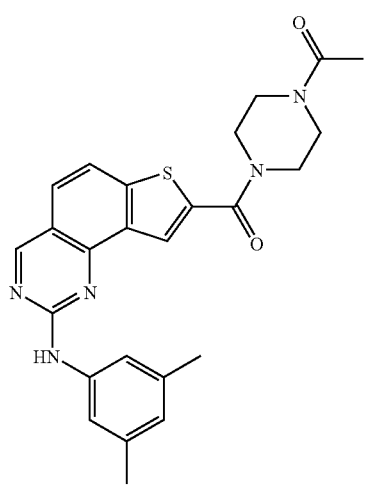
V-8
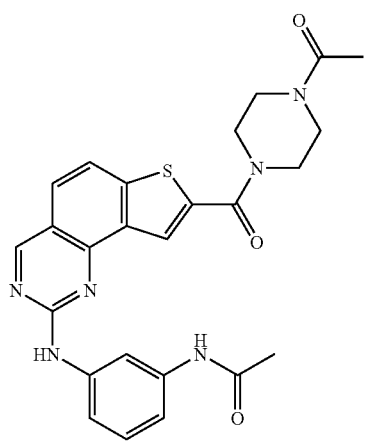
V-9
-continued
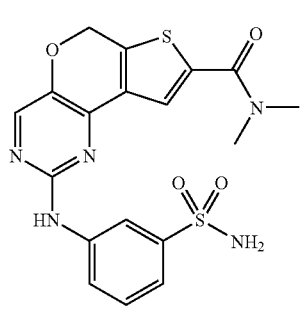
V-10
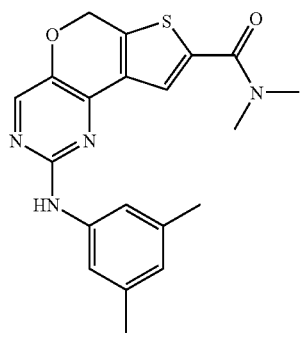
V-11
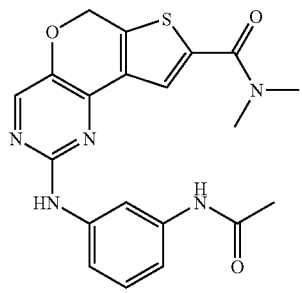
V-12
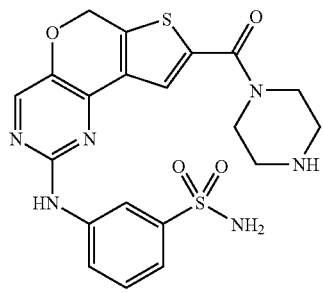
V-13
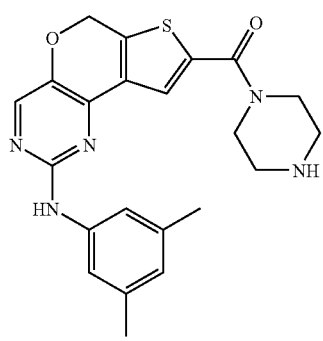
V-14

-continued
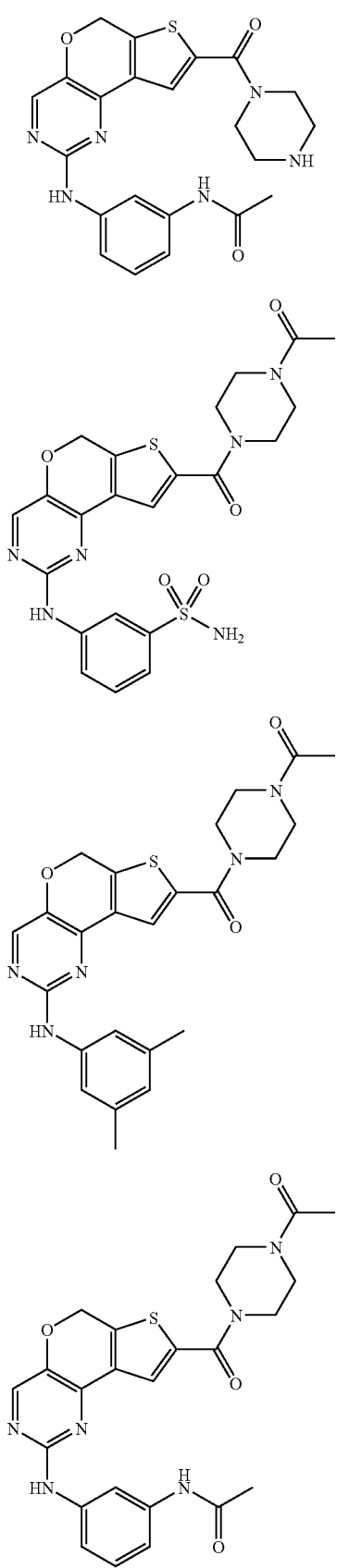
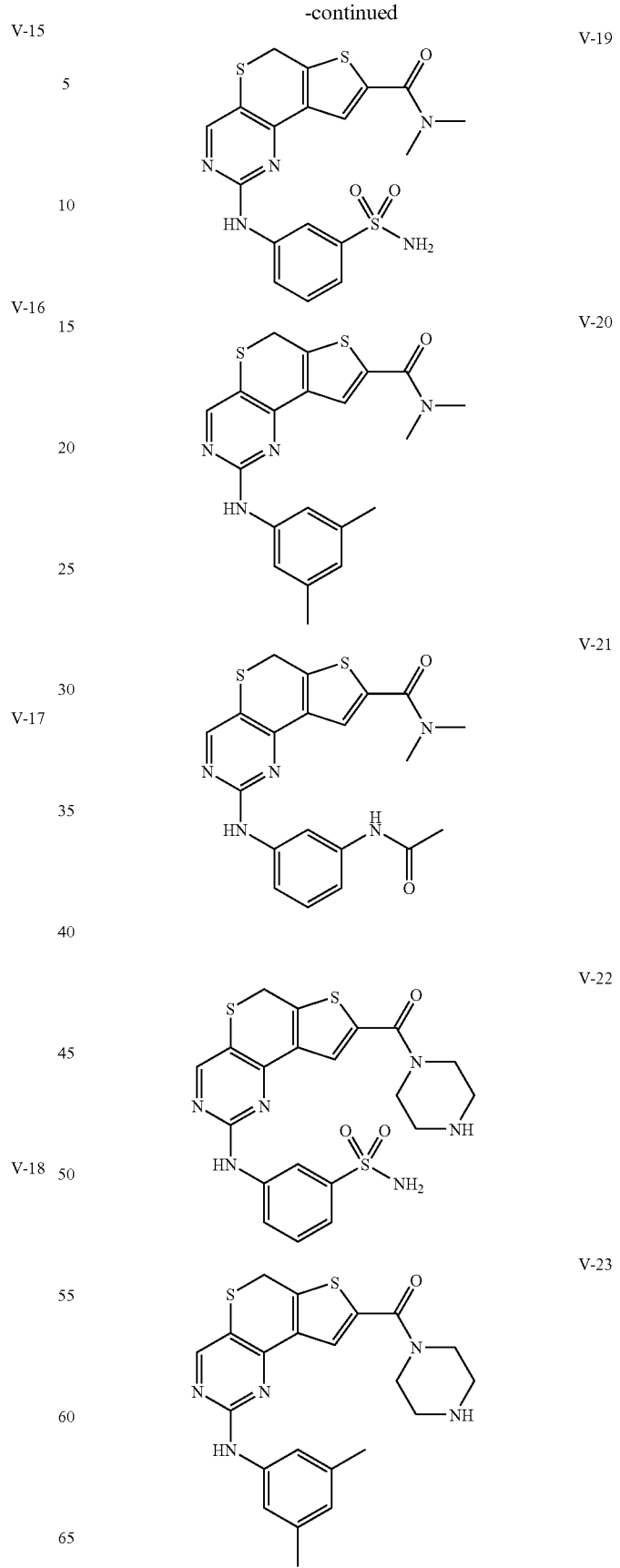

-continued
V-24
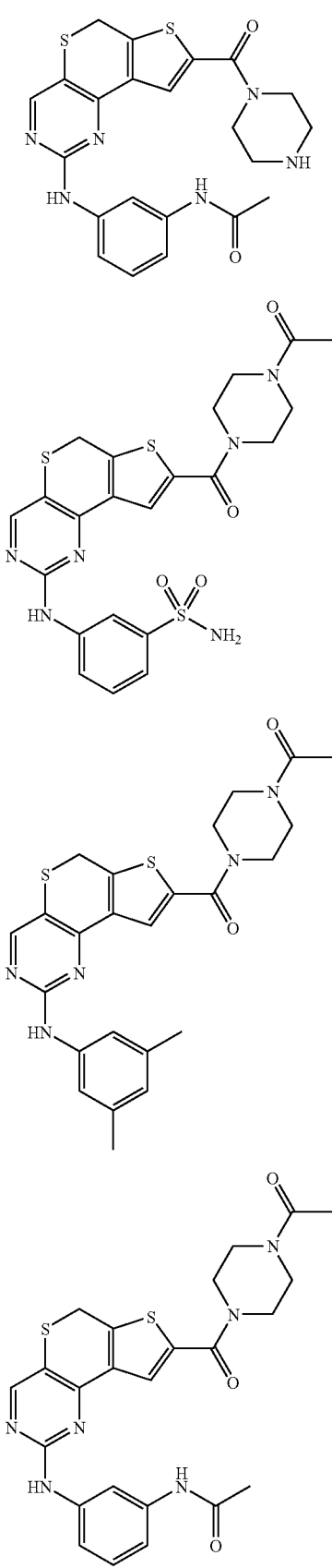
V-25
V-26
V-27
-continued
VI-1
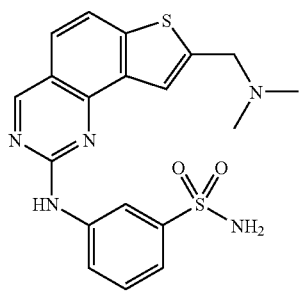
VI-2
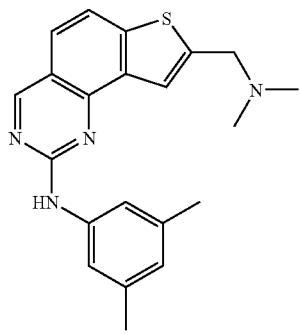
VI-3
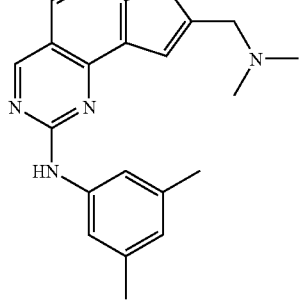
VI-4
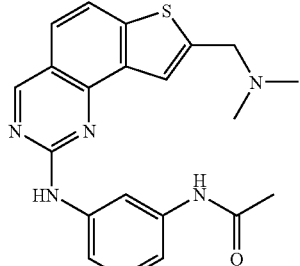
VI-5
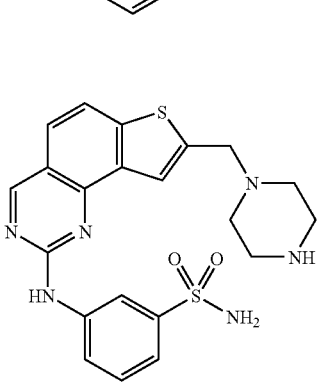

-continued
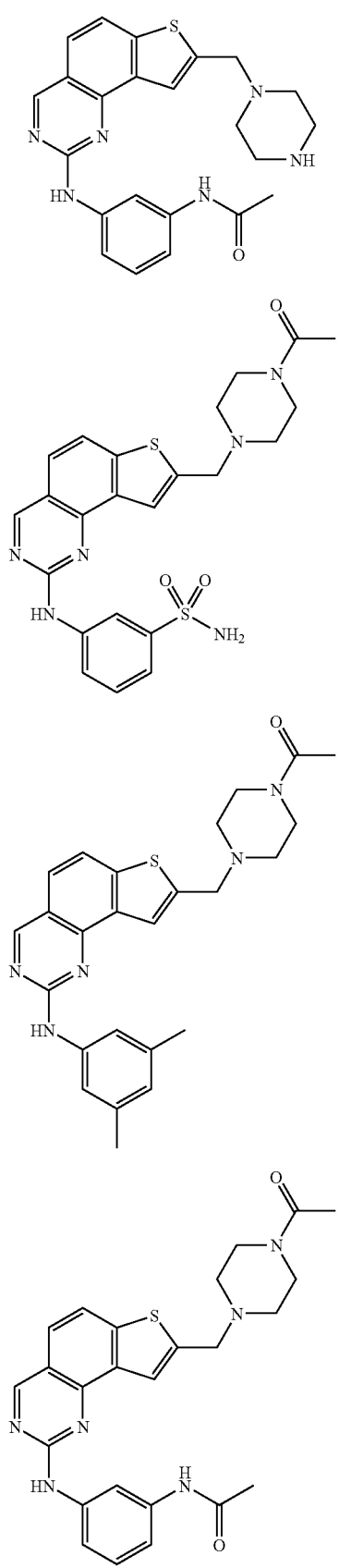
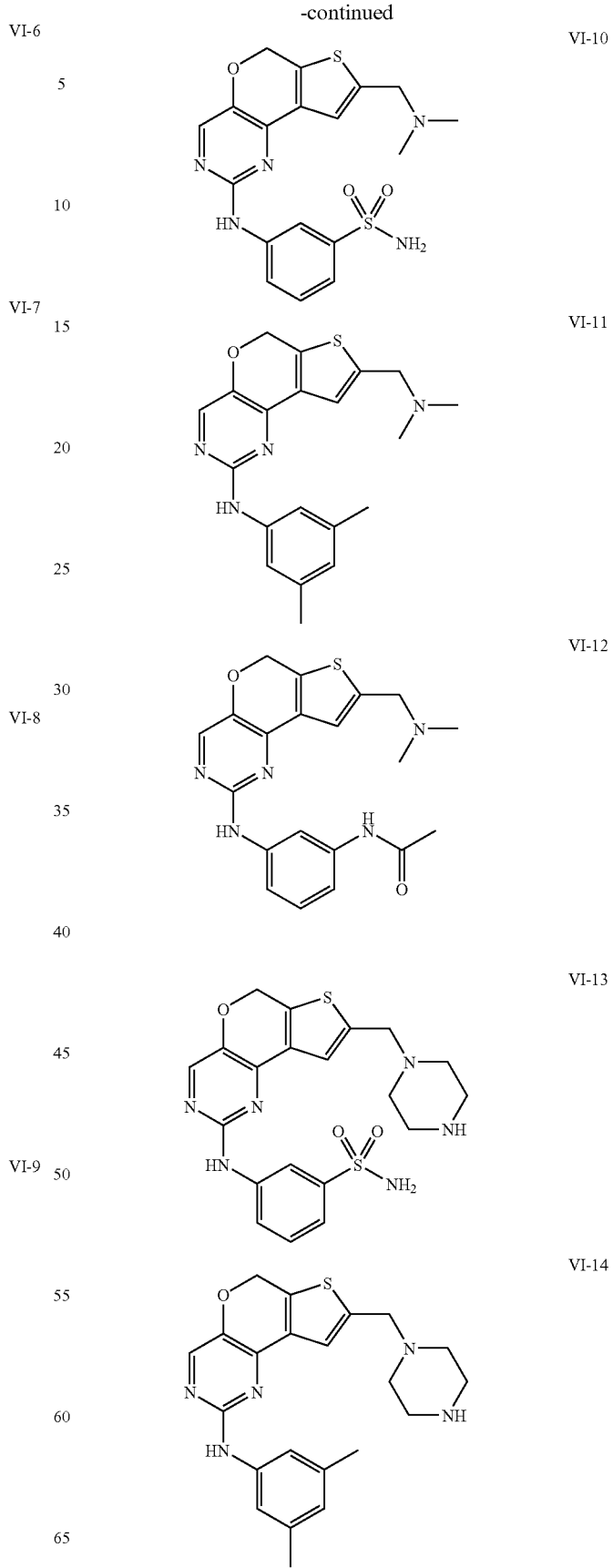

-continued
VI-15
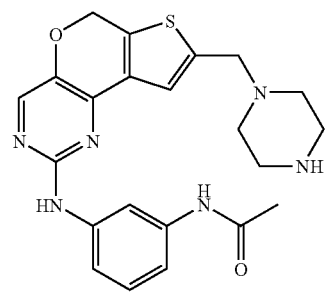
VI-16
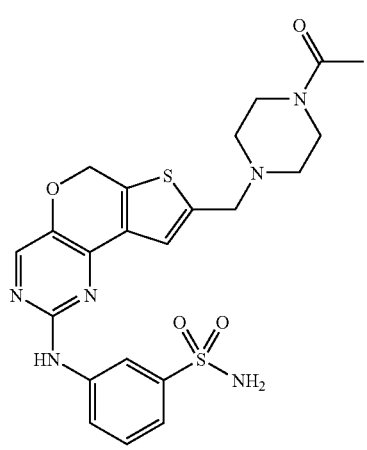
VI-17
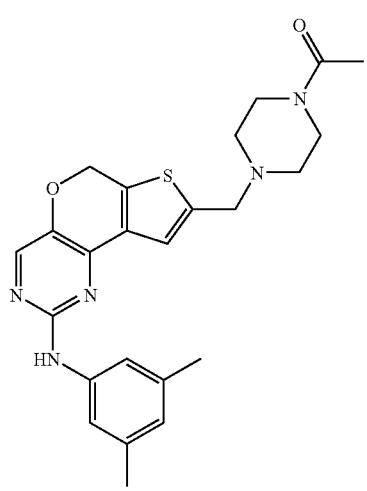
-continued
VI-18
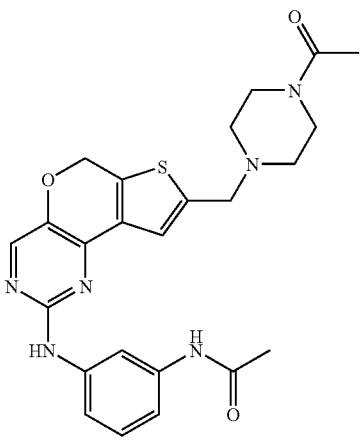
VI-19
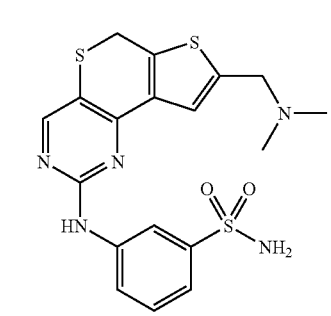
VI-20
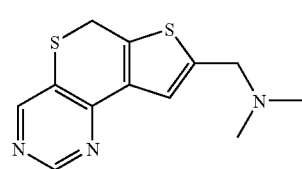
VI-21
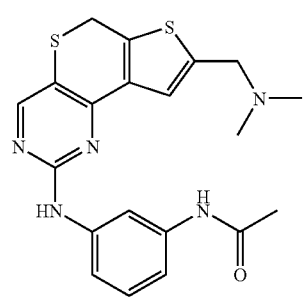

-continued
VI-22
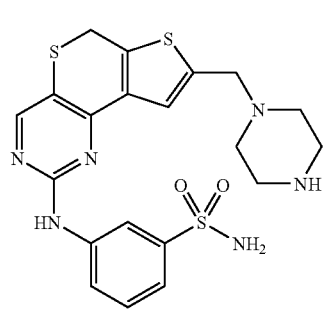
VI-23
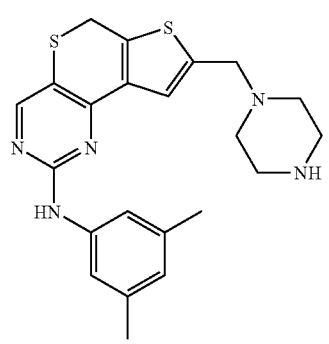
VI-24
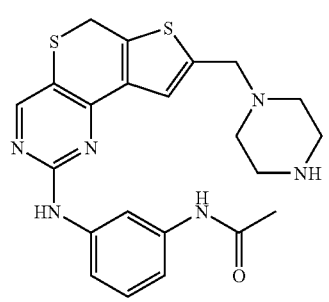
VI-25
VI-26
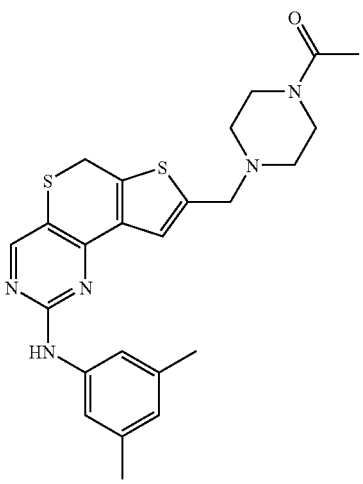
VI-27
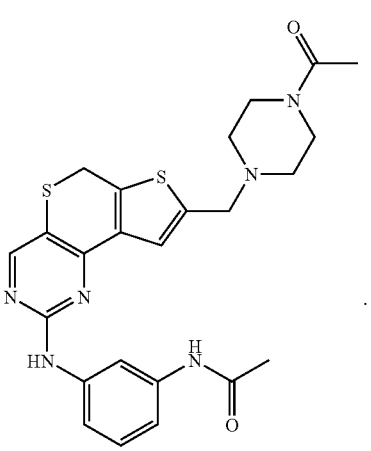
58. The compound of claim 1 or claim 2, wherein the compound is selected from:
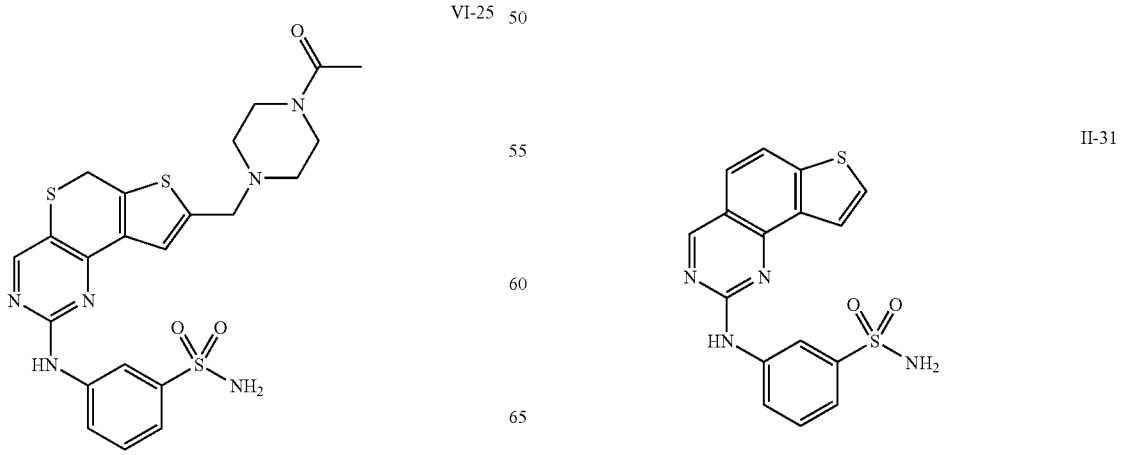
II-31
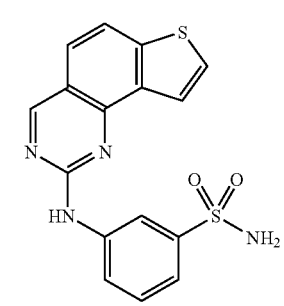

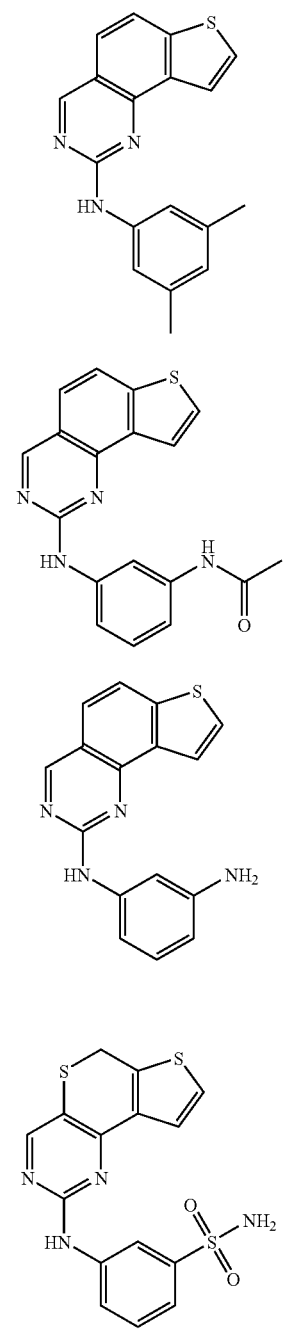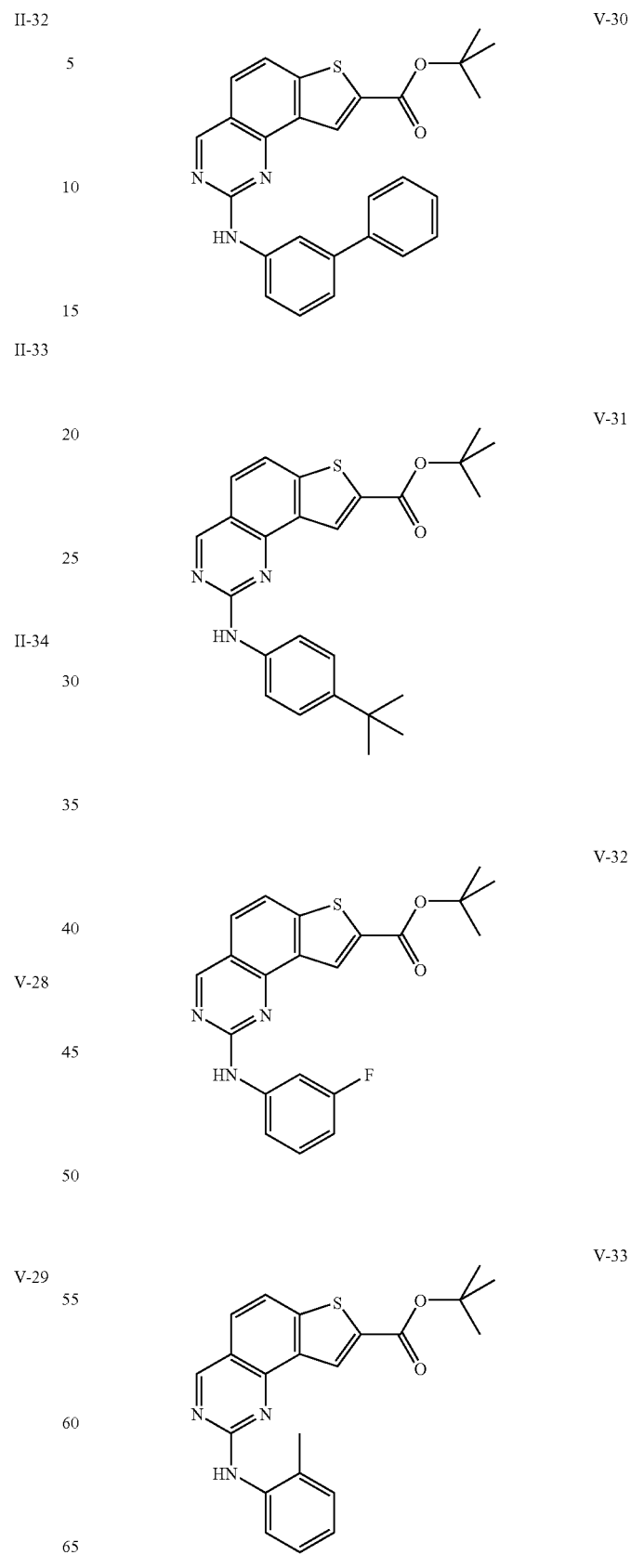

-continued
V-34
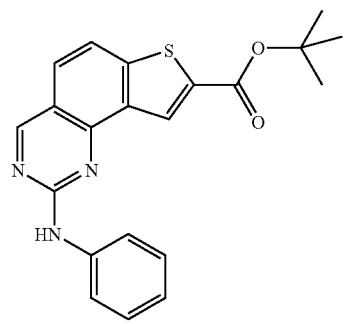
V-35
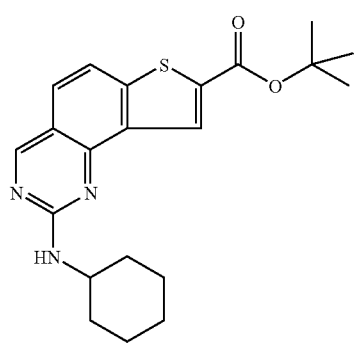
V-36
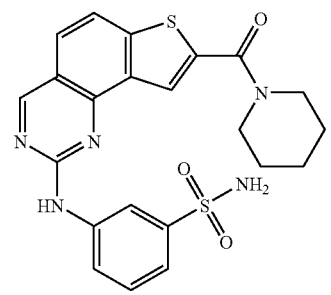
V-37
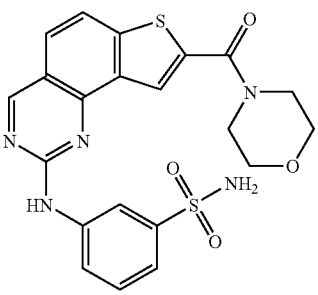
V-38
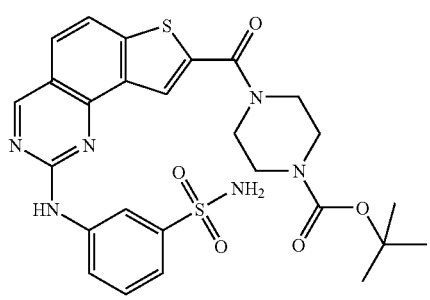
-continued
V-39
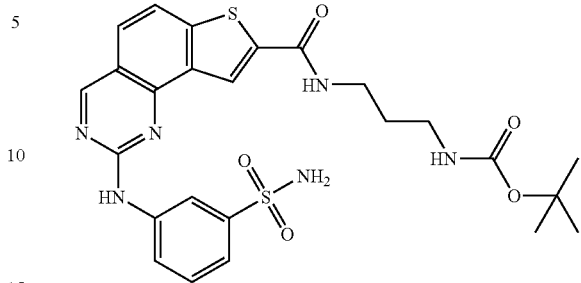
V-40
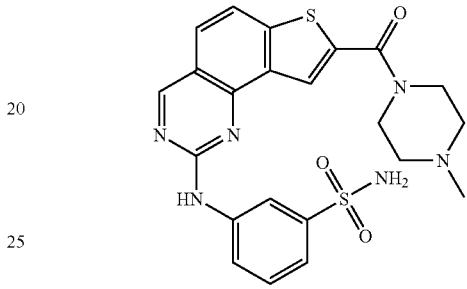
V-41
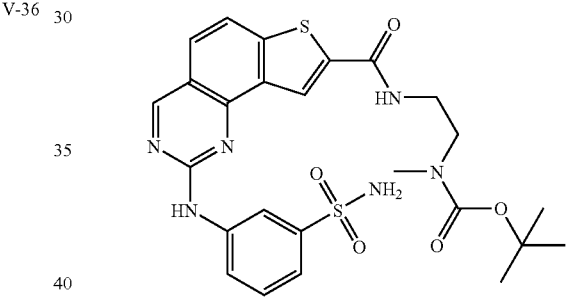
V-42
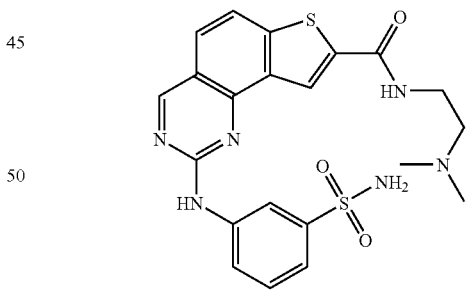
V-43
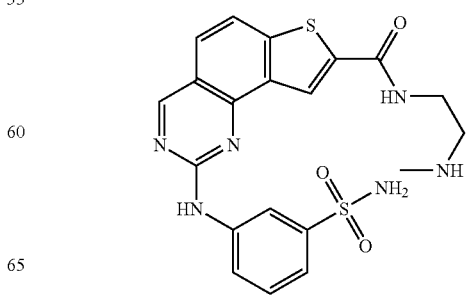

-continued

-continued
V-53
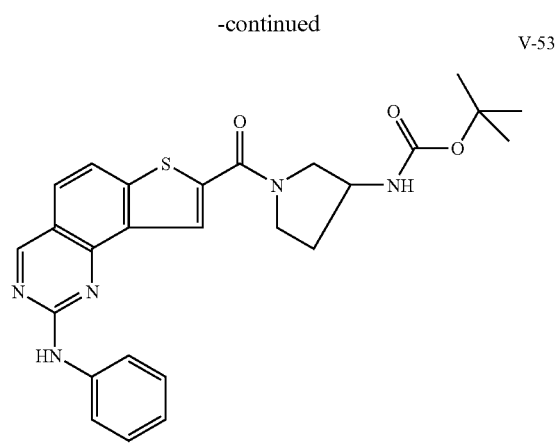
V-54
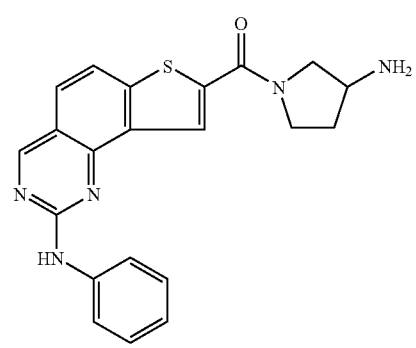
V-55
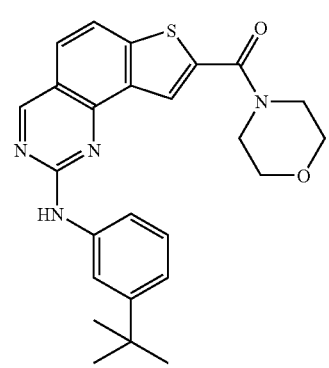
V-56
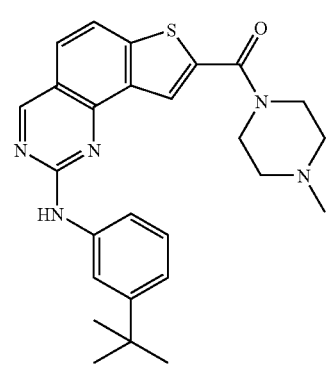
-continued
V-57
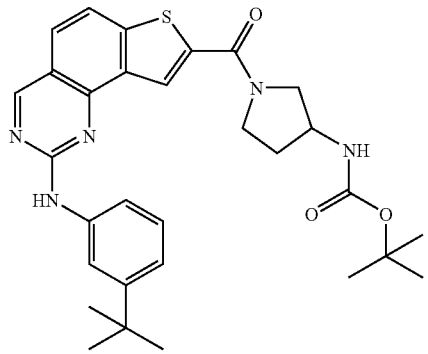
V-58
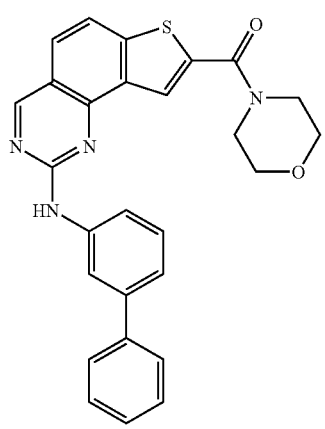
V-59
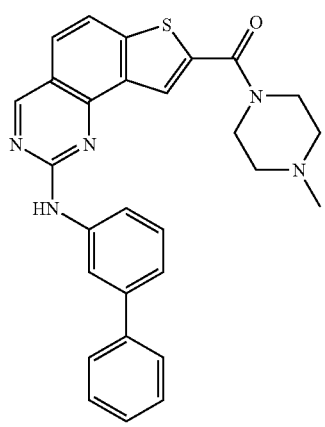
V-60
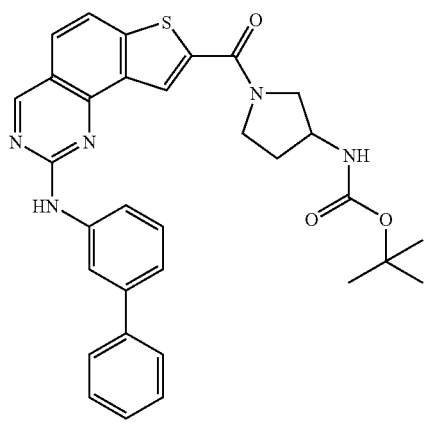

-continued
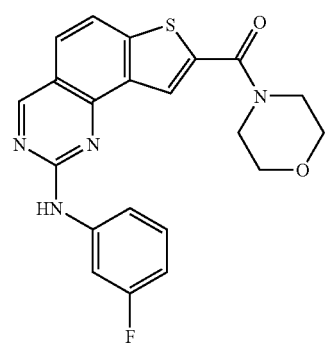
V-61
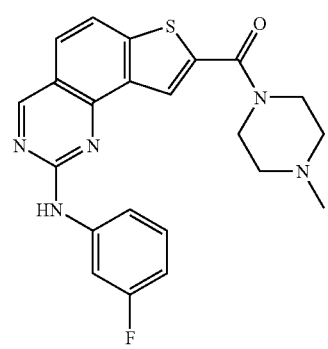
V-62
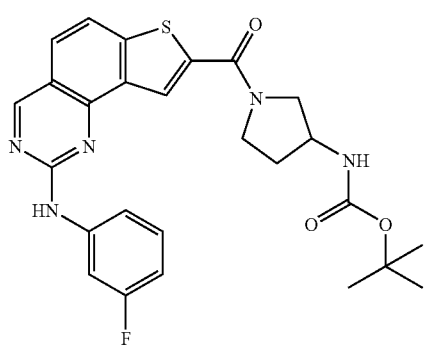
V-63
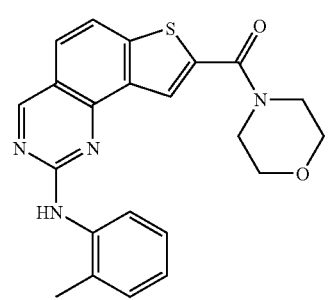
V-64
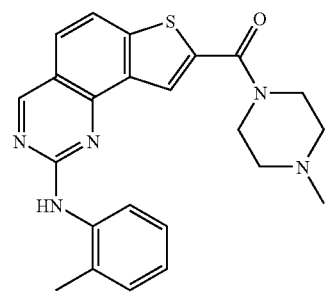
V-65
-continued
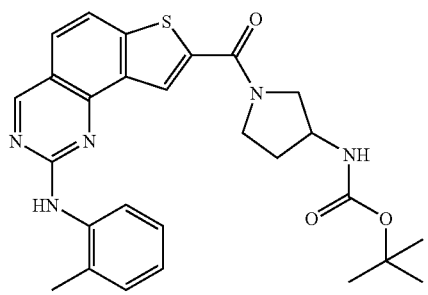
V-66
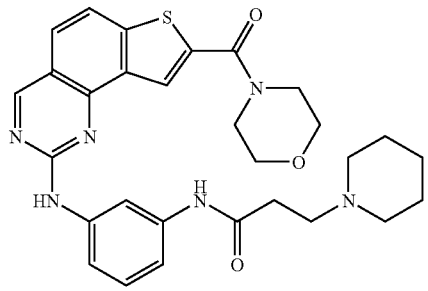
V-67
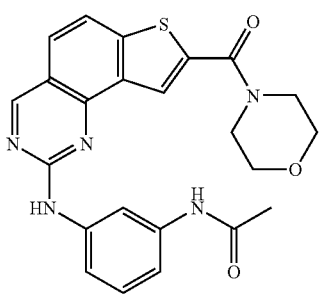
V-68
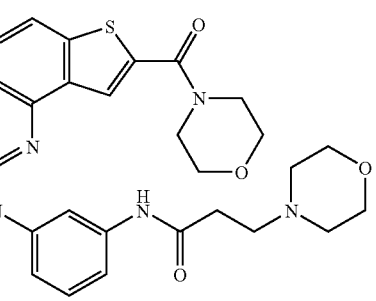
V-69
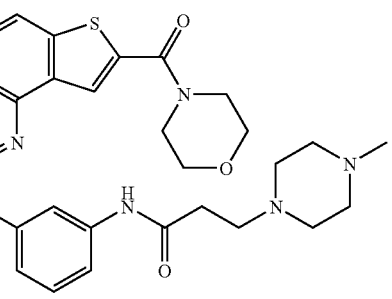
V-70

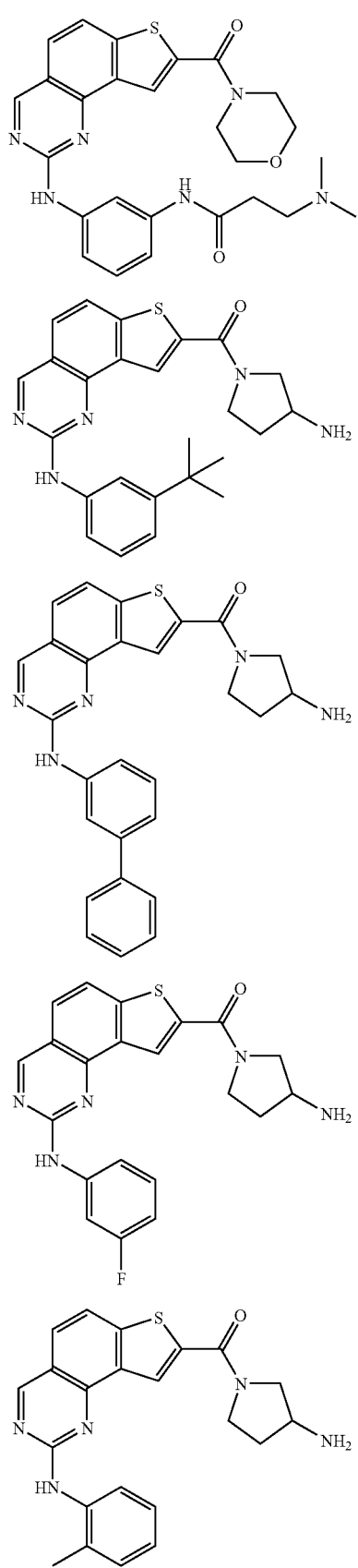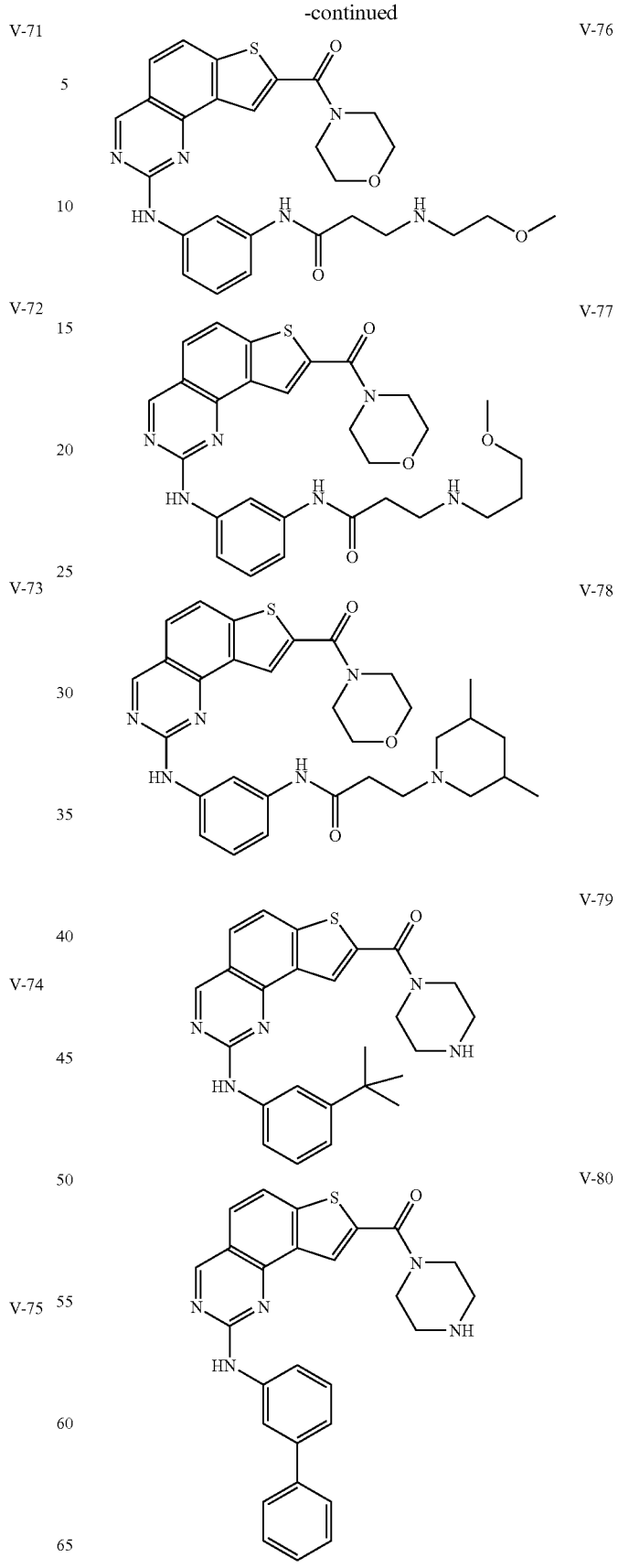

-continued
V-81
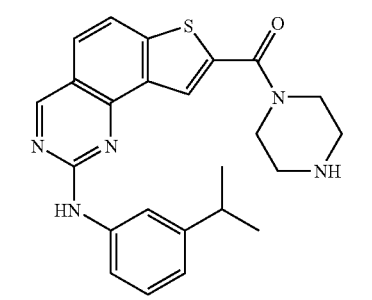
V-82
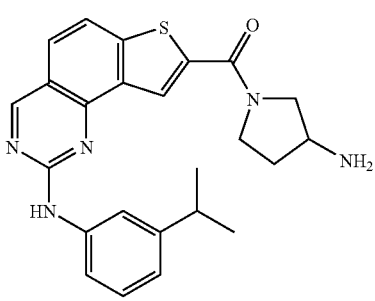
V-83
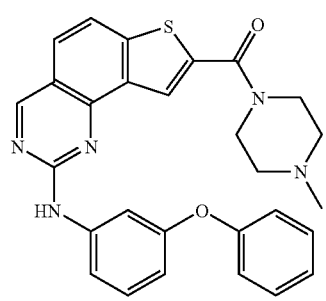
V-84
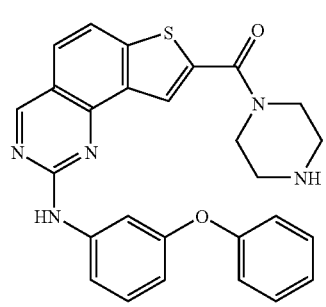
V-85
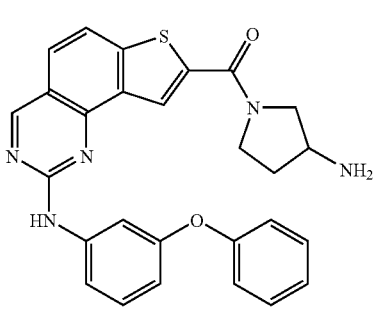
-continued
V-86
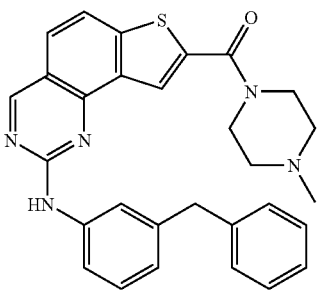
V-87
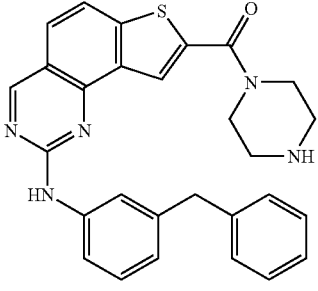
V-88
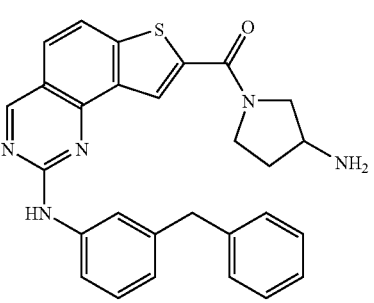
V-89
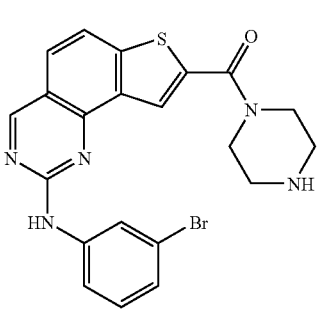
V-90
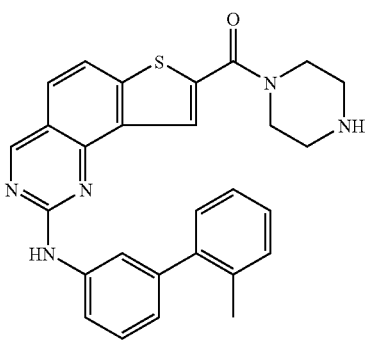

-continued
V-91
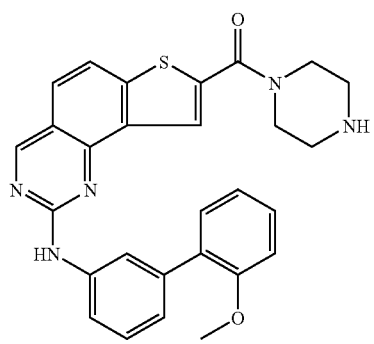
V-92
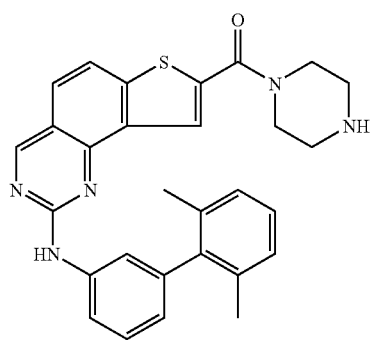
V-93
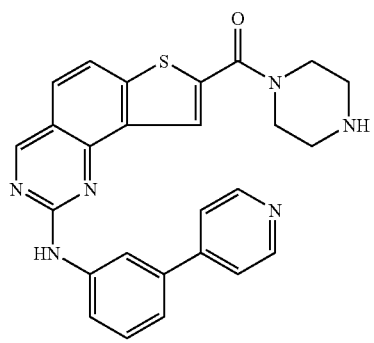
V-94
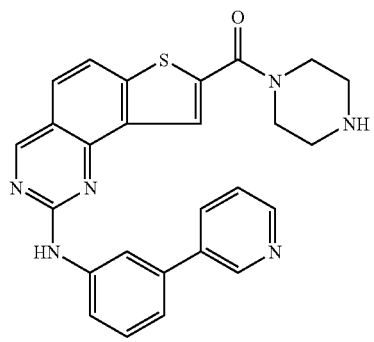
-continued
V-95
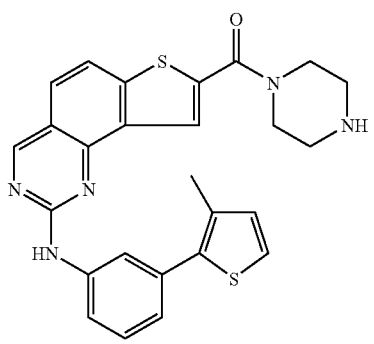
V-96
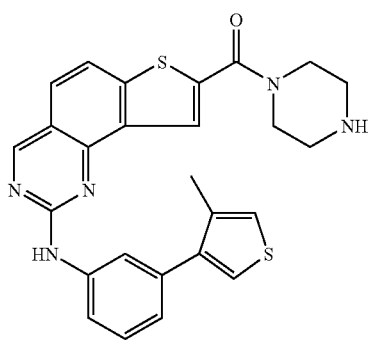
V-97
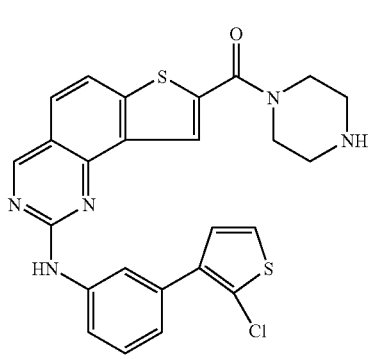
V-98
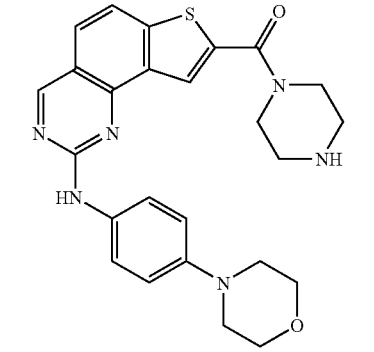

-continued
V-99
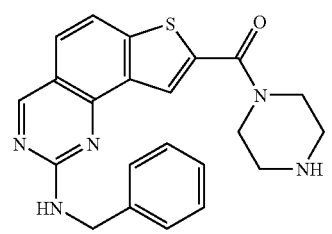
V-100
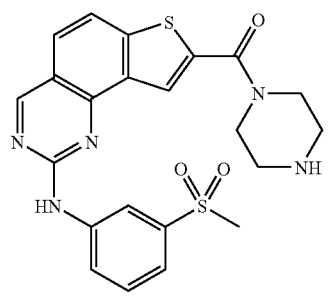
V-101
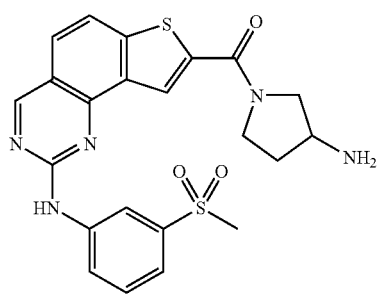
V-102
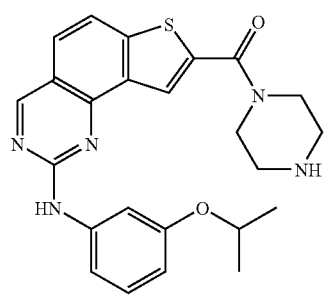
V-103
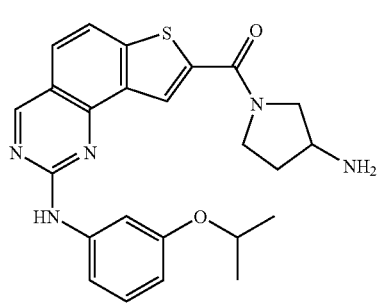
-continued
V-104
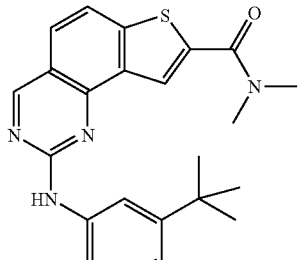
V-105
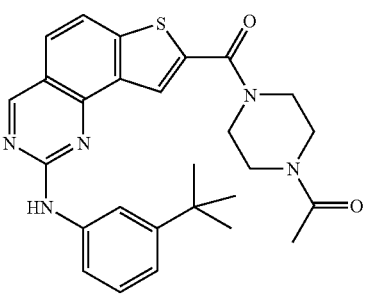
V-106
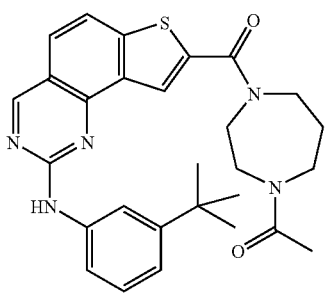
V-107
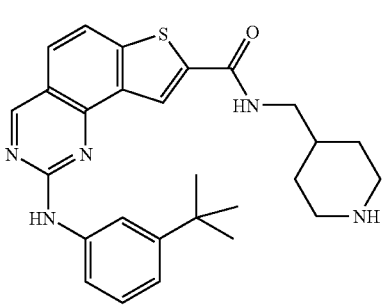
V-108
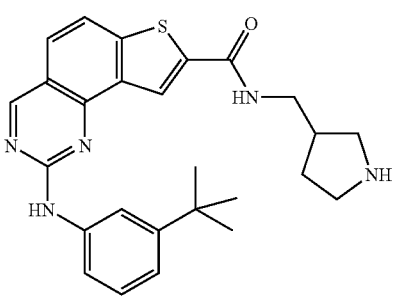

V-109
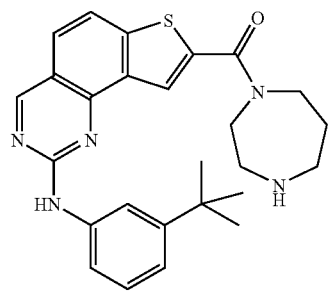
V-110
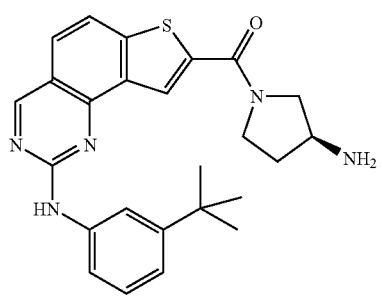
V-111
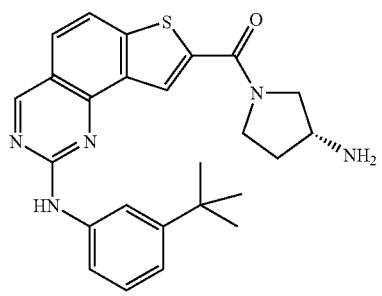
V-112
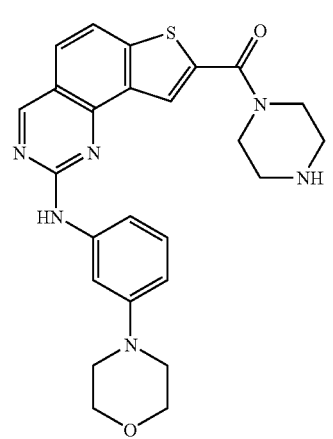
V-113
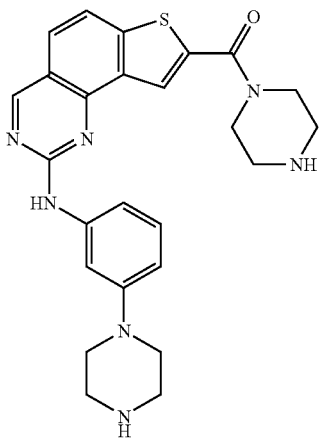
V-114
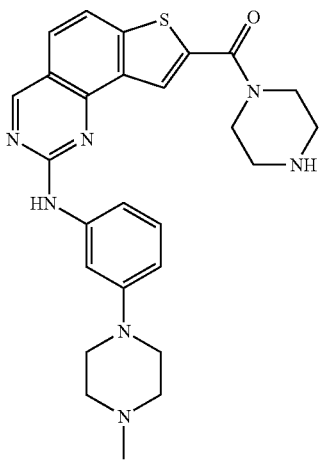
V-115
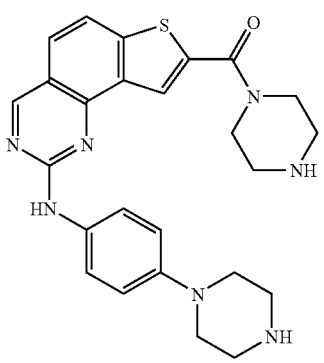
V-116
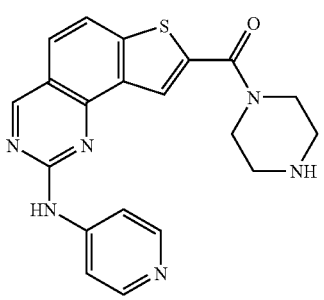

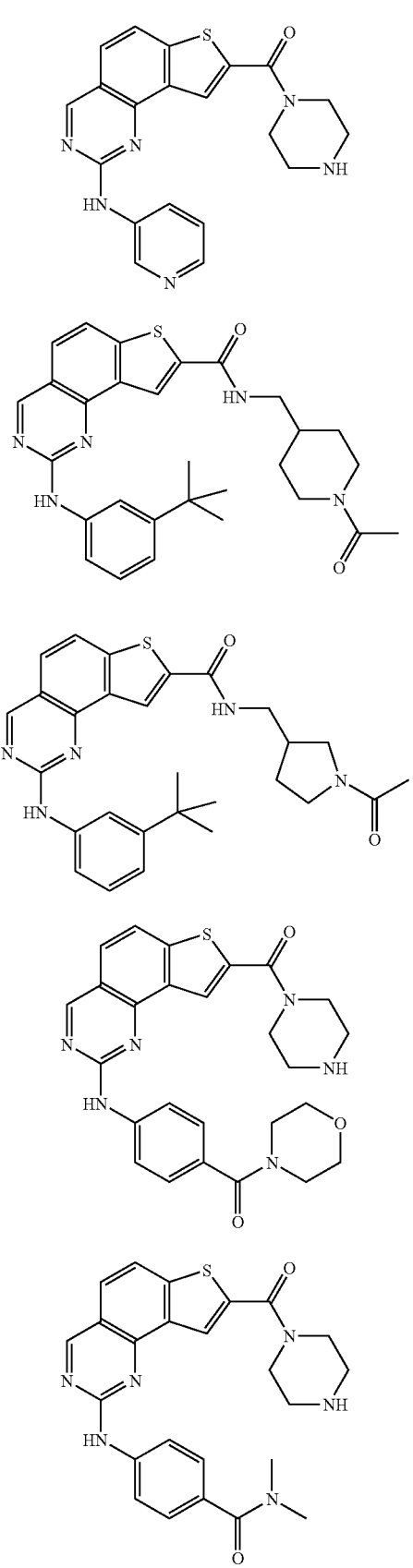
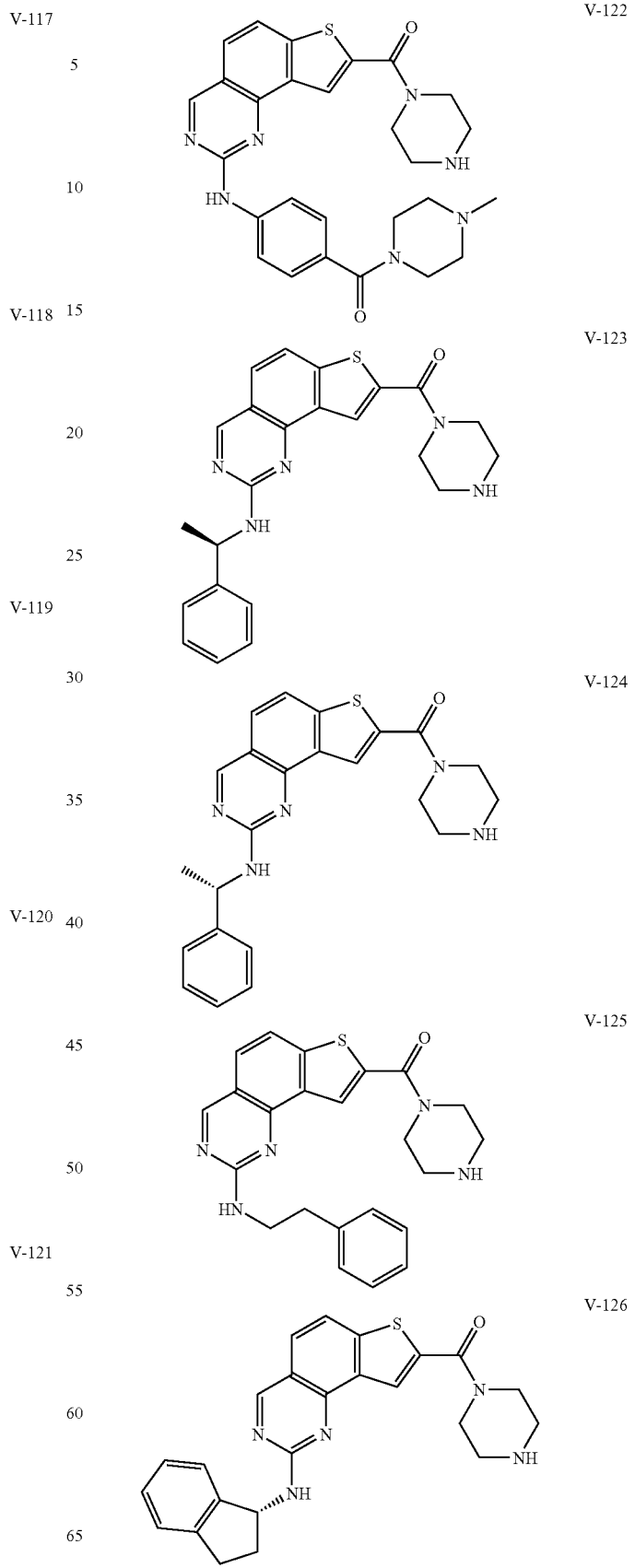

V-127
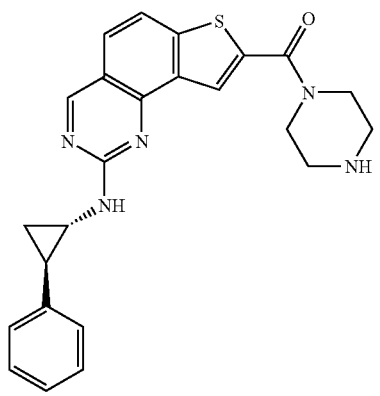
V-128
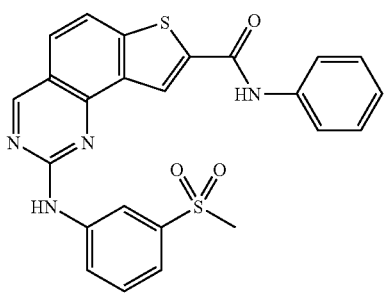
V-129
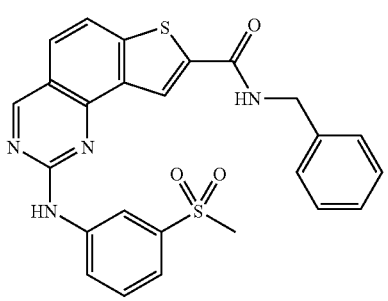
V-130
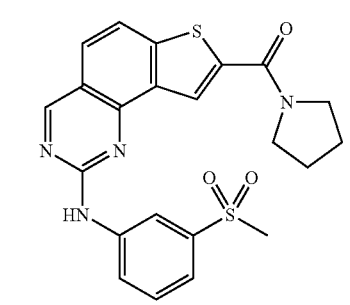
V-131
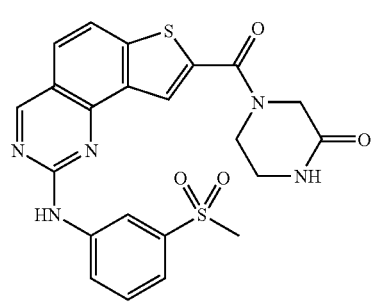
V-132
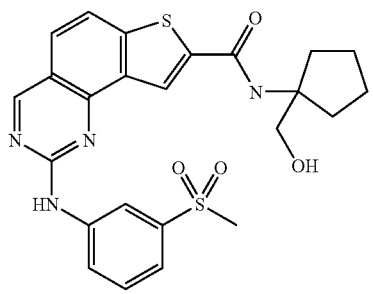
V-133
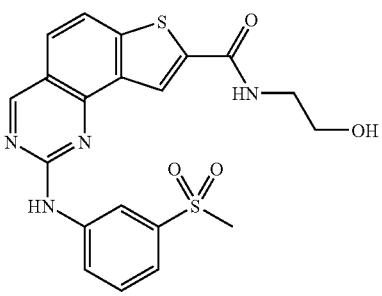
V-134
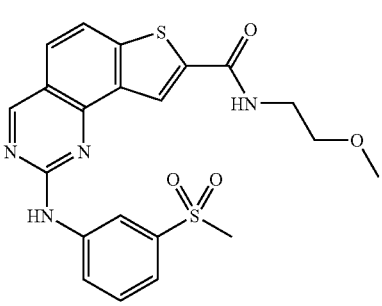
V-135
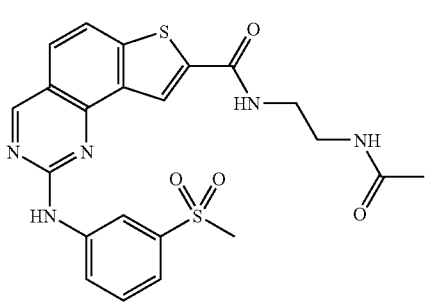
V-136
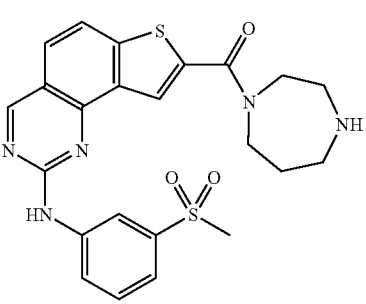

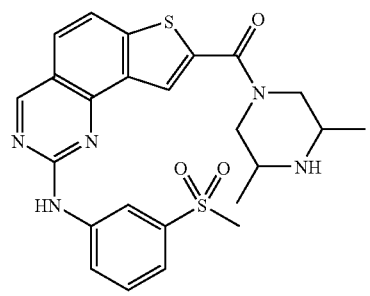 V-137
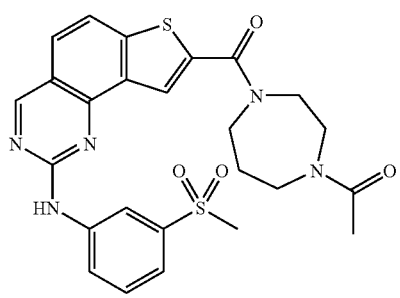 V-138
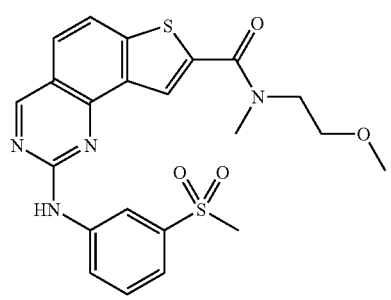 V-139
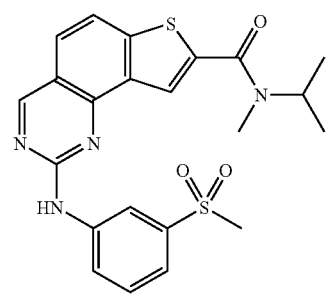 V-140
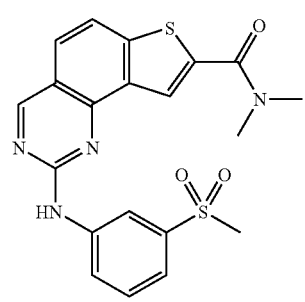 V-141
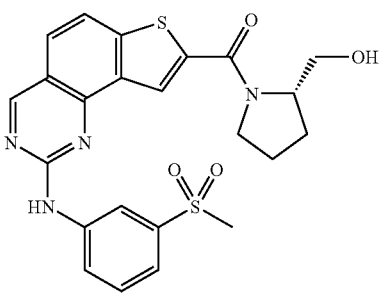 V-142
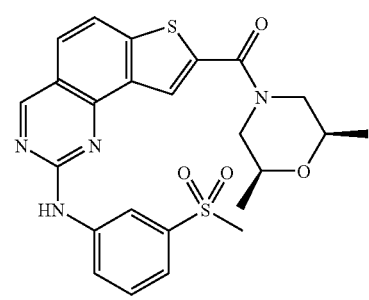 V-143
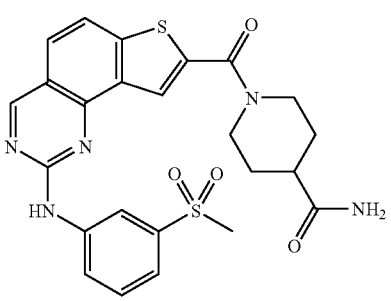 V-144
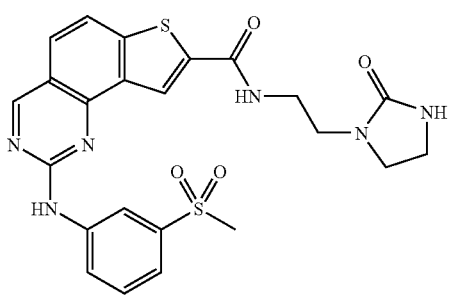 V-145
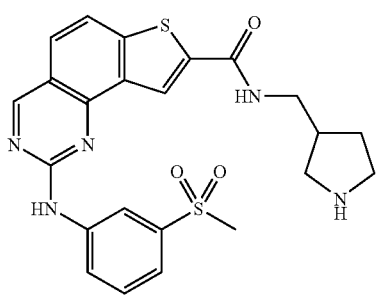 V-146

-continued
V-147
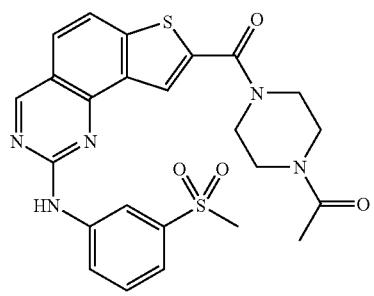
V-148
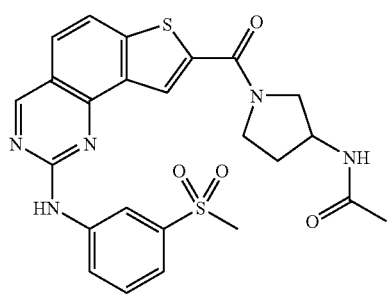
V-149
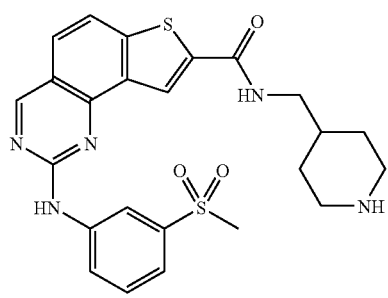
V-150
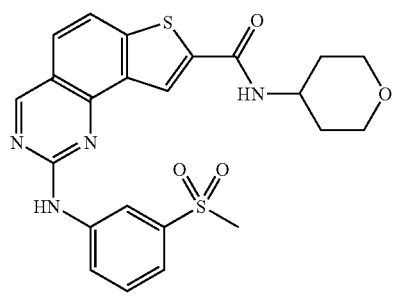
V-151
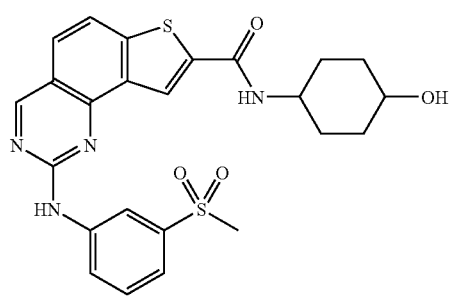
-continued
V-152
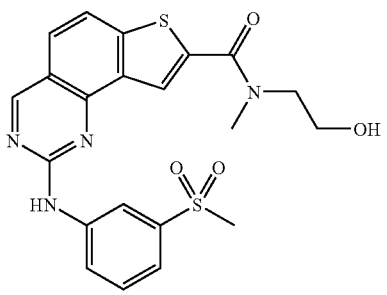
V-153
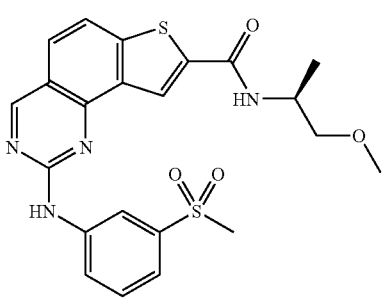
V-154
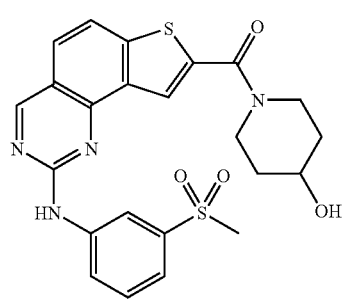
V-155
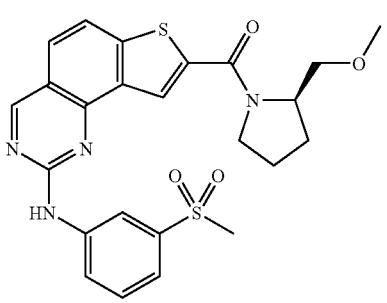
V-156
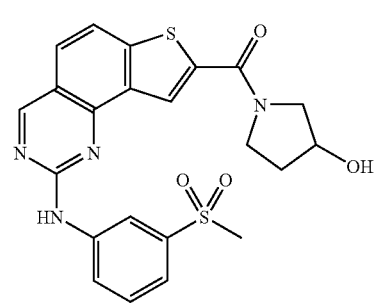

V-157 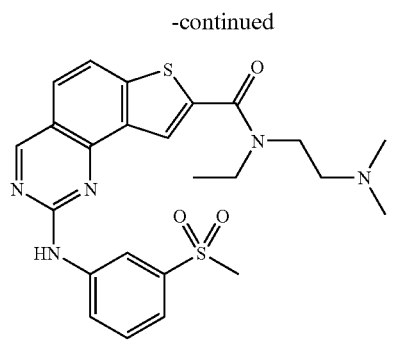
V-158 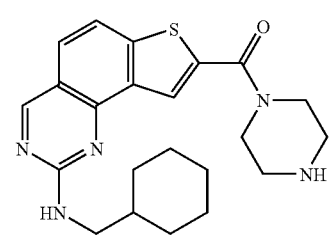
V-159 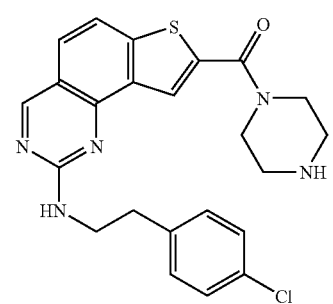
V-160 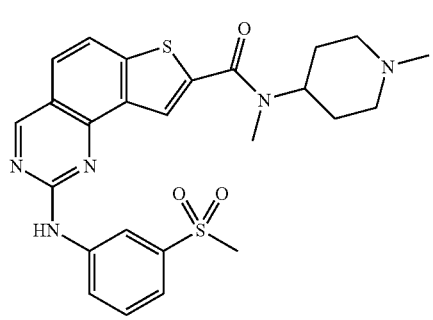
V-161 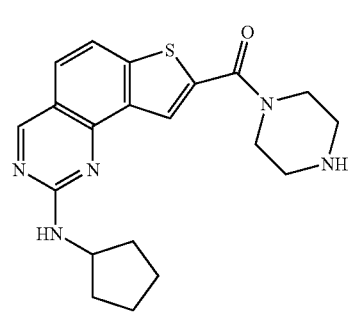
V-162 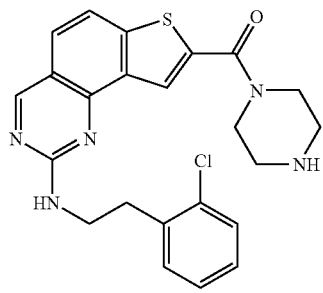
V-163 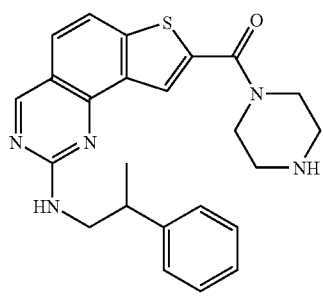
V-164 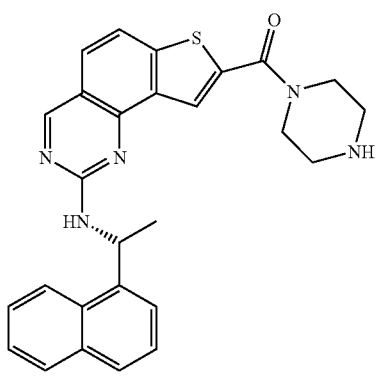
V-165 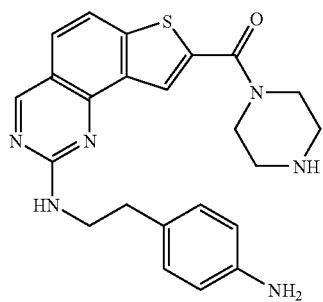

V-166 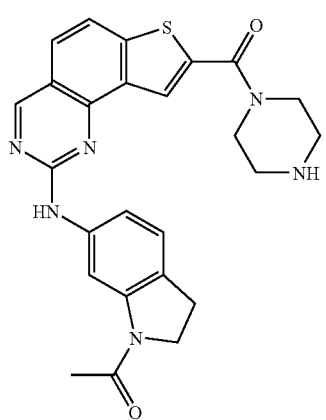
V-170 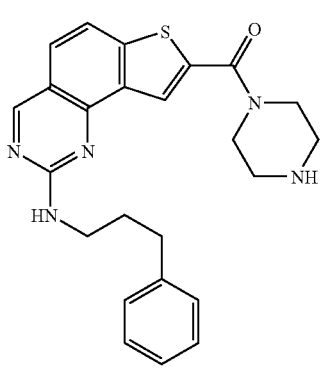
V-167 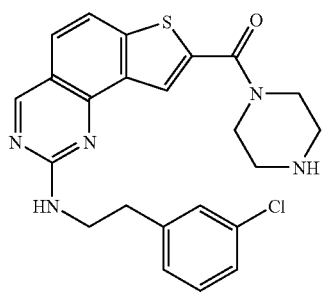
V-171 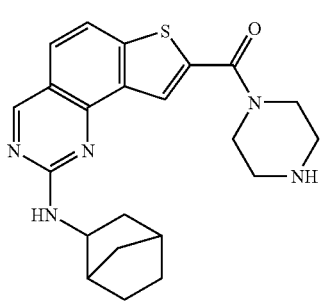
V-168 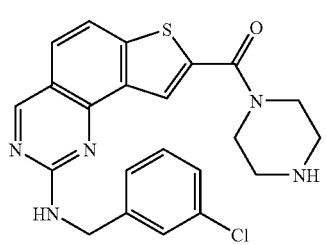
V-172 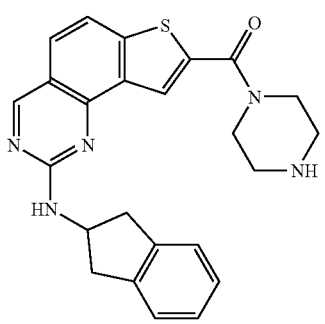
V-169 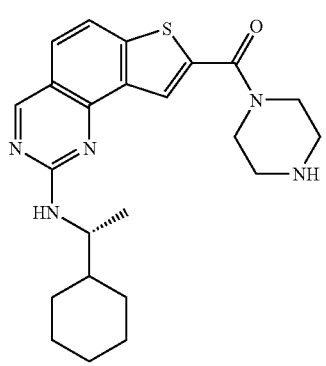
V-173 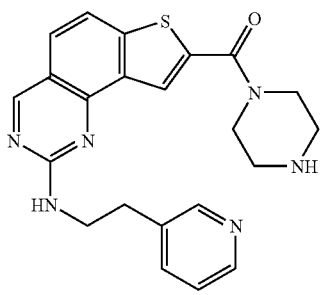

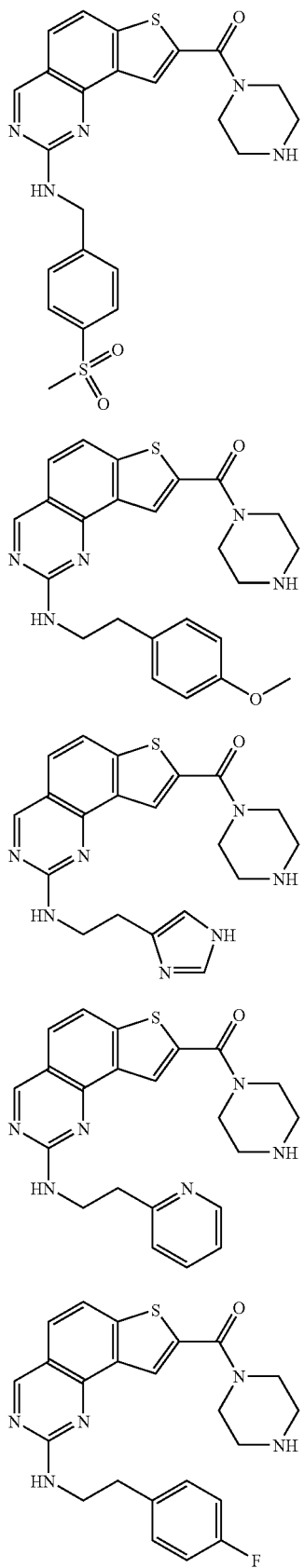
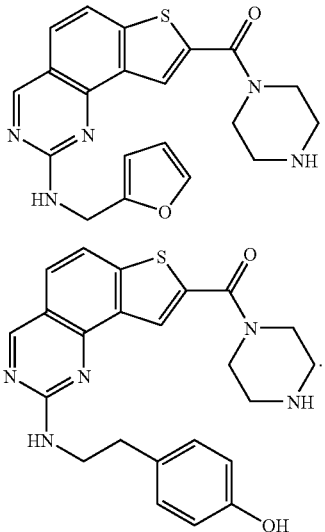
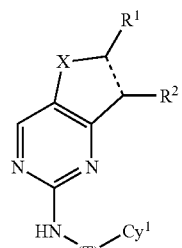

59. A composition comprising a compound of formula I:

$$\text{I}$$

or a pharmaceutically acceptable salt thereof, wherein:
X is —CH=CH—, —S—CH$_2$—, —CH$_2$—S—, —CH$_2$—O—, —O—CH$_2$—, or —(CH$_2$)$_3$—, wherein one or more of the hydrogen substituents are optionally and independently replaced with m occurrences of —WR$^y$, wherein m is an integer selected from 0 to 5;
R$^1$ and R$^2$, taken together with the carbon atoms to which they are bound form an optionally substituted 5-membered heteroaryl thiophene ring,
wherein the ring formed by R$^1$ and R$^2$ taken together is optionally and independently substituted at one or more carbon atoms with m occurrences of —WR$^y$, wherein m is an integer selected from 0 to 5;
each occurrence of W is independently a bond or is a C$_1$-C$_6$ alkylidene chain wherein up to two non-adjacent methylene units of W are independently optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^y$ is independently selected from R', halogen, NO$_2$, or CN, or —WR$^y$ is =O, =S, or =NR';
T is CHR', CH$_2$CH(R'), —S(=O)$_2$, or C(=O);
n is 0 or 1;
Cy$^1$ is a 3-7 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur, wherein $Cy^1$ is optionally and independently substituted at one or more carbon atoms with k occurrences of $-QR^X$, wherein k is an integer selected from 0 to 5; and at one or more substitutable nitrogen atoms with $-R^4$; wherein Q is a bond or is a $C_1$-$C_6$ alkylidene chain wherein up to two non-adjacent methylene units of Q are independently optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, or CN, or -QRX is =O, =S, or =NR';

each occurrence of $R^3$ and $R^4$ is independently R', —COR', —$CO_2$($C_{1-6}$ aliphatic), —CON(R')$_2$, or —$SO_2$R';

each occurrence of R is independently selected from hydrogen or an optionally substituted $C_{1-6}$ aliphatic group; and each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form an optionally substituted 3-8 membered cycloalkyl, heterocyclyl, aryl, or heteroaryl ring having 0-3 heteroatoms independently selected from nitrogen, oxygen, or sulfur; and the dashed bond represents a single or double bond, as valency permits and a pharmaceutically acceptable carrier, adjuvant, or vehicle.

60. The composition of claim 59, wherein the compound is present in a therapeutically effective amount.

61. The composition of claim 59, wherein the compound is present in an amount to detectably inhibit GSK-3, SYK, Aurora-2, CDK-2, JAK-3, and/or Tec family (e.g., Tec, Btk, Itk/Emt/Tsk, Bmx, Txk/Rlk) protein kinase activity.

62. The composition of claim 59, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent an agent for treating blood disorders, an agent for treating diabetes, or an agent for treating immunodeficiency disorders.

63. The compound of claim 30, wherein —$WR^y$ groups are each independently F, Cl, Br, I, Me, Et, —CN, —OMe, —SMe, —$NMe_2$, —$NEt_2$, —COOMe, —COOH, —OH, —$SO_2NH_2$, —CON(CH$_3$)$_2$, —CO(optionally substituted N-piperazinyl), —CO(N-morpholinyl), —CO(N-piperidinyl), —CH$_2$N(Me)$_2$, —CH$_2$N(Et)$_2$, or an optionally substituted group selected from $C_{1-4}$alkoxy, phenyl, phenyloxy, benzyl, benzyloxy, pyridyl, pyrimidinyl, thiophene, N-morpholinyl, N-piperidinyl, N-piperazinyl, or furanyl.

\* \* \* \* \*

UNITED STATES PATENT AND TRADEMARK OFFICE
CERTIFICATE OF CORRECTION

PATENT NO.         : 7,700,609 B2
APPLICATION NO.    : 10/965695
DATED              : April 20, 2010
INVENTOR(S)        : Jimenez et al.

It is certified that error appears in the above-identified patent and that said Letters Patent is hereby corrected as shown below:

Column 21, line 25: replace " 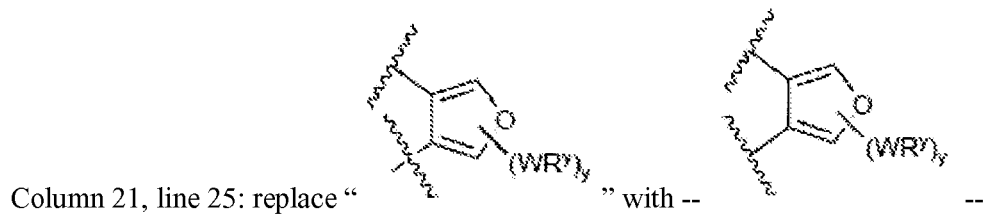 " with -- --

Column 24, line 57: replace " 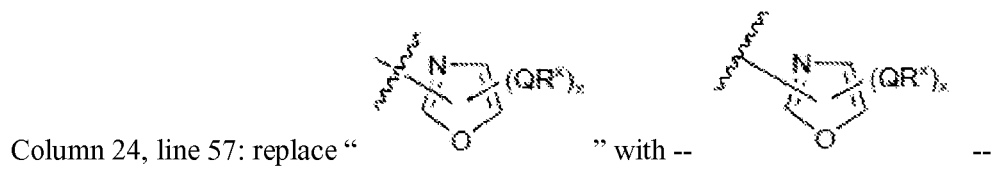 " with -- --

Column 29, line 33: replace " 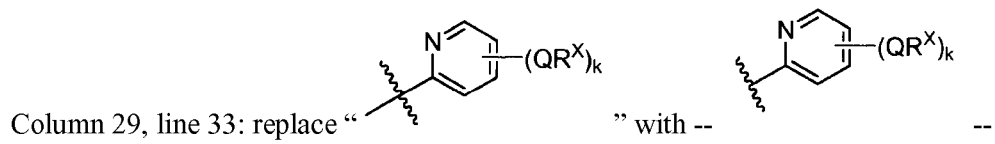 " with -- --

Column 241, line 41: replace "R'is" with -- R' is --

Column 248, line 45: replace " 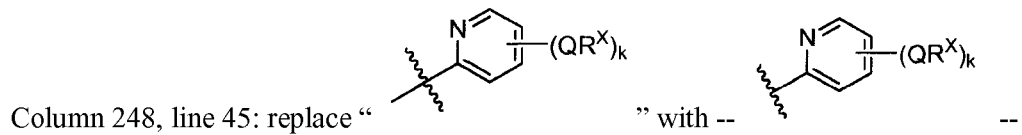 " with -- --

Signed and Sealed this
Twenty-seventh Day of September, 2011

David J. Kappos
*Director of the United States Patent and Trademark Office*